(12) United States Patent
Shin et al.

(10) Patent No.: US 8,530,504 B2
(45) Date of Patent: Sep. 10, 2013

(54) PYRAZOLOTHIAZOLE COMPOUND

(75) Inventors: Kogyoku Shin, Hatfield (GB); Taro Terauchi, Tsukuba (JP); Yoshinori Takahashi, Tsukuba (JP); Minako Hashizume, Tsukuba (JP); Kunitoshi Takeda, Tsukuba (JP); Kodo Shikata, Hatfield (GB); Akira Inomata, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 12/900,026

(22) Filed: Oct. 7, 2010

(65) Prior Publication Data
US 2011/0086882 A1    Apr. 14, 2011

Related U.S. Application Data

(60) Provisional application No. 61/249,817, filed on Oct. 8, 2009, provisional application No. 61/352,970, filed on Jun. 9, 2010.

(30) Foreign Application Priority Data

Oct. 8, 2009 (JP) ............................... P2009-233989
Jun. 9, 2010 (JP) ............................... P2010-132008

(51) Int. Cl.
*A61K 31/429* (2006.01)
*A61P 25/24* (2006.01)

(52) U.S. Cl.
USPC ......................................... 514/368; 548/154

(58) Field of Classification Search
None
See application file for complete search history.

(56) References Cited

U.S. PATENT DOCUMENTS

| | | |
|---|---|---|
| 4,596,872 A | 6/1986 | Davey |
| 4,910,199 A | 3/1990 | Bourguignon et al. |
| 4,925,849 A | 5/1990 | Shiokawa et al. |
| 4,957,925 A | 9/1990 | Gubin et al. |
| 4,985,444 A | 1/1991 | Shiokawa et al. |
| 4,990,516 A | 2/1991 | Ohashi et al. |
| 4,994,453 A | 2/1991 | Shiokawa et al. |
| 5,087,629 A | 2/1992 | Shiokawa et al. |
| 5,102,869 A | 4/1992 | Shiokawa et al. |
| 5,102,878 A | 4/1992 | Shiokawa et al. |
| 5,127,936 A | 7/1992 | Selby |
| 5,155,114 A | 10/1992 | Shiokawa et al. |
| 5,179,103 A | 1/1993 | Shiokawa et al. |
| 5,190,862 A | 3/1993 | Wielinger et al. |
| 5,234,818 A | 8/1993 | Zimmermann et al. |
| 5,296,490 A | 3/1994 | Shiokawa et al. |
| 5,338,743 A | 8/1994 | Shiokawa et al. |
| 5,391,482 A | 2/1995 | Mangold |
| 5,445,943 A | 8/1995 | Hoenes |
| 5,457,200 A | 10/1995 | Zimmermann et al. |
| 5,525,480 A | 6/1996 | Zimmermann et al. |
| 5,565,468 A | 10/1996 | Larsen et al. |
| 5,602,132 A | 2/1997 | Roger et al. |

(Continued)

FOREIGN PATENT DOCUMENTS

| | | |
|---|---|---|
| AU | 2003220190 A1 | 9/2003 |
| CA | 2115805 A1 | 8/1994 |

(Continued)

OTHER PUBLICATIONS

English translation of Chilean Office Action dated Jun. 14, 2011 for Application No. 896-09.

(Continued)

*Primary Examiner* — Kamal Saeed
(74) *Attorney, Agent, or Firm* — Birch, Stewart, Kolasch & Birch, LLP

(57) ABSTRACT

A compound represented by the formula (I) or pharmacologically acceptable salt thereof exhibits an excellent CRF receptor antagonism

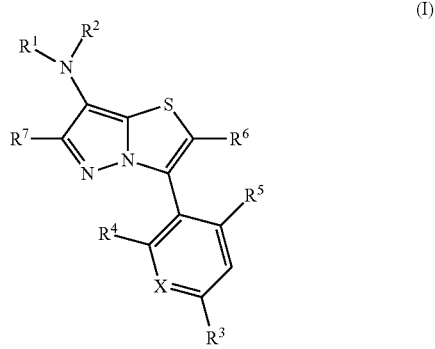

wherein X is a nitrogen atom or CH; $R^1$ is $-A^{11}-A^{12}$; $A^{11}$ is a single bond or a C1-6 alkylene group; $A^{12}$ is a hydrogen atom, a C1-6 alkyl group or a C3-6 cycloalkyl group, etc.; $R^2$ is $-A^{21}-A^{22}$; $A^{21}$ is a single bond or a C1-6 alkylene group; $A^{22}$ is a hydrogen atom, a C1-6 alkyl group, a C3-6 cycloalkyl group, a non-aromatic heterocyclic group, or a heteroaryl group, etc.; $R^3$ is a C1-6 alkyl group, a C3-6 cycloalkyl group, a C1-6 alkoxy group, a C3-6 cycloalkoxy C1-6 alkyl group, di-C1-6 alkyl amino group, a halogen atom, a cyano group, a formyl group, or a carboxyl group, etc; $R^4$ is a hydrogen atom or a C1-6 alkoxy group; $R^5$ is a halogen atom, a C1-6 alkyl group, or a C1-6 alkoxy group; $R^6$ is a hydrogen atom, a C1-6 alkyl group, a C1-6 alkoxy group, a C1-6 alkylthio group, or a C1-6 alkyl sulfinyl group etc.; and $R^7$ is a C1-6 alkyl group, a C1-6 alkoxy group, or a C1-6 alkylthio group.

15 Claims, No Drawings

(56) References Cited

U.S. PATENT DOCUMENTS

| | | | |
|---|---|---|---|
| 5,691,347 | A | 11/1997 | Corbier et al. |
| 6,638,933 | B2 | 10/2003 | Gerlach et al. |
| 6,642,246 | B1 | 11/2003 | Schmiesing |
| 6,657,064 | B2 | 12/2003 | Gerlach et al. |
| 6,664,261 | B2 | 12/2003 | Chen et al. |
| 6,703,404 | B2 | 3/2004 | Maul et al. |
| 6,730,789 | B1 | 5/2004 | Birault et al. |
| 6,849,642 | B2 | 2/2005 | Gerlach et al. |
| 6,900,217 | B2 | 5/2005 | Chen |
| 6,936,631 | B2 | 8/2005 | Gerlach et al. |
| 7,074,797 | B2 | 7/2006 | Chen et al. |
| 7,078,405 | B2 | 7/2006 | Hibi et al. |
| 7,091,215 | B2 | 8/2006 | Hibi et al. |
| 7,176,216 | B2 | 2/2007 | Hibi et al. |
| 7,285,666 | B2 | 10/2007 | Hibi et al. |
| 7,323,569 | B2 | 1/2008 | Hibi et al. |
| 7,625,925 | B2 | 12/2009 | Hibi et al. |
| 7,772,249 | B2 | 8/2010 | Hibi et al. |
| 2004/0122039 | A1 | 6/2004 | Hibi et al. |
| 2004/0224974 | A1 | 11/2004 | Hibi et al. |
| 2006/0211696 | A1 | 9/2006 | Hibi et al. |
| 2006/0235011 | A1 | 10/2006 | Hibi et al. |
| 2006/0270659 | A1 | 11/2006 | Chen et al. |
| 2007/0129382 | A1 | 6/2007 | Grigoriadis et al. |
| 2007/0293511 | A1 | 12/2007 | Luo et al. |
| 2008/0076943 | A1 | 3/2008 | Hibi et al. |
| 2008/0194589 | A1 | 8/2008 | Lanier et al. |
| 2008/0306092 | A1 | 12/2008 | Hossner |
| 2009/0181985 | A1 | 7/2009 | Hibi et al. |
| 2009/0259049 | A1 | 10/2009 | Shibata et al. |

FOREIGN PATENT DOCUMENTS

| | | |
|---|---|---|
| CZ | 301 491 B6 | 3/2010 |
| EP | 0068378 A1 | 1/1983 |
| EP | 0 299 209 A2 | 1/1989 |
| EP | 0353902 A1 | 2/1990 |
| EP | 0 368 343 A2 | 5/1990 |
| EP | 0433853 A1 | 6/1991 |
| EP | 0433854 A2 | 6/1991 |
| EP | 0 497 258 A2 | 8/1992 |
| EP | 0611766 A1 | 8/1994 |
| EP | 0659747 A1 | 6/1995 |
| EP | 0778277 A1 | 6/1997 |
| EP | 0812831 A1 | 12/1997 |
| EP | 1389618 A1 | 2/2004 |
| EP | 1 555 265 A1 | 7/2005 |
| EP | 2266990 A1 | 12/2010 |
| HU | 211684 A9 | 12/1995 |
| IN | 237668 | 1/2010 |
| IN | 246359 | 2/2011 |
| JP | 50-11399 | 4/1975 |
| JP | 2-131424 A | 5/1990 |
| JP | 3-506033 A | 12/1991 |
| JP | 5-58913 A | 3/1993 |
| JP | 6-220345 A | 8/1994 |
| JP | 10-72449 A | 3/1998 |
| JP | 2000-502723 A | 3/2000 |
| JP | 2000-503661 A | 3/2000 |
| JP | 2000-109431 A | 4/2000 |
| JP | 2001-89368 A | 4/2001 |
| JP | 2001-511813 A | 8/2001 |
| JP | 2004-532792 A | 10/2004 |
| JP | 2007-515474 A | 6/2007 |
| JP | 2008-503444 A | 2/2008 |
| JP | 2008-517067 A | 5/2008 |
| JP | 2009-510004 A | 3/2009 |
| JP | 4654325 B2 | 3/2011 |
| NO | 20034788 | 12/2003 |
| RU | 1795971 A3 | 2/1993 |
| RU | 2 007 403 C1 | 2/1994 |
| RU | 2002 110 112 A | 12/2003 |
| WO | WO 90/01030 A1 | 2/1990 |
| WO | WO 94/13643 A1 | 6/1994 |
| WO | WO 94/13644 A1 | 6/1994 |
| WO | WO 94/13661 A1 | 6/1994 |
| WO | WO 94/13676 A1 | 6/1994 |
| WO | WO 94/13677 A1 | 6/1994 |
| WO | WO 95/10506 A1 | 4/1995 |
| WO | WO 95/34563 A1 | 12/1995 |
| WO | WO 97/29109 A1 | 8/1997 |
| WO | WO 97/29110 A1 | 8/1997 |
| WO | WO 98/08847 A1 | 3/1998 |
| WO | WO 98/35967 A2 | 8/1998 |
| WO | WO 99/01454 A1 | 1/1999 |
| WO | WO 99/10350 A1 | 3/1999 |
| WO | WO 99/36393 A1 | 7/1999 |
| WO | WO 99/40090 A1 | 8/1999 |
| WO | WO 00/01697 A1 | 1/2000 |
| WO | WO 00/39127 A1 | 7/2000 |
| WO | WO 00/59907 A2 | 10/2000 |
| WO | WO 00/59908 A2 | 10/2000 |
| WO | WO 01/35917 A1 | 5/2001 |
| WO | WO 01/44248 A1 | 6/2001 |
| WO | WO 02/06286 A2 | 1/2002 |
| WO | WO 02/18320 A2 | 3/2002 |
| WO | WO 02/058704 A1 | 8/2002 |
| WO | WO 02/088121 A1 | 11/2002 |
| WO | WO 03/072536 A1 | 9/2003 |
| WO | WO 03/078435 A1 | 9/2003 |
| WO | WO 2004/037822 A1 | 5/2004 |
| WO | WO 2009/128383 A1 | 10/2009 |
| WO | WO 2010/015628 A1 | 2/2010 |

OTHER PUBLICATIONS

Altemus et al., "Changes in Cerebrospinal Fluid Neurochemistry During Treatment of Obsessive-Compulsive Disorder With Clomipramine", Arch Gen Psychiatry, vol. 51, Oct. 1994, pp. 794-803.

Arase et al., "Effects of Corticotropin Releasing Factor on Genetically Obese (Fatty) Rats", Psychology & Behavior, vol. 45, 1989, pp. 565-570, Pergamon Press.

Arborelius et al., "The Role of Corticotropin-Releasing Factor in Depression and Anxiety Disorders", Journal of Endocrinology, vol. 160, 1999, pp. 1-12.

Bakke et al., "Plasma Corticosterone and Restraint Induced Gastric Pathology: Age-Related Differences After Administration of Corticotropin Releasing Factor", Life Sciences, vol. 45, 1989, pp. 907-916, Pergamon Press.

Baldwin et al., "CRF Antagonist Reverses the 'anxiogenic' Response to Ethanol Withdrawal in the Rat", Psychopharmacology, vol. 103, 1991, pp. 227-232.

Banki et al., "CSF Corticotropin-Releasing Factor-Like Immunoreactivity in Depression and Schizophrenia", American Journal of Psychiatry, vol. 144, No. 7, Jul. 1987, pp. 873-877.

Baram et al., "The CRF1 Receptor Mediates the Excitatory Actions of Corticotropin Releasing Factor (CFR) in the developing Rat Brain: in Vivo Evidence using a Novel, Selective, Non-Peptide CRF Receptor Antagonist", Brain Research, 1997, pp. 89-95, vol. 770.

Barquist et al., "Abdominal Surgery-Induced Delayed Gastric Emptying in Rats: Role of CRF and Sensory Neurons", CRF and Capsaicin Inhibit Delayed Emptying by Surgery, Am. J. Physiol, vol. 262, 1991, pp. G616-G620 (Copyright 1992, The American Physiological Society).

Behan et al., "Displacement of Corticotropin Releasing Factor from Its Binding Protein as a Possible Treatment for Alzheimer's Disease", Nature, vol. 378, Nov. 16, 1995, pp. 284-287.

Blank et al., "The Corticotropin-Releasing Factor Receptor 1 Antagonist CP-154,526 Reverses Stress-induced Learning Deficits in Mice", Behavioral Brain Research, 2003, pp. 207-213, vol. 138, Elsevier Science B.V.

Bohmer et al., "Effects of Corticotropin-Releasing Factor on Central Respiratory Activity", European Journal of Pharmacology, vol. 182, 1990, pp. 405-411.

Bremner et al., "Elevated CSF Corticotropin-Releasing Factor Concentrations in Posttraumatic Stress Disorder", American Journal of Psychiatry, vol. 154, No. 5, May 1997, pp. 624-629.

Briscoe et al., "Antalarmin Blockade of Corticotropin Releasing Hormone-Induced Hypertension in Rats", Brain Research, 2000, pp. 204-207, vol. 881, Elsevier Science B.V.

Butler et al., "Corticotropin-Releasing Factor Produces Fear-Enhancing and Behavioral Activating Effects Following Infusion Into the Locus Coerules", The Journal of Neuroscience, vol. 10, No. 1, Jan. 1990, pp. 176-183.
Chalmers et al., "Corticotrophin-Releasing Factor Receptors: From Molecular Biology to Drug Design", TiPS, vol. 17, Apr. 1996, pp. 166-172, Elsevier Science Ltd.
Chalmers et al., "Localization of Novel Corticotropin-Releasing Factor Receptor (CRF2) mRNA Expression to Specific Subcortical Nuclei in Rat Brain: Comparison with CRF1 Receptor mRNA Expression", The Journal of Neuroscience, vol. 15, No. 10, Oct. 1995, pp. 6340-6350.
Chappell et al., "Elevated Cerebrospinal Fluid Corticotropin-Releasing Factor in Tourette's Syndrome: Comparison to Obsessive Compulsive Disorder and Normal Controls", Biol. Psychiatry, vol. 39, 1996, pp. 776-783.
Chen et al., "Design and Synthesis of a Series of Non-Peptide High Affinity Human Corticotropin-Releasing Factor/ Receptor Antagonists", J. Med. Chem., vol. 39, No. 22, 1996, pp. 4358-4360.
Crofford et al., "Corticotropine-Releasing Hormone in Synovial Fluids and Tissues of Patients with Rhumatoid Arthritis and Osteoarthritis", Journal of Immunology, vol. 151, No. 3, Aug. 1, 1993, pp. 1587-1596.
Crofford et al., "Local Secretion of Corticotropin-Releasing Hormone in the Joints of Lewis Rats with Inflammatory Arthritis", Journal of Clinical Investigation, vol. 90, Dec. 1992, pp. 2555-2564.
Desouza et al., "Corticotropin-Releasing Hormone (CRH) is Decreased in the Basal Ganglia in Huntington's Disease", Brain Research, vol. 437, 1987, pp. 355-359.
Diamant et al., "Structure-Related Effects of CRF and CRF-Derived Peptides: Dissociation of Behavioral, Endocrine and Autonomic Activity", Neuroendocrinology, vol. 57, 1993, pp. 1071-1081.
Dieterich et al., "Cortitropin-Releasing Factor Receptors: An Overview", Experimental and Clinical Endocrinology & Diabetes, vol. 105, 1997, pp. 65-82.
Dörwald, "Side Reactions in Organic Synthesis: A Guide to Successful Synthesis Design", p. IX, Preface, 2005.
Dunn et al., "Physiological and Behavioral Responses to Corticotropin-Releasing Factor Administration: Is CRF a Mediator of Anxiety or Stress Responses?", Brain Research Reviews, vol. 15, 1990, pp. 71-100, Elsevier Science Publishers B.V. (pp. 71-79 only provided).
Ehlers et al., "Cortiicotropin Releasing Factor Produces Increases in Brain Excitabiity and Convulsive Seizures in Rats", Brain Research, vol. 278, 1983, pp. 332-336, Elsevier.
Ford et al., "Psychosensory Modulation of Colonic Sensation in the Human Transverse and Sigmoid Colon", Gastroenterology, vol. 109, No. 6, 1995, pp. 1772-1780.
Fujito et al., "Reaction of Pyridinium and Isoquinolinium N-Imines with Ketenethioacetals", Heterocycles, vol. 6, No. 4, 1977, pp. 379-383.
Fukudo et al., "Impact of Corticotropin-Releasing Hormone on Gastrointestinal Motility and Adrenocorticotropic Hormone in Normal Controls and Patients with Irritable Bowel Syndrome", Gut, vol. 42, 1998, pp. 845-849.
Garrick et al., "Corticotropin-Releasing Factor Acts Centrally to Suppress Stimulated Gastric Contractility in the Rat", Regulatory Peptides, vol. 21, 1988, pp. 173-181, Elsevier.
Gold et al., "Responses to Corticotropin-Releasing Hormone in the Hypercortisolism of Depression and Cushing's Disease", The New England Journal of Medicine, vol. 314, No. 21, May 22, 1986, pp. 1329-1335.
Gubin et al., "Novel Heterocyclic Analogues of the New Potent Class of Calcium Entry Blockers: 1[[4-(Aminoalkoxy)phenyl]sulfonyl]indolizines", Journal of Medicinal Chemistry, vol. 36, No. 10, 1993, pp. 1425-1433.
Gunion et al., "Intrahypothalamic Corticotropin-Releasing Factor Elevates Gastric Bicarbonate and Inhibits Stress Ulcers in Rats", Central CRF and Gastric Bicarbonate, vol. 21, 1989, pp. G152-G157.
Hiroi et al., "Expression of Corticotropin Releasing Hormone Receptors Type I and Type II mRNA in Suicide Victims and Controls", Molecular Psychiatry, vol. 6, 2001, pp. 540-546.
Hotta et al., "Corticotropin-Releasing Factor Receptor Type 1 Mediates Emotional Stress-Induced Inhibition of Food Intake and Behavioral Changes in Rats", Brain Research, 1999, pp. 221-225, vol. 823, Elsevier Science B.V.
Hotta et al., "The Responses of Plasma Adrenocorticotropin and Cortisol to Corticotropin-Releasing Hormone (CRH) and Cerebrospinal Fluid Immunoreactive CRH in Anorexia Nervosa Patients", Journal of Clinical Endocrinology and Metabolism, vol. 62, No. 2, 1986, pp. 319-324.
International Preliminary Report on Patentability, dated Dec. 9, 2010, for Application No. PCT/JP2009/057270.
International Search Report, dated Nov. 16, 2010, for Application No. PCT/JP2010/067556.
Iredale et al., "Role of Corticotropin-Releasing Factor Receptor-1 in Opiate Withdrawal," Journal of Neurochemistry, 2000, pp. 199-208, vol. 74, No. 1, Lippincott Williams & Wilkins, Inc., Philadelphia, PA.
Jain et al., Corticotropin-Releasing Factor Modulates the Immune Response to Stress in the Rat, Endocrinology, vol. 128, No. 3, 1991, pp. 1329-1336.
Jordan, "Tamoxifen: A Most Unlikely Pioneering Medicine", Nature Reviews, vol. 2, Mar. 2003, pp. 205-213.
Kalin et al., "Fear-Motivated Behavior Induced by Prior Shock Experience is Mediated by Corticotropin-Releasing Hormone Systems", Brain Research, vol. 509, 1990, pp. 80-84, Elsevier.
Kang et al., "Acute Stress Increases Interstitial Fluid Amyloid-β via Corticotropin-Releasing Factor and Neuronal Activity", PNAS, Jun. 19, 2007, pp. 10673-10678, vol. 104, No. 25.
Karalis et al., "Autocrine or Paracrine Inflammatory Actions of Corticotropin-Releasing Hormone in Vivo", Science, vol. 254, Oct. 18, 1991, pp. 421-423.
Keck et al., "The Anxiolytic Effect of the CRH1 Receptor Antagonist R121919 Depends on Innate Emotionality in Rats", European Journal of Neuroscience, 2001, pp. 373-380, vol. 13, Federation of European Neuroscience Societies.
Krahn et al., "CRF Antagonist Partially Reverses CRF- and Stress-Induced Effects on Feeding", Brain Research Bulletin, vol. 17, Mar. 24, 1986, pp. 285-289, Ankho International Inc.
Lancel et al., "The CRH1 Receptor Antagonist R121919 Attenuates Stress-Elicited Sleep Disturbances in Rats, Particularly in Those with High Innate Anxiety", Journal of Psychiatric Research, 2002, pp. 197-208, vol. 36, Elsevier Science Ltd.
Lëet al., "The Role of Corticotrophin-Releasing Factor in Stress-Induced Relapse to Alcohol-Seeking Behavior in Rats", Psychopharmacology, 2000, pp. 317-324, vol. 150.
Lee et al., "Behavioral Stress Accelerates Plaque Pathogenesis in the Brain of Tg2576 Mice Via Generation of Metabolic Oxidative Stress", Journal of Neurochemistry, 2009, pp. 165-175, vol. 108, International Society for Neurochemistry.
Lembo et al., "Effects of the Corticotropin-Releasing Factor (CRF) on Rectal Afferent Nerves in Humans", Neurogastroenterology and Motility, vol. 8, No. 1, Mar. 1996, pp. 9-18.
Lenz et al., "Stress-Induced Gastrointestinal Secretory and Motor Responses in Rats are Mediated by Endogenous Corticotropin-Releasing Factor", Gastroenterology, vol. 95, No. 6, Dec. 1988, pp. 1510-1517.
Leonard, "Changes in the Immune System in Depression and Dementia: Causal or Co-Incidental Effects?", International Journal of Developmental Neuroscience, vol. 19, 2001, pp. 305-312, Elsevier Science Ltd.
Levine et al., "Effect of Centrally Administered Corticotropin Releasing Factor (CRF) on Multiple Feeding Paradigms", Neuropharmacology, vol. 22, No. 3A, 1983, pp. 337-339, Pergamon Press, Ltd., Great Britain.
Liaw et al., "Cloning and Characterization of the Human Corticotropin-Releasing Factor-2 Receptor Complementary Deoxyribonucleic Acid", Endocrinology, vol. 137, No. 1, 1996, pp. 72-77.
Luckey et al., "Corticotropin-Releasing Factor Receptor 1-Deficient Mice Do Not Develop Postoperative Gastric Ileus", Gastroenterology, Dec. 2003, pp. 654-659, vol. 125, No. 3.
Lyons et al., "Corticotropin Releasing Factor Antagonist Reduced Ischemic Hippocampal Neuronal Injury", Brain Research, vol. 545, 1991, pp. 338-342.

Maecker et al., "Astressin, a Novel and Potent CFR Antagonist, is Neuroprotective in the Hippocampus When Administered After a Seizure," Brain Research, 1997, pp. 166-170, vol. 744, Elsevier Science B.V.

Martinez et al., "Role of CRF Receptor 1 in Central CRF-Induced Stimulation of Colonic Propulsion in Rats," Brain Research, 2001, pp. 29-35, vol. 893, Elsevier Science B.V.

MENZAGHI et al., "Characterization of a Novel and Potent Corticotropin-Releasing Factor Antagonist in Rats", The Journal of Pharmacology and Experimental Therapeutics, vol. 269, No. 2, Jan. 31, 1994, pp. 564-572.

Monnikes et al., "CRF in the Paraventricular Nucleus of the Hypothalamus Induces Dose-Related Behavioral Profile in Rats", Brain Research, vol. 574, 1992, pp. 70-76, Elsevier Science Publishers B.V.

Morimoto et al., "The Central Role of Corticotrophin-Releasing Factor (CRF-41) in Psychological Stress in Rats", Journal of Psychology, vol. 460, 1993, pp. 221-229, Great Britain.

Murakami et al., "Stimulation by Urocortin of Growth Hormone (GH) Secretion in GH-Producing Human Pituitary Adenoma Cells", Endocrine Journal, vol. 44, No. 4, 1997, pp. 627-629.

Nakazato et al., "Corticotropin-Releasing Factorl Receptor as a Target for Therapeutic Intervention", Drugs of the Future, 1999, pp. 1089-1098, vol. 24, No. 10, Prous Science.

Nemeroff et al., "Reduced Corticotropin Releasing Factor Binding Sites in the Frontal Cortex of Suicide Victims", Arch. Gen. Psychiatry, vol. 45, 1988, pp. 577-579.

Nicholson et al., "Pituitary and Hypothalamic Hormones in Normal and Neoplastic Adrenal Medullae: Biologically Active Corticotropin-Releasing Hormone and Corticotropin", Regulatory Peptides, vol. 18, 1987, pp. 173-188, Elsevier.

Nink et al., "Effects of Corticotropin-Releasing Hormone on the Postoperative Course of Elderly Patients Under Long-term Artificial Respiration", Acta Endocrinologica, vol. 127, 1992, pp. 200-204.

Notice of Allowance for U.S. Appl. No. 10/250,693, dated Mar. 6, 2006.

Notice of Allowance for U.S. Appl. No. 10/451,741, dated Jan. 12, 2006.

Notice of Allowance for U.S. Appl. No. 10/524,662, dated Jun. 11, 2007.

Notice of Allowance for U.S. Appl. No. 10/524,662, dated Oct. 22, 2007.

Notice of Allowance for U.S. Appl. No. 10/689,088, Sep. 29, 2006.

Notice of Allowance for U.S. Appl. No. 11/757,595, dated Aug. 25, 2009.

Ochi et al., "Studies of Heterocyclic Compounds, VIII, Synthesis and Tautomerism of 2-Hydroxypyrazolo[1,5-alpha]pyridine", Bulletin of the Chemical Society of Japan, vol. 49, No. 7, 1976, pp. 1980-1984.

Overstreet et al., "Antidepressant Effects of Citalopram and CRF Receptor Antagonist CP-154,526 in a Rat Model of Depression", European Journal of Pharmacology, 2004, pp. 195-201, vol. 492, Elsevier B.V.

Owens et al., "Physiology and Pharmacology of Corticotropin-Releasing Factor", Pharmacological Reviews, vol. 43, No. 4, 1991, pp. 425-473.

Owens et al., "The Effects of Alprazolam on Corticotropin-Releasing Factor Neurons in the Rat Brain: Acute Time Course, Chronic Treatment and Abrupt Withdrawal", The Journal of Pharmacology and Experimental Therapeutics, vol. 258, No. 1, 1991, pp. 349-356.

Petrusz et al., "Corticotropin-Releasing Factor (CRF)-Like Immunoreactivity in the Gastro-Entero-Pancreatic Endocrine System", Peptides, vol. 5, Suppl. 1, 1984, pp. 71-78, Ankho International Inc.

Plotsky et al., "Hypothalamic-Pituitary-Adrenal Axis Function in the Zucker Obese Rat", Endocrinology, vol. 130, No. 4, 1992, pp. 1931-1941.

Poliak et al., "Stress and Autoimmunity: The Neuropeptides Corticotropin-Releasing Factor and Urocortin Suppress-Encephalomyelitis via Effects on Both the Hypothalamic-Pituitary-Adrenal Axis and the Immune System", The Journal of Immunology, vol. 158, 1997, pp. 5751-5756.

Raadsheer et al., "Corticotropin-Releasing Hormone mRNA Levels in the Paraventricular Nucleus of Patients with Alzheimer's Disease and Depression", American Journal of Psychiatry, vol. 152, No. 9, Sep. 1995, pp. 1372-1376.

Rassnick et al., "Microinjection of a Corticotropin-Releasing Factor Antagonist into the Central Nucleus of the Amygdala Reverses Anxiogenic-Like Effects of Ethanol Withdrawal", Brain Research, 1993, vol. 605, pp. 25-32, Elsevier Science B.V.

Rissman et al., "Corticotropin-Releasing Factor Receptors Differentially regulate Stress-Induced Tau Phosphorylation", Journal of Neuroscience, Jun. 13, 2007, pp. 6552-6562, vol. 27. No. 24.

Rivier et al., "Characterization of Rat Hypothalamic Corticotropin-Releasing Factor", Proc. Natl. Acad. Sci. USA, vol. 80, Aug. 1983, pp. 4851-4855.

Rivier et al., "Synthetic Competitive Antagonists of Corticotropin-Releasing Factor: Effect on ACTH Secretion in the Rat", Science, vol. 224, May 25, 1984, pp. 889-891.

Roy-Byrne et al., "The Corticotropin-Releasing Hormone Stimulation Test in Patients With Panic Disorder", Am. J. Psychiatry, vol. 143, No. 7, Jul. 1986, pp. 896-899.

Sagami et al., "Effect of a Corticotropin Releasing Hormone Receptor Antagonist on Colonic Sensory and Motor Function in Patients with Irritable Bowel Syndrome", Gut, vol. 53, 2004, pp. 958-964.

Sasaki et al., "Immunoreactive Corticotropin-Releasing Hormone Present in Human Plasma May Be Derived From Both Hypothalamic and Extrahypothalamic Sources", Journal of Clinical Endocrinology and Metabolism, vol. 65, No. 1, 1987, pp. 176-182.

Sasaki et al., "Isolation and Characterization of a Corticotropin-Releasing Hormone-Like Peptide From Human Placenta", Journal of Clinical Endocrinology and Metabolism, vol. 67, No. 4, 1988, pp. 768-773.

Sauvage et al., "Detection of Corticotropin—Releasing Hormone Receptor 1 Immunoreactivity in Cholinergic, Dopaminergic and Noradrenergic Neurons of the Murine Basal Forebrain and Brainstem Nuclei-Potential Implication for Arousal and Attention", Neuroscience, vol. 104, No. 3, 2001, pp. 643-652.

Scopa et al., "Presence of Immunoreactive Corticotropin Releasing Hormone in Thyroid Lesions", American Journal of Pathology, vol. 145, No. 5, Nov. 1994, pp. 1159-1167.

Shaham et al., "CP-154,526, a Selective, Non-Peptide Antagonist of the Corticotropin-Releasing Factor1 Receptor Attenuates Stress-Induced Relapse to Drug Seeking in Cocaine- and Heroin-Trained Rats", Psychopharmacology, 1998, pp. 184-190, vol. 137.

Sherman et al., "The Effects of ICV-CRH on Novelty-Induced Behavior", Pharmacology Biochemistry & Behavior, vol. 26, 1987, pp. 699-703, Pergamon Journals Ltd.

Shibahara et al., "Isolation and Sequence Analysis of the Human Corticotropin-Releasing Factor Precursor Gene", The EMBO Journal, vol. 2, No. 5, 1993, pp. 775-779.

Singh et al., "Enhancing Effect of Corticotropin-Releasing Neurohormone on the Production of Interleukin-1 and Interleukin-2", Neuroscience Letters, vol. 120, 1990, pp. 151-154, Elsevier Scientific Publishers Ireland Ltd.

Singh et al., "Potent Mast Cell Degranulation and Vascular Permeability Triggered by Urocortin Through Activation of Corticotropin-Releasing Hormone Receptors", The Journal of Pharmacology and Experimental Therapeutics, vol. 288, No. 3, 1999, pp. 1349-1356.

Singh, "Stimulatory Effect of Corticotropin-Releasing Neurohormone on Human Lymphocyte Proliferation and Interleukin-2 Receptor Expression", Journal of Neuroimmunology, vol. 23, 1989, pp. 257-262, Elsevier Science Publishers B.V.

Sirinathsinghji et al., "Corticotropin-Releasing Factor is a Potent Inhibit of Sexual Receptivity in the Female Rat", Nature, vol. 305, Sep. 15, 1983, pp. 232-235.

Stenzel-Poore et al., "Development of Cushing's Syndrome in Corticotropin-Releasing Factor Transgenic Mice", Endocrinology, vol. 130, No. 6, 1992, pp. 3378-3386.

Stenzel-Poore et al., "Overproduction of Corticotropin-Releasing Factor in Transgenic Mice: A Genetic Model of Anxiogenic Behavior", The Journal of Neuroscience, vol. 14, No. 5, May 1994, pp. 2579-2584.

Strijbos et al., "Corticotrophin-Releasing Factor Antagonist Inhibits Neuronal Damage Induced by Focal Cerebral Ischaemia or Activation of NMDA Receptors in the Rat Brain," Brain Research, 1994, pp. 405-408, vol. 656, Elsevier Science B.V.
Supplemental Notice of Allowance for U.S. Appl. No. 11/446,416, dated Aug. 1, 2007.
Tache et al., "Role of CFR in Stress-Related Alterations of Gastric and Colonic Motor Function", Annals of the New York Academy of Sciences, vol. 697, Corticotrophin-Releasing Factor and Cytokinses: Role in The Stress Response, 1993, cover page, dedication page, pp. 232-243.
Tache et al., "Central Nervous System Action of Corticotropin-Releasing Factor to Inhibit Gastric Emptying in Rats", American Journal of Psychiatry, vol. 253. 1987, pp. G241-G245.
Tazi et al., "Corticotropin-Releasing Factor Antagonist Blocks Stress-Induced Fighting in Rats", Regulatory Peptides, vol. 18, 1987, pp. 37-42, Elsevier Science Publishers B.V.
Theoharides et al., "Corticotropin-Releasing Hormone Induces Skin Mast Cell Degranulation and Increased Vascular Permeability, a Possible Explanation for Its Proinflammatory Effects", Endocrinology, vol. 139, No. 1, 1998, pp. 403-413.
Tominaga et al, "Reaction of Pyridinium and Quinolinium N-Imines with Ketenethioacetals", Yakugaku Zasshi, vol. 104, No. 5, 1984, pp. 440-448.
US Office Action for U.S. Appl. No. 10/250,693, dated Sep. 2, 2005.
US Office Action for U.S. Appl. No. 10/451,741, dated Jan. 28, 2005.
US Office Action for U.S. Appl. No. 10/451,741, dated Sep. 22, 2005.
US Office Action for U.S. Appl. No. 10/524,662, dated Feb. 5, 2007.
US Office Action for U.S. Appl. No. 10/689,088, dated Apr. 28, 2005.
US Office Action for U.S. Appl. No. 10/689,088, dated Mar. 30, 2006.
US Office Action for U.S. Appl. No. 10/689,088, dated Oct. 18, 2005.
US Office Action for U.S. Appl. No. 11/421,740, dated May 19, 2008.
US Office Action for U.S. Appl. No. 11/421,740, dated Sep. 3, 2008.
US Office Action for U.S. Appl. No. 11/446,416, dated Feb. 21, 2007.
US Office Action for U.S. Appl. No. 11/757,595, dated Dec. 8, 2008.
US Office Action for U.S. Appl. No. 11/858,160, dated Jan. 22, 2009.
US Office Action for U.S. Appl. No. 12/397,132, dated Jun. 15, 2009.
US Office Action for U.S. Appl. No. 12/397,132, dated Sep. 16, 2009.
US Office Action for U.S. Appl. No. 12/421,182, dated Nov. 1, 2010.
Valdenaire et al., "A New Functional Isoform of the Human CRF2 Receptor for Corticotropin-Releasing Factor", Biochimica et Biophysica Acta, vol. 1352, 1997, pp. 129-132, Elsevier Science B.V.
Vale et al., "Characterization of a 41-Residue Ovine Hypothalamic Peptide That Stimulates Secretion of Corticotropin and Beta-Endorphin", Science, vol. 213, Sep. 18, 1981, pp. 1394-1397.
Vale et al., "Chemical and Biological Characterization of Corticotropin Releasing Factor", Recent Progress in Hormone Research, vol. 39, 1983, cover page, pp. 245-270.
Whitehouse et al., "Reductions in Corticotropin Releasing Factor-Like Immunoreactivity in Cerebral Cortex in Alzheimer's Disease, Parkinson's Disease, and Progressive Supranuclear Palsy", Neurology, vol. 37, pp. 905-909, Jun. 1987.
Whitten et al., "Rapid Microscale Synthesis, a New Method for Lead Optimization Using Robotics and Solution Phase Chemistry: Application to the Synthesis and Optimization of Corticotropin-Releasing Factor1 Receptor Antagonists", J. Med. Chem., vol. 39, No. 22, 1996, pp. 4354-4357.
Zobel et al., "Effects of the High-Affinity Corticotropin-Releasing Hormone Receptor 1 Antagonist R121919 in Major Depression: the First 20 Patients Treated", Journal of Psychiatric Research, 2000, pp. 171-181, vol. 34, Elsevier Science Ltd.
International Search Report, dated Dec. 21, 2010, for U.S. Appl. No. PCT/JP2010/067564.
European Preliminary Amendment dated Mar. 28, 2012 for EP Appl. No. 10822051.8.
European Preliminary Amendment dated Mar. 28, 2012 for EP Appl. No. 10822057.5.
Chilean Office Action dated Jun. 14, 2011 for U.S. Appl. No. 896-09.
Filipino Notice of Allowability for PH Applicaion No. 1-2000-03412 dated Nov. 29, 2007.
Filipino Office Action for PH Application No. 1-2000-03412 dated Jul. 3, 2007.
Filipino Office Action for PH Application No. 1-2000-03412 dated Mar. 21, 2002.
Filipino Office Action for PH Application No. 1-2000-03412 dated May 5, 2006.
Filipino Response filed for PH Application No. 12000-03412 dated Jul. 23, 2007.
Filipino Voluntary Amendment for PH Application No. 1-2000-03412 dated Jan. 5, 2005.
Filipino Voluntary Amendment for PH Application No. 1-2000-03412 dated Mar. 14, 2005.
Japanese Notice of Allowance for Japanese Application No. 2008-226399 dated Apr. 3, 2012 with English translation.
Polish Office Action dated Apr. 16, 2012 for Polish Application No. P-367067 with English translation.
Chilean Office Action with the English translation dated Jan. 25, 2012, for Application No. 896-09.
Formal Request for Amending Claims dated Feb. 8, 2012, for Indian Application No. 7277/CHENP/2010.
South African Notice of Allowance dated Jan. 5, 2012, for Application No. 2010/06764.
Japanese Amendment and Petition, dated Feb. 21, 2012, for Japanese Application No. 2011-535430.
Response to to US Office Action, dated Mar. 23, 2012, for U.S. Appl. No. 12/900,046.
Taiwanese Amendment, dated Mar. 8, 2012, for Taiwanese Application No. 098112062.
Office Action in U.S. Appl. No. 12/421,182 mailed Feb. 15, 2011.
Argentine Amendment, dated Jul. 26, 2010, for Argentine Application No. P-090101280.
Australian Amendment, dated Apr. 30, 2007, for Australian Appl. No. 2003275589.
Australian Amendment, dated Dec. 9, 2010, for Australian Application No. 2009237050.
Australian Notice of Acceptance, dated Jan. 3, 2007, for Australian Application No. 2002251546.
Australian Notice of Acceptance, dated May 18, 2009, for Australian Application No. 2003275589.
Australian Office Action, dated Aug. 21, 2006, for Australian Application No. 2002251546.
Australian Office Action, dated Aug. 21, 2008, for Australian Application No. 2003275589.
Australian Office Action, dated Sep. 14, 2006, for Australian Application No. 2002251546.
Australian Submission of Search Report, dated Jun. 15, 2005, for Australian Application No. 2002251546.
Bangladeshi Amendment, dated Aug. 1, 2010, for Bangladeshi Application No. 75/2009.
Canadian Notice of Allowance, dated Jan. 13, 2011, for Canadian Application No. 2,494,574.
Canadian Notice of Allowance, dated Nov. 18, 2009, for Canadian Application No. 2,443,802.
Canadian Office Action, dated Apr. 14, 2009, for Canadian Application No. 2,443,802.
Canadian Office Action, dated Apr. 28, 2010, for Canadian Application No. 2,494,574.
Canadian Request for Examination, dated Jun. 10, 2008, for Canadian Application No. 2,494,574.
Chilean Amendment, dated Jul. 23, 2010, for Chilean Application No. 896-2009.
Chinese Amendment, dated Mar. 22, 2006, for Chinese Application No. 200380101417.7.
Chinese Office Action, dated Apr. 24, 2009, for Chinese Application No. 200710128112.5.
Chinese Office Action, dated Feb. 17, 2006, for Chinese Application No. 02808872.7.
Chinese Office Action, dated Jul. 22, 2005, for Chinese Application No. 02808872.7.
Chinese Office Action, dated Jun. 1, 2007, for Chinese Application No. 200380101417.7.
Chinese Office Action, dated Jun. 5, 2009, for Chinese Application No. 200710128111.0.
Chinese Office Action, dated May 26, 2006, for Chinese Application No. 200380101417.7.
Chinese Office Action, dated Oct. 13, 2006, for Chinese Application No. 200380101417.7.

Chinese Office Action, dated Oct. 16, 2009, for Chinese Application No. 200710128111.0.
Chinese Office Action, dated Sep. 22, 2006, for Chinese Application No. 02808872.7.
Czech Office Action, dated Jul. 30, 2009, for Czech Application No. PV 2003-2937.
Czech Office Action, dated Mar. 26, 2009, for Czech Application No. PV 2003-2937.
Czech Office Action, dated Nov. 20, 2009, for Czech Application No. PV 2003-2937.
Czech Office Action, dated Sep. 24, 2008, for Czech Application No. PV 2003-2937.
Dautzenberg et al., "The CRF peptide family and their receptors: yet more partners discovered", TRENDS in Pharmacological Sciences, vol. 23, No. 2, pp. 71-77, Feb. 2002.
European Office Action, dated Apr. 21, 2008, for European Application No. 03758781.3.
European Office Action, dated Apr. 4, 2008, for European Application No. 02711424.8.
European Office Action, dated Feb. 16, 2009, for European Application No. 03758781.3.
European Office Action, dated Feb. 26, 2009, for European Application No. 03758781.3.
European Office Action, dated Jan. 4, 2010, for European Application No. 02720608.5.
European Office Action, dated Jul. 19, 2010, for European Application No. 02711424.8.
European Office Action, dated Jul. 22, 2011, for European Application No. 09732907.2.
European Office Action, dated Jun. 14, 2005, for European Application No. 02720608.5.
European Office Action, dated Jun. 8, 2009, for European Application No. 02711424.8.
European Office Action, dated May 16, 2011, for European Application No. 02711424.8.
European Office Action, dated May 22, 2007, for European Application No. 02711424.8.
European Office Action, dated Nov. 14, 2007, for European Application No. 03758781.3.
European Office Action, dated Nov. 25, 2010, for European Application No. 02720608.5.
European Office Action, dated Sep. 4, 2008, for European Application No. 03758781.3.
European Submission of English translation of priority document, dated Aug. 13, 2007, for European Application No. 02720608.5.
Extended European Search Report, dated Jul. 5, 2011, for European Application No. 09732907.2.
Filipino Notice of Allowability, dated Jul. 18, 2008, for Filipino Application No. 1-2005-500278.
Filipino Notice of Allowability, dated Mar. 21, 2007, for Filipino Application No. 1-2003-501066.
Filipino Office Action, dated Feb. 9, 2004, for Filipino Application No. 1-2003-501066.
Filipino Office Action, dated Jan. 31, 2008, for Filipino Application No. 1-2005-500278.
Filipino Office Action, dated May 23, 2008, for Filipino Application No. 1-2005-500278.
Filipino Office Action, dated Nov. 22, 2006, for Filipino Application No. 1-2003-501066.
Filipino Office Action, dated Oct. 31, 2007, for Filipino Application No. 1-2007-500806.
Hong Kong Request to record a designated patent application for a standard patent, dated Feb. 2, 2006, for Hong Kong Application No. 06101472.9.
Hungarian Office Action, dated Feb. 18, 2011, for Hungarian Application No. P0401292.
Hungarian Request for Amendment, dated Feb. 14, 2005, for Hungarian Application No. P0401292.
Hungarian Search Report, dated Dec. 16, 2010, for Hungarian Application No. P0401292.
Indian Amendment, dated Oct. 16, 2008, for Indian Application No. 961/CHENP/2005.
Indian Office Action, dated May 10, 2007, for Indian Application No. 1748/DELNP/2003.
Indian Office Action, dated Nov. 25, 2008, for Indian Application No. 961/CHENP/2005.
Indian Office Action, dated Nov. 4, 2009, for Indian Application No. 961/CHENP/2005.
Indian Office Action, dated Sep. 15, 2010, for Indian Application No. 1966/CHENP/2007.
Indian Office Action, dated Sep. 17, 2007, for Indian Application No. 1748/DELNP/2003.
Indian Office Action, dated Sep. 27, 2006, for Indian Application No. 1748/DELNP/2003.
Indian Section 8(1) filing, dated Apr. 29, 2011, for Indian Application No. 7277/CHENP/2010.
Indonesian Notice of Allowance, dated Nov. 2, 2009, for Indonesian Application No. W-00200500983.
Indonesian Office Action, dated Apr. 2, 2008, for Indonesian Application No. W-00200500983.
Japanese Amendment and Explanation for Circumstances Concerning Accelerated Examination, dated Oct. 27, 2010, for Japanese Application No. 2010-508183.
Japanese Amendment and Petition, dated Oct. 7, 2008, for Japanese Application No. 2004-546447.
Japanese Amendment and Request for Examination, dated Jan. 13, 2005, for Japanese Application No. 2002-585420.
Japanese Office Action, dated Aug. 5, 2008, for Japanese Application No. 2002-585420.
Japanese Office Action, dated Dec. 14, 2010, for Japanese Application No. 2010-508183.
Japanese Office Action, dated Feb. 16, 2010, for Japanese Application No. 2002-563153.
Japanese Office Action, dated Feb. 27, 2009, for Japanese Application No. 2002-563153.
Japanese Office Action, dated Jun. 2, 2010, for Japanese Application No. 2002-563153.
Japanese Office Action, dated May 26, 2009, for Japanese Application No. 2004-546447.
Japanese Office Action, dated Sep. 30, 2008, for Japanese Application No. 2002-585420.
Jordanian Amendment, dated Aug. 30, 2010, for Jordanian Application No. 127/2009.
Kehne et al., "Non-Peptidic CRF1 Receptor Antagonists for the Treatment of Anxiety, Depression and Stress Disorders", Current Drug Targets—CNS & Neurological Disorders, vol. 1, No. 5, pp. 467-493, 2002.
Korean Amendment, dated Dec. 7, 2010, for Korean Application No. 10-2010-7019769.
Korean Amendment, dated Jun. 19, 2008, for Korean Application No. 10-2008-7006800.
Korean Amendment, dated Oct. 13, 2008, for Korean Application No. 10-2008-7006800.
Korean Office Action, dated Aug. 16, 2010, for Korean Application No. 10-2008-7006800.
Korean Office Action, dated Dec. 4, 2008, for Korean Application No. 10-2003-7013949.
Korean Office Action, dated May 16, 2008, for Korean Application No. 10-2003-7013949.
Korean Office Action, dated May 16, 2008, for Korean Application No. 10-2008-7005209.
Korean Office Action, dated Nov. 4, 2008, for Korean Application No. 10-2008-7005209.
Korean Office Action, dated Oct. 31, 2007, for Korean Application No. 10-2003-7013949.
Korean Request for Examination, dated Jun. 19, 2008, for Korean Application No. 10-2008-7006800.
Kosovo Amendment, dated Mar. 1, 2011, for Kosovo Application No. 329.
Malaysian Statement Justifying the Applicant's Right to a Patent, dated Sep. 27, 2010, for Malaysian Application No. PI2010004527 (Derived from International Application No. PCT/JP2009/057270).
Mexican Notice of Allowance, dated Dec. 3, 2010, for Mexican Application No. PA/a/2007/009752.

Mexican Notice of Allowance, dated Jul. 20, 2007, for Mexican Application No. PA/a/2005/002185.
Mexican Notice of Allowance, dated May 15, 2008, for Mexican Application No. PA/a/2003/009738.
Mexican Office Action, dated Mar. 12, 2008, for Mexican Application No. PA/a/2003/009738.
New Zealand Examination Report and Notice of Acceptance, dated Jun. 8, 2011, for New Zealand Application No. 588376.
New Zealand Examination Report, dated Mar. 29, 2011, for New Zealand Application No. 588376.
New Zealand Examination Report, dated May 26, 2004, for New Zealand Application No. 529333.
New Zealand Examination Report, dated Oct. 25, 2005, for New Zealand Application No. 538860.
New Zealand Notice of Acceptance, dated Dec. 22, 2004, for New Zealand Application No. 529333.
New Zealand Notice of Acceptance, dated Jun. 26, 2006, for New Zealand Application No. 538860.
Norwegian Amendment, dated Oct. 14, 2008, for Norwegian Application No. 20052443.
Norwegian Notice of Allowance, dated Nov. 7, 2008, for Norwegian Application No. 20034788.
Norwegian Notice of Allowance, dated Sep. 6, 2011, for Norwegian Application No. 20052443.
Norwegian Office Action, dated Apr. 13, 2011, for Norwegian Application No. 20052443.
Norwegian Office Action, dated Jan. 14, 2011, for Norwegian Application No. 20052443.
Norwegian Office Action, dated Jun. 3, 2011, for Norwegian Application No. 20052443.
Norwegian Office Action, dated Mar. 25, 2008, for Norwegian Application No. 20034788.
Norwegian Office Action, dated Nov. 12, 2007, for Norwegian Application No. 20034788.
Pakistani Notice of Acceptance, dated Feb. 29, 2012, for Pakistani Application No. 101/2011.
Pakistani Notice of Acceptance, dated Feb. 29, 2012, for Pakistani Application No. 307/2009.
Pakistani Office Action, dated Aug. 3, 2009, for Pakistani Application No. 307/2009.
Peruvian Amendment, dated Aug. 2, 2010, for Peruvian Application No. 000505.2009.
Polish Office Action, dated Apr. 28, 2009, for Polish Application No. P-367067.
Polish Office Action, dated Apr. 29, 2010, for Polish Application No. P-376132.
Polish Office Action, dated Jul. 29, 2011, for Polish Application No. P-367067.
Polish Office Action, dated Mar. 4, 2010, for Polish Application No. P-367067.
Response to Australian Office Action, dated Apr. 23, 2009, for Australian Application No. 2003275589.
Response to Australian Office Action, dated Dec. 18, 2006, for Australian Application No. 2002251546.
Response to Canadian Office Action, dated Jun. 10, 2010, for Canadian Application No. 2,494,574.
Response to Canadian Office Action, dated Jun. 17, 2009, for Canadian Application No. 2,443,802.
Response to Chilean Office Action, dated Sep. 15, 2011, for Chilean Application No. 896-2009.
Response to Chinese Office Action, dated Apr. 17, 2006, for Chinese Application No. 02808872.7.
Response to Chinese Office Action, dated Aug. 1, 2006, for Chinese Application No. 200380101417.7.
Response to Chinese Office Action, dated Dec. 25, 2006, for Chinese Application No. 200380101417.7.
Response to Chinese Office Action, dated Jul. 17, 2009, for Chinese Application No. 200710128111.0.
Response to Chinese Office Action, dated Nov. 23, 2005, for Chinese Application No. 02808872.7 17.
Response to Czech Office Action, dated Feb. 5, 2009, for Czech Application No. PV 2003-2937.
Response to Czech Office Action, dated May 25, 2009, for Czech Application No. PV 2003-2937.
Response to Czech Office Action, dated Oct. 12, 2009, for Czech Application No. PV 2003-2937.
Response to European Office Action, dated Aug. 4, 2005, for European Application No. 02720608.5.
Response to European Office Action, dated Feb. 15, 2010, for European Application No. 02720608.5.
Response to European Office Action, dated Feb. 27, 2008, for European Application No. 03758781.3.
Response to European Office Action, dated May 19, 2008, for European Application No. 03758781.3.
Response to European Office Action, dated Oct. 1, 2007, for European Application No. 02711424.8.
Response to European Office Action, dated Oct. 14, 2008, for European Application No. 02711424.8.
Response to European Office Action, dated Oct. 27, 2010, for European Application No. 02711424.8.
Response to European Office Action, dated Oct. 5, 2009, for European Application No. 02711424.8.
Response to Filipino Office Action, dated Jun. 18, 2008, for Filipino Application No. 1-2005-500278.
Response to Filipino Office Action, dated Mar. 11, 2004, for Filipino Application No. 1-2003-501066.
Response to Filipino Office Action, dated Mar. 2, 2007, for Filipino Application No. 1-2003-501066.
Response to Filipino Office Action, dated Mar. 3, 2008, for Filipino Application No. 1-2005-500278.
Response to Filipino Office Action, dated Nov. 27, 2007, for Filipino Application No. 1-2007-500806.
Response to Hungarian Office Action, dated Jun. 17, 2011, for Hungarian Application No. P0401292.
Response to Indian Office Action, dated Aug. 10, 2007, for Indian Application No. 1748/DELNP/2003.
Response to Indian Office Action, dated Jan. 10, 2011, for Indian Application No. 1966/CHENP/2007.
Response to Indian Office Action, dated Mar. 24, 2009, for Indian Application No. 961/CHENP/2005.
Response to Indian Office Action, dated May 1, 2007, for Indian Application No. 1748/DELNP/2003.
Response to Indian Office Action, dated Nov. 13, 2009, for Indian Application No. 961/CHENP/2005.
Response to Indian Office Action, dated Sep. 24, 2007, for Indian Application No. 1748/DELNP/2003.
Response to Indonesian Office Action, dated Jul. 3, 2008, for Indonesian Application No. W-00200500983.
Response to Indonesian Office Action, dated Oct. 16, 2008, for Indonesian Application No. W-00200500983.
Response to Japanese Office Action, dated Apr. 20, 2010, for Japanese Application No. 2002-563153.
Response to Japanese Office Action, dated Apr. 28, 2009, for Japanese Application No. 2002-563153.
Response to Korean Office Action, dated Feb. 29, 2008, for Korean Application No. 10-2003-7013949.
Response to Korean Office Action, dated Jul. 16, 2008, for Korean Application No. 10-2003-7013949.
Response to Korean Office Action, dated Jul. 16, 2008, for Korean Application No. 10-2008-7005209.
Response to Mexican Office Action, dated May 8, 2008, for Mexican Application No. PA/a/2003/009738.
Response to New Zealand Examination Report, dated Apr. 13, 2006, for New Zealand Application No. 538860.
Response to New Zealand Examination Report, dated May 25, 2011, for New Zealand Application No. 588376.
Response to New Zealand Examination Report, dated Nov. 22, 2004, for New Zealand Application No. 529333.
Response to Norwegian Office Action, dated Aug. 16, 2011, for Norwegian Application No. 20052443.
182 Response to Norwegian Office Action, dated Mar. 12, 2008, for Norwegian Application No. 20034788.
Response to Norwegian Office Action, dated Mar. 30, 2011, for Norwegian Application No. 20052443.

Response to Norwegian Office Action, dated May 24, 2011, for Norwegian Application No. 20052443.
Response to Norwegian Office Action, dated Oct. 27, 2008, for Norwegian Application No. 20034788.
Response to Pakistani Office Action, dated Feb. 17, 2011, for Pakistani Application No. 307/2009.
Response to Pakistani Office Action, dated Jul. 27, 2011, for Pakistani Application No. 307/2009.
Response to Polish Office Action, dated Jul. 5, 2010, for Polish Application No. P-367067.
Response to Polish Office Action, dated Jun. 22, 2010, for Polish Application No. P-376132.
Response to Polish Office Action, dated Jun. 29, 2009, for Polish Application No. P-367067.
Response to Polish Office Action, dated Oct. 25, 2011, for Polish Application No. P-367067.
Response to Russian Office Action, dated Apr. 2, 2004, for Russian Application No. 2003134371.
Response to Russian Office Action, dated Dec. 1, 2006, for Russian Application No. 2003134371.
Response to Russian Office Action, dated Jul. 3, 2006, for Russian Application No. 2003134371.
Response to Russian Office Action, dated Nov. 13, 2007, for Russian Application No. 2005115504.
Response to Taiwanese Office Action, dated Jun. 3, 2005, for Taiwanese Application No. 091108720.
Response to Taiwanese Office Action, dated Sep. 12, 2006, for Taiwanese Application No. 092129327.
Response to Taiwanese Office Action, dated Sep. 8, 2005, for Taiwanese Application No. 091108720.
Response to Thai Office Action, dated Jul. 23, 2010, for Thai Application No. 0901001738.
Response to US Office Action, dated Apr. 19, 2007, for U.S. Appl. No. 10/524,662.
Response to US Office Action, dated Apr. 2, 2009, for U.S. Appl. No. 11/757,595.
Response to US Office Action, dated Apr. 27, 2007, for U.S. Appl. No. 11/446,416.
Response to US Office Action, dated Aug. 2, 2005, for U.S. Appl. No. 10/451,741.
Response to US Office Action, dated Dec. 11, 2009, for U.S. Appl. No. 12/397,132.
Response to US Office Action, dated Dec. 14, 2005, for U.S. Appl. No. 10/689,088.
Response to US Office Action, dated Dec. 2, 2005, for U.S. Appl. No. 10/250,693.
Response to US Office Action, dated Dec. 22, 2005, for U.S. Appl. No. 10/451,741.
Response to US Office Action, dated Feb. 28, 2005, for U.S. Appl. No. 10/451,741.
Response to US Office Action, dated Jul. 10, 2009, for U.S. Appl. No. 12/397,132.
Response to US Office Action, dated Jul. 25, 2005, for U.S. Appl. No. 10/689,088.
Response to US Office Action, dated Jun. 12, 2006, for U.S. Appl. No. 10/689,088.
Response to US Office Action, dated Jun. 19, 2008, for U.S. Appl. No. 11/421,740.
Response to US Office Action, dated Mar. 10, 2010, for U.S. Appl. No. 12/397,132.
Response to Vietnamese Office Action, dated May 26, 2008, for Vietnamese Application No. 1-2005-00679.
Russian Office Action, dated Feb. 1, 2006, for Russian Application No. 2003134371.
Russian Office Action, dated Feb. 13, 2007, for Russian Application No. 2003134371.
Russian Office Action, dated Feb. 2, 2004, for Russian Application No. 2003134371.
Russian Office Action, dated Mar. 12, 2007, for Russian Application No. 2005115504.
Russian Office Action, dated Nov. 22, 2007, for Russian Application No. 2005115504.
Russian Office Action, dated Sep. 29, 2006, for Russian Application No. 2003134371.
Russian Request for Substantial Examination, dated Mar. 22, 2005, for Russian Application No. 2003134371.
Russian Request for Examination, dated Jul. 4, 2006, for Russian Application No. 2005115504.
Singapore Amendment, dated Apr. 20, 2007, for Singapore Application No. 200502609-1.
Singapore Amendment, dated Jul. 28, 2011, for Singapore Application No. 201005623-2.
Singapore Amendment, dated May 28, 2004, for Singapore Application No. 200306355-9.
Singapore Amendment, dated Oct. 18, 2005, for Singapore Application No. 200306355-9.
Singapore Notification of Grant, dated Feb. 28, 2006, for Singapore Application No. 200306355-9.
Singapore Notification of Grant, dated Jul. 31, 2007, for Singapore Application No. 200502609-1.
South African Amendment, dated Feb. 15, 2005, for South African Application No. 2005/01310.
South African Amendment, dated Jan. 19, 2005, for South African Application No. 2003/8860.
South African Office Action, dated Feb. 14, 2005, for South African Application No. 2003/8860.
South African Office Action, dated Jul. 3, 2006, for South African Application No. 2005/01310.
Sri Lankan Certificate of Grant, dated Nov. 25, 2010, for Sri Lankan Patent No. 13600.
Supplementary Partial European Search Report, dated Feb. 11, 2005, for European Application No. 02711424.8.
Supplementary Partial European Search Report, dated Jul. 5, 2006, for European Application No. 03758781.3.
Supplementary Partial European Search Report, dated Jun. 3, 2005, for European Application No. 02720608.5.
Taiwanese Amendment, dated Mar. 3, 2007, for Taiwanese Application No. 092129327.
Taiwanese Amendment, dated Nov. 8, 2007, for Taiwanese Application No. 091108720.
Taiwanese Office Action, dated Apr. 7, 2005, for Taiwanese Application No. 091108720.
Taiwanese Office Action, dated Jul. 11, 2005, for Taiwanese Application No. 091108720.
Taiwanese Office Action, dated Jul. 27, 2006, for Taiwanese Application No. 092129327.
Taiwanese Office Action, dated Mar. 22, 2007, for Taiwanese Application No. 092129327.
Taiwanese Office Action, dated Nov. 23, 2007, for Taiwanese Application No. 091108720.
US Notice of Allowance, dated Jun. 20, 2007, for U.S. Appl. No. 11/446,416.
US Notice of Allowance, dated Mar. 29, 2010, for U.S. Appl. No. 12/397,132.
US Notice of Allowance, dated Oct. 22, 2007, for U.S. Appl. No. 10/524,662.
US Office Action, dated Apr. 1, 2005, for U.S. Appl. No. 10/451,741.
US Office Action, dated Feb. 22, 2012, for U.S. Appl. No. 12/900,046.
Venezuelan Amendment, dated Dec. 21, 2010, for Venezuelan Application No. 2009-000652.
Vietnamese Amendment, dated Oct. 21, 2008, for Vietnamese Application No. 1-2005-00679.
Vietnamese Notice of Acceptance, dated Jun. 27, 2005, for Vietnamese Application No. 1-2005-00679.
Vietnamese Office Action, dated Mar. 25, 2008, for Vietnamese Application No. 1-2005-00679.
Notice of Allowance for U.S. Appl. No. 12/421,182 dated Mar. 21, 2012.
Response to Chilean Office Action for Chilean Application No. 896-09 dated Jan. 25, 2012 with English translation.
Decision on Grant for Russian Patent Application No. 2010146240, dated Dec. 5, 2012.
Submission for Filipino Patent Application No. 1-2010-502102, dated Dec. 12, 2012.

Submission for Indonesian Patent Application No. W-00 2010 03905, dated Dec. 14, 2012.
Notification of the First Office Action for Chinese Patent Application No. 200980113130.3, dated Dec. 3, 2012.
International Preliminary Report on Patentability for corresponding International Patent Application No. PCT/JP2010/067564, date May 18, 2012.
International Preliminary Report on Patentability for International Patent Application No. PCT/JP2010/067556, dated May 18, 2012.
Office Action for Mexican Patent Application No. MX/a/2010/011089, dated May 28, 2012.
Canadian Request for Advanced Examination and Submission of Prior Art for Application No. 2,721,670 dated Jun. 11, 2012.
Chilean official letter of Notification of Acceptance for Application No. 896-09 dated May 24, 2012 (with English translation).
U.S. Office Action for U.S. Appl. No. 12/900,046 dated Jun. 22, 2012.
Amended Vietnamese Specification for Application No. 1-2010-03032 dated Jul. 11, 2012 (with English translation).
Response to Mexican Office Action for Application No. MX/a/2010/011089 dated Jun. 28, 2012 (with English translation).
Takahashi et al., "Synthesis and Structure—Activity Relationships of Pyrazolo[1,5-a]pyridine Derivatives: Potent and Orally Active Antagonists of Corticotropin-Releasing Factor 1 Receptor", Journal of Medicinal Chemistry, vol. 55, No. 11, 2012, pp. 5255-5264.
Takeda et al., "Design, synthesis and structure-activity relationships of 5-alkylaminolquinolines as a novel series of CRF1 receptor antagonists", Bioorganic & Medicinal Chemistry Letters, vol. 22, Iss. 14, Jul. 15, 2012, pp. 4756-4761 (7 pages provided).
Takeda et al., "Design, synthesis, and structure-activity relationships of a series of 2-Ar-8-methyl-5-alkylaminoquinolines as novel CRF1 receptor antagonists", Bioorganic & Medicinal Chemistry Letters, vol. 22, Iss. 17, Sep. 1, 2012, pp. 5372-5376 (10 pages provided).
Notice of Allowance for Mexican Patent Application No. MX/a/2010/011089, dated Jul. 23, 2012.
Notice of Allowance for U.S. Appl. No. 12/421,182, dated Aug. 3, 2012.
Office Action for Indonesian Patent Application No. W-00 2010 03905, dated Aug. 3, 2012.
Submission Document Before the Patent Office for Philippinian Patent Application No. 1-2007-500806, dated Aug. 14, 2012.
Takeda et ai., "Design, synthesis, and structure-activity relationships of a series of 2-Ar-8-methly-5-alkylaminoquinolines as novei CRF1 receptor antagonists," Bioorganic & Medicinal Chemisrty Letters, vol. 22, Jul. 20, 2012, pp. 5372-5376.
Canadian Voluntary Amendment dated Sep. 5, 2012 for Canadian Application No. 2,721,670.
Polish Office Action dated Sep. 17, 2012 for Polish Application No. P-367067 with English translation.
Polish Response to Office Action dated Aug. 17, 2012 for Polish Application No. P-367067 with English translation.
Russian Office Action dated Aug. 23, 2012 for Russian Application No. 2010146240 with English translation.
Takahashi et al., "Design, Synthesis, and Structure—Activity Relationships of Novel Pyrazolo[5,1-b]thiazole Derivatives as Potent and Orally Active Corticotropin-Releasing Factor 1 Receptor Antagonists," Journal of Medicinal Chemistry, Sep. 12, 2012, 47 pages.
Response (Submission Documents), dated Sep. 7, 2012, in Polish Application No. P-376132, including a partical English translation.
Shin et al., "Discovery of a novel, potent, selective and orally active corticotropin-releasing factor1 (CRF1) receptor antagonist, E2508, for the treatment of stress-related disorders such as anxiety and depression," 244th ACS National Meeting, Aug. 19-23, 2012, Poster Presentation & Abstract, 2 pp.
Takeda et al., "Synthesis and Structure—Activity Relationships of 8-Substituted-2-aryl-5-alkylaminoquinolines: Potent, Orally Active Corticotropin-Releasing Factor-1 Receptor Antagonists," Bioorganic & Medicinal Chemistry, Accepted Manuscript, Sep. 2012, pp. 1-43.
Terauchi et al., "Discovery of a novel, potent, selective and orally active corticotropin-releasing factor 1 (CRF1) receptor anagonist, E2009, for the treatment of stress-related disorders such as anxiety and depression,"244th ACS National Meeting, Aug. 19-23, 2012, Poster Presentation & Abstract, 2 pp.
Applicant Submission for Filipino Patent Application No. 1-2010-502102, dated Sep. 24, 2012.
Notice of Allowance for Vietnamese Patent Application No. 1-2010-03032, dated Oct. 26, 2012.
Takeda et al., "Synthesis and structure-activity relationships 8-substituted-2-aryl-5-alkylaminoquinolines: Potent, orally active corticotropin-released factor-1 receptor antagonists," Bioorganic & Medicinal Chemistry, vol. 20, pp. 6559-6578, Sep. 23, 2012.
Notice of Allowance for Polish Patent Application No. P-376 132, dated Sep. 20, 2012.
Office Action for Filipino Patent Application No. 1/2010/502102, mailed Nov. 8, 2012.
Response to Official Action for Russian Patent Application No. 201146240/04, dated Oct. 29, 2012.
Submission for Polish Patent Application No. P-367067, dated Nov. 16, 2012.
Patent Examination Report No. 1 for Australian Patent Application No. 2009237050, dated Nov. 19, 2012.
European Notice of Allowance for Application No. 09732907.2 dated May 11, 2012.
Vietnamese Office Action for Application No. 1-2010-03032 dated May 21, 2012 (with English translation).
Philippine Office Action for Application No. 12010502102 dated Aug. 17, 2012.
Polish Office Action for Application No. P-376132 dated Jul. 3, 2012 (with English translation).
Notice of Allowance for U.S. Appl. No. 12/421,182, dated Dec. 28, 2012.
Decision on Polish Patent Appl. No. P.367067, dated Dec. 20, 2012.
Notice of Allowance for Canadian Appl. No. 2,721,670, dated Jan. 7, 2013.
Notice of Non-Substantive Deficiencies Prior to Allowance for Israeli Appl. No. 208393, dated Jan. 6, 2013.
Notice of Allowance for Indonesian Appl. No. W-00 2010 03905, dated Jan. 11, 2013.
Notice of Allowance for Ukranian Patent Application No. a 2010 13461/M, dated Dec. 24, 2012.
Submission for Chinese Patent Application No. 200980113130.3, dated Jan. 25, 2013.

PYRAZOLOTHIAZOLE COMPOUND

CROSS-REFERENCE TO RELATED APPLICATIONS

This application claims the benefit of the following applications: Japanese patent application No. 2009-233989 filed on Oct. 8, 2009, U.S. provisional application No. 61/249,817 filed on Oct. 8, 2009, Japanese patent application No. 2010-132008 filed on Jun. 9, 2010 and U.S. provisional application No. 61/352,970 filed on Jun. 9, 2010, the disclosures of all of which are herein incorporated by reference in their entireties.

BACKGROUND OF THE INVENTION

1. Field of the Invention

The present invention relates to novel compounds having corticotropin-releasing factor (hereinafter, referred to as "CRF") receptor antagonistic activity, and pharmacologically acceptable salts thereof and to medical use of the same.

2. Related Background Art

CRF is a neuropeptide that consists of 41 amino acids and is produced and secreted in the hypothalamus and promotes release of adrenocorticotropic hormone (ACTH) under stress, and it also functions in the brain as a neurotransmitter or a neuromodulator, integrating electrophysiology, autonomic nerves, behavior, and the like, in response to stress.

There are two subtypes in CRF receptors, CRF1 receptor and CRF2 receptor, and CRF1 receptor has been reported to be widely distributed in the cerebral cortex, cerebellum, olfactory bulb, pituitary gland, amygdaloid nucleus, and the like.

Furthermore, many low molecular compounds having CRF receptor antagonism have been noted as potential therapeutic agents for a variety of diseases including depression, anxiety, stress-related disorders, and the like (see Non-patent Document 1).

Disclosed compounds having CRF receptor antagonism include compounds having a 2,6-dimethoxy-4-methoxymethylphenyl group (see Patent Document 1), but compounds having a pyrazolo[5,1-b]thiazole skeleton according to the invention of the present application have been neither disclosed nor suggested.

As a compound having a pyrazolo[5,1-b]thiazole skeleton, the compound shown below has been disclosed but its use is for colorimetry (see Example 16 of Patent Document 2).

[Chemical Formula 1]

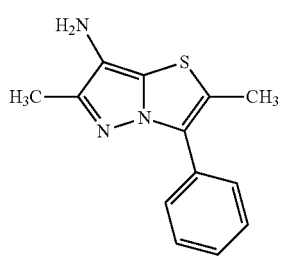

Patent Document 3 (international filing date: Oct. 22, 2009) discloses the following compounds which have a pyrazolo[5,1-b]thiazole skeleton and have CRF receptor antagonism

[Chemical Formula 1a]

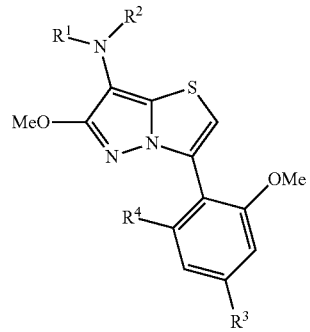

wherein $R^1$ is the formula $-A^{11}-A^{12}$, $R^2$ is tetrahydrofurylmethyl, tetrahydropyranylmethyl or tetrahydropyranyl, $A^{11}$ is a single bond, methylene or 1,2-ethylene, $A^{12}$ is C1-6 alkyl, C3-6 cycloalkyl or C3-6 cycloalkyl having methyl, $R^3$ is methoxy, cyano, cyclobutyloxymethyl, methoxymethyl or ethoxymethyl, and $R^4$ is methoxy or chlorine.

Patent Document 3 was published after the filing date of the earliest priority applications (Japanese patent application No. 2009-233989 and U.S. provisional application No. 61/249,817; both were filed on Oct. 8, 2009) of the present application.

CITATION LIST

Patent Document

[Patent document 1] U.S. Patent Application Publication No. 2004/0224974

[Patent document 2] U.S. Pat. No. 5,234,818

[Patent document 3] WO 2009/128383

Non-Patent Document

[Non-patent document 1] Drugs of the Future, 24:1089-1098 (1999)

SUMMARY OF THE INVENTION

No 3-phenylpyrazolo[5,1-b]thiazole compounds having superior CRF receptor antagonism are known. Furthermore, although compounds having CRF receptor antagonism have been reported, they have not necessarily been sufficient in terms of having superior CRF receptor antagonism, and in terms of having sufficient pharmacological activity, safety and pharmacokinetic properties as medicines.

In view of the above-mentioned current circumstances, the present inventors have intensively studied and, as a result, have discovered novel compounds that are excellent CRF receptor antagonists with sufficient pharmacological activity, safety, and pharmacokinetics, and are useful as prophylactic agents or therapeutic agents for diseases such as depression, anxiety, and irritable bowel syndrome.

Specifically, the present invention relates to the following <1> to <19>.

<1> A compound represented by the formula (I) or pharmacologically acceptable salt thereof:

[Chemical Formula 2]

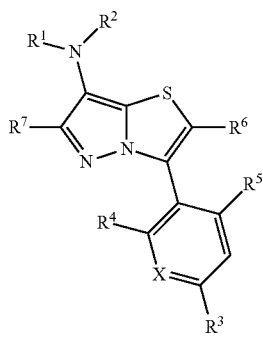

(I)

wherein X is a nitrogen atom or CH;
$R^1$ is $-A^{11}-A^{12}$;
$A^{11}$ is a single bond or a C1-6 alkylene group;
$A^{12}$ is (a) a hydrogen atom, (b) a C1-6 alkyl group optionally having 1 to 3 substituents selected from Substituent group A, or (c) a C3-6 cycloalkyl group optionally having 1 to 3 substituents selected from Substituent group A;
$R^2$ is $-A^{21}-A^{22}$;
$A^{21}$ is a single bond or a C1-6 alkylene group;
$A^{22}$ is (a) a hydrogen atom, (b) a C1-6 alkyl group optionally having 1 to 3 substituents selected from Substituent group A, (c) a C3-6 cycloalkyl group optionally having 1 to 3 substituents selected from Substituent group A; (d) a non-aromatic heterocyclic group selected from a tetrahydropyranyl group, a dihydropyranyl group, a tetrahydrofuryl group, a dioxanyl group, a hexahydrooxepinyl group, an oxabicyclo[3.1.0]hexyl group, a tetrahydrothienyl group, a dithianyl group, and a hexahydrothiepinyl group, which optionally has 1 to 3 substituents selected from Substituent group A, or (e) a heteroaryl group selected from a pyridyl group, a pyrimidinyl group, and a thiazolyl group;
$R^3$ is (a) a C1-6 alkyl group optionally having 1 to 3 substituents selected from Substituent group A, (b) a C3-6 cycloalkyl group, (c) a C1-6 alkoxy group optionally having 1 to 3 substituents selected from Substituent group A, (d) a C3-6 cycloalkoxy C1-6 alkyl group, (e) di-C1-6 alkyl amino group, (f) a halogen atom, (g) a cyano group, (h) a formyl group, or (i) a carboxyl group;
$R^4$ is a hydrogen atom or a C1-6 alkoxy group;
$R^5$ is a halogen atom, a C1-6 alkyl group, or a C1-6 alkoxy group;
$R^6$ is a hydrogen atom, a C1-6 alkyl group, a C1-6 alkoxy group, a C1-6 alkylthio group; or a C1-6 alkyl sulfinyl group; and
$R^7$ is a C1-6 alkyl group, a C1-6 alkoxy group, or a C1-6 alkylthio group;
with the proviso that $R^3$ is (a) a C1-6 alkyl group optionally substituted with a hydroxyl group, (b) a C3-6 cycloalkyl group, (c) a C2-6 alkoxy group optionally having 1 to 3 substituents selected from Substituent group A, (d) a C3-6 alkoxy C1-6 alkyl group, (e) a C1-2 alkoxy C2-6 alkyl group, (f) a di-C1-6 alkyl amino group, (g) a halogen atom, (h) a formyl group or (i) a carboxyl group when X is C11, $A^{12}$ is a C1-6 alkyl group, or a C3-6 cycloalkyl group optionally having a methyl group, $R^2$ is a tetrahydrofurylmethyl group, a tetrahydropyranylmethyl group, or a tetrahydropyranyl group, $R^6$ is a hydrogen atom, and $R^7$ is a methoxy group; and
wherein the Substituent group A consists of a halogen atom, a hydroxyl group, a C1-6 alkyl group and a C1-6 alkoxy group.

<2> The compound or pharmacologically acceptable salt thereof according to <1>, wherein
X is a nitrogen atom or CH;
$A^{11}$ is a single bond, a methylene group or a 1,2-ethylene group;
$A^{12}$ is (a) a hydrogen atom, (b) a C1-6 alkyl group optionally having 1 to 3 substituents selected from Substituent group A, or (c) a C3-6 cycloalkyl group optionally having 1 to 3 substituents selected from Substituent group A;
$A^{21}$ is a single bond, a methylene group, or a 1,2-ethylene group;
$A^{22}$ represents (a) a hydrogen atom, (b) a C1-6 alkyl group optionally having 1 to 3 substituents selected from Substituent group A, (c) a C3-6 cycloalkyl group optionally having 1 to 3 substituents selected from Substituent group A; (d) a tetrahydropyranyl group optionally having 1 to 3 substituents selected from Substituent group A (e) a dihydropyranyl group, (f) a tetrahydrofuryl group, (g) a dioxanyl group, (h) a hexahydrooxepinyl group, (i) an oxabicyclo[3.1.0]hexyl group, or (j) a pyridyl group;
$R^3$ is (a) a methyl group, (b) an ethyl group, (c) a cyclopropyl group, (d) a C1-6 alkoxy group optionally substituted with 1 to 3 halogen atoms, (e) a C1-6 alkoxy methyl group, (f) a cyclobutoxymethyl group, (g) a dimethylamino group, (h) a halogen atom, (i) a cyano group, (j) hydroxymethyl group, (k) a formyl group, or (l) a carboxyl group;
$R^4$ is a hydrogen atom or a methoxy group;
$R^5$ is a halogen atom, a methyl group or a methoxy group;
$R^6$ is a hydrogen atom, a methyl group or an ethyl group; and
$R^7$ is a methoxy group.

<3> The compound or pharmacologically acceptable salt thereof according to <2>, wherein
X is CH;
$R^3$ is (a) a methyl group, (b) an ethyl group, (c) a cyclopropyl group, (d) a C1-6 alkoxy group optionally substituted with 1 to 3 halogen atoms, (e) a C1-6 alkoxy methyl group, or (f) a cyclobutoxymethyl group.

<4> The compound or pharmacologically acceptable salt thereof according to <1>, wherein
X is CH;
$R^1$ is a hydrogen atom, a C1-6 alkyl group, a C3-6 cycloalkyl group, or a C3-6 cycloalkyl methyl group;
$R^2$ is a hydrogen atom, a C1-6 alkyl group, a tetrahydropyranyl group, a tetrahydropyranylmethyl group, or a tetrahydrofurylmethyl group;
$R^3$ is a C1-6 alkoxy methyl group;
$R^4$ is a methoxy group;
$R^5$ is a methoxy group;
$R^6$ is a hydrogen atom, a methyl group, a methylthio group, or a methylsulfinyl group; and
$R^7$ is a methyl group, an ethyl group, an ethoxy group, or a methylthio group.

<5> The compound or pharmacologically acceptable salt thereof according to <4>, wherein $R^7$ is a methyl group.

<6> The compound or pharmacologically acceptable salt thereof according to <4>, wherein $R^7$ is an ethoxy group.

<7> A pharmaceutical composition comprising a compound or pharmacologically acceptable salt thereof according to <1> as an active ingredient <8> The pharmaceutical composition according to <7>, which is a CRF1 receptor antagonist <9> A therapeutic or prophylactic agent for depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia, comprising a compound or pharmacologically acceptable salt thereof according to <1> as an active ingredient.

<10> A therapeutic or prophylactic agent for depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, or dementia, comprising a compound or pharmacologically acceptable salt thereof according to <1> as an active ingredient.

<11> A therapeutic or prophylactic agent for depression, depressive symptoms, anxiety, or irritable bowel syndrome, comprising a compound or pharmacologically acceptable salt thereof according to <1> as an active ingredient.

<12> The compound or pharmacologically acceptable salt thereof according to <1>, wherein the compound is N-(cyclopropylmethyl)-3-[2,6-dimethoxy-4-(inethoxymethyl)phenyl]-6-methyl-N-(tetrahydro-2H-pyran-4-ylmethyl)pyrazolo[5,1-b][1,3]thiazole-7-amine:

[Chemical Formula 3]

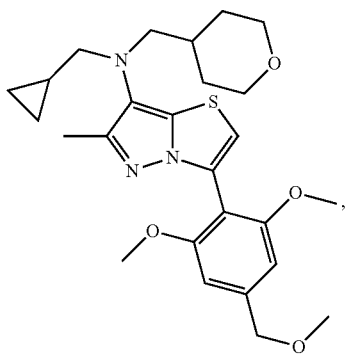

cyclopropylmethyl-[3-(2,6-dimethoxy-4-methoxymethyl-phenyl)-6-methoxy-pyrazolo[5,1-b][1,3]thiazol-7-yl]-[1,3]dioxan-5-ylmethyl-amine:

[Chemical Formula 4]

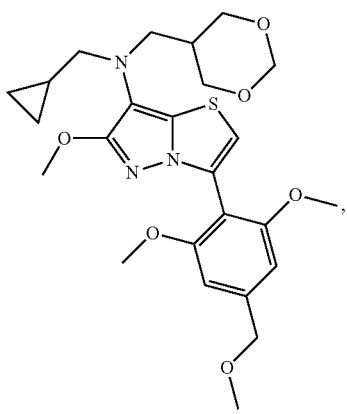

or
N-butyl-3-[2,6-dimethoxy-4-(methoxymethyl)phenyl]-6-(methylthio)-N-(tetrahydro-2H-pyran-4-yl)pyrazolo[5,1-b][1,3]thiazole-7-amine:

[Chemical Formula 5]

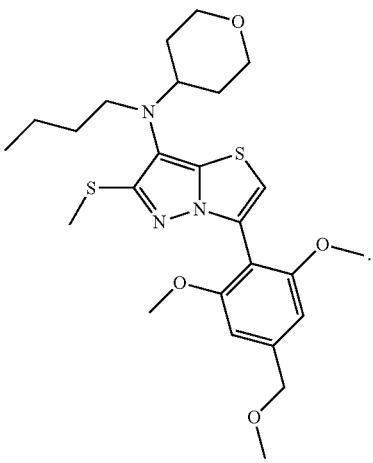

<13> The compound or pharmacologically acceptable salt thereof according to <1>, wherein the compound is N-(cyclopropylmethyl)-3-[2,6-dimethoxy-4-(methoxymethyl)phenyl]-6-methyl-N-(tetrahydro-2H-pyran-4-ylmethyl)pyrazolo[5,1-b][1,3]thiazole-7-amine:

[Chemical Formula 6]

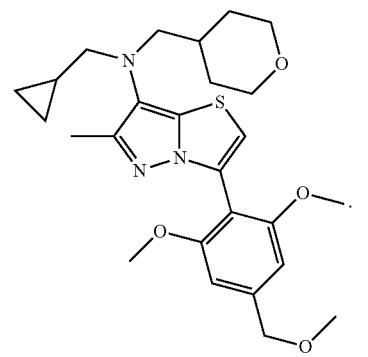

<14> The compound or pharmacologically acceptable salt thereof according to claim 1, wherein the compound is cyclopropylmethyl-[3-(2,6-dimethoxy-4-methoxymethyl-phenyl)-6-methoxy-pyrazolo[5,1-b][1,3]thiazol-7-yl]-[1,3]dioxan-5-ylmethyl-amine:

[Chemical Formula 7]

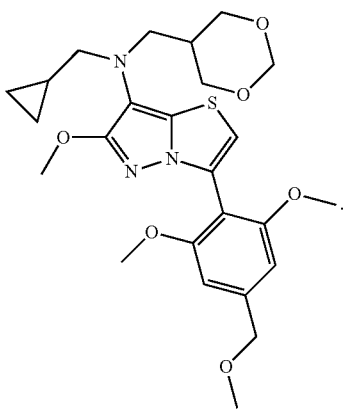

<15> The compound or pharmacologically acceptable salt thereof according to claim 1, wherein the compound is N-butyl-3-[2,6-dimethoxy-4-(methoxymethyl)phenyl]-6-(methylthio)-N-(tetrahydro-2H-pyran-4-yl)pyrazolo[5,1-b][1,3]thiazole-7-amine:

[Chemical Formula 8]

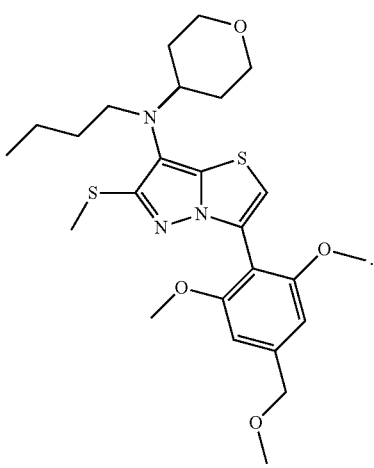

<16> A method for treating or preventing depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia, comprising administering a compound or pharmacologically acceptable salt thereof according to <1> to a patient.

<17> Use of a compound or pharmacologically acceptable salt thereof according to <1> for the manufacture of a therapeutic or prophylactic agent for depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia.

<18> A compound or pharmacologically acceptable salt thereof according to <1> for treating or preventing depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia.

<19> Use of a compound or pharmacologically acceptable salt thereof according to <1> for treating or preventing depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia,

ADVANTAGEOUS EFFECTS OF INVENTION

CRF receptor antagonists have been reported to be effective for a variety of diseases as mentioned below.

(1) Depression, Depressive Symptoms, Anxiety

CRF1 receptor antagonist R121919 is effective for ameliorating depression, depressive symptoms, anxiety, and the like (Journal of Psychiatric Research, 34:171-181 (2000)).

CRF1 receptor antagonist R121919 exhibits an anti-anxiety action in rats (European Journal of Neuroscience, 13:373-380 (2001)).

CRF1 receptor antagonist CP-154526 exhibits anti-depressant and anti-anxiety actions in rats. (European Journal of Pharmacology, 492:195-201 (2004)).

(2) Irritable Bowel Syndrome (IBS)

CRF1 receptor antagonist α-helical CRF (9-41) inhibits colon intestinal hyperkinesis in IBS patients and reduces abdominal pain and anxiety (Gut 2004; 53:958-964).

(3) Sleep Disorder, Insomnia

CRF1 receptor antagonist R121919 inhibits stress-related sleep disorder particularly in high-anxiety rats (Journal of Psychiatric Research, 36:197-208 (2002)).

(4) Alcohol Dependence, Alcohol Withdrawal Symptoms, Drug Dependence, Drug Withdrawal Symptoms CRF1 receptor antagonist CP-154526 inhibits recurrence of stress-elicited alcohol-seeking behavior in rats (Psychopharmacology, 150:317-324 (2000)).

CRF1 receptor antagonist α-helical CRF (9-41) inhibits anxiety behavior in ethanol withdrawal rats (Brain Research, 605:25-32 (1993)).

CRF1 receptor antagonist CP-154526 inhibits recurrence of stress-elicited drug (heroin, cocaine)-seeking behavior in rats (Psychopharmacology, 137:184-190 (1998)).

Pretreatment of CRF1 receptor antagonist CP-154526 inhibits naltrexone-induced morphine withdrawal symptoms (Journal of Neurochemistry, 74: 199-208 (2000)).

(5) Stress-Related Gastrointestinal Dysfunction

CRF1 receptor antagonist NM-27914 inhibits water avoidance stress-related rat catharsis (Brain Research, 893:29-35 (2001)).

(6) Anorexia Nervosa, Eating Disorder CRF1 receptor antagonists α-helical CRF (9-41) and CRA1000 inhibit stress-related reduction in food intake (Brain Research, 823: 221-225 (1999)).

(7) Postoperative Ileus

CRF1 receptor antagonist CP-154526 recovers gastric emptying retardation after surgery (Gastroenterology, 125: 654-659 (2003)).

(8) Dementia, Senile Dementia of Alzheimer type, Multi-infarct Dementia, Senile Dementia CRF1 receptor antagonist CP-154526 inhibits learning disability following acute stress (Behavioural Brain Research, 138: 207-213 (2003)).

CRF1 receptor antagonist α-helical CRF (9-41) suppresses stress-related increase in intracerebral amyloid-β (Proceedings of the National Academy of Sciences of the United States of America, 104: 10673-10678 (2007)).

CRF1 receptor antagonist NBI27914 inhibits increased levels of Aβ and Aβ plaque deposition induced by stress in Tg2576 transgenic mice (Journal of Neurochemistry, 108: 165-175 (2009)).

CRF1 receptor antagonist antalarmin inhibits stress-induced hippocampal tau phosphorylation (Journal of Neuroscience, 27 (24): 6552-6562 (2007)).

(9) Ischemic Neuropathy, Apoplexy

CRF1 receptor antagonist α-helical CRF (9-41) inhibits ischemic and excitotoxic encephalopathy (Brain Research, 656: 405-408 (1994)).

(10) Excitotoxic Neuropathy

CRF1 receptor antagonist Asressin inhibits kainic acid-induced excitotoxic neuropathy (Brain Research, 744: 166-170 (1997)).

(11) Convulsion, Epilepsy

CRF1 receptor antagonist NBI27914 inhibits limbic system seizure (convulsion and epilepsy induced by CRF administration) (Brain Research, 770:89-95 (1997)).

(12) Hypertension

CRF1 receptor antagonist antalarmin inhibits hypertension induced by intraventricular administration of CRF (Brain Research, 881: 204-207 (2000)).

The compounds or pharmacologically acceptable salts thereof according to the present invention have excellent CRF receptor antagonism, as shown in the activity data in the Pharmacological Test Examples described below. Thus, based on the above-mentioned documents demonstrating a nexus between CRF receptor antagonism and effects of treating or preventing diseases, the compounds or pharmacologically acceptable salts thereof according to the present invention are useful for treatment or prevention of diseases associated with CRF and/or CRF receptors, and are particularly useful as therapeutic agents or prophylactic agents for depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia, etc.

DESCRIPTION OF THE PREFERRED EMBODIMENTS

Hereinafter, the present invention is described in detail.

In the present specification, the structural formulae for compounds will show a certain isomer for convenience, but the present invention includes all isomers such as geometric isomers, optical isomers, stereoisomers, and tautomers generated by the compound structures, as well as their isomer mixtures, and the compounds may not be limited to the formulae that are shown for convenience and may be any of the isomers or mixtures including isomers in any arbitrary proportions. Thus, for example, the compounds of the present invention may exist as optically active substances or racemic mixtures, but they are not limited to any of them, they may be racemic mixtures or optically active substances, and they may also be mixtures with the optically active substances in any arbitrary ratio.

The present invention may include polymorphic crystals, but similarly include single substances of any crystal forms or a mixture thereof without any restrictions, as well as it may include amorphous forms, and the compounds of the present invention also include both anhydrate and solvate (especially, hydrate). The present invention further encompasses metabolites of compound (I) according to the present invention that are produced by metabolism (oxidation, reduction, hydrolysis, conjugation, and the like) in the living body. The present invention still further encompasses compounds that produce the compound (I) according to the present invention by metabolism (oxidation, reduction, hydrolysis, conjugation, and the like) in the living body (so-called prodrugs).

Hereinafter, the meanings of the terms and symbols used throughout the present specification are described, and the present invention is described in detail.

The term "halogen atom" used in the present specification means a fluorine atom, a chlorine atom, a bromine atom or an iodine atom. Preferable example of the "halogen atom" can include a fluorine atom, and a chlorine atom.

The term "C1-6 alkyl group" used in the present specification means C1-6 straight- or branched-chain alkyl groups, and the specific examples thereof may include a methyl group, an ethyl group, a 1-propyl group (a n-propyl group), a 2-propyl group (an i-propyl group), a 2-methyl-1-propyl group (an i-butyl group), a 2-methyl-2-propyl group (a tert-butyl group), a 1-butyl group (an n-butyl group), a 2-butyl group (an s-butyl group), a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2 butyl group, a 2,3-dimethyl-2-butyl group, and the like.

The term "C1-6 alkoxy group" used in the present specification means an oxygen atom to which the above-defined "C1-6 alkyl group" is bonded, and specific examples thereof may include a methoxy group, an ethoxy group, a 2-propyloxy group, a 1-pentyloxy group, a 1-hexyloxy group, and the like.

The term "C1-6 alkylthio group" used in the present specification means a sulfur atom to which the above-defined "C1-6 alkyl group" is bonded, and specific examples thereof may include a methylthio group, an ethylthio group, a 2-propylthio group, a 1-pentylthio group, a 1-hexylthio group, and the like.

The term "C1-6 alkyl sulfinyl group" used in the present specification means a sulfinyl group to which the above-defined "C1-6 alkyl group" is bonded, and specific examples thereof may include a methylsulfinyl group, an ethylsulfinyl group, a 2-propylsulfinyl group, a 1-pentylsulfinyl group, a 1-hexylsulfinyl group, and the like.

The term "C1-6 alkylene group" means a divalent group derived by further removing any one hydrogen atom from the above-defined "C1-6 alkyl group," and specific examples thereof may include a methylene group, an ethylene group, a methylethylene group, a propylene group, an ethylethylene group, a 1,1-dimethylethylene group, a trimethylene group, a pentamethylene group, a hexamethylene group, and the like.

The term "C1-6 alkoxy C1-6 alkyl group" used in the present specification means the above-defined "C1-6 alkyl group" to which the above-defined "C1-6 alkoxy group" is bonded, and specific examples thereof may include a methoxy methyl group, an ethoxymethyl group, a 2-methoxyethyl group, a (2-propyloxy)methyl group, a 6-hexyloxyhexyl group, and the like.

The term "C3-6 cycloalkyl group" used in the present specification means a monocycle saturated aliphatic hydrocarbon group having 3 to 6 carbon atoms, and specific examples thereof may include a cyclopropyl group, a cyclobutyl group, a cyclopentyl group, and a cyclohexyl group.

The term "C3-6 cycloalkyl C1-6 alkyl group" used in the present specification means the above-defined "C1-6 alkyl group" to which the above-defined "C3-6 cycloalkyl group" is bonded, and specific examples thereof may include a cyclopropylmethyl group, a cyclobutylmethyl group, a 2-cyclopropylethyl group, and the like.

The term "C3-6 cycloalkoxy group" used in the present specification means an oxygen atom to which the above-defined "C3-6 cycloalkyl group" is bonded, and specific examples thereof may include a cyclopropyloxy group, a cyclobutyloxy group, a cyclopentyloxy group, a cyclohexyloxy group, and the like.

The term "C3-6 cycloalkoxy C1-6 alkyl group" used in the present specification means the above-defined "C1-6 alkyl group" to which the above-defined "C3-6 cycloalkoxy group" is bonded, and specific examples thereof may include a cyclopropyloxymethyl group, a cyclobutyloxymethyl group, 1-(cyclopropyloxy)ethyl group, a cyclohexyloxymethyl group, and the like.

Specific examples of a "tetrahydropyranyl group" used in the present specification may include a tetrahydropyran-4-yl group and a tetrahydropyran-3-yl group, and a preferable example is a tetrahydropyran-4-yl group.

Specific examples of a "tetrahydropyranylmethyl group" used in the present specification may include a (tetrahydropyran-4-yl)methyl group, a (tetrahydropyran-3-yl)methyl group, a (tetrahydropyran-2-yl)methyl group, and a preferable example is a (tetrahydropyran-4-yl)methyl group.

Specific examples of a "tetrahydrofuryl group" used in the present specification may include a tetrahydrofuran-3-yl group, and a tetrahydrofuran-2-yl group, and a preferable example is a tetrahydrofuran-3-yl group.

Specific examples of a "tetrahydrofurylmethyl group" used in the present specification may include a (tetrahydrofuran-3-yl)methyl group and a (tetrahydrofuran-2-yl)methyl group, and a preferable example is a (tetrahydrofuran-3-yl) methyl group.

The term "anxiety" used in the present specification means not only anxiety in the strict sense, but also to conditions within the general concept of anxiety, such as generalized anxiety disorder, panic disorder, phobia, obsessive compulsive disorder and post-traumatic stress disorder, as well as diseases closely related to anxiety.

The term "dementia" used in the present specification means not only dementia in the strict sense, but also conditions within the general concept of dementia, such as Alzheimer-type senile dementia, multi-infarct dementia and senile dementia, as well as diseases closely related to dementia.

A "pharmacologically acceptable salt" used in the present specification is not particularly limited as long as it is formed with the compound of the present invention, and as specific examples thereof may include inorganic acid salts, organic acid salts, and acidic amino acid salts.

A "pharmacologically acceptable salt" used in the present specification, unless otherwise specified, may form a salt with an appropriate ratio, and the number of the acid molecule to one molecule of the compound is not particularly limited in the formed salt, but preferably about 0.1 to about 5 molecules of the acid exists with respect to one molecule of the compound, more preferably approximately 0.5 to approximately 2 molecules of the acid exists with respect to one molecule of the compound, and further preferably about 0.5, about 1 or about 2 molecules of the acid exists with respect to one molecule of the compound.

Preferable examples of inorganic acid salts may include hydrochloride, hydrobromide, sulfate, nitrate, phosphate and the like; preferable examples of organic acid salts may include acetate, succinate, fumarate, maleate, tartrate, citrate, lactate, stearate, benzoate, methanesulfonate, p-toluenesulfonate and the like.

Preferable examples of acidic amino acid salts may include aspartate, glutamate and the like.

(General Production Process)

Hereinafter, General Production Processes of compounds according to the present application are shown, but they are not intended to be limited to these processes. Furthermore, the raw material compounds and reagents used in the general production processes for compounds of the present invention may also form salts or solvates (especially hydrates).

The compounds represented by the formula (I) of the present invention can be produced by the following production methods.

[General Production Process]

<Production Method A>

[Chemical Formula 9]

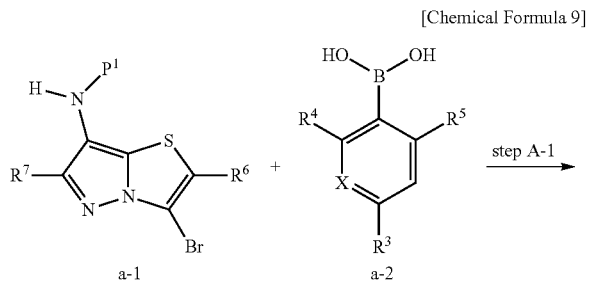

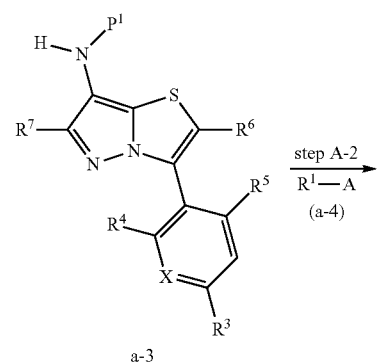

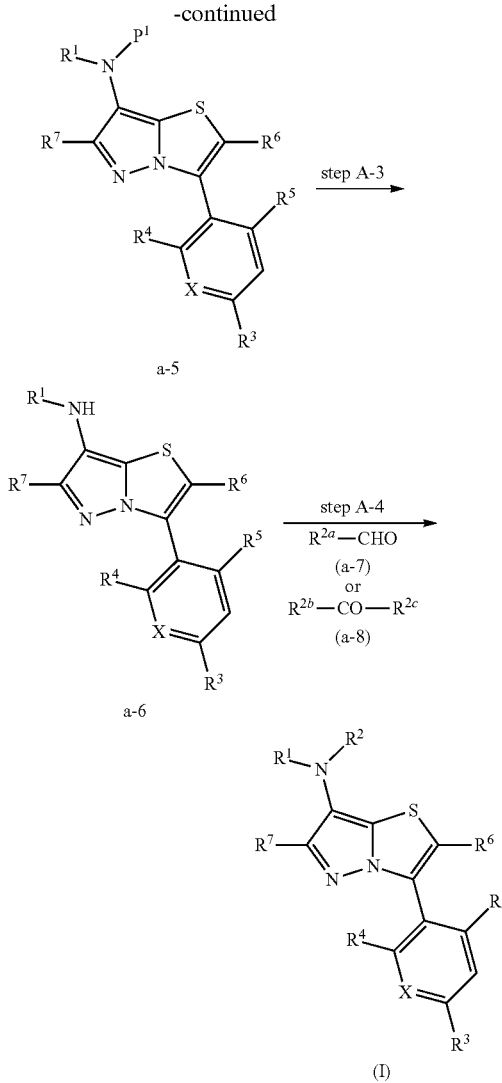

[wherein $R^1$, $R^2$, $R^3$, $R^4$, $R^5$, $R^6$, $R^7$ and X have the same definitions as above, respectively, $P^1$ is a protecting group of an amino group such as a tert-butoxycarbonyl group, and A is a halogen atom. $R^{2a}$, $R^{2b}$, and $R^{2c}$ are substituents in which $R^{2a}CH_2$— or $R^{2b}R^{2c}CH$— is $R^2$.]

Step A-1

This is a step of reacting a compound represented by the formula a-1 (hereinafter, also referred to as Compound a-1) and Compound a-2 in a solvent in the presence or in the absence of a base and in the presence of a palladium catalyst to yield Compound a-3.

This step can be carried out according to the reaction conditions, operations after reaction, and purification method described in, for example, the below-mentioned Example 1.

Compound a-1 can be obtained according to the below-mentioned Production Method B, C and the like.

Compound a-2 can be prepared according to Production Method 10 and Production Method 11 described in WO2004/037822.

The reaction may be carried out in a stream or in an atmosphere of an inert gas such as nitrogen or argon.

The solvent to be used in the reaction is not particularly limited as long as it dissolves the starting materials to some extent and does not inhibit the reaction, but examples of the solvents include alcohol solvents such as methanol and ethanol, ether solvents such as tetrahydrofuran, 1,2-dimethoxyethane, methyl-tert-butyl ether, cyclopentyl methyl ether, diethyl ether, diisopropyl ether, dibutyl ether, dicyclopentyl ether, and 1,2-dimethoxyethane, aromatic hydrocarbon solvents such as benzene, toluene, xylene and mesitylene, amide solvents such as N,N-dimethylformamide, aliphatic hydrocarbon solvents such as heptane and hexane, water, or mixture solvents thereof, and preferable solvents are alcohol solvents, aromatic hydrocarbon solvents, water or mixtures thereof; and more preferable solvents are a mixed solvent of ethanol and toluene, or a mixture solvent of 1,2-dimethoxymethane and water.

The base is not particularly limited and differs depending on the starting material and solvent to be used, and examples thereof may include inorganic bases such as lithium hydroxide, sodium hydroxide, potassium hydroxide, lithium carbonate, sodium carbonate, potassium carbonate, sodium hydrogencarbonate, potassium hydrogencarbonate, cesium carbonate, cesium fluoride and potassium fluoride, organic bases such as imidazole, pyridine, triethylamine and N,N-diisopropylethylamine, and preferable base is sodium carbonate.

The palladium catalyst is not particularly limited as long as it does not inhibit the reaction, and differs depending on the starting material and solvent used, but preferable examples thereof may include tetrakis(triphenylphosphine)palladium (0), palladium(II) acetate/triphenylphosphine, palladium(II) acetate/2-dicyclohexylphosphino-2',4',6'-triisopropylbiphenyl, palladium(II) chloride, tris(dibenzylideneacetone)dipalladium(0)/tri-tert-butylphosphine and dichloro[1,1'-bis(diphenylphosphine)-ferrocene]palladium(0).

The reaction temperature generally differs depending on the starting material, solvent, and other reagents to be used in the reaction, but it is preferably between 0° C. and the reflux temperature of the solvent (the internal temperature of the reactor), and more preferably 60° C. to 100° C.

The reaction time also generally differs depending on the starting material, solvent, and other reagents to be used in the reaction, and on the reaction temperature, but it is preferably 1-48 hours and more preferably 1-6 hours at the above-mentioned temperature after addition of the reagent.

Compound a-2 may be used at 1 to 5 molar equivalents and preferably 1 to 3 molar equivalents with respect to Compound a-1.

The base can be used at 1 to 10 molar equivalents and preferably 2 to 5 molar equivalents with respect to Compound a-1.

The palladium catalyst may be used at 0.05 to 1 molar equivalents and preferably 0.05 to 0.1 molar equivalents with respect to Compound a-1.

Step A-2

This is a step of reacting Compound a-3 and Compound a-4 in a solvent in the presence of a base to yield Compound a-5.

The reaction may be carried out in a stream or in an atmosphere of an inert gas such as nitrogen and argon.

The solvent to be used in the reaction is not particularly limited as long as it dissolves the starting materials to some degree and does not inhibit the reaction, but examples of the solvent may include nitrile solvents such as acetonitrile, ether solvents such as tetrahydrofuran, 1,2-dimethoxyethane, methyl-tert-butyl ether, cyclopentyl methyl ether, diethyl ether, diisopropyl ether, dibutyl ether and dicyclopentyl ether, aromatic hydrocarbon solvents such as benzene and toluene, amide solvents such as N,N-dimethylformamide, sulfoxide solvents such as dimethyl sulfoxide, aliphatic hydrocarbon solvents such as heptane and hexane, or mixture solvents thereof, among which N,N-dimethylformamide and dimethyl sulfoxide are preferred.

The base used is not particularly limited and differs depending on the starting material and solvent to be used, but examples of the base may include inorganic bases such as lithium hydroxide, sodium hydroxide, potassium hydroxide, lithium carbonate, sodium carbonate, potassium carbonate, sodium hydrogencarbonate, potassium hydrogencarbonate, cesium carbonate, potassium-tert-butoxide, organometallic bases such as butyllithium, methyllithium, lithium bis(trimethylsilyl)amide, sodium bis(trimethylsilyl)amide, and potassium bis(trimethylsilyl)amide, metal hydride bases such as lithium hydride, sodium hydride and potassium hydride, organic bases such as imidazole, pyridine, 4-dimethylaminopyridine, triethylamine, and N,N-diisopropylethylamine, and preferable base is sodium hydride. The base can be used at 1 to 3 molar equivalents and preferably 1 to 2 molar equivalents with respect to Compound a-3.

The reaction temperature generally differs depending on the starting material, solvent, and other reagents to be used in the reaction, but it is preferably between 0° C. and the reflux temperature of the solvent (the internal temperature of the reactor), and more preferably room temperature.

The reaction time generally differs depending on the starting material, solvent, and other reagents to be used in the reaction, and on the reaction temperature, but it is preferably 1-48 hours and more preferably 1-6 hours at the above-mentioned temperature after addition of the reagent.

Compound a-4 may be used at 1 to 5 molar equivalents and preferably 1 to 2 molar equivalents with respect to Compound a-3.

Step A-3

This is a step of deprotecting the protecting group of an amino group of Compound a-5 to yield Compound a-6. The deprotection reaction of the protecting group of the amino group differs depending on the type of the protecting group and is not particularly limited, but the deprotection reaction can be carried out under acidic conditions if the protecting group is, for example, a carbamate protecting group such as a tert-butoxycarbonyl group.

In the reaction, a solvent may be used or may not be used, and the solvent is not particularly limited as long as it dissolves the starting materials to some degree and does not inhibit the reaction, and examples of the solvent may include alcohol solvents such as methanol and ethanol, ether solvents such as tetrahydrofuran, 1,2-dimethoxyethane, methyl-tert-butyl ether, cyclopentyl methyl ether, diethyl ether, diisopropyl ether, dibutyl ether, and dicyclopentyl ether, halogenated hydrocarbon solvents such as dichloromethane and chloroform, acetic acid, and the like, and they can be used alone or as mixed solvents.

Examples of acid may include trifluoroacetic acid, hydrochloric acid, sulfuric acid, and the like, among which trifluoroacetic acid is preferred. The acid can be used in a volume of 1 to 100 times with respect to Compound as The reaction temperature generally differs depending on the starting material, solvent, and other reagents to be used in the reaction, but it is preferably between 0° C. and the reflux temperature of the solvent (the internal temperature of the reactor), and more preferably room temperature.

The reaction time generally differs depending on the starting material, solvent, and other reagents to be used in the reaction, and on the reaction temperature, but it is preferably 0.1-12 hours and more preferably 0.5-2 hours at the above-mentioned temperature after addition of the reagent.

Step A-4

This is a step of carrying out reductive amination reaction of Compound a-6 and Compound a-7 or a-8 that is aldehyde or ketone corresponding to $R^2$ in the presence of a reducing agent to yield a compound (I).

The reaction may be carried out in a stream or in an atmosphere of an inert gas such as nitrogen or argon.

The solvent to be used in the reaction is not particularly limited as long as it dissolves the starting materials to some extent and does not inhibit the reaction, and examples of the solvent include alcohol solvents such as methanol and ethanol, ether solvents such as tetrahydrofuran, 1,2-dimethoxyethane, methyl-tert-butyl ether, cyclopentyl methyl ether, diethyl ether, diisopropyl ether, dibutyl ether, and dicyclopentyl ether, and acetic acid, and the like, and these can be used alone or as mixed solvents.

The reducing agent is not limited in the reaction and may be those commonly used in reductive amination reactions between carbonyl compounds and amine compounds, and examples of the reducing agent include borane and borohydride complex compound, and the preferable reducing agent is α-picolineborane or sodium triacetoxyborohydride. The reducing agent may be used at 0.5 to 3 molar equivalents and preferably 1 to 2 molar equivalents with respect to Compound a-6.

The reaction temperature generally differs depending on the starting material, solvent, and other reagents to be used in the reaction, but it is preferably between 0° C. and the reflux temperature of the solvent (the internal temperature of the reactor), and more preferably room temperature.

The reaction time generally differs depending on the starting material, solvent, and other reagents to be used in the reaction, and on the reaction temperature, but it is preferably 1 to 48 hours and more preferably 1 to 6 hours at the above-mentioned temperature after addition of the reagent.

Compound a-7 or Compound a-8 may be used at 1 to 5 molar equivalents and preferably 1 to 2 molar equivalents with respect to Compound a-6.

<Production Method B>

[Chemical Formula 10]

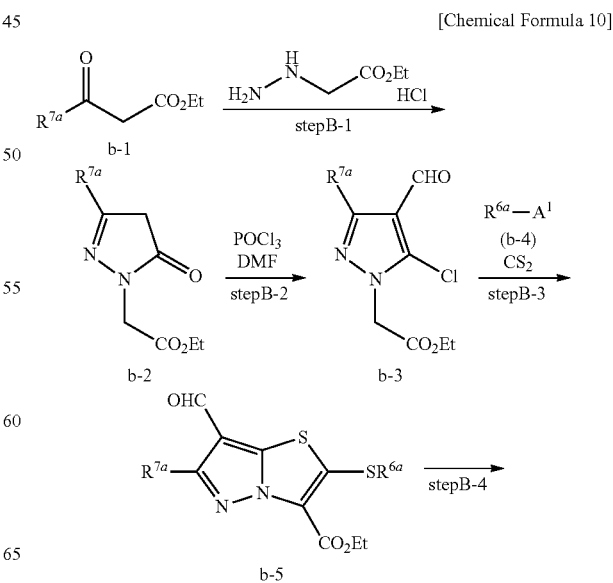

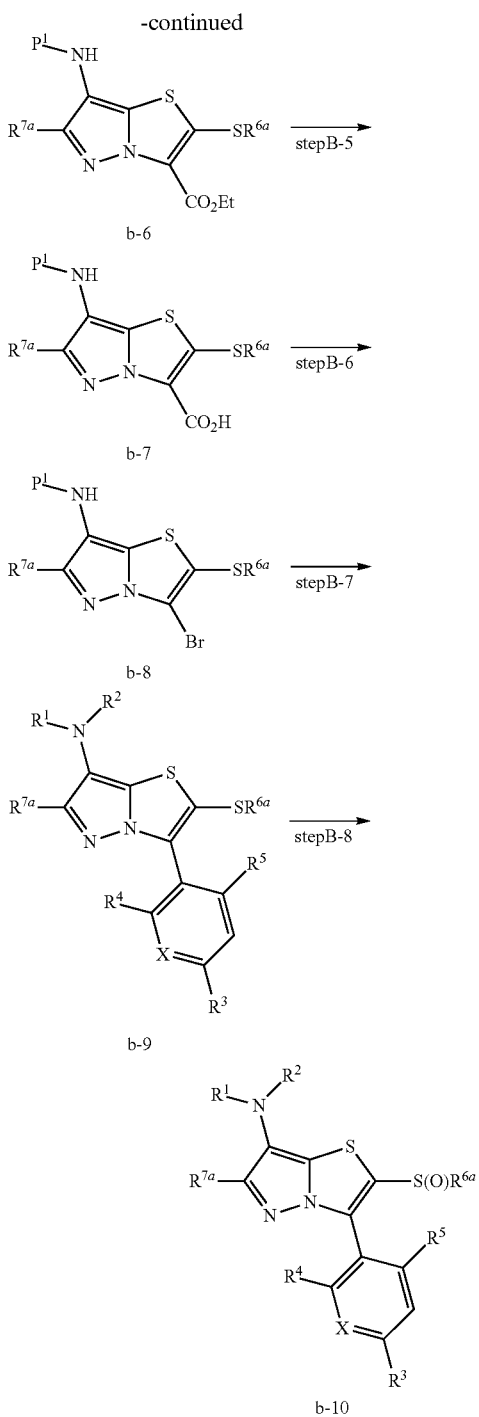

[wherein $R^1$, $R^2$, $R^3$, $R^4$, $R^5$, X, and $P^1$ have the same definitions as above, respectively, and $A^1$ is a leaving group such as a halogen atom, an alkylsulfonyloxy group and a toluenesulfonyloxy group, $R^{6a}$ is a C1-6 alkyl group and $R^{7a}$ is a C1-6 alkyl group.]

Step B-1

This is a step of reacting Compound b-1 and ethyl hydrazinoacetate monohydrochloride in a solvent in the presence of a base to yield Compound b-2.

The reaction may be carried out in a stream or in an atmosphere of an inert gas such as nitrogen or argon.

The solvent to be used in the reaction is not particularly limited as long as it dissolves the starting materials to some extent and does not inhibit the reaction, and examples include alcohol solvents such as methanol and ethanol, ether solvents such as tetrahydrofuran, 1,2-dimethoxyethane, methyl-tert-butyl ether, cyclopentyl methyl ether, diethyl ether, diisopropyl ether, dibutyl ether, dicyclopentyl ether, and 1,2-dimethoxyethane, aromatic hydrocarbon solvents such as benzene, toluene, xylene and mesitylene, amide solvents such as N,N-dimethylformamide, aliphatic hydrocarbon solvents such as heptane and hexane, and they are alone or as mixed solvents. Preferable solvents are the alcohol solvent or the aromatic hydrocarbon solvents or a mixed solvent thereof, and more preferable solvents are methanol or ethanol.

The base is not particularly limited and differs depending on the starting material and solvent used, but examples include inorganic bases such as lithium carbonate, sodium carbonate, potassium carbonate, sodium hydrogencarbonate, potassium hydrogencarbonate, cesium carbonate, and potassium-tert-butoxide, organic bases such as imidazole, pyridine, 4-dimethylaminopyridine, triethylamine and N,N-diisopropylethylamine, among which triethylamine is preferred. The base can be used at 1 to 3 molar equivalents and preferably 1 to 1.5 molar equivalents with respect to Compound b-1.

The reaction temperature generally differs depending on the starting material, solvent, and other reagents to be used in the reaction, but it is preferably between 0° C. and the reflux temperature of the solvent (the internal temperature of the reactor), and more preferably 100° C.

The reaction time generally differs depending on the starting material, solvent, and other reagents to be used in the reaction, and on the reaction temperature, but it is preferably 1-24 hours and more preferably 1-5 hours at the above-mentioned temperature after addition of the reagent.

The ethyl hydrazinoacetate monohydrochloride can be used at 0.9 to 5 molar equivalents and preferably 0.9 to 1.1 molar equivalents with respect to Compound b-1.

Step B-2

This is a step of reacting phosphorus oxychloride in a N,N-dimethylformamide solvent to yield Compound b-3 from Compound b-2.

The reaction may be carried out in a stream or in an atmosphere of an inert gas such as nitrogen or argon.

Phosphorus oxychloride may be used at 2 to 20 molar equivalents and preferably 5 to 10 molar equivalents with respect to Compound b-2.

The reaction temperature generally differs depending on the starting material, and other reagents to be used in the reaction, but it is preferably between 0° C. and 150° C. (the internal temperature of the reactor), and more preferably 100° C. to 120° C.

The reaction time generally differs depending on the starting material, and other reagents to be used in the reaction, and on the reaction temperature, but it is preferably 1-24 hours and more preferably 3-5 hours at the above-mentioned temperature after addition of the reagent.

Step B-3

This is a step of reacting Compound b-3, carbon disulfide and Compound b-4 in a solvent in the presence of a base to yield Compound b-5.

The reaction may be carried out in a stream or in an atmosphere of an inert gas such as nitrogen or argon.

The solvent to be used in the reaction is not particularly limited as long as it dissolves the starting materials to some extent and does not inhibit the reaction, and examples include ether solvents such as 1,2-dimethoxyethane, methyl-tert-butyl ether, cyclopentyl methyl ether, diethyl ether, diisopropyl ether, dibutyl ether, dicyclopentyl ether, and 1,2-dimethoxyethane, aromatic hydrocarbon solvents such as benzene, toluene, xylene and mesitylene, amide solvents such as N,N-dimethylformamide, sulfoxide solvents such as dimethyl sulfoxide, and aliphatic hydrocarbon solvents such as heptane and hexane. The preferable solvent is dimethyl sulfoxide.

The base is not particularly limited and differs depending on the starting material and solvent to be used, but examples of the base may include inorganic bases such as lithium hydroxide, sodium hydroxide, potassium hydroxide, lithium carbonate, sodium carbonate, potassium carbonate, sodium hydrogencarbonate, potassium hydrogencarbonate, and cesium carbonate, metal alkoxide base such as potassium-tert-butoxide, and organic bases such as imidazole, pyridine, 4-dimethylaminopyridine, triethylamine, N,N-diisopropylethylamine, and the like, among which potassium hydroxide is preferred. The base can be used at 2 to 5 molar equivalents and preferably 3 molar equivalents with respect to Compound b-3.

The carbon disulfide can be used at 1 to 3 molar equivalents and preferably 1 to 2 molar equivalents with respect to Compound b-3.

Examples of Compound b-4 include dimethylsulfuric acid, diethylsulfuric acid, C1-6 alkyl halide, and the like. Compound b-4 can be used at 1 to 3 times equivalents and preferably 1 to 2 equivalents with respect to Compound b-3.

The reaction temperature generally differs depending on the starting material, solvent, and other reagents to be used in the reaction, but it is preferably between 0° C. and the reflux temperature of the solvent (the internal temperature of the reactor), and more preferably room temperature.

The reaction time generally differs depending on the starting material, solvent, and other reagents to be used in the reaction, and on the reaction temperature, but it is preferably 1-48 hours and more preferably 20-30 hours at the above-mentioned temperature after addition of the reagent.

Step B-4

This is a step of reacting Compound b-5 and an oxidizing agent to yield carboxylic acid and subjecting the resultant carboxylic acid to a rearrangement reaction such as Curtius rearrangement reaction in the presence of a base to yield Compound b-6.

(Oxidation Reaction)

The reaction may be carried out in a stream or in an atmosphere of an inert gas such as nitrogen or argon.

The solvent to be used in the reaction is not particularly limited as long as it dissolves the starting materials to some extent and does not inhibit the reaction, and preferable examples of such solvents include acetone, dichloromethane, n-hexane, toluene, xylene, acetonitrile, water, and the like, which can be used alone or as a mixture.

The oxidizing agent to be used is not particularly limited and differs depending on the starting material and reagents, but preferable examples thereof include potassium permanganate, silver oxide, activated manganese dioxide, pyridinium dichromate, sodium chlorite, and the like, which can be used alone or as a mixture. The oxidizing agent may be used at 1 to 3 molar equivalents and preferably 1 to 2 molar equivalents with respect to Compound b-5.

The reaction temperature generally differs depending on the starting material, solvent, and other reagents to be used in the reaction, but it is preferably between −10° C. and 200° C., and more preferably room temperature.

The reaction time generally differs depending on the starting material, solvent, and other reagents to be used in the reaction, and on the reaction temperature, but it is preferably 0.5-48 hours and more preferably 0.5-1 hours at the above-mentioned temperature after addition of the reagent.

(Rearrangement Reaction)

The carboxylic acid obtained by the above-mentioned oxidization reaction and an azidating agent (for example, diphenylphosphoryl azide (DPPA)) are heated in or without a solvent and in the presence or in the absence of a base and are subjected to a reaction with, for example, tert-butanol via acid azide to yield Compound b-6 that is protected by, for example, a carbamate group such as a tert-butoxycarbonyl (BOC).

The reaction may be carried out in a stream or in an atmosphere of an inert gas such as nitrogen or argon.

The solvent to be used in the reaction is not particularly limited as long as it dissolves the starting materials to some extent and does not inhibit the reaction, but preferable examples of such a solvent include benzene, toluene, xylene, diphenyl ether, tert-butanol, tetrahydrofuran, dioxane, acetonitrile, N,N-dimethylformamide, and the like, which can be used alone or as a mixture.

The base to be used is not particularly limited and differs depending on the starting material and reagent, but preferable examples thereof include triethylamine, N,N-diisopropylethylamine, 4-dimethylaminopyridine, pyridine, and the like, which can be used alone or as a mixture. The base can be used at 1 to 3 molar equivalents and preferably 1 to 2 molar equivalents with respect to Compound b-5.

The reaction temperature generally differs depending on the starting material, solvent, and other reagents to be used in the reaction, but it is generally between −10° C. and 250° C., and preferably 100° C. and 200° C.

The reaction time generally differs depending on the starting material, solvent, and other reagents to be used in the reaction, and on the reaction temperature, but it is preferably 1-24 hours and more preferably 1-10 hours at the above-mentioned temperature after addition of the reagent.

As an alternative method, for synthesis of the acid azide, the carboxylic acid may be induced to acid chloride or mixed acid anhydride and then subjected to reaction with an azidating agent (for example, sodium azide, trimethylsilyl azide, and the like) to yield the acid azide. As yet another alternative method, Compound b-6 may be obtained by Hofmann rearrangement or Schmidt rearrangement reaction. In this case, it is desirable that the azidation agent is used at 1 to 3 molar equivalents, the base is used at 1 to 5 molar equivalents, and tert-butanol is used at 1 to 50 molar equivalents or as a solvent with respect to Compound b-5, respectively.

Step B-5

This is a step of subjecting Compound b-6 to hydrolysis in the presence of a base so to yield Compound b-7.

The reaction may be carried out in a stream or in an atmosphere of an inert gas such as nitrogen or argon.

The solvent to be used in the reaction is not particularly limited as long as it dissolves the starting materials to some extent and does not inhibit the reaction, but preferable examples of such solvents include methanol, ethanol, n-butanol, tert-butanol, tetrahydrofuran, dioxane, water, and the like, which can be used alone or as a mixture.

The base is not particularly limited and differs depending on the starting material and solvent to be used, and examples thereof include lithium hydroxide, sodium hydroxide, potassium hydroxide, lithium carbonate, sodium carbonate, potassium carbonate, sodium hydrogencarbonate, potassium hydrogencarbonate, cesium carbonate, potassium-tert-butoxide, and the like. The base can be used at 1 to 10 molar equivalents with respect to Compound b-6.

The reaction temperature generally differs depending on the starting material, solvent, and other reagents to be used in the reaction, but it is preferably between 0° C. and the reflux temperature of the solvent (the internal temperature of the reactor), and more preferably room temperature.

The reaction time generally differs depending on the starting material, solvent, and other reagents to be used in the reaction, and on the reaction temperature, but it is preferably 1-24 hours and more preferably 1-3 hours at the above-mentioned temperature after addition of the reagent.

Step B-6

This is a step of reacting Compound b-7 with silver nitrate in water as a solvent in the presence of a base to yield a silver salt of carboxylic acid, and bromine is allowed to act thereon in carbon tetrachloride, thus yielding Compound b-8 (Hunsdiecker reaction).

The reaction may be carried out in a stream or in an atmosphere of an inert gas such as nitrogen or argon.

The base is not particularly limited and differs depending on the starting material and solvent to be used, but preferable examples of the base include lithium hydroxide, sodium hydroxide, potassium hydroxide, and the like. The base can be used at 1 to 2 molar equivalents with respect to Compound b-7.

The reaction temperature generally differs depending on the starting material, and other reagents to be used in the reaction, but it is preferably between 0° C. and the reflux temperature of the solvent (the internal temperature of the reactor).

The reaction time generally differs depending on the starting material, and other reagents to be used in the reaction, and on the reaction temperature, but it is preferably 1-12 hours at the above-mentioned temperature after addition of the reagent.

Step B-7

This step corresponds to step A-2 to step A-4 of Production Method A, and it can be carried out in the same conditions as those in the steps.

Step B-8

This is a step of oxidizing Compound b-9 in a solvent with an oxidizing agent such as m-chloroperbenzoic acid to yield Compound b-10.

The reaction may be carried out in a stream or in an atmosphere of an inert gas such as nitrogen or argon.

Preferable examples of the solvent to be used include dichloromethane, benzene, toluene, and the like.

The oxidizing agent is not particularly limited and differs depending on the starting material and solvent to be used, and examples thereof include m-chloroperbenzoic acid, trifluoroperacetic acid, sodium periodate, dinitrogen tetraoxide, mixed acid of nitric acid-sulfuric acid, chromic acid, and the like. In this case, the oxidizing agent is desirably used at 1 to 2 molar equivalents with respect to Compound b-9.

The reaction temperature generally differs depending on the starting material, solvent, and other reagents to be used in the reaction, but it is preferably between 0° C. and the reflux temperature of the solvent (the internal temperature of the reactor).

The reaction time generally differs depending on the starting material, solvent, and other reagents to be used in the reaction, and on the reaction temperature, but it is preferably 10 minutes to 1 hour after addition of the reagent.

<Production Method C>

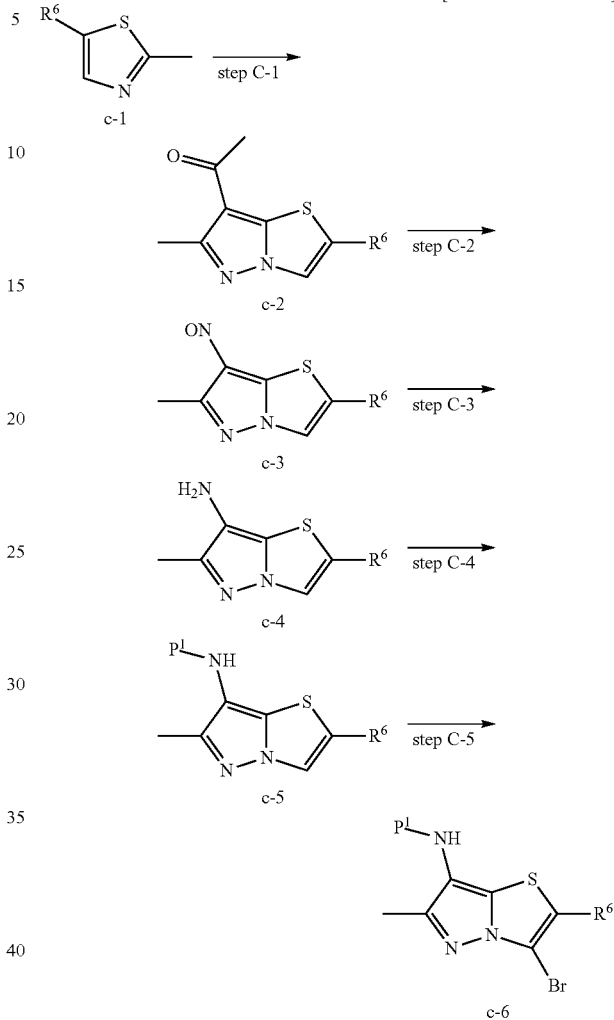

[Chemical Formula 11]

[wherein $R^6$ and $P^1$ have the same definitions as above, respectively.]

Step C-1

This is a step of reacting Compound c-1 and an N-amination agent (for example, hydroxylamine-O-sulfonic acid, O-mesitylenesulfonyl hydroxylamine) at 0° C. to 40° C. in a solvent, and isolating the resultant N-aminothiazolium salt by filtration and the like, and reacting it in acetic anhydride in the presence of sodium acetate at 0° C. to 250° C., thus yielding Compound c-2.

The reaction may be carried out in a stream or in an atmosphere of an inert gas such as nitrogen or argon.

The N-amination agent is not particularly limited and differs depending on the starting material and solvent to be used, but examples of the N-amination agent may include hydroxylamine-O-sulfonic acid, O-mesitylenesulfonyl hydroxylamine. In this case, the N-amination agent is preferably used at 1 to 2 molar equivalents with respect to Compound c-1.

The solvent to be used in the N-amination reaction is not particularly limited as long as it dissolves the starting materials to some extent and does not inhibit the reaction, but preferable examples thereof may include toluene, xylene, anisole, 1,2-dimethoxyethane, tetrahydrofuran, dioxane, dichloromethane, and the like, which can be used alone or as a mixture.

The reaction time generally differs depending on the starting material, solvent, and other reagents to be used in the reaction, and on the reaction temperature, but it is preferably 1 to 24 hours at the above-mentioned temperature after addition of the reagent.

The reaction with acetic anhydride is generally carried out in 5 to 20 times volume of acetic anhydride in the presence of 1 to 5 molar equivalents of sodium acetate with respect to Compound c-1 for 1 to 24 hours at the above-mentioned temperature.

Step C-2

This is a step of reacting Compound c-2 with a nitrosating agent in the presence of an acid to yield Compound c-3.

The solvent is not particularly limited as long as it dissolves the starting materials to some extent and does not inhibit the reaction, but preferable examples may include water, acetic acid, and the like, which may be used alone or as a mixture.

The nitrosating agent is not particularly limited and differs depending on the starting material, solvent to be used, and the like, but preferable examples thereof include sodium nitrite, and the like. In this case, it is preferable that the nitrosating agent is used at 2 to 3 molar equivalents with respect to Compound c-2.

The acid to be used is not particularly limited and differs depending on the starting material, solvent to be used, and the like, but preferable examples thereof include acetic acid, hydrochloric acid, sulfuric acid, and the like. The nitrosating agent can be used at 1 to 5 molar equivalents with respect to Compound c-2.

The reaction temperature generally differs depending on the starting material, solvent, and other reagents to be used in the reaction, but it is generally between 0° C. and room temperature.

The reaction time generally differs depending on the starting material, solvent, and other reagents to be used in the reaction, and on the reaction temperature, but it is preferably 1 to 24 hours at the above-mentioned temperature after addition of the reagent.

Step C-3

This is a step of reducing Compound c-3 to yield Compound c-4. Compound c-3 can be reduced in the presence of 1 to 10 molar equivalents of zinc, iron, tin(II) chloride, and nickel(II) chloride as well as 1 to 20 molar equivalents of acid.

The acid to be used is not particularly limited and differs depending on the starting material, solvent to be used, and the like, but preferable examples thereof include acetic acid, hydrochloric acid, sulfuric acid, ammonium chloride, and the like. It is preferable that the acid is used at 2 to 10 molar equivalents with respect to Compound c-3.

The reduction can be carried out with hydrogen in the presence of a catalyst such as palladium-carbon. It is preferable that the catalyst is used at the weight ratio of 5-50% with respect to Compound c-3.

The solvent to be used is not particularly limited and differs depending on the starting material and solvent to be used, but preferable examples may include methanol, ethanol, n-butanol, water, and the like, which can be used alone or as a mixture.

The reaction temperature generally differs depending on the starting material, solvent, and other reagents to be used in the reaction, but it is preferably between 0° C. to room temperature.

The reaction time generally differs depending on the starting material, solvent, and other reagents to be used in the reaction, and on the reaction temperature, but it is preferably 1-24 hours at the above-mentioned temperature after addition of the reagent.

Step C-4

This is a step of reacting Compound c-4 with an amino-group protecting reagent in a solvent in the presence or in the absence of a base to yield Compound c-5.

This step can be carried out by using a well-known introduction reaction of a amino-group protecting group, but specifically, this step can be carried out according to the method of Production Example 19-3 mentioned below.

As the amino-group protecting reagent, well-known reagents can be used, and examples thereof may include di-tert-butyl dicarbonate. The amino-group protecting reagent can be used at 1 to 1.5 molar equivalents with respect to Compound c-4.

The solvent to be used in the reaction is not particularly limited as long as it dissolves the starting materials to some extent and does not inhibit the reaction, but preferable examples of such a solvent include ether solvents such as tetrahydrofuran, diethyl ether, and 1,4-dioxane, halogenated hydrocarbon solvents such as dichloromethane, 1,2-dichloroethane, and chloroform, amide solvents such as N,N-dimethylformamide, and the like, among which the halogenated hydrocarbon solvent is preferred and dichloromethane is more preferred.

The base is not particularly limited and differs depending on the starting material and solvent to be used and the like, but preferable examples thereof may include inorganic bases such as lithium hydroxide, sodium hydroxide, potassium hydroxide, lithium carbonate, sodium carbonate, potassium carbonate, sodium hydrogencarbonate, potassium hydrogencarbonate, cesium carbonate, organic bases such as imidazole, pyridine, triethylamine, and N,N-diisopropylethylamine, and the like, among which triethylamine is preferred. It can be used at 1 to 2 molar equivalents with respect to Compound c-4.

The reaction temperature generally differs depending on the starting material, solvent, and other reagents to be used in the reaction, but it is preferably between 0° C. and the reflux temperature of the solvent (the internal temperature of the reactor), and more preferably room temperature.

The reaction time generally differs depending on the starting material, solvent, and other reagents to be used in the reaction, and on the reaction temperature, but it is preferably 1-48 hours and more preferably 12 hours at the above-mentioned temperature after addition of the reagent Step C-5

This is a step of reacting Compound c-5 with a brominating agent in a solvent in the presence of an alkyllithium reagent to yield Compound c-6.

The reaction may be carried out in a stream or in an atmosphere of an inert gas such as nitrogen or argon.

The alkyllithium reagent is not particularly limited and differs depending on the starting material and solvent to be used, and the like, but examples of the reagent include n-butyllithium, sec-butyllithium, tert-butyllithium, and the like. In this case, it is preferable that the alkyllithium reagent is used at 1 to 2 molar equivalents with respect to Compound c-5.

The solvent to be used is not particularly limited as long as it dissolves the starting materials to some extent and does not inhibit the reaction, but preferable examples thereof include hexane, pentane, tetrahydrofuran, diethyl ether, and the like, which can be used alone or as a mixture.

The brominating agent is not particularly limited and differs depending on the starting material, solvent to be used, and the like, but preferable examples thereof include bromine, N-bromosuccinimide, 1,2-dibromoethane, 1,2-dibromo-1,1,2,2-tetrafluoroethane, and the like. In this case, it is preferable that the brominating agent is used at 1 to 3 molar equivalents with respect to Compound c-5.

The reaction temperature generally differs depending on the starting material, solvent, and other reagents to be used in the reaction, but it is preferably between −100° C. and 40° C.

The reaction time generally differs depending on the starting material, solvent, and other reagents to be used in the reaction, and on the reaction temperature, but it is preferably 1 to 24 hours at the above-mentioned temperature after addition of the reagent.

Note here that the compound c-1 can be prepared from the well-known compound or commercially available compound according to, for example, the method of Production Example 20-1.

<Production Method D>

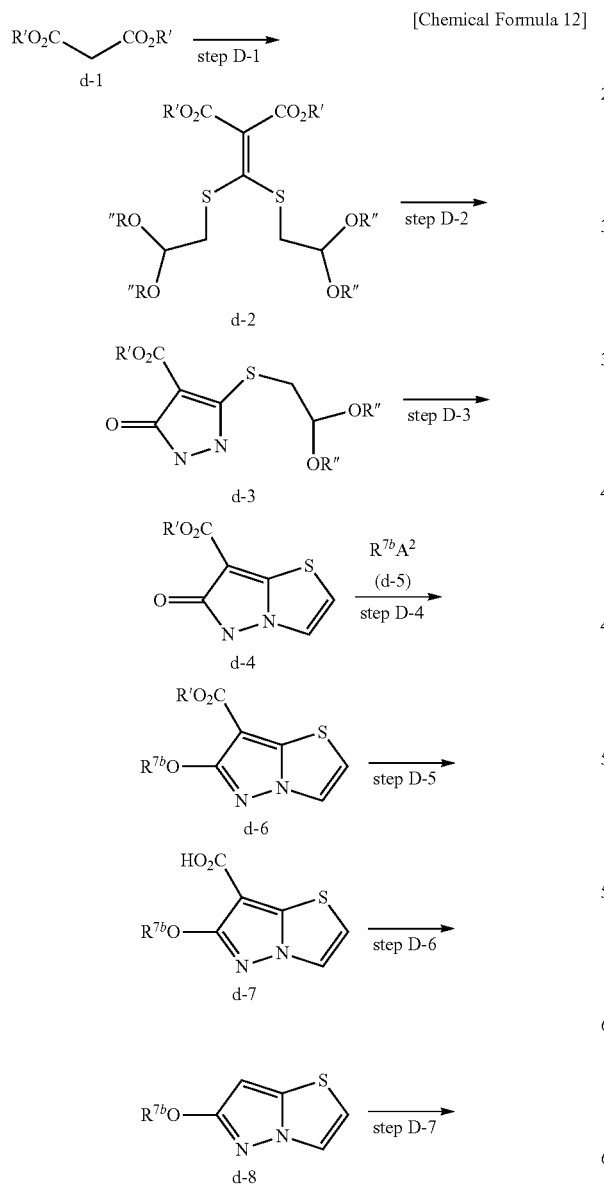

[Chemical Formula 12]

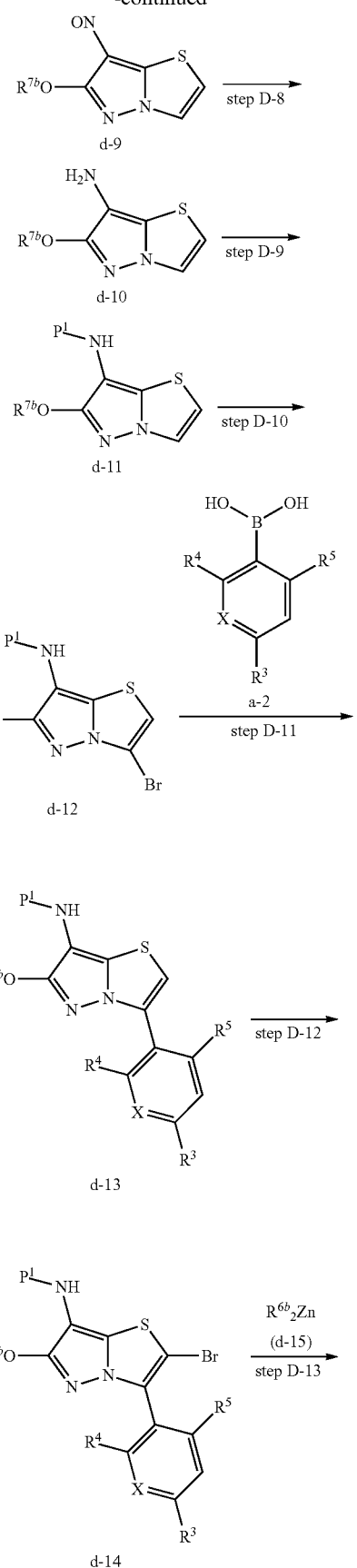

-continued

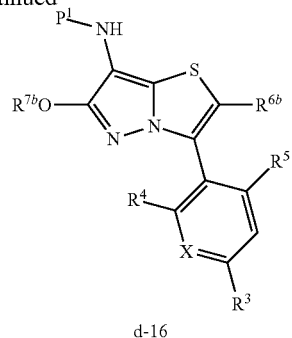

d-16

[wherein $R^3$, $R^4$, $R^5$, X, and $P^1$ have the same definition as above, respectively, $A^2$ is a leaving group such as a halogen atom and a sulfonyloxy group, $R^{6b}$ is a C1-6 alkyl group, $R^{7b}$ is a C1-6 alkyl group, R' and R'' independently are a methyl group or an ethyl group.]

Step D-1

This is a step of reacting Compound d-1, carbon disulfide, and dialkoxyethyl halide in a solvent in the presence of a base to yield Compound d-2, and, specifically, this step can be carried out according to the method of the below-mentioned Production Example 21-1.

The solvent to be used in the reaction is not particularly limited as long as it dissolves the starting materials to some extent and does not inhibit the reaction, but examples of the solvents include ether solvents such as tetrahydrofuran and 1,4-dioxane, amide solvents such as N,N-dimethylformamide and N-methylpyrolidone, and the like, among which the amide solvents are preferable, and N,N-dimethylformamide is more preferable.

The base is not particularly limited and differs depending on the starting material and solvent to be used, and desirable examples thereof include cesium carbonate, potassium carbonate, sodium carbonate, and the like. The base can be used at 2 to 10 molar equivalents and preferably 2 to 4 molar equivalents with respect to Compound d-1.

The reaction temperature generally differs depending on the starting material, solvent, and other reagents to be used in the reaction, but it is preferably between 0° C. and the reflux temperature of the solvent (the internal temperature of the reactor), and more preferably room temperature to 80° C.

The reaction time generally differs depending on the starting material, solvent, and other reagents to be used in the reaction, and on the reaction temperature, but it is preferably 1-24 hours and more preferably 2-10 hours at the above-mentioned temperature after addition of the reagent.

Carbon disulfide can be used at 1 to 5 molar equivalents and preferably 1 to 3 molar equivalents with respect to Compound d-1.

Dialkoxyethyl halide can be used at 2 to 10 molar equivalents and preferably 2 to 4 molar equivalents with respect to Compound d-1.

Step D-2

This is a step of reacting Compound d-2 and hydrazine hydrate in a solvent to yield Compound d-3, and, specifically, this step can be carried out according to the method of the below-mentioned Production Example 21-1.

The solvent to be used in the reaction is not particularly limited as long as it dissolves the starting materials to some extent and does not inhibit the reaction, and examples of the solvents include ether solvents such as tetrahydrofuran and 1,4-dioxane, alcohol solvents such as ethanol and methanol, amide solvents such as N,N-dimethylformamide, N-methylpyrolidone, and the like, among which the alcohol solvents are preferable.

Hydrazine hydrate can be used at 1 to 5 molar equivalents and preferably 1 to 2 molar equivalents with respect to Compound d-2.

The reaction temperature generally differs depending on the starting material, solvent, and other reagents to be used in the reaction, but it is preferably between 0° C. and the reflux temperature of the solvent (the internal temperature of the reactor), and more preferably room temperature.

The reaction time generally differs depending on the starting material, solvent, and other reagents to be used in the reaction, and on the reaction temperature, but it is preferably 1-24 hours and more preferably 5-15 hours at the above-mentioned temperature after addition of the reagent.

Step D-3

This is a step of treating Compound d-3 with an acid in a solvent to yield Compound d-4, and, specifically, this step can be carried out according to the method of the below-mentioned Production Example 21-1.

The solvent to be used in the reaction is not particularly limited as long as it dissolves the starting materials to some extent and does not inhibit the reaction, and examples of the solvents include ether solvents such as tetrahydrofuran and 1,4-dioxane, amide solvents such as N,N-dimethylformamide and N-methylpyrolidone, aromatic hydrocarbon solvents such as benzene and toluene, halogenated hydrocarbon solvents such as dichloromethane, 1,2-dichloroethane and chloroform, and water or a mixture solvent thereof, among which a mixture solvent of 1,4-dioxane and water is preferable.

The acid to be used is not particularly limited and differs depending on the starting material and solvent to be used, but the desirable examples thereof include hydrochloric acid, trifluoroacetic acid, sulfuric acid, and the like, and more preferable acid is 1 to 5 times volume of 5N hydrochloric acid with respect to Compound d-3.

The reaction temperature generally differs depending on the starting material, solvent, and other reagents to be used in the reaction, but it is preferably between 0° C. and the reflux temperature of the solvent (the internal temperature of the reactor), and more preferably room temperature to 80° C.

The reaction time generally differs depending on the starting material, solvent, and other reagents to be used in the reaction, and on the reaction temperature, but it is preferably 1-24 hours and more preferably 2-10 hours at the above-mentioned temperature after addition of the reagent.

Step D-4

This is a step of reacting Compound d-4 and Compound d-5 in a solvent in the presence of a base to yield Compound d-6, and, specifically, this step can be carried out according to the method of the below-mentioned Production Example 21-2.

The solvent to be used in the reaction is not particularly limited as long as it dissolves the starting materials to some extent and does not inhibit the reaction, but examples of the solvents include ether solvents such as tetrahydrofuran and 1,4-dioxane, amide solvents such as N,N-dimethylformamide and N-methylpyrolidone, and the like, among which amide solvents are preferable, and N,N-dimethylformamide is more preferable.

The base is not particularly limited and differs depending on the starting material and solvent to be used, but desirable examples thereof include cesium carbonate, potassium carbonate, sodium carbonate, lithium carbonate, sodium hydride, and the like. The base can be used at 1 to 5 molar equivalents and preferably 1 to 3 molar equivalents with respect to Compound d-4.

The reaction temperature generally differs depending on the starting material, solvent, and other reagents to be used in the reaction, but it is preferably between 0° C. and the reflux temperature of the solvent (the internal temperature of the reactor), and more preferably room temperature.

The reaction time generally differs depending on the starting material, solvent, and other reagents to be used in the reaction, and on the reaction temperature, but it is preferably 0.5-12 hours and more preferably 1-2 hours at the above-mentioned temperature after addition of the reagent.

Compound d-5 can be used at 1 to 5 molar equivalents and preferably 1 to 2 molar equivalents with respect to Compound d-4.

Step D-5

This is a step of subjecting Compound d-6 in a solvent to hydrolysis to yield Compound d-7, and, specifically, this step can be carried out according to the method of the below-mentioned Production Example 21-3.

The solvent to be used in the reaction is not particularly limited as long as it dissolves the starting materials to some extent and does not inhibit the reaction, but examples of the solvents include ether solvents such as tetrahydrofuran and 1,4-dioxane, alcohol solvents such as methanol and ethanol, and the like, among which alcohol solvents are preferable and ethanol is more preferable.

The reagent to be used in the hydrolysis may include a reagent that is used in usual ester hydrolysis, and is not particularly limited, but the preferable reagent is 1 to 10 times volume of 5N aqueous solution of sodium hydroxide, 5N aqueous solution of potassium hydroxide, or the like, with respect to Compound d-6.

The reaction temperature generally differs depending on the starting material, solvent, and other reagents to be used in the reaction, but it is preferably between 0° C. and the reflux temperature of the solvent (the internal temperature of the reactor), and more preferably room temperature to 80° C.

The reaction time generally differs depending on the starting material, solvent, and other reagents to be used in the reaction, and on the reaction temperature, but it is preferably 1-12 hours and more preferably 1-3 hours at the above-mentioned temperature after addition of the reagent.

Step D-6

This is a step of subjecting Compound d-7 to decarbonation in a solvent to yield Compound d-8, and, specifically, this step can be carried out according to the method of the below-mentioned Production Example 21-3.

The solvent to be used in the reaction is not particularly limited as long as it dissolves the starting materials to some extent and does not inhibit the reaction, but examples of the solvents include ether solvents such as tetrahydrofuran and 1,4-dioxane, amide solvents such as N,N-dimethylformamide and N-methylpyrolidone, and the like, among which 1,4-dioxane is preferable.

The reagent to be used in the decarbonation may include hydrochloric acid, sulfuric acid, phosphoric acid, hydrobromic acid, and the like, and preferably concentrated hydrochloric acid that is 3-10 times volume with respect to Compound d-7.

The reaction temperature generally differs depending on the starting material, solvent, and other reagents to be used in the reaction, but it is preferably between 0° C. and the reflux temperature of the solvent (the internal temperature of the reactor), and more preferably 40° C. to 80° C.

The reaction time generally differs depending on the starting material, solvent, and other reagents to be used in the reaction, and on the reaction temperature, but it is preferably 0.5-12 hours and more preferably 1-3 hours at the above-mentioned temperature after addition of the reagent.

Step D-7

This is a step of nitrosating Compound d-8 in a solvent to yield Compound d-9, and, specifically, this step can be carried out according to the method of the below-mentioned Production Example 21-4. This step can be carried out in the same conditions as in step C-2.

Step D-8

This is a step of reducing Compound d-9 with a metal (powder) to yield Compound d-10. This step can be carried out in the same conditions as in step C-3.

Step D-9

This is a step of reacting Compound d-10 with an amino-group protecting reagent in a solvent in the presence or in the absence of a base to yield Compound d-11. This step can be carried out in the same conditions as in step C-4.

Step D-10

This is a step of reacting Compound d-11 with a brominating agent in a solvent in the presence an alkyllithium reagent to yield Compound d-12. This step can be carried out in the same conditions as in step C-5.

Step D-11

This is a step of reacting Compound d-12 with Compound a-2 in a solvent in the presence or in the absence of a base and in the presence of a palladium catalyst to yield Compound d-13. This step can be carried out in the same conditions as in step A-1.

Step D-12

This is a step of reacting Compound d-13 with a brominating agent in a solvent in the presence an alkyllithium reagent to yield Compound d-14. This step can be carried out in the same conditions as in step C-5.

Step D-13

This is a step of reacting Compound d-14 with Compound d-15 in a solvent in the presence a palladium catalyst to yield Compound d-16.

The reaction may be carried out in a stream or in an atmosphere of an inert gas such as nitrogen or argon.

The solvent to be used in the reaction is not particularly limited as long as it dissolves the starting materials to some extent and does not inhibit the reaction, and examples of the solvents include 1,4-dioxane, tetrahydrofuran, 1,2-dimethoxyethane, methyl-tert-butyl ether, cyclopentyl methyl ether, diethyl ether, diisopropyl ether, dibutyl ether, dicyclopentyl ether, 1,2-dimethoxyethane, benzene, toluene, xylene, mesitylene heptane, hexane, and the like.

Compound d-15 is not particularly limited and differs depending on the starting material and solvent to be used, and examples thereof include dimethyl zinc, diethyl zinc, and the like. In this case, it is preferable that Compound d-15 is used at 1 to 3 molar equivalents with respect to Compound d-14.

The palladium catalyst is not particularly limited as long as it does not inhibit the reaction, and differs depending on the starting material and solvent used, but examples thereof include tetrakis(triphenylphosphine)palladium(0), palladium (II) acetate/triphenylphosphine, palladium(II) acetate/2-dicyclohexylphosphino-2',4',6'-triisopropylbiphenyl, palladium(II) chloride, bis(tri-tert-butylphosphine)palladium(0), bis-tris(dibenzylideneacetone)dipalladium(0)/tri-tert-butylphosphine, dichloro[1,1'-bis(diphenylphosphine)-ferrocene]palladium(0), and the like, among which bis(tri-tert-butylphosphine)palladium(0) is preferable. In this case, it is preferable that the palladium catalyst can be used at 0.05 to 0.1 molar equivalents with respect to Compound d-14.

The reaction temperature generally differs depending on the starting material, solvent, and other reagents to be used in the reaction, but it is preferably between 0° C. and the reflux temperature of the solvent (the internal temperature of the reactor), and more preferably 60° C. to 100° C.

The reaction time generally differs depending on the starting material, solvent, and other reagents to be used in the reaction, and on the reaction temperature, but it is preferably 1-48 hours and more preferably 1-6 hours at the above-mentioned temperature after addition of the reagent.

<Production Method E>

[Chemical Formula 13]

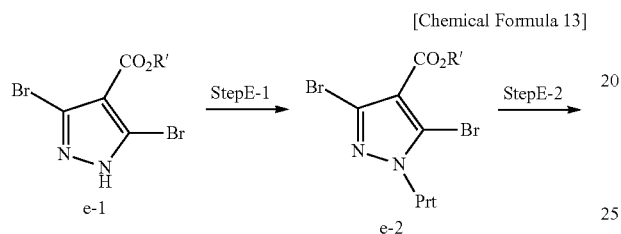

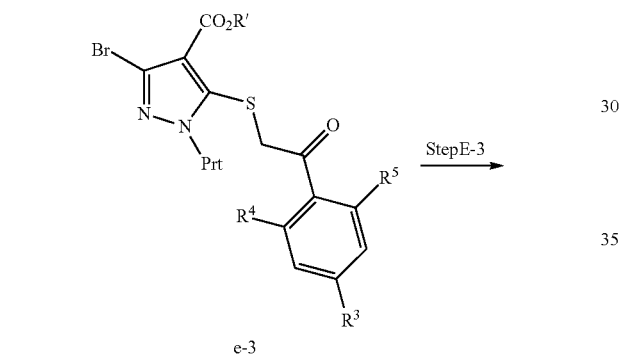

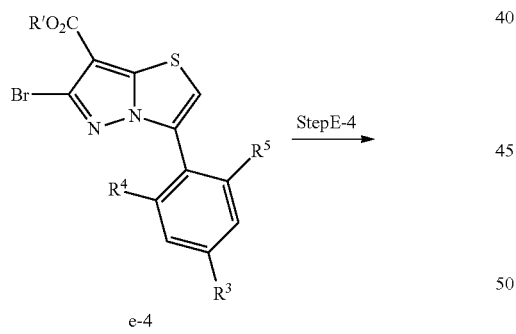

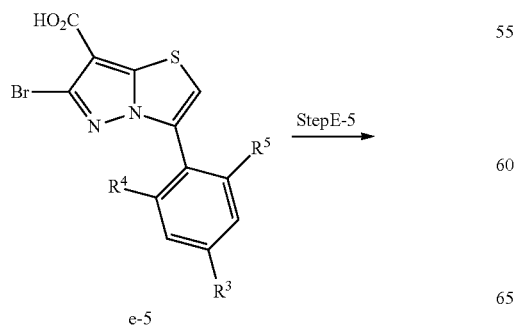

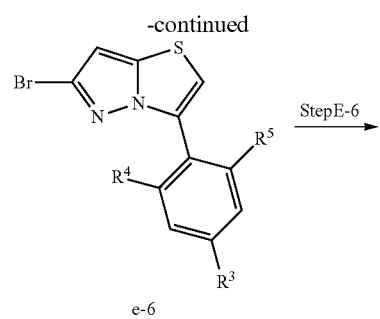

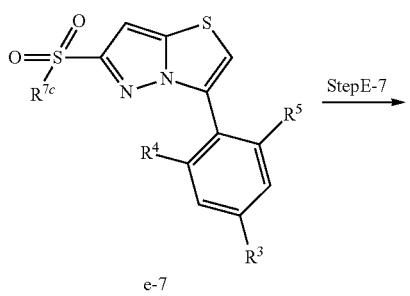

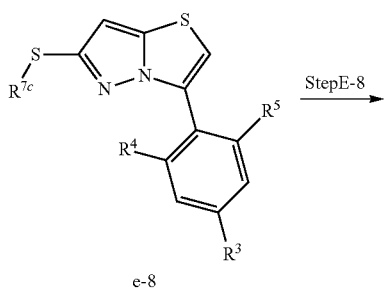

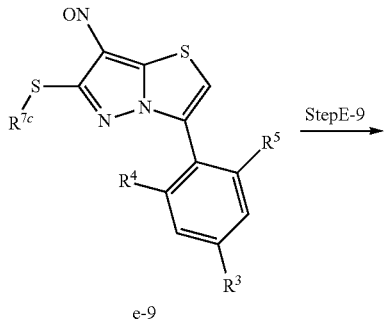

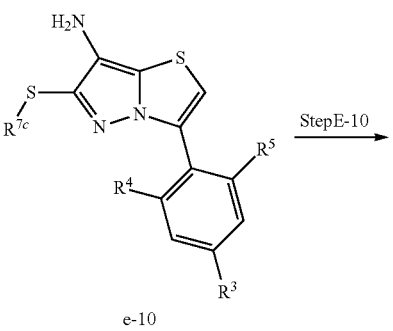

-continued

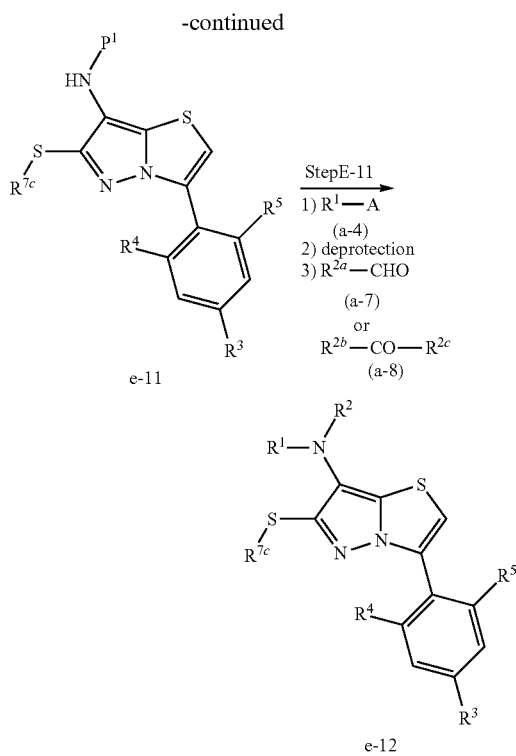

[wherein Prt is a protecting group such as a methoxymethyl group and a methoxyethoxymethyl group and $R^{7c}$ is a C1-6 alkyl group, and $R^1$, $R^2$, $R^3$, $R^4$, $R^5$, $R^{2a}$; $R^{2b}$, $R^{2c}$, R', and $P^1$ have the same definition as above, respectively.]

Step E-1

This is a step of reacting Compound e-1 with an amino-group protecting reagent in a solvent in the presence or in the absence of a base to yield Compound e-2, and, specifically, this step can be carried out according to the method of the below-mentioned Production Example 23-2.

The reaction may be carried out in a stream or in an atmosphere of an inert gas such as nitrogen or argon.

As the amino-group protecting reagent, well-known reagents can be used, and examples thereof include chloromethyl methyl ether, methoxyethoxymethyl chloride, and the like.

The solvent to be used in the reaction is not particularly limited as long as it dissolves the starting materials to some extent and does not inhibit the reaction, but examples of the solvents include ether solvents such as tetrahydrofuran, diethyl ether, and 1,4-dioxane, halogenated hydrocarbon solvents such as dichloromethane, 1,2-dichloroethane and chloroform, and the like, among which ether solvents are preferable and tetrahydrofuran is more preferable.

The base is not particularly limited and differs depending on the starting material and solvent to be used, and examples thereof may include inorganic bases such as lithium hydroxide, sodium hydroxide, potassium hydroxide, lithium carbonate, sodium carbonate, potassium carbonate, sodium hydrogencarbonate, potassium hydrogencarbonate, and cesium carbonate, organic bases such as imidazole, pyridine, triethylamine, and N,N-diisopropylethylamine, and metal hydride bases such as lithium hydride, sodium hydride, and potassium hydride, and the like, among which sodium hydride or N,N-diisopropylethylamine is preferable. The base can be used at 1 to 5 molar equivalents and preferably 1 to 3 molar equivalents with respect to Compound e-1.

The reaction temperature generally differs depending on the starting material, solvent, and other reagents to be used in the reaction, but it is preferably between 0° C. and the reflux temperature of the solvent (the internal temperature of the reactor), and more preferably room temperature.

The reaction time generally differs depending on the starting material, solvent, and other reagents to be used in the reaction, and on the reaction temperature, but it is preferably 1-48 hours and more preferably 1-3 hours at the above-mentioned temperature after addition of the reagent.

Step E-2

This is a step of reacting Compound e-2 and sodium sulfide in a solvent, then adding a phenacyl bromide derivative into the reaction mixture to yield Compound e-3, and this step can be specifically carried out by the method according to the below mentioned Production Example 23-3.

The reaction may be earned out in a stream or in an atmosphere of an inert gas such as nitrogen or argon.

The solvent to be used in the reaction is not particularly limited as long as it dissolves the starting materials to some extent and does not inhibit the reaction, and examples of the solvents include ether solvents such as tetrahydrofuran, 1,2-dimethoxyethane, methyl-tert-butyl ether, cyclopentyl methyl ether, diethyl ether, diisopropyl ether, dibutyl ether, dicyclopentyl ether, and 1,2-dimethoxyethane, aromatic hydrocarbon solvents such as benzene, toluene, xylene and mesitylene, amide solvents such as N,N-dimethylformamide and sulfoxide solvents such as dimethyl sulfoxide, among which the amide solvents are preferable and N,N-dimethylformamide is more preferable.

Sodium sulfide is used at 0.9 to 12 molar equivalents with respect to Compound e-2; the reaction temperature is preferably between 50° C. and the reflux temperature of the solvent (the internal temperature of the reactor), and more preferably 80 to 100° C. The reaction time is 1 to 24 hours and more preferably 1 to 5 hours.

The phenacyl bromide derivative is used at 0.9 to 1.2 molar equivalents with respect to Compound e-2; and the reaction temperature is preferably between 10° C. and 50° C. and more preferably room temperature. The reaction time is 1 to 24 hours and more preferably 1 to 5 hours.

Step E-3

This is a step of treating Compound e-3 with an acid in a solvent to yield Compound e-4, and specifically, the step can be carried out by the method in the below-mentioned Production Example 23-4.

The reaction may be carried out in a stream or in an atmosphere of an inert gas such as nitrogen or argon.

The solvent to be used in the reaction is not particularly limited as long as it dissolves the starting materials to some extent and does not inhibit the reaction, and examples of the solvents include ether solvents such as tetrahydrothran and 1,4-dioxane, alcohol solvents such as methanol, ethanol, and isopropanol, aromatic hydrocarbon solvents such as benzene and toluene, and the like, among which the alcohol solvents are preferable and isopropanol is more preferable.

The acid to be used is not particularly limited and differs depending on the starting material and solvent to be used, but desirable examples thereof include hydrochloric acid, trifluoroacetic acid, and sulfuric acid, and more preferable example is concentrated hydrochloric acid or 5N hydrochloric acid, which is 5 to 10 times volume with respect to Compound e-3.

The reaction temperature generally differs depending on the starting material, solvent, and other reagents to be used in the reaction, and it is preferably between 0° C. and the reflux temperature of the solvent (the internal temperature of the reactor), and more preferably heat reflux temperature.

Step E-4

This is a step of subjecting Compound e-4 to hydrolysis in a solvent to yield Compound e-5, and this step can be specifically carried out by the method in the below-mentioned Production Example 23-5.

The solvent to be used in the reaction is not particularly limited as long as it dissolves the starting materials to some extent and does not inhibit the reaction, and examples of the solvents include ether solvents such as tetrahydrofuran and 1,4-dioxane, alcohol solvents such as methanol and ethanol, among which the alcohol solvents are preferable and ethanol is more preferable.

As the reagents to be used in hydrolysis are not particularly limited and reagents to be used in usual ester hydrolysis can be used, and preferable reagents are 1 to 10 times volume of 5N aqueous solution of sodium hydroxide and 5N aqueous solution potassium hydroxide with respect to Compound e-4.

The reaction temperature generally differs depending on the starting material, solvent, and other reagents to be used in the reaction, but it is preferably between 0° C. and the reflux temperature of the solvent (the internal temperature of the reactor), and more preferably heat reflux temperature.

The reaction time generally differs depending on the starting material, solvent, and other reagents to be used in the reaction, and on the reaction temperature, but it is preferably 1-12 hours and more preferably 1-3 hours at the above-mentioned temperature after addition of the reagent.

Step E-5

This is a step of subjecting Compound e-5 to decarbonation in a solvent to yield Compound e-6, and this step can be specifically carried out by the method in the below-mentioned Production Example 23-6.

The solvent to be used in the reaction is not particularly limited as long as it dissolves the starting materials to some extent and does not inhibit the reaction, but examples of the solvents include ether solvents such as tetrahydrofuran and 1,4-dioxane, amide solvents such as N,N-dimethylformamide and N-methylpyrolidone, and the like, among which 1,4-dioxane is preferable.

The examples of the reagent to be used in decarbonation include acids such as hydrochloric acid, sulfuric acid, phosphoric acid, and hydrobromic acid, and preferable example is 3 to 10 times volume of concentrated hydrochloric acid with respect to Compound e-5.

The reaction temperature generally differs depending on the starting material, solvent, and other reagents to be used in the reaction, but it is preferably between 0° C. and the reflux temperature of the solvent (the internal temperature of the reactor), and more preferably heat reflux temperature.

The reaction time generally differs depending on the starting material, solvent, and other reagents to be used in the reaction, and on the reaction temperature, but it is preferably 1-15 hours and more preferably 10-13 hours at the above-mentioned temperature after addition of the reagent.

Step E-6

This is a step of reacting Compound e-6, sodium methanesulphinate, L-proline, and copper iodide in a solvent in the presence of a base by using Microwave Synthesizer to yield Compound e-7, and this step can be specifically carried out by the method in the below-mentioned Production Example 23-7.

It is preferable that sodium methanesulphinate is used at 2 to 20 molar equivalents, L-proline is used at 0.5 to 1 molar equivalents, and copper iodide is used at 0.5 to 1 molar equivalents, respectively, with respect to Compound e-6.

The solvent to be used in the reaction is not particularly limited as long as it dissolves the starting materials to some extent and does not inhibit the reaction, but examples of the solvents include aromatic hydrocarbon solvents such as benzene and toluene, amide solvent such as N,N-dimethylformamide, and sulfoxide solvents such as dimethyl sulfoxide, among which the sulfoxide solvents are preferable and dimethyl sulfoxide is more preferable.

The base to be used is not particularly limited and differs depending on the starting material and solvent to be used, but examples thereof may include inorganic bases such as lithium hydroxide, sodium hydroxide, potassium hydroxide, lithium carbonate, sodium carbonate, potassium carbonate, sodium hydrogencarbonate, potassium hydrogencarbonate, and cesium carbonate, and preferable base is sodium hydroxide. Preferably, the base is used 1 to 2 molar equivalents to Compound e-6.

The reaction temperature generally differs depending on the starting material, solvent, and other reagents to be used in the reaction, but it is preferably between 100° C. and 150° C., and more preferably 140° C.

The reaction time generally differs depending on the starting material, solvent, and other reagents to be used in the reaction, and on the reaction temperature, and it is preferably 1-5 hours and more preferably 3 hours at the above-mentioned temperature after addition of the reagent.

Step E-7

This is a step of treating Compound e-7 with a reducing agent in a solvent in the presence of titanium tetrachloride to yield Compound e-8, and this step can be specifically carried out by the method in the below-mentioned Production Example 23-8.

The reaction may be carried out in a stream or in an atmosphere of an inert gas such as nitrogen or argon.

The solvent to be used in the reaction is not particularly limited as long as it dissolves the starting materials to some extent and does not inhibit the reaction, but examples of the solvents include ether solvents such as tetrahydrofuran, 1,2-dimethoxy ethane, methyl-tert-butyl ether, cyclopentyl methyl ether, diethyl ether, diisopropyl ether, dibutyl ether, dicyclopentyl ether, and 1,2-dimethoxyethane, among which tetrahydrofuran is preferable.

The reducing agent to be used is not particularly limited and differs depending on the starting material and solvent to be used, but examples thereof include lithium aluminum hydride, diisopropyl aluminum hydride, and lithium tri-tert-butoxy aluminum hydride, among which lithium aluminum hydride is preferable.

Titanium tetrachloride is preferably used at 4 to 20 molar equivalents with respect to Compound e-7, and the reducing agent as hydride is preferably used at 4 to 20 molar equivalents with respect to titanium tetrachloride.

The reaction temperature generally differs depending on the starting material, solvent, and other reagents to be used in the reaction, but it is preferably −78° C. to 50° C.

Step E-8

This is a step of nitrosating Compound e-8 in a solvent to yield Compound e-9, and, specifically, this step can be carried out according to the method of the below-mentioned Production Example 23-9. This step can be carried out in the same conditions as in step C-2.

Step E-9

This is a step of reducing Compound e-9 to yield Compound e-10. This step can be carried out in the same conditions as in step C-3.

Step E-10

This is a step of reacting Compound e-10 with an amino-group protecting reagent in a solvent in the presence or in the absence of a base to yield Compound e-11. Well-known introduction reaction of a protecting group of an amino group can be used, and this step can be carried out according to the method of the below-mentioned Production Example 23-9. This step can be carried out in the same conditions as in step C-4.

Step E-11

This is a step of reacting Compound e-11 with a halogenated alkyl, Compound a-4, in a solvent in the presence of a base, subjecting a protecting group of an amino group to deprotection, and subjecting an aldehyde or ketone corresponding to $R^2$, Compound a-7 or a-8, to a reductive amination reaction in the presence of a reducing agent to yield Compound e-12. This step can be carried out in the same conditions as in the step A-2 to step A-4.

[Reaction Treatment Method]

When the entire reaction mixture is a liquid, for example, the reaction mixture is returned to room temperature or cooled on ice as desired, and appropriately neutralized with an acid, an alkali, an oxidizing agent or a reducing agent, followed by addition of water and an organic solvent such as acetic acid which is immiscible with water and does not react with the target compound. After thoroughly shaking the mixture, the mixture is allowed to stand still and the layer containing the target compound is separated from the resulting two layers. Next, a solvent that is immiscible with the obtained layer and does not react with the target compound is added, and then the layer containing the target compound is washed and separated. When the layer is an organic layer, it may be dried with a desiccant such as anhydrous magnesium sulfate or anhydrous sodium sulfate, and the solvent is distilled off to yield the target compound. When the layer is an aqueous layer, it is electrically desalted and then freeze-dried, and thereby the target compound can be obtained.

When the entire reaction mixture is a liquid, and if possible, it may be possible to collect the target compound simply by distilling off the components other than the target compound (for example, solvent, reagents, and the like) at ordinary pressure or under reduced pressure.

When only the target compound precipitates as a solid, or when the entire reaction mixture is a liquid and only the target compound precipitates as a solid during the collecting process, the target compound are first collected by a filtration method, the collected target compound are washed with a suitable organic or inorganic solvent and dried appropriately to yield the target compound.

Furthermore, when only the reagent or the catalyst is present as a solid, or when only the reagent or the catalyst precipitates as a solid during treatment of the reaction mixture, and the target compound is dissolved in a solution, the reagent or the catalyst is firstly removed by a filtration method, the removed reagent or catalyst is washed with a suitable organic or inorganic solvent, and the resultant washing solution is combined with the mother solution to yield a mixed solution, which is then treated in the same manner as in the case that the entire reaction mixture is a liquid, so that the target compound can be obtained.

The reaction mixture may be used directly for subsequent steps without isolation of the target compound in the case where components other than the target compound contained in the reaction mixture will not inhibit the reaction in the subsequent steps.

[Purifying Method]

Purity of the target compound collected by the above-mentioned methods can be improved by appropriately carrying out recrystallization, various chromatography methods, or distillation.

When the collected target compound is a solid, purity of the target compound can be usually improved by recrystallization. For recrystallization, a simple solvent or a mixed solvent of a plurality of solvents, which does not react with the target compound, can be used. Specifically, firstly, the target compound is dissolved in the simple solvent or the mixed solvent of a plurality of solvents, which does not react with the target compound, at mom temperature or with heating. The obtained mixture is cooled with ice water or the like or allowed to stand at room temperature to allow the target compound to precipitate from the mixed solution When the collected target compound is a solid or liquid, purity of the target compound can be improved by various chromatography methods. In general, a weakly acidic silica gel such as silica gel 60 (70-230 mesh or 340-400 mesh) by Merck, Ltd. or BW-300 (300 mesh) by Fuji Silysia Chemical, Ltd. may be used. If the target compound is basic, propylamine-coated silica gel (200-350 mesh) by Fuji Silysia Chemical, Ltd., or the like, may be used. If the target compound is bipolar or requires elution with a highly polar solvent such as methanol, NAM-200H or NAM-300H by Nagana Science Co., Ltd. may be used. By using these silica gels, the target compound may be eluted in the simple solvent or the mixed solvent of a plurality of solvents, which does not react with the target compound, and the solvent is distilled off to yield the target compound with improved purity.

When the collected target compound is a liquid, purity of the target compound can also be improved by distillation. The temperature and degree of reduced pressure are appropriately adjusted depending on the target compound, and the target compound can be obtained by an ordinary distillation method.

When a compound of the present invention is obtained in free form, it may be converted to an acceptable salt of the compound by an ordinary method.

On the contrary, when a compound of the present invention is obtained as a salt, it can be converted into the free form of the compound by an ordinary method.

Furthermore, various isomers (for example, geometric isomers, optical isomers, rotational isomers, stereoisomers, tautomers, and the like) obtained for compounds of the present invention can be purified and isolated using ordinary separation means such as, for example, recrystallization, a diastereomer salt method, enzymatic separation method, or various chromatography methods (for example, thin-layer chromatography, column chromatography, gas chromatography, etc.).

[Formulation]

When a compound of the present invention is used as a medicine, the compound of the present invention is usually used after it is mixed and formulated with appropriate additives. However, this does not negate the use of the compounds of the present invention in bulk forms as a medicine.

As additives there may be mentioned excipients, binders, lubricants, disintegrators, coloring agents, taste correctives, emulsifiers, surfactants, dissolving aids, suspending agents, isotonizing agents, buffering agents, antiseptic agents, antioxidants, stabilizers, absorption accelerators and the like which are commonly used in medicines, and these may also be used in appropriate combinations as desired.

As examples of excipients there may be mentioned lactose, white soil sugar, glucose, corn starch, mannitol, sorbitol, starch, pregelatinized starch, dextrin, crystalline cellulose, light silicic anhydride, aluminum silicate, calcium silicate, magnesium aluminometasilicate, calcium hydrogenphosphate and the like.

As examples of binders there may be mentioned polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol and the like.

As examples of lubricants there may be mentioned magnesium stearate, calcium stearate, sodium stearyl fumarate, talc, polyethylene glycol, colloidal silica and the like.

As examples of disintegrators there may be mentioned crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, carboxymethyl starch sodium and the like.

As coloring agents there may be mentioned those approved for addition to pharmaceuticals, such as iron sesquioxide, yellow iron sesquioxide, calamine, caramel, β-carotene, titanium oxide, talc, riboflavin sodium phosphate, yellow aluminum lake and the like.

As taste correctives there may be mentioned cocoa powder, menthol, aromatic powders, peppermint oil, camphor, cinnamon powder and the like.

As emulsifying agents or surfactants there may be mentioned stearyl triethanolamine, sodium lauryl sulfate, lauryl aminopropionic acid, lecithin, glycerin monostearate, sucrose fatty acid esters, glycerin fatty acid esters and the like.

As dissolving aids there may be mentioned polyethylene glycol, propylene glycol, benzyl benzoate, ethanol, cholesterol, triethanolamine, sodium carbonate, sodium citrate, polysorbate 80, nicotinamide and the like.

As suspending agents there may be mentioned the aforementioned surfactants, as well as hydrophilic polymers such as polyvinyl alcohol, polyvinylpyrrolidone, methylcellulose, hydroxymethylcellulose, hydroxyethylcellulose and hydroxypropylcellulose.

As isotonizing agents there may be mentioned glucose, sodium chloride, mannitol, sorbitol and the like.

As buffering agents there may be mentioned phosphate, acetate, carbonate and citrate buffering solutions.

As antiseptic agents there may be mentioned methylparaben, propylparaben, chlorobutanol, benzyl alcohol, phenethyl alcohol, dehydroacetic acid, sorbic acid and the like.

As antioxidants there may be mentioned sulfite, ascorbic acid, α-tocopherol and the like.

As stabilizers there may be mentioned those commonly used in drugs.

As absorption accelerators there may also be mentioned those commonly used in medicines.

As formulations there may be mentioned oral forms such as tablets, powders, granules, capsules, syrups, lozenges and inhalants; topical formulations such as suppositories, ointments, eye salves, tapes, eye drops, nose drops, ear drops, poultices, lotions, and the like; or injections.

The aforementioned oral forms may be formulated with appropriate combinations of the additives mentioned above. Their surfaces may also be coated if necessary.

The aforementioned topical formulations may be formulated with appropriate combinations of the additives mentioned above, and especially excipients, binders, taste correctives, emulsifiers, surfactants, dissolving aids, suspending agents, isotonizing agents, antiseptic agents, antioxidants, stabilizers and absorption accelerators.

Injections may also be formulated with appropriate combinations of the additives mentioned above, and especially emulsifiers, surfactants, dissolving aids, suspending agents, isotonizing agents, buffering agents, antiseptic agents, antioxidants, stabilizers and absorption accelerators.

The dosage of a medicine according to the invention will differ depending on the severity of symptoms, patient age, gender and body weight, type of dosage form/salt, patient drug sensitivity and specific nature of the disease, but the dosage per day for adults will generally be 30 µg to 10 g (preferably 0.1 mg to 1 g) for oral administration, 30 µg to 20 g (preferably 100 µg to 10 g) for topical formulation and 30 µg to 1 g (preferably 100 µg to 1 g) for injection, either administered at a single time or divided into several dosages.

These values are the actual administered amounts in the case of oral formulations and injections, and are the amounts actually absorbed by the body in the case of topical formulations.

EXAMPLES

The compounds of the present invention may be produced by the processes described in the following Examples, and the effects of the compounds may be confirmed by the methods described in the following testing examples. However, these specific examples are merely illustrative and not intended to limit the present invention in any way, while various modifications may be implemented within the scope of the present invention.

Compounds mentioned with reference to published documents were produced in the manner described in those documents.

The symbols used in the present specification stand for the followings.

$^1$H-NMR: proton nuclear magnetic resonance
δ: chemical shift
s: singlet
d: doublet
t: triplet
q: quartet
m: multiplet
dd: double doublet
br. s: broad singlet
sept: septet
J: coupling constant
Hz: Hertz
M: mol/L
n-: normal
s-: secondary
tert-: tertiary
N: normality
$CDCl_3$: deuterio-chloroform
DMSO-$d_6$: deuterio-dimethyl sulfoxide
DMF: N,N-dimethylformamide
DME: 1,2-dimethoxyethane
THF: tetrahydrofuran
DMSO: dimethyl sulfoxide
NMP: N-methylpyrrolidinone
Me: a methyl group
Ac: an acetyl group
EGTA: Glycol ether diamine tetraacetic acid (O,O'-bis(2-aminoethyl)ethyleneglycol-N,N,N,N'-tetraacetic acid)
BSA: Bovine serum albumin "Under reduced pressure" means conditions with approximately 1 to 50 mmHg by using a vacuum pump, a water-jet pump, and the like.

Unless otherwise specified, the "silica gel" in "silica gel column chromatography" mentioned throughout the examples is Silica Gel 60 (70-230 mesh or 340-400 mesh) by Merck, Ltd., FLASH+Cartridge (KP-SIL, pore size: 60 Å, particle size: 32-63 μm) by Biotage, or Cartridge (Hi-Flash, pore size: 60 Å, particle size: 40 μm) by Yamazen.

Also unless otherwise specified, the "(NH)silica gel" in "(NH)silica gel column chromatography" mentioned throughout the examples is propylamine-coated silica gel (200-350 mesh) by Fuji Silysia Chemical, Ltd., or Cartridge (Hi-Flash Amino, pore size: 60 Å, particle size: 40 μm) by Yamazen.

The term "room temperature" refers to a range from about 10° C. to 35° C. The % denotes weight percent unless otherwise specified.

Production Example 1

Dihydro-2H-pyran-3(4H)-one

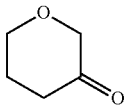

[Chemical Formula 14]

To a mixture of oxalyl chloride (2.28 mL, 26.6 mmol) and dichloromethane (40 mL) was added a mixture of DMSO (3.78 mL, 53.2 mmol) and dichloromethane (20 mL) while stirring at −78° C., and the mixture was stirred at −78° C. for 30 minutes. After then adding to this mixture a mixture of tetrahydropyran-3-ol (synthesized according to the method described in Tetrahedron, 60, 10411-10418, 2004) (136 g, 13.3 mmol) and dichloromethane (20 mL) at −78° C., the resulting mixture was stirred at −78° C. for 30 minutes, after which triethylamine (11.1 mL, 79.8 mmol) was added and stirring was continued for 2 hours while slowly raising the temperature to 0° C.

Brine and diethyl ether were added to the mixture, and after sufficient shaking, the organic layer was separated and the organic layer was washed with brine and dried over anhydrous magnesium sulfate. The mixture was then filtered, and the solvent in the filtrate was distilled off under reduced pressure to obtain the title compound (1.62 g, 162 mmol).

$^1$H-NMR (CDCl$_3$) δ: 2.07-2.14 (m, 2H), 2.54 (t, J=6.8 Hz, 2H), 3.82-3.88 (m, 2H), 4.03 (s, 2H).

Production Example 2

2-Cyclopropylethyl methanesulfonate

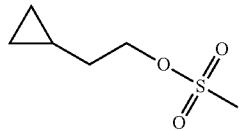

[Chemical Formula 15]

To a mixture of 2-cyclopropylethanol (5.35 g, 62.1 mmol) and dichloromethane (107 mL) were added methanesulfonyl chloride (5.29 mL, 68.3 mmol) and triethylamine (13.1 mL, 93.1 mmol) in that order while stirring on ice, and the resulting mixture was stirred for 1 hour. Water and ethyl acetate were then added to the reaction mixture. After thoroughly shaking the mixture, the organic layer was separated and the organic layer was washed with brine and dried over anhydrous magnesium sulfate. The mixture was then filtered, and the solvent in the filtrate was distilled off under reduced pressure to obtain the title compound (10.3 g, 62.7 mmol).

$^1$H-NMR (CDCl$_3$) δ: 0.10-0.16 (m, 2H), 0.48-0.55 (m, 2H), 0.72-0.83 (m, 1H), 1.65 (q, J=6.8 Hz, 2H), 3.01 (s, 3H), 4.29 (t, J=6.8 Hz, 2H).

Production Example 3

Tetrahydrofuran-3-yl-4-methylbenzenesulfonate

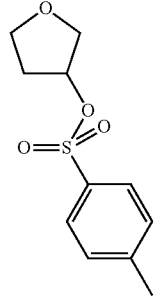

[Chemical Formula 16]

To a mixture of 3-hydroxytetrahydrofuran (7.00 g, 79.5 mmol) and pyridine (100 mL), was added p-toluenesulfonyl chloride (18.2 g, 95.4 mmol) while stirring at room temperature, and the resulting mixture was stirred for 8.5 hours. To the mixture, were added water and ethyl acetate. After thoroughly shaking the mixture, the organic layer was separated, and the organic layer was washed with brine and dried over anhydrous magnesium sulfate. The mixture was filtered, and then the solvent in the filtrate was distilled off under reduced pressure. The residue was purified by silica gel column chromatography (a mixed solvent of n-heptane and ethyl acetate: n-heptane/ethyl acetate=4/1) to obtain the title compound (13.0 g, 53.7 mmol).

$^1$H-NMR (CDCl$_3$) δ: 2.08-2.11 (m, 2H), 2.46 (s, 3H), 3.78-3.91 (m, 4H), 5.09-5.13 (m, 1H), 7.35 (d, J=8.0 Hz, 2H), 7.78 (d, J=8.0 Hz, 2H).

Production Example 4

3-Methoxypropyl methanesulfonate

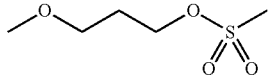

[Chemical Formula 17]

To a dichloromethane (50 mL) mixture of 3-methoxy-1-propanol (2.70 g, 30.0 mmol) and triethylamine (4.62 mL, 33.0 mmol), was added methanesulfonyl chloride (2.45 mL, 31.5 mmol) while stirring on ice, and the resulting mixture was stirred at room temperature for 30 minutes. Water and ethyl acetate were added to the reaction mixture. After thoroughly shaking the mixture, the organic layer was separated, and the organic layer was washed with brine and dried over anhydrous magnesium sulfate. The mixture was filtered, and the solvent in the filtrate was then distilled off under reduced pressure.

$^1$H-NMR (CDCl$_3$) δ: 2.00 (quit., J=6.0 Hz, 2H), 3.01 (s, 3H), 3.34 (s, 3H), 3.49 (t, J=6.0 Hz, 2H), 4.33 (t, J=6.0 Hz, 2H).

Production Example 5

2-Isopropoxyethyl methanesulfonate

[Chemical Formula 18]

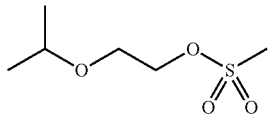

To a dichloromethane (50 mL) mixture of 2-isopropoxyethanol (5.21 g, 50.0 mmol) and triethylamine (7.70 mL, 55.0 mmol), was added methanesulfonyl chloride (4.30 mL, 55.0 mmol) while stirring on ice, and the resulting mixture was stirred for 30 minutes. Water and ethyl acetate were added to the mixture. After the mixture was thoroughly shaken, the organic layer was separated, and the organic layer was washed with brine and dried over anhydrous magnesium sulfate. The mixture was filtered, and the solvent in the filtrate was then distilled off under reduced pressure.

$^1$H-NMR (CDCl$_3$) δ: 1.17 (d, J=6.4 Hz, 6H), 3.06 (s, 3H), 3.61 (sept, J=6.4 Hz, 1H), 3.77 (t, J=4.4 Hz, 2H), 4.35 (t, J=4.4 Hz, 2H).

Production Example 6-1

2-Methoxypropan-1-ol

[Chemical Formula 19]

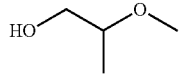

To a diethyl ether (60.0 mL) solution of lithium aluminum hydride (641 mg, 16.9 mmol), was added methyl 2-methoxypropionate (2.00 g, 16.9 mmol) while stirring on ice, and the mixture was stirred at room temperature over one day and night. After the reaction was completed, aqueous ammonia was added while cooling on ice, and the mixture was filtered with Celite and the solvent was distilled off under reduced pressure to obtain a crude compound (1.60 g, 17.8 mmol)

$^1$H-NMR (CDCl$_3$) δ: 1.12 (d, J=6.0 Hz, 3H), 3.38 (s, 3H), 3.41-3.49 (m, 2H), 3.55-3.63 (m, 1H).

Production Example 6-2

2-Methoxypropyl 4-methylbenzenesulfonate

[Chemical Formula 20]

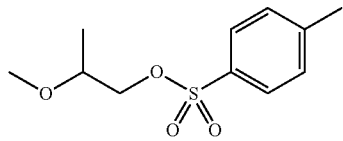

To dichloromethane (30 mL) mixture of 2-methoxypropan-1-ol (1.6 g, 17.8 mmol) and pyridine (20.0 mL), was added p-toluenesulfonyl chloride (4.07 g, 21.4 mmol) while stirring on ice, and the mixture was stirred at room temperature for five hours. To the mixture, were added water and ethyl acetate. After thoroughly shaking the mixture, the organic layer was separated, and the organic layer was washed with brine and dried over anhydrous magnesium sulfate. The mixture was filtered, and the solvent in the filtrate was then distilled off under reduced pressure. The residue was purified by silica gel column chromatography (a mixed solvent of n-heptane and ethyl acetate: n-heptane/ethyl acetate=2/1) to obtain the title compound (3.12 g, 12.8 mmol).

$^1$H-NMR (CDCl$_3$) δ: 1.12 (d, J=6.0 Hz, 3H), 2.45 (s, 3H), 3.29 (s, 3H), 3.49-3.59 (m, 1H), 3.95 (d, J=5.2 Hz, 2H), 7.32-7.36 (m, 2H), 7.76-7.81 (m, 2H).

Production Example 7

3-Methoxybutyl methanesulfonate

[Chemical Formula 21]

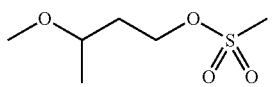

To a dichloromethane (30 mL) mixture of 3-methoxy-1-butanol (3.12 g, 30.0 mmol) and triethylamine (4.62 mL, 33.0 mmol), was added methanesulfonyl chloride (4.62 mL, 33.0 mmol) while stirring on ice, and the mixture was stirred at room temperature for 30 minutes. To the mixture, were added water and ethyl acetate. After thoroughly shaking the mixture, the organic layer was separated, and the organic layer was washed with brine and dried over anhydrous magnesium sulfate. The mixture was then filtered, and the solvent in the filtrate was then distilled off under reduced pressure.

$^1$H-NMR (CDCl$_3$) δ: 1.18 (d, J=6.0 Hz, 3H), 1.80-1.92 (m, 2H), 3.00 (s, 3H), 3.33 (s, 3H), 3.43-3.52 (m, 1H), 4.26-4.42 (m, 2H).

Production Example 8-1

3-[(Benzyloxy)methyl]cyclobutanone

[Chemical Formula 22]

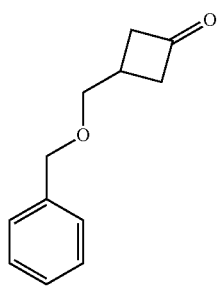

(J. Org, Chem, 1990, 55(24), 6058-6061.)

To a diethyl ether (100 mL) solution of allyl benzyl ether (11.1 g, 75.0 mmol), was added zinc copper couple (74.5 g, 33.0 mmol) while stirring at room temperature, a dimethoxyethane (100 mL) solution of trichloroacetyl chloride (43.6 mL, 375 mmol) was added dropwise, and the mixture was stirred at mom temperature for six hours. The reaction mixture was poured into ice-cooled aqueous sodium hydrogencarbonate (500 mL), extracted with ethyl acetate, and dried over anhydrous magnesium sulfate. The mixture was filtered and then the solvent in the filtrate was distilled off under reduced pressure. The residue was purified by silica gel column chromatography (a mixed solvent of n-heptane and ethyl acetate: n-heptane/ethyl acetate=15/1). The obtained dichloro product was dissolved in methanol (200 mL), ammonium chloride (20.0 g, 375 mmol) was added and zinc powder (30.0 g, 450 mmol) was added little by little while vigorously stirring. After the reaction was completed, the insoluble matters were filtered off with Celite, the filtrate was distilled off under reduced pressure. Water was added to the residue, which was extracted with ethyl acetate, and dried over anhydrous magnesium sulfate. The mixture was filtered, and the solvent in the filtrate was then distilled off under reduced pressure. The residue was purified by silica gel column chromatography (a mixed solvent of n-heptane and ethyl acetate: n-heptane/ethyl acetate=15/1 then 12/1) to obtain the title compound (7.20 g, 37.9 mmol).

$^1$H-NMR (CDCl$_3$) δ: 2.64-2.76 (m, 1H), 2.84-2.94 (m, 2H), 3.09-3.19 (m, 2H), 3.60 (d, J=6.4 Hz, 2H), 4.57 (s, 2H), 7.25-7.40 (m, 5H).

Production Example 8-2

{[(3,3-(Difluorocyclobutyl)methoxy]methyl}benzene

[Chemical Formula 23]

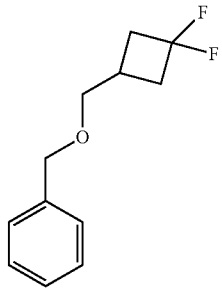

To a dichloromethane (25 mL) solution of 3-[(benzyloxy) methyl]cyclobutanone (2.50 g, 13.1 mmol), was added dropwise diethylaminosulfur trifluoride (OAST) (5.24 mL, 39.3 mmol) while stirring at −78° C., which was warmed to room temperature and stirred at room temperature for two days. The reaction mixture was poured into ice-cooled aqueous sodium hydrogencarbonate, extracted with ethyl acetate, and dried over anhydrous magnesium sulfate. The mixture was filtered and then the solvent in the filtrate was distilled off under reduced pressure. The residue was purified by silica gel column chromatography (a mixed solvent of n-heptane and ethyl acetate: n-heptane/ethyl acetate=15/1) to obtain the title compound (2.60 g, 12.1 mmol)

$^1$H-NMR (CDCl$_3$) δ: 228-2.47 (m, 3H), 2.56-2.70 (m, 2H), 3.50 (d, J=6.0 Hz, 2H), 4.53 (s, 2H), 7.25-7.40 (m, 5H).

Production Example 8-3

(3,3-Difluorobutyl)methyl methanesulfonate

[Chemical Formula 24]

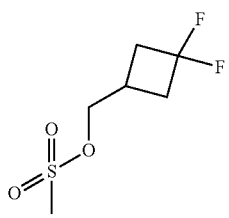

To a dichloromethane (16.6 mL) solution of {[(3,3-difluorocyclobutyl)methoxy]methyl}benzene (2.40 g, 11.3 mmol), was added dropwise iodotrimethylsilane (2.46 mL, 16.9 mmol) while stirring on ice, and stirred at room temperature for one hour. The reaction mixture was poured into ice-cooled aqueous sodium hydrogencarbonate, extracted with ethyl acetate, and dried over anhydrous magnesium sulfate. To the reaction mixture, were added ice and sodium thiosulfate, extracted with dichloromethane, and dried over anhydrous magnesium sulfate. The mixture was filtered, then the solvent in the filtrate was distilled off under reduced pressure, and the resultant crude product was dissolved in dichloromethane (100 mL), triethylamine (2.02 mL, 14.4 mmol) and methanesulfonyl chloride (1.31 mL, 14.5 mmol) were added while stirring on ice, and stirred at room temperature over one day and night. To the mixture, were added water and ethyl acetate. After thoroughly shaking the mixture, the organic layer was then separated, and the organic layer was washed with brine and dried over anhydrous magnesium sulfate. The mixture was filtered, and then the solvent in the filtrate was distilled off under reduced pressure. The residue was purified by silica gel column chromatography (a mixed solvent of n-heptane and ethyl acetate:n-heptane/ethyl acetate=11/4) to obtain the title compound (2.10 g, 10.49 mmol).

$^1$H-NMR (CDCl$_3$) δ: 2.36-2.49 (m, 2H), 2.52-2.64 (m, 1H), 2.67-2.80 (m, 2H), 3.05 (s, 3H), 4.27 (d, J=6.4 Hz, 2H).

Production Example 9

3-(Hydroxymethyl)cyclobutanone

[Chemical Formula 25]

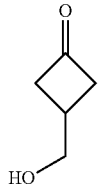

To a methanol (90 mL) solution of 3-[(benzyloxy)methyl] cyclobutanone (4.55 g, 23.9 mmol), was added 10% palladium-carbon (50% water wet, 4.55 g), and catalytic hydrogen reduction was carried out at room temperature for one hour in an atmosphere of one atmosphere of hydrogen. The reaction mixture was filtered with Celite, the filtrate was concentrated under reduced pressure, and the residue was purified by medium pressure silica gel column chromatography (n-heptane/ethyl acetate: 5% then 65%) to obtain the title compound (1.34 g, 13.4 mmol).

$^1$H-NMR (CDCl$_3$) δ: 2.58-2.70 (m, 1H), 2.83-2.94 (m, 2H), 3.08-3.20 (m, 2H), 3.81 (d, J=6.8 Hz, 2H).

Production Example 10-1

5-Hydroxymethyl-1,3-dioxane

[Chemical Formula 26]

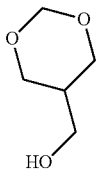

To a dichloromethane (4.9 mL) suspension of 2-hydroxymethyl-1,3-propanediol (1.00 g, 9.41 mmol), were added formaldehyde dimethyl acetal (2.94 mL, 33.3 mmol), lithium bromide (159 mg, 1.84 mmol) and p-toluenesulfonic acid monohydrate (160 mg, 0.843 mmol), and the mixture was stirred at room temperature for three days. To the mixture, was added triethylamine (1.0 mL), the solvent was distilled off under reduced pressure, and the residue was purified by silica gel column chromatography to obtain the title compound (380 mg, 3.22 mmol) from fraction of n-heptane:ethyl acetate (4:1).

$^1$H-NMR (400 MHz, CDCl$_3$) δ: 1.55 (br.s, 1H), 1.92-2.00 (m, 1H), 3.75 (dd, J=4.8, 6.8 Hz, 2H), 3.79 (dd, J=6.0, 11.6 Hz, 2H), 4.01 (dd, J=4.0, 11.6 Hz, 2H), 4.80 (d, J=6.4 Hz, 1H), 4.86 (d, J=6.4 Hz, 1H).

Production Example 10-2

5-Iodomethyl-1,3-dioxane

[Chemical Formula 27]

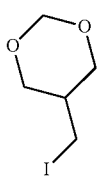

To a dichloromethane (30 mL) solution of 5-hydroxymethyl-1,3-dioxane (2.30 g, 19.5 mmol) obtained by Production Example 10-1 or well-known methods (see Japanese Patent Application Unexamined Publication No. 2003-238884 and No. 2003-183569), was added N,N-diisopropylethylamine (4.01 mL, 23.4 mmol). Methanesulfonyl chloride (1.66 mL, 21.4 mmol) was added dropwise thereto while ice cooling, which was warmed to room temperature and stirred for 40 minutes. A saturated aqueous solution of sodium hydrogencarbonate was added thereto, which was extracted with ethyl acetate, then washed with brine and dried over anhydrous magnesium sulfate, and the solvent was distilled off under reduced pressure. To an acetonitrile (200 mL) solution of the residue, was added sodium iodide (17.5 g, 117 mmol), and the mixture was heated to reflux for seven hours. After returning the mixture to room temperature, the solvent was distilled off under reduced pressure. Water was added to the residue, which was extracted with ethyl acetate, washed with a saturated aqueous solution of sodium thiosulfate and brine, dried over anhydrous magnesium sulfate, and the solvent was then distilled off under reduced pressure. The residue was purified by silica gel column chromatography to obtain the title compound (2.60 g, 11.4 mmol) from a fraction of n-heptane:ethyl acetate (10:1).

$^1$H-NMR (400 MHz, CDCl$_3$) δ: 2.01-2.07 (m, 1H), 3.19 (d, J=7.2 Hz, 2H), 3.69 (dd, J=6.4, 11.6 Hz, 2H), 4.06 (dd, J=3.6, 11.6 Hz, 2H), 4.75 (d, J=6.2 Hz, 1H), 4.84 (d, J=6.2 Hz, 1H).

Production Example 11-1

3-Oxa-bicyclo[3.1.0]hexane-6-carboxylic acid ethyl ester (diastereomer 1 and diastereomer 2)

[Chemical Formula 28]

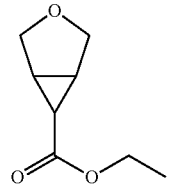

2,5-Dihydro-furan (25 g, 156 mmol) was dissolved in dichloromethane (350 mL), and Rh(II)(OAc$_2$ (320 mg, 1.34 mmol) was added to the reaction mixture, and diazoacetic acid ethyl (312 mL, 297 mmol) was added dropwise at room temperature. The mixture was stirred at room temperature for one hour, to which silica gel was added, and the mixture was distilled off under reduced pressure, and the residue was purified by column chromatography (heptane:ethyl acetate=to 15% ethyl acetate) to obtain diastereomer 1 (25.9 g, 166 mmol) as a low polar component and diastereomer 2 (5.1 g, 32.7 mmol) as a high polar component as a colorless oil, respectively.

(Diastereomer 1)

$^1$H-NMR (CDCl$_3$) δ: 1.27 (t, J=7.3 Hz, 3H), 1.61 (t, J=3.6 Hz, 1H), 2.16 (m, 2H), 3.75 (br.d, J=9.3 Hz, 2H), 3.93 (d, J=8.5 Hz, 2H), 4.13 (q, J=7.3 Hz, 2H)

(Diastereomer 2)

$^1$H-NMR (CDCl$_3$) δ: 1.26 (t, J=7.5 Hz, 3H), 1.72 (t, J=7.8 Hz, 1H), 1.89 (br.d, J=7.8 Hz, 2H), 3.73 (br.d, J=10.9 Hz, 2H), 4.06 (d, J=10.9 Hz, 2H), 4.14 (q, J=7.5 Hz, 2H).

Production Example 11-2

(3-Oxa-bicyclo[3.1.0]hex-6-yl)methanol diastereomer 1

[Chemical Formula 29]

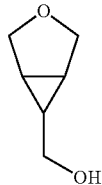

3-Oxa-bicyclo[3.1.0]hexane-6-carboxylic acid ethyl ester diastereomer 1 (10 g, 64.1 mmol) was dissolved in THF (100 mL), and to the mixture, was added dropwise a 0.99M toluene (180 mL, 178 mmol) solution of DIBAL while cooling on ice, and stirred at room temperature for one hour. To the reaction mixture, were added a small amount of water and ethyl acetate, and the mixture was filtered with Celite, washed with ethyl acetate, and then the filtrate was distilled off under reduced pressure, and the residue was purified by column chromatography (heptane:ethyl acetate to 75% ethyl acetate) to obtain the title compound (2.6 g, 228 mmol) as a colorless oil.

¹H-NMR (CDCl₃) δ: 1.10 (dt, J=3.6 Hz, 6.8 Hz, 1H), 1.53-1.56 (m, 2H), 3.53 (d, J=6.8 Hz, 2H), 3.70 (d, J=8.0 Hz, 2H), 3.88 (d, J=8.4 Hz, 2H)

Production Example 11-3

(3-Oxa-bicyclo[3.1.0]hex-6-yl)methanol diastereomer 2

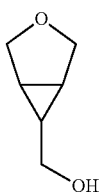

[Chemical Formula 30]

From 3-oxa-bicyclo[3.1.0]hexane-6-carboxylic acid ethyl ester diastereomer 2 (5 g, 32.1 mmol), the title compound (2.1 g, 18.4 mmol) was obtained as a colorless oil according to the same procedure as in (3-oxa-bicyclo[3.1.0]hex-6-yl)methanol diastereomer 1.

¹H-NMR (CDCl₃) δ: 1.23 (t, J=3.6 Hz, 1H), 1.80 (d, J=3.6 Hz, 2H), 3.79 (d, J=7.6 Hz, 2H), 3.91 (m, 4H)

Production Example 11-4

3-Oxa-bicyclo[3.1.0]hexane-6-carbaldehyde diastereomer 1

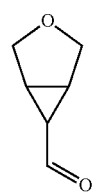

[Chemical Formula 31]

A dichloromethane (50 mL) solution of oxalyl chloride (1.54 mL, 17.3 mmol) was cooled to −78° C., to which a dichloromethane (8 mL) solution of DMSO (2.51 mL) was added dropwise, and the mixture was stirred for 30 minutes. Then, a dichloromethane (5 mL) solution of (3-oxa-bicyclo[3.1.0]hex-6-yl)methanol diastereomer 1 (1 g, 8.77 mmol) was added dropwise to the mixture, and the mixture was stirred for 30 minutes, followed by addition of TEA (7.4 mL, 53.1 mmol), and the mixture was gradually warmed to 0° C. Water was added to the reaction mixture, which was extracted with ethyl acetate and dried over magnesium sulfate, and distilled off under reduced pressure with silica gel added, and the residue was purified by column chromatography (heptane:ethyl acetate=to 110:40) to obtain the title compound (500 mg, 4.46 mmol) as a colorless oil.

1H-NMR (CDCl₃) δ: 1.94 (dt, J=3.2 Hz, 4.4 Hz, 1H), 2.30 (m, 2H), 3.80 (br.d, J=8.4 Hz, 2H), 3.96 (d, J=8.8 Hz, 2H), 9.42 (d, J=4.4 Hz, 1H)

Production Example 11-5

3-Oxa-bicyclo[3.1.0]hexane-6-carbaldehyde diastereomer 2

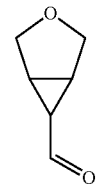

[Chemical Formula 32]

From (3-oxa-bicyclo[3.1.0]hex-6-yl)methanol diastereomer 1(1 g, 8.77 mmol), the title compound (680 mg, 6.07 mmol) was obtained as a colorless oil according to the same procedure as in 3-oxa-bicyclo[3.1.0]hexane-6-carbaldehyde diastereomer 1.

¹H-NMR (CDCl₃) δ: 1.73 (dt, J=6.4 Hz, 7.6 Hz, 1H), 2.21 (m, 2H), 4.05 (d, J=8.8 Hz, 2H), 4.24 (d, J=10.0 Hz, 2H), 9.57 (d, J=7.6 Hz, 1H)

Production Example 12-1

4-Bromo-3,5-dimethoxybenzamide

[Chemical Formula 33]

To a mixture of 4-bromo-3,5-dimethoxybenzoic acid (15 g, 57.6 mmol) and THF (200 mL), were added triethylamine (9.63 mL, 69.0 mmol) and ethyl chloroformate (5.79 mL, 60.6 mmol) while stirring on ice, and the mixture was stirred on ice for 20 minutes. To the mixture, 28% aqueous ammonia was added and stirred at room temperature for two hours, followed by addition of ethyl acetate. After thoroughly shaking the mixture, the organic layer was separated, and the organic layer was washed with brine and dried over anhydrous magnesium sulfate. The mixture was filtered, and then the solvent in the filtrate was distilled off under reduced pressure. The obtained residue (solid) was washed with diethyl ether, collected by filtration to obtain the title compound (11.8 g, 45.4 mmol).

¹H-NMR (CDCl₃) δ: 3.95 (s, 6H), 7.00 (s, 2H).

Production Example 12-2

4-Bromo-3,5-dimethoxybenzonitrile

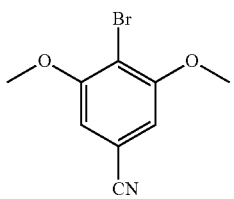

[Chemical Formula 34]

To 4-bromo-3,5-dimethoxybenzamide (4 g, 15.4 mmol), were added toluene (20 mL), DMF (5 mL), and thionyl chloride (3.36 mL, 46.1 mmol) in this order, and the mixture was stirred at 50° C. for one hour. To the mixture, was added ice water at room temperature, and ethyl acetate was then added. After thoroughly shaking the mixture, the organic layer was separated, and the organic layer was washed with brine and dried over anhydrous magnesium sulfate. The mixture was filtered, and then the solvent in the filtrate was distilled off under reduced pressure.

The obtained residue (solid) was washed with diethyl ether/n-heptane (1/1) to obtain the title compound (2.08 g, 8.59 mmol)

$^1$H-NMR (CDCl$_3$) δ: 3.93 (s, 6H), 6.82 (s, 2H).

Production Example 12-3

(4-Cyano-2,6-dimethoxyphenyl)boronic acid

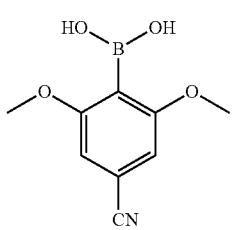

[Chemical Formula 35]

To a mixture of 4-bromo-3,5-dimethoxybenzonitrile (2 g, 8.26 mmol) and THF (60 mL), was added n-butyllithium (1.58 M, n-hexane solution: 5.48 mL, 8.68 mmol) while stirring at −100° C., and the mixture was further stirred at −100° C. for 30 minutes. To the mixture, was added trimethyl borate (1.84 mL, 16.5 mmol), and the mixture was stirred for four hours while gradually warming to −20° C. To the mixture, were added a saturated aqueous solution of ammonium chloride and 1N hydrochloric acid, and then ethyl acetate was added.

After thoroughly shaking the mixture, the organic layer was separated, and the organic layer was washed with brine and dried over anhydrous magnesium sulfate. The mixture was filtered, and then the solvent in the filtrate was distilled off under reduced pressure. The obtained residue (solid) was washed with n-heptane to obtain the title compound (1.43 g, 6.91 mmol).

$^1$H-NMR (CDCl$_3$) δ: 3.96 (s, 6H), 6.89 (s, 2H), 7.01 (s, 2H).

Production Example 13-1

Ethyl 4-amino-3-methoxybenzoate

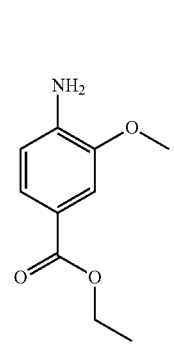

[Chemical Formula 36]

To a mixture of 4-amino-3-methoxybenzoic acid (15 g, 89.7 mmol) and ethanol (170 mL), was added concentrated sulfuric acid (5 mL), and the mixture was heated to reflux for seven hours. The reaction mixture was returned to mom temperature. The solvent in the mixture was distilled off under reduced pressure. To the residue, were added water, a saturated aqueous solution of sodium hydrogencarbonate and ethyl acetate.

After thoroughly shaking the mixture, the organic layer was separated, and the organic layer was washed with brine and dried over anhydrous magnesium sulfate. The mixture was filtered, and then the solvent in the filtrate was distilled off under reduced pressure to obtain the title compound (17.8 g, 91.2 mmol).

$^1$H-NMR (CDCl$_3$) δ: 1.37 (t, J=6.8 Hz, 3H), 3.90 (s, 3H), 4.32 (q, J=6.8 Hz, 2H), 6.66 (d, J=8.0 Hz, 1H), 7.45 (d, J=1.6 Hz, 1H), 7.54 (dd, J=1.6, 8.0 Hz, 1H).

Production Example 13-2

Ethyl 4-amino-3-chloro-5-methoxybenzoate

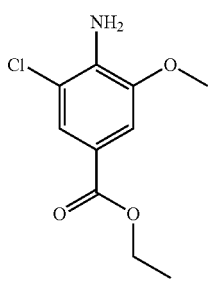

[Chemical Formula 37]

To ethyl 4-amino-3-methoxybenzoate (17.8 g, 91.2 mmol), were added acetonitrile (170 mL) and N-chlorosuccinimide (13.4 g, 100 mmol) in this order, and the mixture was stirred at 60° C. for two hours. The mixture was returned to room temperature, and the solvent in the mixture was distilled off under reduced pressure. The residue was purified by silica gel column chromatography (a mixed solvent of n-heptane and ethyl acetate:n-heptane/ethyl acetate=8/1 then 4/1) to obtain the title compound (158 g, 68.8 mmol).

$^1$H-NMR (CDCl$_3$) δ: 1.37 (t, J=6.8 Hz, 3H), 3.91 (s, 3H), 4.32 (q, J=6.8 Hz, 2H), 4.58 (br.s, 2H), 7.36 (d, J=1.8 Hz, 1H), 7.65 (d, J=1.8 Hz, 1H).

Production Example 13-3

Ethyl 3-chloro-4-iodo-5-methoxybenzoate

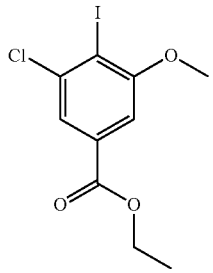

[Chemical Formula 38]

To ethyl 4-amino-3-chloro-5-methoxybenzoate (15.8 g, 68.8 mmol), were added acetonitrile (40 mL) and diiodomethane (22.2 mL, 275 mmol) in this order, and the mixture was stirred at 70° C., and then isoamyl nitrite (13.9 mL, 103 mmol) was added dropwise thereto over 10 minutes. The mixture was stirred at 70° C. for 40 minutes. The mixture was returned to room temperature, the solvent was then distilled off under reduced pressure, and the residue was purified by silica gel column chromatography (a mixed solvent of n-heptane and ethyl acetate: n-heptane/ethyl acetate=8/1 then 5/1) to obtain the title compound (15.6 g, 45.8 mmol)

1H-NMR (CDCl$_3$) δ: 1.40 (t, J=7.2 Hz, 3H), 3.95 (s, 3H), 4.38 (q, J=7.2 Hz, 2H), 7.30 (d, J=1.6 Hz, 1H), 7.73 (d, J=1.6 Hz, 1H).

Production Example 13-4

(3-Chloro-4-iodo-5-methoxyphenyl)methanol

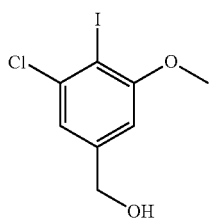

[Chemical Formula 39]

To a mixture of ethyl 3-chloro-4-iodo-5-methoxybenzoate (15.6 g, 45.8 mmol) and toluene (150 mL), was added diisobutyl aluminum hydride (1.01M toluene solution: 95.2 mL, 96.2 mmol) while stirring at −78° C., and the mixture was stirred while warming to −30° C. for three hours. To the mixture, an aqueous solution (400 mL) of Rochelle salt (potassium sodium (+)-tartrate tetrahydrate) (77.6 g, 275 mmol) was added, the mixture was stirred at room temperature for five hours, followed by addition of ethyl acetate. After thoroughly shaking the mixture, the organic layer was separated, and the organic layer was washed with brine and dried over anhydrous magnesium sulfate. The mixture was filtered, and then the solvent in the filtrate was distilled off under reduced pressure to obtain the title compound (13.7 g, 45.8 mmol).

$^1$H-NMR (CDCl$_3$) δ: 3.90 (s, 3H), 4.66 (s, 2H), 6.72 (d, J=1.2 Hz, 1H), 7.09 (br.s, 1H).

Production Example 13-5

1-Chloro-2-iodo-3-methoxy-5-(methoxymethyl)benzene

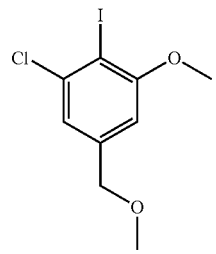

[Chemical Formula 40]

To a mixture of (3-chloro-4-iodo-5-methoxyphenyl)methanol (13.7 g, 45.9 mmol) and NMP (90 mL) were added sodium hydride (60% oil dispersion: 2.02 g, 50.5 mmol) and iodomethane (3.14 mL, 50.4 mmol), and the mixture was stirred at room temperature for four hours. To the mixture, water and diethyl ether were added. After thoroughly shaking the mixture, the organic layer was separated, and the organic layer was washed with brine and dried over anhydrous magnesium sulfate. The mixture was filtered, and then the solvent in the filtrate was distilled off under reduced pressure.

The residue was purified by silica gel column chromatography (a mixed solvent of n-heptane and ethyl acetate: n-heptane/ethyl acetate=8/1 then 4/1) to obtain the title compound (13.2 g, 422 mmol).

$^1$H-NMR (CDCl$_3$) δ: 3.40 (s, 3H), 3.90 (s, 3H), 4.40 (s, 2H), 6.69 (s, 1H), 7.07 (s, 1H).

Production Example 13-6

[2-Chloro-6-methoxy-4-(methoxymethyl)phenyl]boronic acid

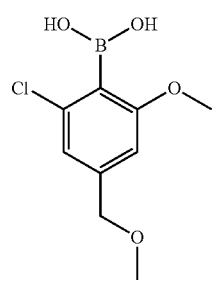

[Chemical Formula 41]

To a mixture of 1-chloro-2-iodo-3-methoxy-5-(methoxymethyl)benzene (4.72 g, 15.1 mmol) and THF (150 mL) was added n-butyllithium (1.58 M, n-hexane solution: 10.5 mL, 16.6 mmol) while stirring at −100° C., and the mixture was further stirred at −100° C. to −85° C. for 30 minutes. To the mixture was added trimethyl borate (4.21 mL, 37.8 mmol), and the mixture was stirred for four hours while gradually warming to −20° C. To the mixture were added a saturated aqueous solution of ammonium chloride and 1N hydrochloric acid, and then ethyl acetate was added.

After thoroughly shaking the mixture, the organic layer was separated, and the organic layer was washed with brine and dried over anhydrous magnesium sulfate. The mixture was filtered, and then the solvent in the filtrate was distilled off under reduced pressure. The obtained residue (solid) was washed with n-heptane to obtain the title compound (2.65 g, 11.5 mmol).

$^1$H-NMR (CDCl$_3$) δ: 3.42 (s, 3H), 3.92 (s, 3H), 4.44 (s, 2H), 6.23 (s, 2H), 6.86 (s, 1H), 7.00 (br.s, 1H).

Production Example 14-1

(4-Bromo-3,5-dimethoxyphenyl)methanol

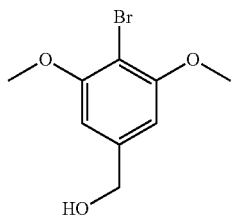

[Chemical Formula 42]

To a mixture of 4-bromo-3,5-dimethoxybenzoic acid (50.0 g, 192 mmol) and THF (1 L) was added borane methyl sulfide (27.1 mL, 286 mmol) while cooling on ice, and the mixture was heated to reflux for one hour. Water was gradually added to the mixture while cooling on ice, and the solvent in the mixture was then distilled off under reduced pressure. To the residue, water and ethyl acetate were added. After thoroughly shaking the mixture, the organic layer was separated, and the organic layer was washed with brine and dried over anhydrous magnesium sulfate. The mixture was filtered, and then the solvent in the filtrate was distilled off under reduced pressure to obtain the title compound (47.3 g, 191 mmol).

$^1$H-NMR (CDCl$_3$) δ: 1.80 (s, 1H), 3.91 (s, 6H), 4.68 (s, 2H), 6.60 (s, 2H).

Production Example 14-2

2-Bromo-5-(chloromethyl)-1,3-dimethoxybenzene

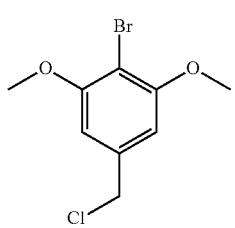

[Chemical Formula 43]

To a mixture of (4-bromo-3,5-dimethoxyphenyl)methanol (10.0 g, 40.6 mmol) and dichloromethane (100 mL) were added triethylamine (12.4 mL, 89.3 mmol) and methanesulfonyl chloride (3.46 mL, 44.7 mmol) in this order while cooling on ice, and the mixture was stirred at room temperature for 14 hours. To the mixture was added water, and then ethyl acetate was added. After thoroughly shaking the mixture, the organic layer was separated, and the organic layer was washed with brine and dried over anhydrous magnesium sulfate. The mixture was filtered, and then the solvent in the filtrate was distilled off under reduced pressure. The residue was purified by silica gel column chromatography (a mixed solvent of n-heptane and ethyl acetate: n-heptane/ethyl acetate=4/1) to obtain the title compound (2.47 g, 9.30 mmol).

$^1$H-NMR (CDCl$_3$) δ: 3.92 (s, 6H), 4.55 (s, 2H), 6.60 (s, 2H).

Production Example 14-3

2-Bromo-5-[(cyclobutyloxy)methyl]-1,3-dimethoxybenzene

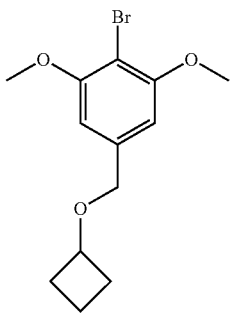

[Chemical Formula 44]

To a mixture of cyclobutyl alcohol (4.16 g, 57.7 mmol) and DMF (30 mL) was added sodium hydride (60% oil dispersion: 2.31 g, 57.7 mmol) while cooling on ice, and the mixture was stirred at room temperature for one hour. To the mixture was gradually added dropwise a mixture of 2-bromo-5-(chloromethyl)-1,3-dimethoxybenzene (2.47 g, 9.3 mmol) and DMF (30 mL), and the mixture was stirred at room temperature for one hour. Water was added to the mixture while cooling on ice, and then ethyl acetate was added. After thoroughly shaking the mixture, the organic layer was separated, and the organic layer was washed with brine and dried over anhydrous magnesium sulfate. The mixture was filtered, and then the solvent in the filtrate was distilled off under reduced pressure. The residue was purified by silica gel column chromatography (a mixed solvent of n-heptane and ethyl acetate: n-heptane/ethyl acetate=4/1) to obtain the title compound (2.39 g, 7.94 mmol).

$^1$H-NMR (CDCl$_3$) δ: 1.43-1.60 (m, 1H), 1.65-1.80 (m, 1H), 1.92-2.08 (m, 2H), 2.15-2.28 (m, 2H), 3.90 (s, 6H), 3.96-4.07 (m, 1H), 4.38 (s, 2H), 6.56 (s, 2H).

Production Example 14-4

{4-[(Cyclobutyloxy)methyl]-2,6-dimethoxyphenyl}boronic acid

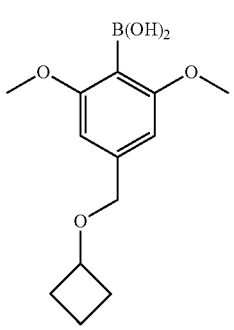

[Chemical Formula 45]

To a mixture of 2-bromo-5-[(cyclobutyloxy)methyl]-1,3-dimethoxybenzene (2.39 g, 7.94 mmol) and THF (20 mL) was added n-butyllithium (2.73M n-hexane solution: 3.49 mL, 9.53 mmol) at −78° C. (internal temperature), and the mixture was stirred for one hour. To the mixture was added trimethyl borate (1.07 mL, 9.53 mmol) and the mixture was gradually warmed to room temperature while stirring. Thereafter, a saturated aqueous solution of ammonium chloride was added to the mixture while cooling on ice, and then ethyl acetate was added. After thoroughly shaking the mixture, the organic layer was separated, and the organic layer was washed with brine and dried over anhydrous magnesium sulfate. The mixture was filtered, and then the solvent in the filtrate was distilled off under reduced pressure. To the residue, heptane (30 mL) was added, the precipitated solid was filtered and then dried under reduced pressure to obtain the title compound (905 mg, 3.40 mmol).

$^1$H-NMR (CDCl$_3$) δ: 1.45-1.60 (m, 1H), 1.67-1.80 (m, 1H), 1.94-2.08 (m, 2H), 2.18-2.30 (m, 2H), 3.92 (s, 6H), 3.96-4.07 (m, 1H), 4.41 (s, 2H), 6.61 (s, 2H), 7.18 (s, 2H).

Production Example 15-1

2-Bromo-5-(isopropoxymethyl)-1,3-dimethoxybenzene

[Chemical Formula 46]

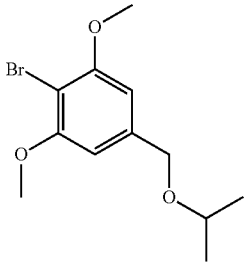

To an N,N-dimethylformamide (15 ml) solution of 2-propanol (7.81 ml, 102 mmol) was added sodium hydride (4.08 g, 102 mmol) at room temperature and the mixture was stirred for 30 minutes. To the mixture was added an N,N-dimethylformamide (15 ml) solution of 2-bromo-5-(chloromethyl)-1,3-dimethoxybenzene (2.70 g, 10.2 mmol) and the mixture was stirred for one hour. After the reaction was completed, water was added to the reaction mixture while cooling on ice, which was extracted with ethyl acetate and dried over anhydrous magnesium sulfate, and the solvent was then distilled off under reduced pressure. The residue was purified by silica gel column chromatography (n-heptane/ethyl acetate: 3/1) to obtain the title compound (1.85 g, 6.40 mmol).

$^1$H-NMR (CDCl$_3$) δ: 1.23 (d, J=8.4 Hz, 6H), 3.63-3.74 (m, 1H), 3.91 (s, 6H), 4.48 (s, 2H), 6.58 (s, 2H).

Production Example 15-2

[4-(Isopropoxymethyl)-2,6-dimethoxyphenyl]boronic acid

[Chemical Formula 47]

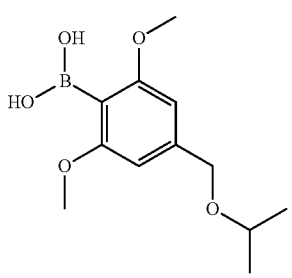

To a tetrahydrofuran (20 ml) solution of 2-bromo-5-(isopropoxymethyl)-1,3-dimethoxybenzene (1.85 g, 6.40 mmol) was added dropwise 2.77M n-butyllithium (2.77 ml, 7.68 mmol) at −78° C., and the mixture was stirred for one hour. To the mixture was added trimethyl borate (0.86 ml, 7.68 mmol), and the mixture was warmed to room temperature. After the reaction was completed, a saturated aqueous solution of ammonium chloride was added while cooling on ice, which was extracted with ethyl acetate and dried over anhydrous magnesium sulfate, and the solvent was then distilled off under reduced pressure. The residue was purified by silica gel column chromatography (n-heptane/ethyl acetate: 3/1 then 1/1) to obtain the title compound (571 mg, 2.25 mmol).

$^1$H-NMR (CDCl$_3$) δ: 1.24 (d, J=5.0 Hz, 6H), 3.64-3.75 (m, 1H), 3.92 (s, 6H), 4.52 (s, 2H), 6.63 (s, 2H), 7.19 (s, 2H).

Production Example 16-1

1-(4-Bromo-3,5-dimethoxyphenyl)ethanol

[Chemical Formula 48]

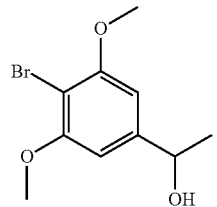

To a solution of (4-bromo-3,5-dimethoxyphenyl)methanol (14.5 g, 58.7 mmol) in dichloroethane (100 ml) and toluene (140 mL) was added manganese dioxide (25.5 g, 294 mmol) and the mixture was stirred at 80° C. for three hours. After the reaction was completed, the mixture was filtered with Celite and the solvent was distilled off under reduced pressure to obtain a crude compound. To a tetrahydrofuran (153 mL) solution of the crude compound (13.8 g, 56.3 mmol) was added dropwise 1.04M methyllithium (59.5 mL, 61.9 mmol) at −78° C., and the mixture was stirred for four hours. After the reaction was completed, a saturated aqueous solution of ammonium chloride was added to the reaction mixture, which was extracted with ethyl acetate, and dried over anhydrous magnesium sulfate, and the solvent was then distilled off under reduced pressure. The residue was purified by silica gel column chromatography (n-heptane/ethyl acetate: 4/1 then 1/1) to obtain the title compound (11.4 g, 43.7 mmol).

$^1$H-NMR (CDCl$_3$) δ: 1.50 (d, J=6.4 Hz, 3H), 1.86 (br.s, 1H), 3.91 (s, 6H), 4.85-4.91 (m, 1H), 6.60 (s, 2H).

Production Example 16-2

2-Bromo-1,3-dimethoxy-5-(1-methoxyethyl)benzene

[Chemical Formula 49]

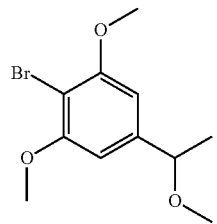

To a tetrahydrofuran (100 mL) solution of 1-(4-bromo-3,5-dimethoxyphenyl)ethanol (7.24 g, 27.7 mmol) was added sodium hydride (1.33 g, 33.2 mmol) at 0° C., and the mixture was stirred for 10 minutes. To the mixture was added dropwise iodomethane (1.90 mL, 30.5 mmol), and the mixture was stirred at room temperature for one hour. After the reaction was completed, water was added to the reaction mixture while cooling on ice, which was extracted with ethyl acetate and dried over anhydrous magnesium sulfate, and the solvent was then distilled off under reduced pressure. The residue was purified by silica gel column chromatography (n-heptane/ethyl acetate: 10/1 then 1/4) to obtain the title compound (7.39 g, 26.9 mmol).

$^1$H-NMR (CDCl$_3$) δ: 1.43 (d, J=6.4 Hz, 3H), 3.25 (s, 3H), 3.90 (s, 6H), 4.22-4.28 (m, 1H), 6.53 (s, 2H).

Production Example 16-3

[2,6-Dimethoxy-4-(1-methoxyethyl)phenyl]boronic acid

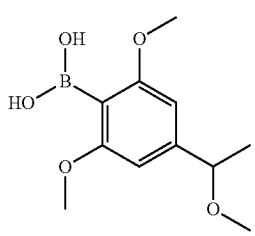

[Chemical Formula 50]

To a tetrahydrofuran (200 ml) solution of 2-bromo-1,3-dimethoxy-5-(1-methoxyethyl)benzene (7.39 g, 26.9 mmol), was added dropwise 1.57M n-butyl lithium (18.8 ml, 29.6 mmol) at −78° C., and the mixture was stirred for 30 minutes. To the mixture, was added dropwise trimethyl borate (6.00 ml, 53.8 mmol), and warmed to room temperature. After the reaction was completed, a saturated aqueous solution of ammonium chloride was added while cooling on ice, which was extracted with ethyl acetate and dried over anhydrous magnesium sulfate, and the solvent was then distilled off under reduced pressure. The residue was purified by silica gel column chromatography (n-heptane/ethyl acetate=1/1) to obtain the title compound (4.97 g, 20.7 mmol)

$^1$H-NMR (CDCl$_3$) δ: 1.44 (d, J=6.4 Hz, 3H), 3.27 (s, 3H), 3.92 (s, 6H), 4.28 (q, 6.4 Hz, 1H), 6.58 (s, 2H), 7.18 (s, 2H).

Production Example 17-1

1-Cyclopropyl-3,5-dimethoxybenzene

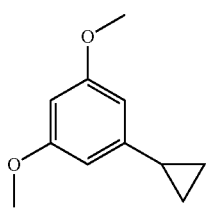

[Chemical Formula 51]

To a solution of 1-bromo-3,5-dimethoxybenzene (2.00 g, 9.21 mmol) in dioxane (30 mL) and water (10 mL) were added potassium cyclopropyl trifluoroborate (2.73 g, 18.4 mmol), 2-dicyclohexylphosphino-2',6'-dimethoxybiphenyl (756 mg, 1.84 mmol), palladium(II) acetate (207 mg, 0.92 mmol) and cesium carbonate (18.0 g, 55.3 mmol), and the mixture was heated at 100° C. for 16 hours. After the reaction was completed, water was added to the reaction mixture, which was extracted with ethyl acetate and dried over anhydrous magnesium sulfate, and the solvent was distilled off under reduced pressure. The residue was purified by silica gel column chromatography (n-heptane/ethyl acetate: 3/1) to obtain the title compound (1.61 g, 9.03 mmol).

$^1$H-NMR (CDCl$_3$) δ: 0.66-0.71 (m, 2H), 0.90-0.96 (m, 2H), 1.80-1.90 (m, 1H), 3.77 (s, 6H), 6.20-6.30 (m, 3H).

Production Example 17-2

(4-Cyclopropyl-2,6-dimethoxyphenyl)boronic acid

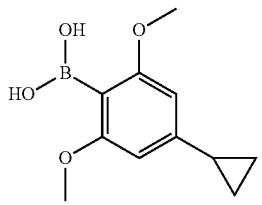

[Chemical Formula 52]

To a tetrahydrofuran (45 ml) solution of 1-cyclopropyl-3,5-dimethoxybenzene (1.59 g, 8.92 mmol) was added N,N,N,N-tetramethylethylenediamine (2.01 ml, 13.4 mmol) at room temperature and 2.77M n-butyllithium (4.83 ml, 13.4 mmol) was added dropwise at −78° C., and the mixture was stirred at room temperature for two hours. The temperature was returned to −78° C. again, trimethyl borate (1.49 ml, 13.4 mmol) was added dropwise and warmed to room temperature, and the mixture was stirred for 13 hours. After the reaction was completed, a saturated aqueous solution of ammonium chloride was added to the reaction mixture while cooling on ice, which was extracted with ethyl acetate and dried over anhydrous magnesium sulfate, and the solvent was distilled off under reduced pressure. The residue was purified by silica gel column chromatography (n-heptane/ethyl acetate: 3/1) to obtain the title compound (1.36 g, 6.12 mmol).

$^1$H-NMR (CDCl$_3$) δ: 0.73-0.78 (m, 2H), 1.00-1.06 (m, 2H), 1.84-1.98 (m, 1H), 3.89 (s, 6H), 6.33 (s, 2H), 7.14 (s,

Production Example 18-1

Ethyl(3-methyl-5-oxo-4,5-dihydro-1H-pyrazol-1-yl)acetate

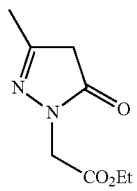

[Chemical Formula 53]

To an ethanol (250 mL) solution of ethyl hydrazinoacetate monohydrochloride (19.4 g, 125 mmol) was added triethylamine (19.2 mL, 138 mmol), and the mixture was stirred at room temperature for 10 minutes, and then ethyl acetoacetate (16.6 mL, 131 mmol) was added, and the mixture was heated to reflux for four hours. After returning the mixture to room temperature, the solvent was distilled off under reduced pressure. N-heptane (100 mL) was added to the residue to yield a solid, and the obtained solid was filtered and washed with n-heptane to obtain primary crystals of the title compound (17.1 g, 93.0 mmol). Furthermore, the solvent in the filtrate was distilled off under reduced pressure, and to the residue, n-heptane/acetone mixture (1:1) was added to yield a solid, and the obtained solid was filtered. Thus, secondary crystals of the title compound (0.44 g, 2.39 mmol) were obtained.

$^1$H-NMR (CDCl$_3$) δ: 1.28 (t, J=7.2 Hz, 3H), 2.12 (s, 3H), 3.26 (s, 2H), 4.22 (q, 2H), 4.42 (s, 2H).

Production Example 18-2

Ethyl(5-chloro-4-formyl-3-methyl-1H-pyrazol-1-yl)acetate

[Chemical Formula 54]

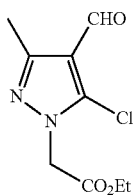

DMF (2.01 mL) was cooled to 0° C. and phosphorus oxychloride (5.67 mL, 60.8 mmol) was added dropwise. This reaction mixture was warmed to room temperature, and then ethyl(3-methyl-5-oxo-4,5-dihydro-1H-pyrazol-1-yl)acetate (1.60 g, 8.69 mmol) was added slowly, and then the mixture was stirred at 110° C. for 3.5 hours. After the reaction was completed, the mixture was poured into ice water, a 5N aqueous solution of sodium hydroxide and sodium hydrogencarbonate were added to the mixture for neutralization. The extraction with ethyl acetate was carried out, the organic layer was washed with brine and dried over anhydrous magnesium sulfate. The mixture was filtered to obtain filtrate, and the solvent was distilled off under reduced pressure to yield a solid, and the obtained solid was washed with n-heptane/diisopropyl ether mixture (1:1), and dried to obtain the title compound 1.28 g (5.55 mmol).

$^1$H-NMR (CDCl$_3$) δ: 1.30 (t, J=7.2 Hz, 3H), 2.47 (s, 3H), 4.26 (q, J=7.2 Hz, 2H), 4.88 (s, 2H), 9.88 (s, 1H).

Production Example 18-3

Ethyl 7-formyl-6-methyl-2-(methylthio)pyrazolo[5,1-b][1,3]thiazole-3-carboxylate

[Chemical Formula 55]

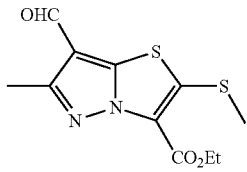

To a mixture of ethyl(5-chloro-4-formyl-3-methyl-1H-pyrazol-1-yl)acetate (560 mg, 2.43 mmol), potassium hydroxide (495 mg, 7.5 mmol) and DMSO (9.72 mL) was added carbon disulfide (194 μL, 3.21 mmol), and the mixture was stirred at room temperature for 18 hours. To the reaction mixture, methyl iodide (182 μL, 2.92 mmol) was added, and the mixture was further stirred at room temperature for 8 hours. This reaction mixture was poured into ice water to yield a solid, and the obtained solid was filtered, and then washed with water and dried to obtain the title compound (346.1 mg, 1.22

$^1$H-NMR (CDCl$_3$) δ: 1.47 (t, J=7.2 Hz, 3H), 2.65 (s, 3H), 2.68 (s, 3H), 4.53 (q, J=7.2 Hz, 2H), 9.90 (s, 1H).

Production Example 18-4

Ethyl 7-[(tert-butoxycarbonyl)amino]-6-methyl-2-(methylthio)pyrazolo[5,1-b][1,3]thiazole-3-carboxylate

[Chemical Formula 56]

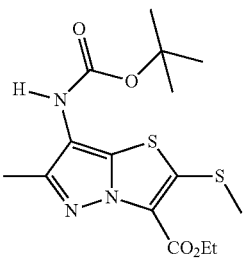

To an acetone (7 mL) solution of ethyl 7-formyl-6-methyl-2-(methylthio)pyrazolo[5,1-b][1,3]thiazole-3-carboxylate (100 mg, 0.35 mmol), was added aqueous (3 mL) solution of potassium permanganate (83.4 mg, 0.53 mmol), and the mixture was stirred at room temperature for 45 minutes. To the reaction mixture, aqueous hydrogen peroxide was added, and insoluble matters were filtered off and then the organic solvent in the filtrate was distilled off under reduced pressure. The residue was subjected to cotton filtration, and a 2N aqueous solution of hydrochloric acid was added thereto to yield a solid, the obtained solid was filtered and dried. To a toluene (2 mL) solution of the obtained white solid (80.3 mg, 0.27 mmol) were added diphenylphosphoryl azide (63.1 μL, 0.29 mmol), triethylamine (44.7 μL, 0.32 mmol) and tert-butyl alcohol (122 μL, 1.33 mmol), and the mixture was stirred at 110° C. for two hours. The solvent in the reaction mixture was distilled off under reduced pressure, and the residue was purified by medium pressure silica gel column chromatography (n-heptane/ethyl acetate: 25% then 66%) to obtain 35.7 mg (0.096 mmol) of the title compound.

$^1$H-NMR (CDCl$_3$) δ: 1.45 (t, J=7.2 Hz, 3H), 1.52 (s, 9H), 2.35 (s, 3H), 2.61 (s, 3H), 4.49 (q, J=7.2 Hz, 2H), 6.09 (br.s, 1H).

Production Example 18-5

7-[(tent-Butoxycarbonyl)amino]-6-methyl-2-(methylthio)pyrazolo[5,1-b][1,3]thiazole-3-carboxylic acid

[Chemical Formula 57]

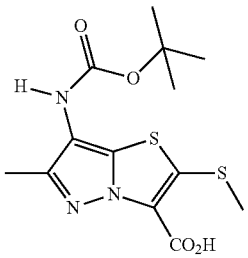

To an ethanol (30 mL) solution of ethyl 7-[(tert-butoxycarbonyl)amino]-6-methyl-2-(methylthio)pyrazolo[5,1-b][1,3]thiazole-3-carboxylate (775 mg, 2.09 mmol) was added sodium hydroxide (836 mg, 20.9 mmol), water (20 mL) and ethanol (10 mL) were further added, and the mixture was stirred at room temperature for 1.5 hours. To the reaction mixture, a 2N aqueous solution of hydrochloric acid and ethyl acetate were added, and a substance of interest was extracted with ethyl acetate. The organic layer was washed with brine, and dried over magnesium sulfate, and the solvent was distilled off under reduced pressure and dried to obtain 718 mg (2.09 mmol) of the title compound.

$^1$H-NMR (CDCl$_3$) δ: 1.53 (s, 9H), 2.32 (s, 3H), 2.64 (s, 3H), 6.13 (br s, 1H).

Production Example 18-6 tert-Butyl[3-bromo-6-methyl-2-(methylthio)pyrazolo[5,1-b][1,3]thiazol-7-yl]carbamate

[Chemical Formula 58]

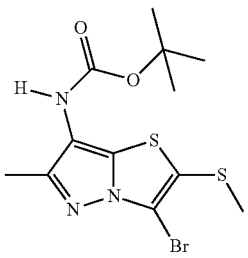

To an aqueous solution (10 mL) of 7-[(tert-butoxycarbonyl)amino]-6-methyl-2-(methylthio)pyrazolo[5,1-b][1,3]thiazole-3-carboxylic acid (180 mg, 0.53 mmol), were added potassium hydroxide (34.7 mg, 0.53 mmol) and silver carbonate (93.6 mg, 0.55 mmol), and the mixture was stirred at room temperature for 1.5 hours. The solid was filtered, washed with water, and then dried. To a mixture of the obtained solid and carbon tetrachloride (3.6 mL) was added bromine (29.6 μL, 0.58 mmol), and the mixture was stirred at 75° C. for five hours. To the reaction mixture was added chloroform, and the insoluble matters were filtered off, and then the solvent was distilled off under reduced pressure. The residue was purified by medium pressure silica gel column chromatography (n-heptane/ethyl acetate: 33% then 66%) to obtain 94.0 mg (0.25 mmol) of the title compound.

$^1$H-NMR (CDCl$_3$) δ: 1.53 (s, 9H), 2.35 (s, 3H), 2.45 (s, 3H), 6.08 (br.s, 1H).

Production Example 19-1

1-(6-Methylpyrazolo[5,1-b][1,3]thiazol-7-yl)ethanone

[Chemical Formula 59]

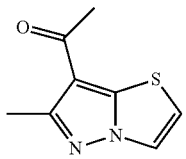

To a dichloromethane (35 mL) solution of 2-methylthiazole (5.77 g, 58.2 mmol), was added a dichloromethane (35 mL) solution of O-(mesitylenesulfonyl)hydroxylamine (12.53 g, 58.2 mmol) at 0° C., and the mixture was stirred at room temperature for 9.5 hours. The solvent in the reaction mixture was distilled off under reduced pressure, and the obtained white solid (14.66 g, 46.6 mmol) was dried under reduced pressure over one day and night.

A mixture of the white solid (15.6 g, 49.6 mmol) obtained in the above-mentioned procedure, sodium acetate (6.1 g, 74.4 mmol) and acetic anhydride (125 mL) was heated to reflux at 130° C. for five hours. The solvent in the reaction mixture was distilled off under reduced pressure, and water was added to the residue. After cooling to 0° C., a saturated aqueous solution of potassium carbonate was added, and a substance of interest was extracted with ethyl acetate. The organic layer was washed with brine and dried over anhydrous magnesium sulfate. The mixture was filtered to yield a filtrate, and then a solvent was distilled off under reduced pressure. To the residue, diisopropyl ether (40 mL) was added, and the obtained solid was filtered and dried to obtain 5.25 g (29.13 mmol) of the title compound.

$^1$H-NMR (CDCl$_3$) δ: 2.51 (s, 3H), 2.65 (s, 3H), 7.00 (d, J=4.0 Hz, 1H), 7.76 (d, J=4.0 Hz, 1H).

Production Example 19-2

6-Methylpyrazolo[5,1-b][1,3]thiazole-7-amine

[Chemical Formula 60]

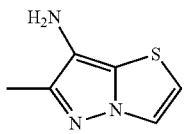

A mixture of 1-(6-methylpyrazolo[5,1-b][1,3]thiazol-7-yl)ethanone (1.02 g, 5.66 mmol) and a 5N aqueous solution of hydrochloric acid (23.8 mL) was cooled to 0° C., and an aqueous (1.5 mL) solution of sodium nitrite (781 mg, 11.3 mmol) was added. This reaction mixture was stirred at 0° C. for two hours, then, warmed to room temperature, and further stirred at room temperature over one day and night. A 5N aqueous solution of sodium hydroxide was added to the mixture so that the solution became basic, and a produced blue solid was filtered and washed with a small amount of water. The obtained blue solid was dissolved in a 2N aqueous solution of hydrochloric acid (22 mL), zinc powder (370 mg, 5.66 mmol) was added thereto, and the mixture was stirred at room temperature for 15 minutes. To the mixture, zinc powder (370 mg, 5.66 mmol) was added again, and the mixture was stirred at room temperature for one hour. The insoluble matters were filtered off and then a 5N aqueous solution of sodium hydroxide was added to the filtrate at 0° C. for neutralization. A substance of interest was extracted with ethyl acetate, and the organic layer washed with brine, and dried over magnesium sulfate. The mixture was filtered to yield a filtrate, and the solvent was distilled off under reduced pressure, and the obtained solid was dried to obtain 605.8 mg (3.95 mmol) of the title compound.

$^1$H-NMR (CDCl$_3$) δ: 2.34 (s, 3H), 2.72 (br.s, 2H), 6.65 (d, J=4.0 Hz, 1H), 7.56 (d, J=4.0 Hz, 1H).

Production Example 19-3 tert-Butyl(6-methylpyrazolo[5,1-b][1,3]thiazol-7-yl)carbamate

[Chemical Formula 61]

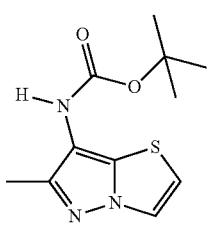

To a dichloromethane (20 mL) solution of 6-methylpyrazolo[5,1-b][1,3]thiazole-7-amine (606 mg, 3.96 mmol) were added di-tert-butyl dicarbonate (951 mg, 4.36 mmol) and methylamine (829 μl, 5.94 mmol), and the mixture was stirred at room temperature over one day and night. Water was added to the reaction mixture, and a substance of interest was extracted with dichloromethane, and the organic layer was dried over anhydrous magnesium sulfate. The mixture was filtered to yield a filtrate, and then a solvent was distilled off under reduced pressure, and the residue was purified by medium pressure silica gel column chromatography (n-heptane/ethyl acetate: 50%) to obtain 808.4 mg (3.19 mmol) of the title compound.

$^1$H-NMR (CDCl$_3$) δ: 1.53 (s, 9H), 2.33 (s, 3H), 6.03 (br.s, 1H), 6.71 (d, J=4.0 Hz, 1H), 7.59 (d, J=4.0 Hz, 1H).

Production Example 19-4 tert-Butyl(3-bromo-6-methylpyrazolo[5,1-b][1,3]thiazol-7-yl)carbamate

[Chemical Formula 62]

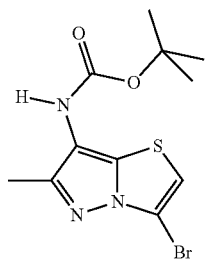

A tetrahydrofuran (40 mL) solution of tert-butyl(6-methylpyrazolo[5,1-b][1,3]thiazol-7-yl)carbamate (1.20 g, 4.74 mmol) was cooled to −78° C., and n-butyllithium (1.57 M, 6.64 mL, 10.4 mmol) was added dropwise thereto, and the mixture was stirred for 30 minutes. Then, 1,2-dibromotetrafluoroethane (619 μl, 5.21 mmol) was added to the mixture, and the reaction mixture was warmed to room temperature, and stirred at room temperature for one hour. To the reaction mixture, a saturated aqueous solution of ammonium chloride was added, and a substance of interest was extracted with ethyl acetate. The organic layer was washed with brine and dried over magnesium sulfate, and the solvent was distilled off under reduced pressure. The residue was purified by medium pressure silica gel column chromatography (n-heptane/ethyl acetate: 50% then 66%) to obtain 1.39 g (4.32 mmol) of the title compound.

$^1$H-NMR (CDCl$_3$) δ: 1.52 (s, 9H), 2.37 (s, 3H), 6.07 (br.s, 2H), 6.68 (s, 1H).

Production Example 20-1

2,5-Dimethyl-1,3-thiazole

[Chemical Formula 63]

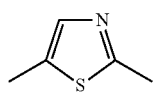

To a tetrahydrofuran (30 mL) solution of 2-methylthiazole (1.00 g, 10.1 mmol) was added n-butyllithium (4.02 mL, 10.6 mmol) dropwise at −78° C. and the mixture was stirred for 30 minutes. To the mixture was added iodomethane (0.69 mL, 11.1 mmol) and the mixture was warmed to room temperature. After the reaction was completed, water was added to the reaction mixture while cooling on ice, which was extracted with ethyl acetate. The organic layer was washed with brine and dried over anhydrous magnesium sulfate. The mixture was filtered to yield a filtrate, and distilled off under reduced pressure to obtain the title compound (864 mg, 7.63 mmol).

$^1$H-NMR (CDCl$_3$) δ: 2.41 (s, 3H), 2.64 (s, 3H), 7.24 (s, 1H).

Production Example 20-2

1-(2,6-Dimethylpyrazolo[5,1-b][1,3]thiazol-7-yl)ethanone

[Chemical Formula 64]

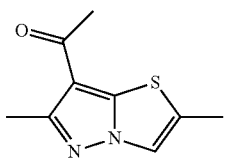

To a dichloromethane (5 mL) solution of 2,5-dimethyl-1,3-thiazole (864 mg, 7.63 mmol) was added a dichloromethane (6 mL) solution of O-(mesitylenesulfonyl)hydroxylamine (1.64 g, 7.63 mmol) at 0° C., and the mixture was stirred at room temperature for four hours. The solvent in the reaction mixture was distilled off under reduced pressure to obtain a crude compound (2.51 g, 7.63 mmol).

A mixture of the crude compound (2.51 g, 7.63 mmol), sodium acetate (940 mg, 11.5 mmol) and acetic anhydride (19.5 mL) was heated at 130° C. to reflux for five hours. The solvent in the reaction mixture was distilled off under reduced pressure, and then water was added to the residue. The mixture residue was cooled to 0° C., then, a saturated aqueous solution of potassium carbonate was added to the mixture, and a substance of interest was extracted with ethyl acetate. The organic layer was washed with brine and dried over anhydrous magnesium sulfate. The mixture was filtered to yield a filtrate, and then the solvent was distilled off under reduced pressure. The residue was purified by silica gel column chromatography (n-heptane/ethyl acetate: 2/1 then 1/1) to obtain the title compound (655 mg, 3.37 mmol).

$^1$H-NMR (CDCl$_3$) δ: 2.48 (s, 6H), 2.62 (s, 3H), 7.46 (s, 1H).

Production Example 20-3

2,6-Dimethylpyrazolo[5,1-b][1,3]thiazole-7-amine

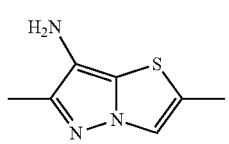

[Chemical Formula 65]

A mixture of 1-(2,6-dimethylpyrazolo[5,1-b][1,3]thiazol-7-yl)ethanone (655 mg, 3.37 mmol) and a 5N aqueous solution of hydrochloric acid (14.2 mL) was cooled to 0° C., and an aqueous (1.0 mL) solution of sodium nitrite (465 mg, 6.74 mmol) was added. This reaction mixture was stirred at room temperature over one day and night. To the mixture was added a 5N aqueous solution of sodium hydroxide at 0° C. to make the solution basic, and produced blue solid was filtered and washed with a small amount of water. The obtained blue solid was dissolved in a 2N aqueous solution of hydrochloric acid (13.5 mL), zinc powder (220 mg, 3.37 mmol) was added to the mixture, and the mixture was stirred at room temperature for 15 minutes. To the mixture, zinc powder (220 mg, 3.37 mmol) was added again, and the mixture was stirred at room temperature for 1.5 hours. The insoluble matters were filtered off and then a 5N aqueous solution of sodium hydroxide was added to the filtrate at 0° C. to neutralize the mixture. A substance of interest was extracted with ethyl acetate, and the organic layer was washed with brine, and dried over magnesium sulfate. The mixture was filtered to yield a filtrate, the solvent was distilled off under reduced pressure, and the obtained solid was dried to obtain the title compound (306 mg, 1.83 mmol).

$^1$H-NMR (CDCl$_3$) δ: 2.30 (s, 3H), 2.37 (s, 3H), 7.27 (s, 1H).

Production Example 20-4 tert-Butyl(2,6-dimethylpyrazolo[5,1-b][1,3]thiazol-7-yl)carbamate

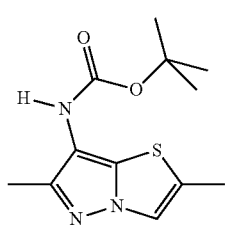

[Chemical Formula 66]

To a dichloromethane (10 mL) solution of 2,6-dimethylpyrazolo[5,1-b][1,3]thiazole-7-amine (306 mg, 1.83 mmol) were added di-tert-butyl dicarbonate (439 mg, 2.01 mmol) and triethylamine (0.383 ml, 2.75 mmol), and the mixture was stirred at room temperature over one day and night. Water was added to the reaction mixture, a substance of interest was extracted with dichloromethane, and the organic layer was dried over anhydrous magnesium sulfate. The mixture was filtered to yield a filtrate, the solvent was distilled off under reduced pressure, and the residue was purified by medium pressure silica gel column chromatography (n-heptane/ethyl acetate: 1/1) to obtain the title compound (266 mg, 0.995 mmol).

$^1$H-NMR (CDCl$_3$) δ: 1.52 (s, 9H), 2.28 (s, 3H), 2.36 (s, 3H), 5.98 (br.s, 1H), 7.29 (s, 1H).

Production Example 20-5 tert-Butyl(3-bromo-2,6-dimethylpyrazolo[5,1-b][1,3]thiazol-7-yl)carbamate

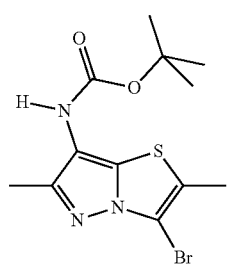

[Chemical Formula 67]

A tetrahydrofuran (10 mL) solution of tert-butyl(2,6-dimethylpyrazolo[5,1-b][1,3]thiazol-7-yl)carbamate (266 mg, 0.995 mmol) was cooled to −78° C., and n-butyllithium (2.64M, 0.829 mL, 2.19 mmol) was added dropwise and the mixture was stirred for 10 minutes. Then, 1,2-dibromotetrafluoroethane (0.142 ml, 1.19 mmol) was added to the mixture, and the reaction mixture was warmed to room temperature and stirred at room temperature over one day and night. To the reaction mixture, a saturated aqueous solution of ammonium chloride was added, and a substance of interest was extracted with ethyl acetate. The organic layer was washed with brine and dried over magnesium sulfate, and the solvent was distilled off under reduced pressure. The residue was purified by medium pressure silica gel column chromatography (n-heptane/ethyl acetate: 3/1 then 2/1) to obtain the title compound (203 mg, 0.586 mmol).

$^1$H-NMR (CDCl$_3$) δ: 1.52 (s, 9H), 2.34 (s, 6H), 6.04 (s, 1H).

Production Example 21-1

Ethyl 6-oxo-5,6-dihydropyrazolo[5,1-b][1,3]thiazole-7-carboxylate

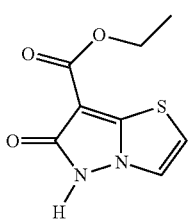

[Chemical Formula 68]

To a mixture of diethyl malonate (100 g, 624 mmol) and DMF (900 mL) were added cesium carbonate (488 g, 1.5 mol) and carbon disulfide (45.3 mL, 749 mmol) while stirring at room temperature, and the mixture was stirred at room temperature for five minutes. Bromoacetaldehyde diethyl acetal (290 mL, 1.87 mol) was added dropwise to the mixture at room temperature, and then sodium iodide (9.34 g, 62.4 mmol) was added and the mixture was stirred at 60° C. for eight hours. To the mixture were added water and diethyl ether at room temperature.

After thoroughly shaking the mixture, the organic layer was separated, the organic layer was washed with brine and dried over anhydrous magnesium sulfate. The mixture was filtered, and then the solvent in the filtrate was distilled off under reduced pressure.

To a mixture of the obtained residue and ethanol (900 mL) was added hydrazine hydrate (60.7 mL, 1.25 mol) while stirring in a water bath, and the mixture was stirred at room temperature for 13 hours. The mixture was filtered, the solvent in the filtrate was distilled off under reduced pressure.

To the obtained residue, were added 1,4-dioxane (1 L) and 5N hydrochloric acid (200 mL) in this order, and the mixture was stirred at 60° C. for four hours. After returning the mixture to room temperature, the solvent in the mixture was distilled off under reduced pressure. Water was added to the obtained residue, and the mixture was filtered, and the filtered residue and filtrate were obtained. The residue was further washed with water and dried under reduced pressure to obtain the title compound (42.5 g, 200 mmol).

To the above-mentioned obtained filtrate was added ethyl acetate. After thoroughly shaking the mixture, the organic layer was separated, and the organic layer was washed with brine and dried over anhydrous magnesium sulfate. The mixture was filtered, and then the solvent in the filtrate was distilled off under reduced pressure. To the obtained residue, diethyl ether was added, and precipitated solid was collected by filtration and dried under reduced pressure to further obtain the title compound (2.6 g, 12.3 mmol).

$^1$H-NMR (CDCl$_3$) δ: 1.41 (t, J=7.0 Hz, 3H), 4.40 (q, J=7.0 Hz, 2H), 6.89 (d, J=4.0 Hz, 1H), 7.69 (d, J=4.4 Hz, 1H).

Production Example 21-2

Ethyl 6-methoxypyrazolo[5,1-b][1,3]thiazole-7-carboxylate

[Chemical Formula 69]

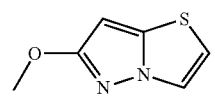

To a mixture of ethyl 6-oxo-5,6-dihydropyrazolo[5,1-b][1,3]thiazole-7-carboxylate (41.3 g, 195 mmol) and DMR (624 mL) were added cesium carbonate (127 g, 389 mmol) and iodomethane (24.2 mL, 389 mmol) while stirring at room temperature. After the mixture was stirred at room temperature for one hour, a mixed solvent of water and ethyl acetate/diethyl ether (1/1) was added.

After thoroughly shaking the mixture, the organic layer was separated, and the organic layer was washed with brine and dried over anhydrous magnesium sulfate. The mixture was filtered, and then the solvent in the filtrate was distilled off under reduced pressure. The residue was purified by silica gel column chromatography (a mixed solvent of n-heptane and ethyl acetate: n-heptane/ethyl acetate=9/1 then 1/2.3) to obtain the title compound (30.7 g, 136 mmol).

$^1$H-NMR (CDCl$_3$) δ: 1.39 (t, J=7.0 Hz, 3H), 4.08 (s, 3H), 4.35 (q, J=7.0 Hz, 2H), 6.87 (d, J=4.4 Hz, 1H), 7.66 (d, J=4.4 Hz, 1H).

Production Example 21-3

6-Methoxypyrazolo[5,1-b][1,3]thiazole

[Chemical Formula 70]

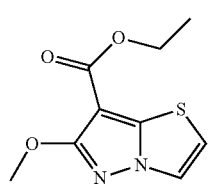

To a mixture of ethyl 6-methoxypyrazolo[5,1-b][1,3]thiazole-7-carboxylate (30.7 g, 136 mmol) and ethanol (407 mL) was added a 5N aqueous solution of sodium hydroxide (136 mL) while stirring at room temperature, and the mixture was stirred at 80° C. for two hours. 5N hydrochloric acid was appropriately added while stirring on ice so that the mixture became substantially neutral. Ethanol in the mixture was distilled off under reduced pressure. A solid precipitated in the mixture was collected by filtration, and washed with water.

To the obtained residue, were added 1,4-dioxane (400 mL) and concentrated hydrochloric acid (200 mL) in this order and stirred at 60° C. for 1.5 hours. 1,4-Dioxane in the mixture was distilled off under reduced pressure. Sodium hydroxide was appropriately added while stirring on ice so that the mixture became weak acidic and then ethyl acetate was added.

After thoroughly shaking the mixture, the organic layer was separated, and the organic layer was washed with brine and dried over anhydrous magnesium sulfate. The mixture was filtered, and then the solvent in the filtrate was distilled off under reduced pressure. The residue was purified by silica gel column chromatography (a mixed solvent of n-heptane and ethyl acetate: n-heptane/ethyl acetate=1/0 then 2.3/1) to obtain the title compound (15.8 g, 103 mmol).

$^1$H-NMR (CDCl$_3$) δ: 3.95 (s, 3H), 5.81 (d, J=0.8 Hz, 1H), 6.60 (d, J=4.0 Hz, 1H), 7.58 (dd, J=0.8, 4.4 Hz, 1H).

Production Example 21-4 tert-Butyl(6-methoxypyrazolo[5,1-b][1,3]thiazol-7-yl)carbamate

[Chemical Formula 71]

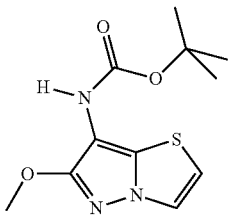

To a mixture of 6-methoxypyrazolo[5,1-b][1,3]thiazole (15.8 g, 103 mmol) and 5N hydrochloric acid (350 mL), was added a mixture of sodium nitrite (10.6 g, 154 mmol) and water (115 mL) while stirring on ice. The mixture was stirred at room temperature for 0.5 hours, and then an appropriate amount of a 5N aqueous solution of sodium hydroxide was added while stirring on ice so that the mixture became substantially neutral. The precipitate in the mixture was collected by filtration, and washed with water.

To the obtained residue were added ethanol (200 mL), TI-IF (300 mL) and 10% palladium-carbon (50% wet: 16 g) in this order, and the mixture was stirred in a normal-pressure hydrogen atmosphere at room temperature for five hours. The mixture was filtered with Celite, and the solvent in the obtained filtrate was distilled off under reduced pressure.

To a mixture of the obtained residue and dichloromethane (425 mL), di-tert-butyl dicarbonate (24.1 g, 111 mmol) and triethylamine (17.8 mL, 128 mmol) were added while stirring at room temperature, and the mixture was stirred at room temperature for 11 hours. The solvent in the mixture was distilled off under reduced pressure, and the residue was purified by silica gel column chromatography (a mixed solvent of n-heptane and ethyl acetate: n-heptane/ethyl acetate=2/1) to obtain the title compound (16.5 g, 61.4 mmol).

$^1$H-NMR (CDCl$_3$) δ: 1.51 (s, 9H), 3.98 (s, 3H), 6.12 (br.s, 1H), 6.54 (d, J=4.0 Hz, 1H), 7.48 (d, J=4.4 Hz, 1H).

Production Example 21-4-2

Alternative synthesis method of tert-butyl(6-methoxy-pyrazolo[5,1-b][1,3]thiazol-7-yl)carbamate To a mixture of 6-methoxypyrazolo[5,1-b]thiazole-7-carboxylic acid (300 mg, 1.51 mmol) and 1,4-dioxane (4 mL) were added triethylamine (0.215 mL, 1.54 mmol) and diphenylphosphoryl azide (0.325 mL, 1.51 mmol) while stirring at room temperature, and the resulting mixture was stirred and heated to reflux for three hours. After returning the mixture to room temperature, triethylamine (0.631 mL, 4.53 mmol) and tert-butanol (0.289 mL, 3.02 mmol) were added, and the resulting mixture was stirred and heated to reflux for three hours. After returning the mixture to room temperature, the solvent was distilled off under reduced pressure and the residue was purified by silica gel column chromatography (mixture solvent of n-heptane and ethyl acetate: n-heptane/ethyl acetate=1/4) to obtain the title compound (144 mg, 0.535 mmol).

$^1$H-NMR (CDCl$_3$) δ: 1.51 (s, 9H), 3.98 (s, 3H), 6.12 (br.s, 1H), 6.54 (d, J=-4.0 Hz, 1H), 7.48 (d, J=4.4 Hz, 1H)

Production Example 21-5 tert-Butyl(3-bromo-6-methoxypyrazolo[5,1-b][1,3]thiazol-7-yl)carbamate

[Chemical Formula 72]

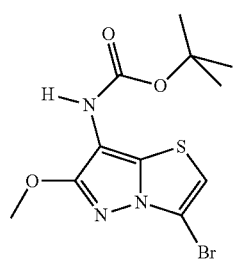

To a mixture of tert-butyl(6-methoxypyrazolo[5,1-b][1,3]thiazol-7-yl)carbamate (16.5 g, 61.4 mmol) and THF (410 mL) was added n-butyllithium (2.77 M n-hexane solution: 62.1 mL, 172 mmol) while stirring at −78° C. After stirring the mixture at −78° C. for 40 minutes, 1,2-dibromotetrafluoroethane (10.2 mL, 86 mmol) was added, and the mixture was stirred for two hours while warming to mom temperature. A saturated aqueous solution of ammonium chloride and ethyl acetate were added to the mixture, and then acetic acid was added so that the mixture became weakly acidic. After thoroughly shaking the mixture, the organic layer was separated and the organic layer was washed with brine and dried over anhydrous magnesium sulfate. The mixture was filtered, and then the solvent in the filtrate was distilled off under reduced pressure. The residue was purified by silica gel column chromatography (a mixed solvent of n-heptane and ethyl acetate: n-heptane/ethyl acetate=1/0 then 4/1) to obtain the title compound (14.3 g, 41.1 mmol).

$^1$H-NMR (CDCl$_3$) δ: 1.51 (s, 9H), 4.04 (s, 3H), 6.16 (br.s, 1H), 6.50 (s, 1H).

Production Example 22-1

6-Ethoxypyrazolo[5,1-b][1,3]thiazole-7-carboxylic acid ethyl ester

[Chemical Formula 73]

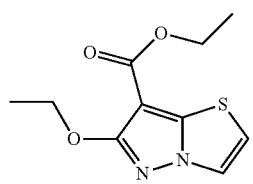

To a DMF (119 mL) solution of 6-oxo-5,6-dihydro-pyrazolo[5,1-b][1,3]thiazole-7-carboxylic acid ethyl ester (8.5 g, 40.2 mmol), cesium carbonate (26.1 g, 80.2 mmol) and iodo-ethane (8.3 mL, 80.2 mmol) were added while stirring at room temperature. The mixture was stirred at room temperature for one hour, was extracted with diethyl ether, washed with brine, and dried over anhydrous magnesium sulfate, and then the solvent was distilled off under reduced pressure. The residue was purified by medium pressure amino silica gel column chromatography (n-heptane/ethyl acetate: 10% then 40%) to obtain the title compound (7.01 g, 29.2 mmol).

$^1$H-NMR (CDCl$_3$) δ: 1.38 (t, J=7.0 Hz, 3H), 1.49 (t, J=7.2 Hz, 3H), 4.34 (q, J=7.0 Hz, 2H), 4.41 (q, J=7.2 Hz, 2H), 6.84 (d, J=4.0 Hz, 1H), 7.64 (d, J=4.0 Hz, 1H).

Production Example 22-2

6-Ethoxy-pyrazolo[5,1-b][1,3]thiazole

[Chemical Formula 74]

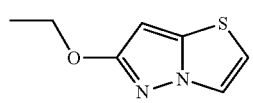

To an ethanol (88 mL) solution of 6-ethoxypyrazolo[5,1-b][1,3]thiazole-7-carboxylic acid ethyl ester (7.01 g, 29.2 mmol), was added a 5N aqueous solution of sodium hydroxide (29.2 mL) while stirring at room temperature, and the mixture was stirred at 80° C. for two hours. The reaction mixture was returned to room temperature, and neutralized with 5N hydrochloric acid while stirring on ice, and ethanol in the reaction mixture was distilled off under reduced pressure. The precipitated solid was collected by filtration and washed with water.

The obtained solid was suspended in 1,4-dioxane (80 mL), and concentrated hydrochloric acid (40 mL) was added to the suspension, which was stirred at 60° C. for one hour. The reaction mixture was returned to room temperature, and 1,4-dioxane was distilled off under reduced pressure, and then neutralized with potassium carbonate while stirring on ice. The reaction mixture was extracted with ethyl acetate, washed with a saturated aqueous solution of sodium hydrogencarbonate and brine and dried over anhydrous magnesium sulfate, and the solvent was distilled off under reduced pressure to obtain 6 g (35.7 mmol) of the title compound.

$^1$H-NMR (CDCl$_3$) δ: 1.42 (t, J=7.0 Hz, 3H), 4.26 (q, J=7.0 Hz, 2H), 5.80 (s, 1H), 6.60 (d, J=4.4 Hz, 1H), 7.59 (d, J=4.4 Hz, 1H).

Production Example 22-3

6-Ethoxy-pyrazolo[5,1-b][1,3]thiazol-7-yl)-carbamic acid tert-butyl ester

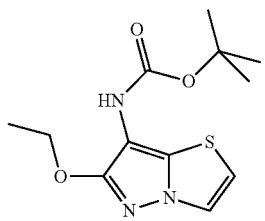

[Chemical Formula 75]

To a 5N hydrochloric acid (90 mL) solution of 6-ethoxy-pyrazolo[5,1-b][1,3]thiazole (4.91 g, 29.2 mmol) was added an aqueous (30 mL) solution of sodium nitrite (3.02 g, 43.8 mmol) while stirring on ice. The mixture was stirred at room temperature for 0.5 hours, and neutralized with a 5N aqueous solution of sodium hydroxide while stirring on ice, and the precipitated solid was collected by filtration and washed with water.

The obtained solid was dissolved in ethanol (60 mL) THE (90 mL), and 10% palladium carbon powder (4.97 g, 50% water wet) was added thereto, followed by catalytic hydrogen reduction under normal pressure at room temperature for five hours. The mixture was filtered with Celite, and the solvent was distilled off under reduced pressure.

The obtained residue was dissolved in dichloromethane (150 mL), di-tert-butyl dicarbonate (8.06 g, 36.9 mmol) and triethylamine (5.94 mL, 42.6 mmol) were added while stirring at room temperature, and the mixture was stirred at room temperature for 25 hours. The solvent was distilled off from the reaction mixture under reduced pressure, and the residue was purified by medium pressure silica gel column chromatography to obtain the title compound (4.44 g, 15.7 mmol) from fraction of n-heptane:ethyl acetate=3:2.

$^1$H-NMR (CDCl$_3$) δ: 1.42 (t, J=7.0 Hz, 3H), 1.52 (s, 9H), 4.31 (q, J=7.0 Hz, 2H), 6.14 (br.s, 1H), 6.52 (d, J=4.0 Hz, 1H), 7.47 (d, J=3.2 Hz, 1H).

Production Example 22-4

(3-Bromo-6-ethoxy-pyrazolo[5,1-b][1,3]thiazol-7-yl)-carbamic acid tert-butyl ester

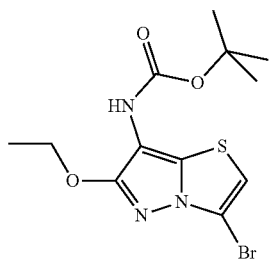

[Chemical Formula 76]

To a THF (150 mL) solution of (6-ethoxy-pyrazolo[5,1-b][1,3]thiazol-7-yl)-carbamic acid tert-butyl ester (16.5 g, 61.4 mmol), was added a 2.77M n-hexane solution of n-butyl-lithium (15.9 mL, 44 mmol) while stirring at −78° C. The mixture was stirred at −78° C. for one hour, and then 1,2-dibromotetrafluoroethane (2.61 mL, 22 mmol) was added, and the mixture was stirred while heating to room temperature for three hours. A saturated aqueous solution of ammonium chloride was added and acetic acid was added, and the mixture was extracted with ethyl acetate and washed with brine, dried over magnesium sulfate, and the solvent was distilled off under reduced pressure. The residue was purified by medium pressure silica gel column chromatography (n-heptane/ethyl acetate: 0% then 30%) to obtain 4.95 g (13.7 mmol) of the title compound.

$^1$H-NMR (CDCl$_3$) δ: 1.42 (t, J=7.0 Hz, 3H), 1.51 (s, 9H), 4.38 (q, J=7.0 Hz, 2H), 6.19 (br.s, 1H), 6.49 (s, 1H).

Production Example 23-1

Ethyl 3,5-dibromo-1H-pyrazole-4-carboxylate (Synthetic Communications, 38, 674-683, 2008)

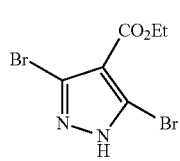

[Chemical Formula 77]

To an ethanol (200 mL) solution of ethyl 1H-pyrazole-4-carboxylate (10.0 g, 71.4 mmol), was added an aqueous (300 mL) solution of sodium acetate (40.4 g, 486 mmol) while stirring at room temperature, and bromine (14.6 mL, 286 mmol) was added dropwise at the same temperature for five hours. After the reaction was completed, water was added while cooling on ice, the reaction mixture was extracted with ethyl acetate, and the organic layer was washed with a saturated aqueous sodium hydrogencarbonate and brine and dried over anhydrous magnesium sulfate, and then the solvent was distilled off under reduced pressure to obtain the title compound (20.9 g, 70.3 mmol).

Production Example 23-2

Ethyl 3,5-dibromo-1-(methoxymethyl)-1H-pyrazole-4-carboxylate

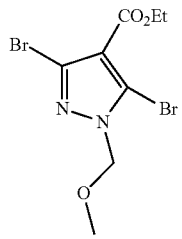

[Chemical Formula 78]

To a tetrahydrofuran (262 mL) solution of ethyl 3,5-dibromo-1H-pyrazole-4-carboxylate (20.93 g, 703 mmol) was added N,N-diisopropylethylamine (24.5 mL, 141 mmol), and chloromethyl methyl ether (6.42 mL, 84.3 mmol) was added dropwise while cooling on ice, and stirred at room temperature for one hour. After the reaction was completed, water was added while cooling on ice, the reaction mixture was extracted with ethyl acetate, the organic layer was dried over magnesium sulfate, and then the solvent was distilled off under reduced pressure. The residue was purified by silica gel column chromatography (n-heptane/ethyl acetate=3/1) to obtain the title compound (23.4 g, 68.5 mmol).

$^1$H-NMR (400 MHz, CDCl$_3$) δ: 1.40 (t, J=7.2 Hz, 3H), 3.41 (s, 3H), 4.37 (q, J=7.2 Hz, 2H), 5.48 (s, 2H).

Production Example 23-3

Ethyl 3-bromo-5-({2-[2,6-dimethoxy-4-methoxymethyl)phenyl]-2-oxoethyl}thio)-1-(methoxymethyl)-1H-pyrazole-4-carboxylate

[Chemical Formula 79]

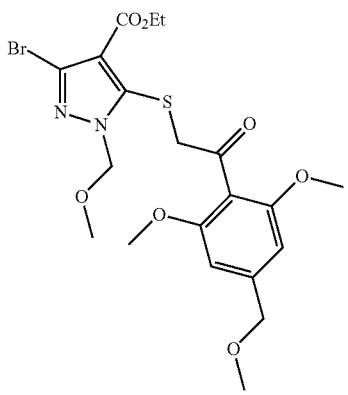

To a N,N-dimethylformamide (70.0 mL) solution of ethyl 3,5-dibromo-1-(methoxymethyl)-1H-pyrazole-4-carboxylate (6.25 g, 18.3 mmol) was added sodium sulfide (1.50 g, 19.2 mmol) and heated at 90° C. for two hours. The temperature of the reaction mixture was returned to room temperature, 2-bromo-1-[2,6-dimethoxy-4-(methoxymethyl)phenyl]ethanone (purity: 86.5%, 6.74 g, 19.3 mmol) was added thereto, and the mixture was stirred for two hours. After the reaction was completed, water was added while cooling on ice, the reaction mixture was extracted with ethyl acetate and dried over magnesium sulfate, and then the solvent was distilled off under reduced pressure. The residue was purified by silica gel column chromatography (n-heptane/ethyl acetate=2/1 then 1/1) to obtain the title compound (7.50 g, 14.5 mmol)

$^1$H-NMR (400 MHz, CDCl$_3$) δ: 1.40 (t, J=7.2 Hz, 3H), 3.35 (s, 3H), 3.41 (s, 3H), 3.72 (s, 6H), 4.30 (s, 2H), 4.36 (q, J=7.2 Hz, 2H), 4.42 (s, 2H), 5.60 (s, 2H), 6.48 (s, 2H).

Production Example 23-4

Ethyl 6-bromo-3-[2,6-dimethoxy-4-(methoxymethyl)phenyl]pyrazolo[5,1-b][1,3]thiazole-7-carboxylate

[Chemical Formula 80]

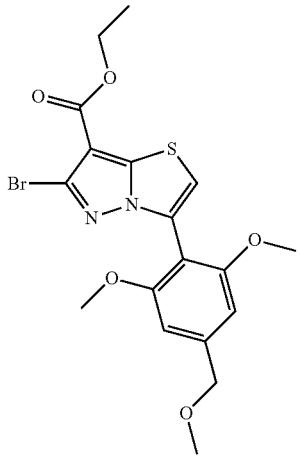

To an isopropanol (50.0 mL) solution of ethyl 3-bromo-5-({2-[2,6-dimethoxy-4-methoxymethyl)phenyl]-2-oxoethyl}thio)-1-(methoxymethyl)-1H-pyrazole-4-carboxylate (4.60 g, 8.89 mmol) was added concentrated hydrochloric acid (1.38 mL, 45.2 mmol) and heated to reflux for 20 hours. After the reaction was completed, the solvent was distilled off under reduced pressure, water (30 mL) was added to the residue, and the obtained solid was subjected to suction filtration, washed with water, and then dried to obtain the title compound (3.84 g, 8.43 mmol).

$^1$H-NMR (400 MHz, CDCl$_3$) δ: 1.41 (t, J=7.2 Hz, 3H), 3.45 (s, 3H), 3.75 (s, 6H), 4.39 (q, J=7.2 Hz, 2H), 4.49 (s, 2H), 6.63 (s, 2H), 6.90 (s, 1H).

Production Example 23-5

6-Bromo-3-[2,6-dimethoxy-4-(methoxymethyl)phenyl]pyrazolo[5,1-b][1,3]thiazole-7-carboxylic acid

[Chemical Formula 81]

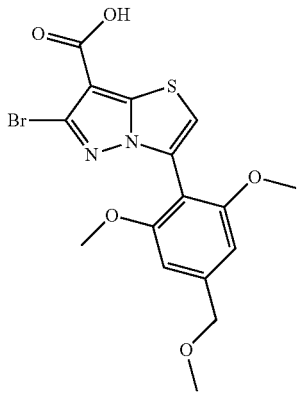

To an ethanol (60.0 mL) solution of ethyl 6-bromo-3-[2,6-dimethoxy-4-(methoxymethyl)phenyl]pyrazolo[5,1-b][1,3]thiazole-7-carboxylate (3.84 g, 8.45 mmol) was added a 5N aqueous solution of sodium hydroxide (5.07 mL, 25.3 mmol) and heated to reflux for two hours. After the reaction was completed, the solvent was distilled off under reduced pressure, water (30 mL) was added to the residue, a 5N aqueous solution of hydrochloric acid was added while cooling on ice so that the solution became acidic, and the precipitated solid was subjected to suction filtration and dried to obtain the title compound (3.4 g, 7.96 mmol).

$^1$H-NMR (400 MHz, DMSO-$d_6$) δ: 3.38 (s, 3H), 3.71 (s, 6H), 4.50 (s, 2H), 6.77 (s, 2H), 7.45 (s, 1H), 13.0 (s, 1H).

Production Example 23-6

6-Bromo-3-[2,6-dimethoxy-4-(methoxymethyl)phenyl]pyrazolo[5,1-b][1,3]thiazole

[Chemical Formula 82]

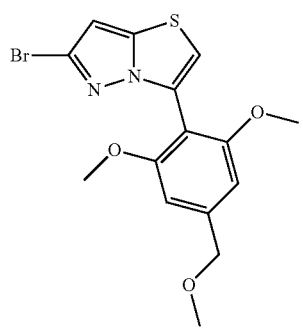

To a 1,4-dioxane (90.0 mL) solution of 6-bromo-3-[2,6-dimethoxy-4-(methoxymethyl)phenyl]pyrazolo[5,1-b][1,3]thiazole-7-carboxylic acid (5.00 g, 11.7 mmol) was added concentrated hydrochloric acid (14.9 mL) and the mixture was heated to reflux for 13 hours. After the reaction was completed, the solvent was distilled off under reduced pressure, water (50 mL) was added to the residue, and the precipitated solid was subjected to suction filtration and dried to obtain the title compound (1.12 g, 2.92 mmol).

$^1$H-NMR (400 MHz, CDCl$_3$) δ: 3.45 (s, 3H), 3.76 (s, 6H), 4.49 (s, 2H), 6.43 (s, 1H), 6.63 (s, 2H), 6.72 (s, 1H).

Production Example 23-7

3-[2,6-Dimethoxy-4-(methoxymethyl)phenyl]-6-(methylsulfonyl)pyrazolo[5,1-b][1,3]thiazole

[Chemical Formula 83]

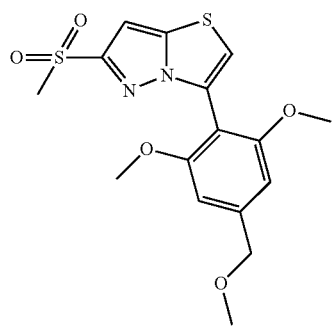

To a dimethyl sulfoxide (28.0 mL) solution of 6-bromo-3-[2,6-dimethoxy-4-(methoxymethyl)phenyl]pyrazolo[5,1-b][1,3]thiazole (1.12 g, 2.92 mmol) were added sodium methanesulphinate (2.38 g, 23.3 mmol), L-proline (268 mg, 2.33 mmol), sodium hydroxide (184 mg, 4.61 mmol), and copper iodide (444 mg, 2.33 mmol) and the mixture was heated at 140° C. for three hours by using Biotage Initiator™ Microwave Synthesizer. After the reaction was completed, water was added, the reaction mixture was extracted with ethyl acetate, the organic layer was dried over magnesium sulfate, and the solvent was distilled off under reduced pressure. To the residue, ethyl acetate was added, and the obtained solid was subjected to suction filtration and dried to obtain the title compound (1.00 g, 2.62 mmol).

$^1$H-NMR (400 MHz, CDCl$_3$) δ: 3.17 (s, 3H), 3.47 (s, 3H), 3.77 (s, 6H), 4.51 (s, 2H), 6.65 (s, 2H), 6.97 (s, 1H), 6.99 (s, 1H).

Production Example 23-8

3-[2,6-Dimethoxy-4-(methoxymethyl)phenyl]-6-(methylthio)pyrazolo[5,1-b][1,3]thiazole

[Chemical Formula 84]

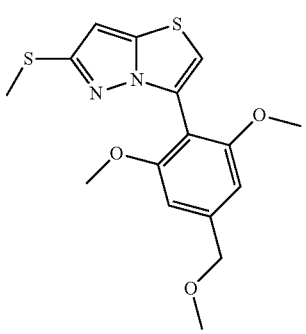

To tetrahydrofuran (20 mL) was added dropwise titanium tetrachloride (1.10 mL, 10.1 mmol) at −78° C., and the mixture was stirred for 10 minutes. At the same temperature, a tetrahydrofuran (20 mL) solution of lithium aluminum hydride (767 mg, 20.1 mmol) was gradually added dropwise and stirred for 30 minutes. To the mixture was added 3-[2,6-dimethoxy-4-(methoxymethyl)phenyl]-6-(methylsulfonyl)pyrazolo[5,1-b][1,3]thiazole (384 mg, 1.01 mmol), and the mixture was stirred at room temperature for 30 minutes. The mixture was heated at 50° C. for one hour. After the reaction was completed, 5N sodium hydroxide was gradually added dropwise while cooling on ice to stop the reaction. The reaction mixture was filtered with Celite and extracted with ethyl acetate, the organic layer was dried over magnesium sulfate, and the solvent was distilled off under reduced pressure. The residue was purified by silica gel column chromatography (n-heptane/ethyl acetate=1/1) to obtain the title compound (32.8 mg, 0.094 mmol).

$^1$H-NMR (400 MHz, CDCl$_3$) δ: 2.49 (s, 3H), 3.45 (s, 3H), 3.76 (s, 6H), 4.49 (s, 2H), 6.36 (s, 1H), 6.63 (s, 2H), 6.66 (s, 1H).

Production Example 23-9 tert-Butyl[3-[2,6-dimethoxy-4-(methoxymethyl)phenyl]-6-(methylthio)pyrazolo[5,1-b][1,3]thiazol-7-yl]carbamate

[Chemical Formula 85]

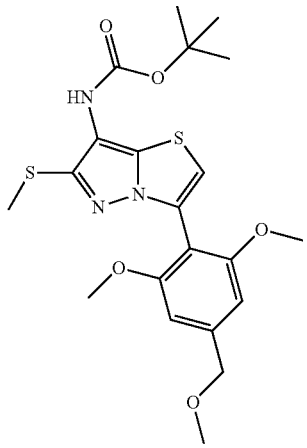

To a 5N aqueous solution of hydrochloric acid (3.00 mL) of 3-[2,6-dimethoxy-4-(methoxymethyl)phenyl]-6-(methylthio)pyrazolo[5,1-b][1,3]thiazole (23.5 mg, 0.067 mmol) was added sodium nitrite (9.24 mg, 0.134 mmol) at 0° C., and the mixture was stirred at room temperature for three hours. After the reaction was completed, 5N sodium hydroxide was added to the mixture while cooling on ice to neutralize the mixture, and the reaction mixture was extracted with ethyl acetate, the organic layer was dried over magnesium sulfate, and the solvent was distilled off under reduced pressure.

To an ethanol (2.50 mL) solution of the obtained residue, 50% palladium-carbon (30.0 mg, 0.282 mmol) was added, and the mixture was stirred at room temperature for one hour under a stream of hydrogen. After the reaction was completed, the reaction mixture was filtered with Celite, and the solvent was distilled off under reduced pressure.

To a dichloromethane (2.50 mL) solution of the obtained residue, triethylamine (11.0 μl, 0.080 mmol) and di-tert-butyl dicarbonate (13.9 mg, 0.064 mmol) were added, and the mixture was stirred at room temperature for 15 hours. After the reaction was completed, the solvent was distilled off under reduced pressure, and the residue was purified by silica gel column chromatography (n-heptane/ethyl acetate 1/1) to obtain the title compound (23.0 mg, 0.049 mmol).

MS [M+H]$^+$=466

Production Example 24

2-Bromo-[2,6-dimethoxy-4-(methoxymethyl)phenyl]ethanone

[Chemical Formula 86]

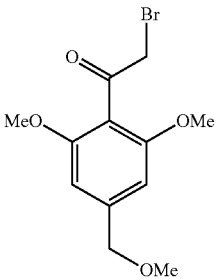

To a tetrahydrofuran (120 mL) solution of 1-[2,6-dimethoxy-4-(methoxymethyl)phenyl]ethanone (10.0 g, 44.9 mmol) was added triethylamine (18.8 ml, 135 mmol), and tert-butyldimethylsilyl trifluoromethanesulfonate (15.5 ml, 67.4 mmol) was added dropwise while cooling on ice, and the mixture was stirred for 30 minutes. N-bromosuccinimide (12.0 g, 67.4 mmol) was added and the mixture was stirred for 1.5 hours. To the reaction mixture, a saturated aqueous solution sodium hydrogencarbonate was added, and the reaction mixture was extracted with ethyl acetate, and dried over magnesium sulfate, and the solvent was distilled off under reduced pressure. To a tetrahydrofuran (80 mL) solution was added dropwise tetrabutylammonium fluoride (1M, 40.4 ml, 40.4 mmol) while cooling on ice, and the mixture was stirred for 30 minutes. To the mixture was added a saturated aqueous solution of ammonium chloride and the mixture was extracted with ethyl acetate and dried over magnesium sulfate, and then the solvent was distilled off under reduced pressure. The residue was purified by silica gel column chromatography (a mixed solvent of n-heptane and ethyl acetate: n-heptane/ethyl acetate 3/1 then 2/1) to obtain the title compound (12.0 g, 39.6 mmol).

$^1$H-NMR (CDCl$_3$) δ: 3.42 (s, 3H), 3.82 (s, 6H), 4.35 (s, 2H), 4.44 (s, 2H), 6.54 (s, 2H).

Example 1

N-(Cyclopropylmethyl)-3-[2,6-dimethoxy-4-(methoxymethyl)phenyl]-6-methyl-2-(methylthio)-N-(tetrahydro-2H-pyran-4-ylmethyl)pyrazolo[5,1-b][1,3]thiazole-7-amine (1a) tert-Butyl[3-[2,6-dimethoxy-4-(methoxymethyl)phenyl]-6-methyl-2-(methylthio)pyrazolo[5,1-b][1,3]thiazol-7-yl]carbamate

[Chemical Formula 87]

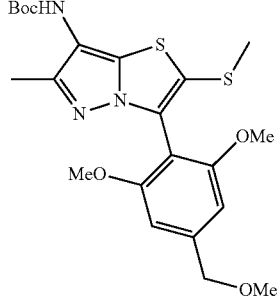

To a mixture of tert-butyl[3-bromo-6-methyl-2-(methylthio)pyrazolo[5,1-b][1,3]thiazol-7-yl]carbamate (397 mg, 1.03 mmol), toluene (6.8 mL) and ethanol (3.4 mL) were added 2,6-dimethoxy-4-(methoxymethyl)phenylboric acid (349 mg, 1.55 mmol) synthesized by the method described in WO2004/037822, a 1M aqueous solution of sodium carbonate (2.06 mL, 2.06 mmol) and tetrakis(triphenylphosphine)palladium (119 mg, 0.10 mmol) in this order, and the mixture was heated to reflux at 110° C. for three hours. Water was added to the reaction mixture and then ethyl acetate was added. After thoroughly shaking the mixture, the organic layer was separated, and the organic layer was stirred at 75° C. for five hours. Chloroform was added to the reaction mixture, insoluble matters were filtered off, and then the solvent was distilled off under reduced pressure. The residue was purified by medium pressure silica gel column chromatography (n-heptane/ethyl acetate: 33% then 66%) to obtain 450.9 mg (0.94 mmol) of the title compound.

¹H-NMR (CDCl₃) δ: 1.54 (s, 9H), 2.25 (s, 3H), 2.31 (s, 3H), 3.46 (s, 3H), 3.73 (s, 6H), 4.50 (s, 2H), 6.01 (br.s, 1H), 6.63 (s, 2H).

(1b) N-(Cyclopropylmethyl)-3-[2,6-dimethoxy-4-(methoxymethyl)phenyl]-6-methyl-2-(methylthio)-N-(tetrahydro-2H-pyran-4-ylmethyl)pyrazolo[5,1-b][1,3]thiazole-7-amine

[Chemical Formula 88]

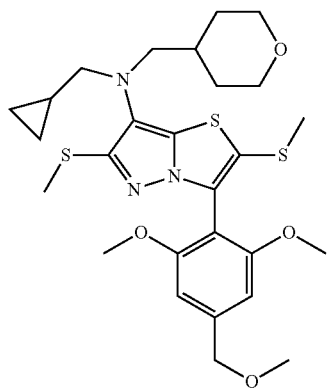

To a DMF (5 mL) solution of tert-butyl[3-[2,6-dimethoxy-4-(methoxymethyl)phenyl-6-methyl-2-(methylthio)pyrazolo[5,1-b][1,3]thiazol-7-yl]carbamate (322 mg, 0.67 mmol) were added sodium hydride (32.1 mg, 0.80 mmol) and cyclopropylmethyl bromide (130 μl, 1.34 mmol) and the mixture was stirred at room temperature for 2.5 hours. Water was added to the reaction mixture and then ethyl acetate was added, and a substance of interest was extracted with ethyl acetate. The organic layer was washed with water and brine, and dried over anhydrous magnesium sulfate. The mixture was filtered to yield a filtrate, and the solvent in the filtrate was distilled off under reduced pressure.

To the obtained residue was added dichloromethane (5 mL) and then trifluoroacetic acid (2.2 mL) was added, and the mixture stirred at room temperature for one hour. The solvent in the reaction mixture was distilled off under reduced pressure. To the obtained residue was added THF (5 mL) and then tetrahydro-4H-pyran-4-carbaldehyde (153 μl, 1.34 mmol) and sodium triacetoxyborohydride (213 mg, 1.01 mmol) were added in this order, and the mixture was stirred at room temperature for 10 minutes. To the reaction mixture was added a saturated aqueous solution of sodium hydrogencarbonate and then ethyl acetate was added. After thoroughly shaking the mixture, the organic layer was separated, the organic layer was washed with brine and dried over anhydrous magnesium sulfate. The mixture was filtered to yield a filtrate, and the solvent in the filtrate was distilled off under reduced pressure. The residue was purified by silica gel column chromatography (a mixed solvent of n-heptane and ethyl acetate: n-heptane/ethyl acetate=25% to 66%) to obtain 281.8 mg (0.53 mmol) of the title compound.

¹H-NMR (CDCl₃) δ: 0.02-0.05 (m, 2H), 0.40-0.44 (m, 2H), 0.81-0.90 (m, 1H), 1.23-1.33 (m, 2H), 1.50-1.62 (m, 1H), (1.71-1.78 (m, 2H), 2.32 (s, 3H), 2.26 (s, 3H), 2.72 (d, J=6.4 Hz, 2H), 2.86 (d, J=7.2 Hz, 2H), 3.30-3.38 (m, 2H), 3.47 (s, 3H), 3.76 (s, 6H), 3.91-3.97 (m, 2H), 4.51 (s, 2H), 6.65 (s, 2H).

Example 2

3-[2,6-Dimethoxy-4-(methoxymethyl)phenyl-6-methyl-2-(methylthio)-N,N-dipropylpyrazolo[5,1-b][1,3]thiazole-7-amine

[Chemical Formula 89]

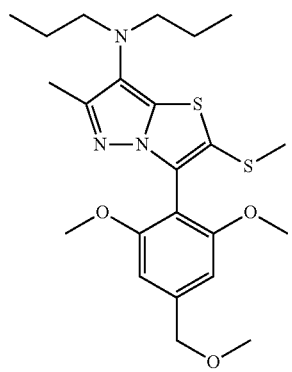

The title compound was obtained according to the procedure similar to Example 1.

¹H-NMR (CDCl₃) δ: 0.89 (t, J=7.2 Hz, 6H), 1.37-4.60 (m, 4H), 2.25 (s, 3H), 2.32 (s, 3H), 2.83 (t, J=7.2 Hz, 4H), 3.46 (s, 3H), 3.75 (s, 6H), 4.50 (s, 2H), 6.63 (s, 2H).

Example 3

3-[2,6-Dimethoxy-4-(methoxymethyl)phenyl]-6-methyl-2-(methylsulfinyl)-N,N-dipropylpyrazolo[5,1-b][1,3]thiazole-7-amine

[Chemical Formula 90]

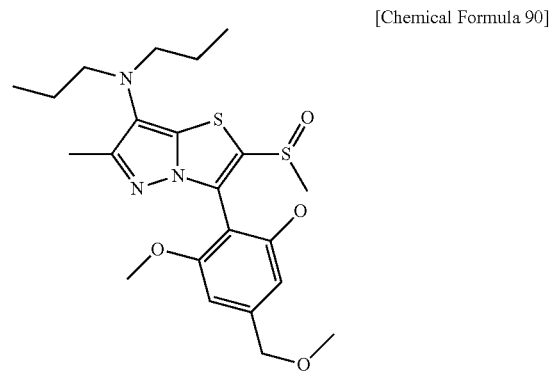 [SMILES: CCCN(CCC)c1c(C)nn2c(-c3c(O)cc(COC)cc3OC)c(S(C)=O)sc12]

To a dichloromethane (670 μl) solution of 3-[2,6-dimethoxy-4-(methoxymethyl)phenyl]-6-methyl-2-(methylthio)-N,N-dipropylpyrazolo[5,1-b][1,3]thiazole-7-amine (31.5 mg, 0.068 mmol) was added 3-chloroperbenzoic acid (23.4 mg, 0.136 mmol), and the mixture was stirred at room temperature for 10 minutes. To the reaction mixture, a saturated aqueous solution of sodium carbonate was added, the mixture was extracted with dichloromethane, and then, the organic layer was dried over anhydrous magnesium sulfate. The mixture was filtered to yield a filtrate, and the solvent in the filtrate was distilled off under reduced pressure. The residue was purified by thin-layer silica gel chromatography (chloroform:methanol=12:1) to obtain 7.3 mg (0.0152 mmol) of the title compound.

$^1$H-NMR (CDCl$_3$) δ: 0.96 (t, J=7.6 Hz, 6H), 2.10-2.33 (m, 4H), 3.51-3.61 (m, 4H), 2.33 (s, 3H), 2.35 (s, 3H), 3.46 (s, 3H), 3.74 (s, 6H), 4.50 (s, 2H), 6.63 (s, 2H).

Example 4

N-(Cyclopropylmethyl)-3-[2,6-dimethoxy-4-(methoxymethyl)phenyl]-6-methyl-N-(tetrahydro-2H-pyran-4-ylmethyl)pyrazolo[5,1-b][1,3]thiazole-7-amine

[Chemical Formula 91]

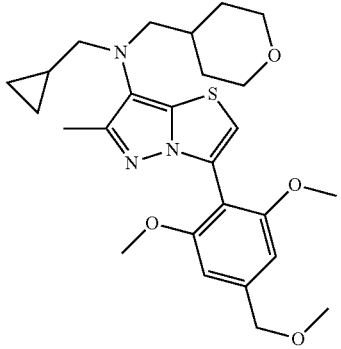

This compound was synthesized according to the procedure similar to Example 1 by using the compound obtained in Production Example 19-4.

$^1$H-NMR (CDCl$_3$) δ: 0.01-0.05 (m, 2H), 0.38-0.44 (m, 2H), 0.81-0.92 (m, 1H), 1.22-1.34 (m, 2H), 1.49-1.61 (m, 1H), 1.71-1.78 (m, 2H), 2.28 (s, 3H), 2.74 (d, J=6.8 Hz, 2H), 2.88 (d, J=7.2 Hz, 2H), 3.36 (br.dd, J=11.6, 10.4 Hz, 2H), 3.45 (s, 3H), 3.76 (s, 6H), 3.93 (br.dd, J=11.2, 2.8 Hz, 2H), 4.49 (s, 2H), 6.52 (s, 1H), 6.64 (s, 2H).

Example 5

N-(Cyclopropylmethyl)-3-[2,6-dimethoxy-4-(methoxymethyl)phenyl]-2,6-dimethyl-N-(tetrahydro-2H-pyran-4-ylmethyl)pyrazolo[5,1-b][1,3]thiazole-7-amine

[Chemical Formula 92]

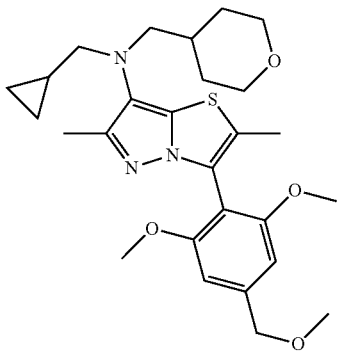

This compound was synthesized according to the procedure similar to Example 1 by using the compound obtained in Production Example 20-5.

$^1$H-NMR (CDCl$_3$) δ: 0.01-0.04 (m, 2H), 0.38-0.43 (m, 2H), 0.80-0.90 (m, 1H), 1.22-1.34 (m, 2H), 1.48-1.62 (m, 1H), 1.74 (br d, J=13.2 Hz, 2H), 2.14 (s, 3H), 2.25 (s, 3H), 2.71 (d, J=6.8 Hz, 2H), 2.85 (d, J=7.2 Hz, 2H), 3.32 (ddd, J=-11.6, 11.6, 1.6 Hz, 2H), 3.47 (s, 3H), 3.76 (s, 6H), 3.93 (br.dd, J=11.6, 4.4 Hz, 2H), 4.49 (s, 2H), 6.64 (s, 2H).

Example 6

N-(Cyclopropylmethyl)-3-[2,6-dimethoxy-4-(methoxymethyl)phenyl]-2,6-dimethyl-N-(tetrahydro-2H-pyran-4-yl)pyrazolo[5,1-b][1,3]thiazole-7-amine

[Chemical Formula 93]

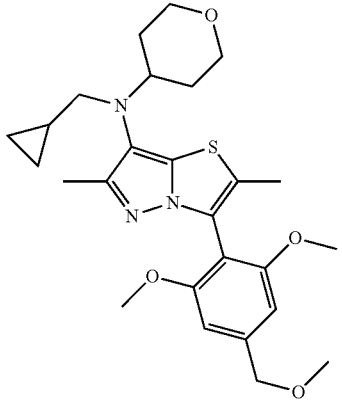

This compound was synthesized according to the procedure similar to Example 5.

$^1$H-NMR (CDCl$_3$) δ: 0.00-0.04 (m, 2H), 0.32-0.38 (m, 2H), 0.72-0.83 (m, 1H), 1.52-1.65 (m, 2H), 1.77-1.85 (m, 2H), 2.16 (s, 3H), 2.27 (s, 3H), 2.84 (d, J=8 Hz, 2H), 3.05-3.15 (m, 1H), 3.40 (ddd, J=11.6, 11.6, 12 Hz, 2H), 3.49 (s, 3H), 3.78 (s, 6H), 3.96-4.03 (m, 2H), 4.51 (s, 2H), 6.66 (s, 2H).

Example 7

[3-(2,6-Dimethoxy-4-methoxymethyl-phenyl)-6-methoxy-2-methyl-pyrazolo[5,1-b][1,3]thiazol-7-yl]-propyl-(tetrahydro-pyran-4-yl)-amine (7a) tert-Butyl{2-bromo-3-[2,6-dimethoxy-4-(methoxymethyl)phenyl]-6-methoxypyrazolo[5,1-b][1,3]thiazol-7-yl}carbamate

[Chemical Formula 94]

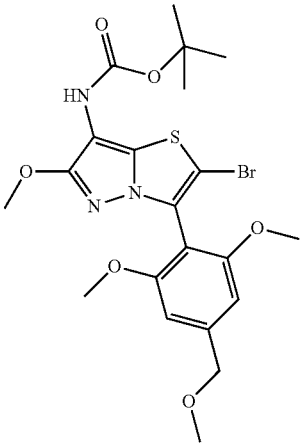

To a THF (40 mL) solution of tert-butyl{3-[2,6-dimethoxy-4-(methoxymethyl)phenyl]-6-methoxypyrazolo[5,1-b][1,3]thiazol-7-yl}carbamate (1.22 g, 2.71 mmol) was added dropwise 2.77M n-butyllithium (2.74 mL, 7.59 mmol) at −78° C., and the mixture was stirred for one hour. 1,2-Dibromotetrafluoroethane (0.10 mL, 7.59 mmol) was added, and the mixture was warmed to room temperature. After the reaction was completed, a saturated aqueous solution of ammonium chloride was added while cooling on ice, and then, ethyl acetate was added.

After thoroughly shaking the mixture, the organic layer was separated, the organic layer was washed with brine and dried over anhydrous magnesium sulfate. The mixture was filtered, and then the solvent in the filtrate was distilled off under reduced pressure. The residue was purified by silica gel column chromatography (a mixed solvent of n-heptane and ethyl acetate: n-heptane/ethyl acetate=1/1) to obtain the title compound (441 mg, 0.835 mmol).

$^1$H-NMR (CDCl$_3$) δ: 1.51 (s, 9H), 3.48 (s, 3H), 3.77 (s, 6H), 3.85 (s, 3H), 4.50 (s, 2H), 6.13 (br.s, 1H), 6.64 (s, 2H).

(7b) tert-Butyl{3-[2,6-dimethoxy-4-(methoxymethyl)phenyl]-6-methoxy-2-methoxypyrazolo[5,1-b][1,3]thiazol-7-yl}carbamate

[Chemical Formula 95]

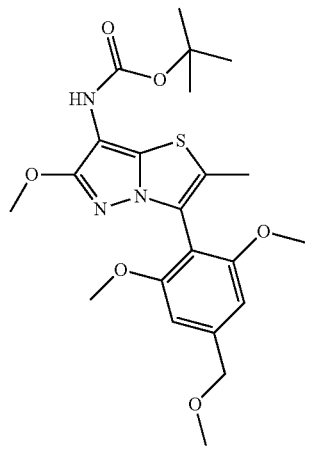

To a dioxane (15 mL) solution of tert-butyl{2-bromo-3-[2,6-dimethoxy-4-(methoxymethyl)phenyl]-6-methoxypyrazolo[5,1-b][1,3]thiazol-7-yl}carbamate (323 mg, 0.612 mmol) were added 2M dimethyl zinc (0.612 mL, 1.22 mmol) and bis(tri-tert-butylphosphine)palladium(0) (15.6 mg, 0.031 mmol), and the mixture was heated at 60° C. for one hour. After the reaction was completed, the solvent was directly distilled off under reduced pressure. The residue was purified by silica gel column chromatography (a mixed solvent of n-heptane and ethyl acetate: n-heptane/ethyl acetate=1/1) to obtain the title compound (205 mg, 0.442 mmol).

$^1$H-NMR (CDCl$_3$) δ: 1.52 (s, 9H), 2.11 (s, 3H), 3.48 (s, 3H), 3.75 (s, 6H), 3.85 (s, 3H), 4.50 (s, 2H), 6.06 (br.s, 1H), 6.64 (s, 2H).

(7c) [3-(2,6-Dimethoxy-4-methoxymethyl-phenyl)-6-methoxy-2-methyl-pyrazolo[5,1-b][1,3]thiazol-7-yl]-propyl-tetrahydro-pyran-4-yl-amine

[Chemical Formula 96]

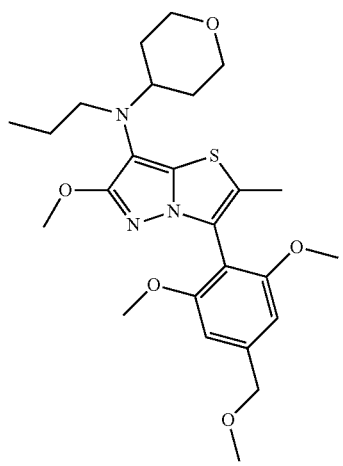

This compound was synthesized according to the procedure similar to Example 1b.

$^1$H-NMR (CDCl$_3$) δ: 0.87 (t, J=−7.2 Hz, 3H), 1.30-1.46 (m, 2H), 1.50-1.68 (m, 2H), 1.74-1.88 (m, 2H), 2.14 (s, 3H), 2.92 (t, J=7.6 Hz, 2H), 2.96-3.10 (m, 1H), 3.37 (t, J=12.0 Hz, 2H), 3.49 (s, 3H), 3.79 (s, 6H), 3.83 (s, 3H), 3.90-4.04 (m, 2H), 4.51 (s, 2H), 6.65 (s, 2H).

Example 8

Cyclopropylmethyl-[3-(2,6-dimethoxy-4-methoxymethyl-phenyl)-6-methoxy-2-methyl-pyrazolo[5,1-b][1,3]thiazol-7-yl]-(tetrahydro-furan-3-ylmethyl)-amine

[Chemical Formula 97]

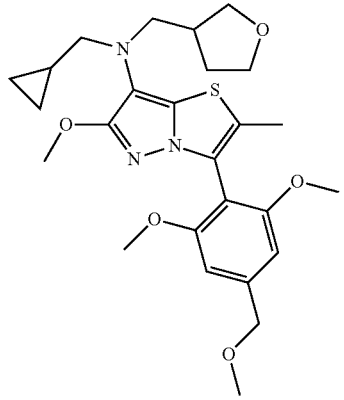

This compound was synthesized according to the procedure similar to Example 7.

$^1$H-NMR (CDCl$_3$) δ: −0.01-0.10 (m, 2H), 0.35-0.46 (m, 2H), 0.83-0.97 (m, 1H), 1.56-1.71 (m, 1H), 1.90-2.04 (m, 1H), 2.14 (s, 3H), 2.27-2.40 (m, 1H), 2.79 (d, J=6.8 Hz, 2H), 2.93 (dd, J=8.0, 11.6 Hz, 1H), 3.04 (dd, J=6.8, 11.6 Hz, 1H), 3.48 (s, 3H), 3.55 (dd, J=6.4, 8.0 Hz, 1H), 3.62-3.76 (m, 1H), 3.78 (s, 6H), 3.76-3.90 (m, 2H), 3.84 (s, 3H), 4.50 (s, 2H), 6.65 (s, 2H).

Example 9

[3-(2,6-Dimethoxy-4-methoxymethyl-phenyl)-2-ethyl-6-methoxy-pyrazolo[5,1-b][1,3]thiazol-7-yl]-propyl-(tetrahydro-pyran-4-yl)-amine (9a) tert-Butyl{3-[2,6-dimethoxy-4-(methoxymethyl)phenyl]-2-ethyl-6-methoxymethylpyrazolo[5,1-b][1,3]thiazol-7-yl}carbamate

[Chemical Formula 98]

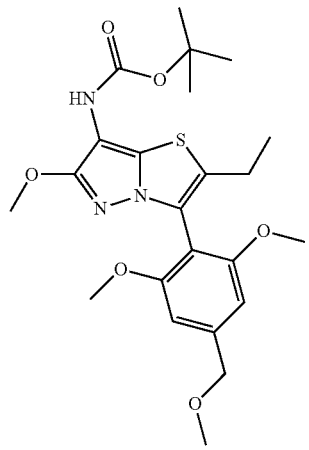

To a dioxane (5 mL) solution of tert-butyl{2-bromo-3-[2,6-dimethoxy-4-(methoxymethyl)phenyl]-6-methoxypyrazolo[5,1-b][1,3]thiazol-7-yl}carbamate (118 mg, 0.224 mmol), 1M diethyl zinc (0.448 mL, 0.448 mmol) and bis(tri-tert-butylphosphine)palladium(0) (5.70 mg, 0.011 mmol) were added, and the mixture was heated at 60° C. for one hour. After the reaction was completed, the solvent was directly distilled off under reduced pressure. The residue was purified by silica gel column chromatography (a mixed solvent of n-heptane and ethyl acetate: n-heptane/ethyl acetate=1/1) to obtain the title compound (84 mg, 0.176 mmol).

$^1$H-NMR (CDCl$_3$) δ: 1.16 (t, J=7.6 Hz, 3H), 1.52 (s, 9H), 2.47 (q, J=7.6 Hz, 2H), 3.48 (s, 3H), 3.74 (s, 6H), 3.84 (s, 3H), 4.49 (s, 2H), 6.07 (br.s, 1H), 6.63 (s, 2H).

(9b) [3-(2,6-Dimethoxy-4-methoxymethyl-phenyl)-2-ethyl-6-methoxy-pyrazolo[5,1-b][1,3]thiazol-7-yl]-propyl-(tetrahydro-pyran-4-yl)-amine

[Chemical Formula 99]

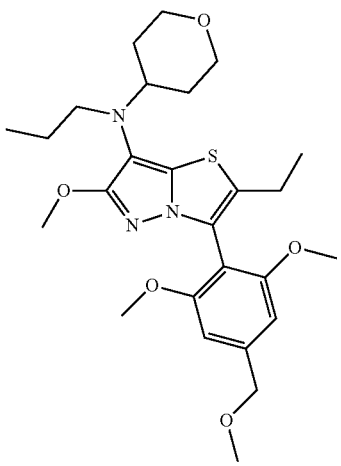

This compound was synthesized according to the procedure similar to Example 1b.

$^1$H-NMR (CDCl$_3$) δ: 0.87 (t, J=7.6 Hz, 3H), 1.18 (t, J=7.2 Hz, 3H), 1.32-1.45 (m, 2H), 1.52-1.68 (m, 2H), 1.77-1.88 (m, 2H), 2.51 (q, J=7.2 Hz, 2H), 2.92 (dd, J=7.6, 9.2 Hz, 2H), 2.98-3.12 (m, 1H), 3.38 (td, J=1.6, 12.0 Hz, 2H), 3.49 (s, 3H), 3.77 (s, 6H), 3.82 (s, 3H), 3.92-4.04 (m, 2H), 4.50 (s, 2H), 6.65 (s, 2H).

Example 10

[3-(2,6-Dimethoxy-4-methoxymethyl-phenyl)-6-methoxy-pyrazolo[5,1-b][1,3]thiazol-7-yl]-(3-fluoro-propyl)-(tetrahydro-pyran-4-yl)amine (10a) tert-Butyl{3-[4-(ethoxymethyl)-2,6-dimethoxyphenyl]-6-methoxypyrazolo[5,1-b][1,3]thiazol-7-yl}carbamate

[Chemical Formula 100]

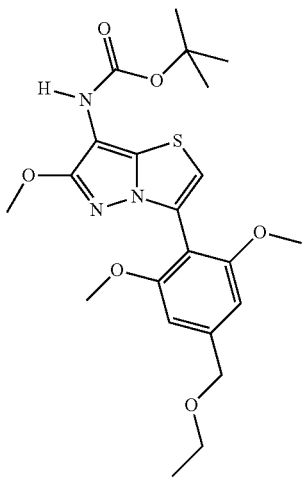

To a mixture of tert-butyl(3-bromo-6-methoxypyrazolo[5,1-b][1,3]thiazol-7-yl)carbamate (2.00 g, 5.74 mmol), DME (200 mL) and water (70 mL) were added 2,6-dimethoxy-4-(ethoxymethyl)phenylboric acid (Production Example 33 in WO04/037822) (2.07 g, 8.64 mmol), potassium carbonate (1.59 g, 11.5 mmol), triphenyl phosphine (0.75 g, 2.87 mmol) and palladium(II) acetate (0.13 g, 0.57 mmol) in this order, and the mixture was heated at 90° C. (internal temperature) for four hours. Water was added to the reaction mixture, and then ethyl acetate was added.

After thoroughly shaking the mixture, the organic layer was separated, the organic layer was washed with brine and dried over anhydrous magnesium sulfate. The mixture was filtered, and then the solvent in the filtrate was distilled off under reduced pressure. The residue was purified by silica gel column chromatography (a mixed solvent of n-heptane and ethyl acetate: n-heptane/ethyl acetate=2/1 then 1/1) to obtain the title compound (2.49 g, 5.37 mmol).

¹H-NMR (CDCl₃) δ: 1.29 (t, J=7.2 Hz, 3H), 1.52 (s, 9H), 3.61 (q, J=7.2 Hz, 2H), 3.75 (s, 6H), 3.87 (s, 3H), 4.53 (s, 2H), 6.09 (br.s, 1H), 6.42 (s, 1H), 6.64 (s, 2H).

(10b) [3-(2,6-Dimethoxy-4-methoxymethyl-phenyl)-6-methoxy-pyrazolo[5,1-b][1,3]thiazol-7-yl]-(3-ffluoro-propyl)-(tetrahydro-pyran-4-yl)-amine

[Chemical Formula 101]

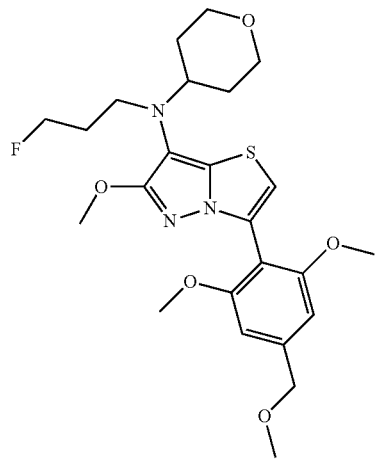

This compound was synthesized according to the procedure similar to Example 1b.

¹H-NMR (CDCl₃) δ: 1.50-1.90 (m, 6H), 2.99-3.12 (m, 1H), 3.13 (t, J=7.2 Hz, 2H), 3.37 (td, J=1.6, 11.6 Hz, 2H), 3.47 (s, 3H), 3.79 (s, 6H), 3.85 (s, 3H), 3.92-4.04 (m, 2H), 4.46 (t, J=6.0 Hz, 1H), 4.50 (s, 2H), 4.58 (t, J=6.0 Hz, 1H), 6.43 (s, 1H), 6.65 (s, 2H).

Hereinafter, the compounds of Examples 11 to 75 were synthesized according to the procedure similar to Example 10.

Example 11

Cyclopropylmethyl-3[3-(2,6-dimethoxy-4-methoxymethyl-phenyl)-6-methoxy-pyrazolo[5,1-b][1,3]thiazol-7-yl]-[1,3]dioxan-5-ylmethyl-amine

[Chemical Formula 102]

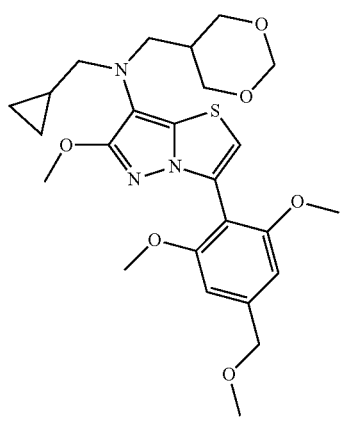

¹H-NMR (CDCl₃) δ: 0.01-0.10 (m, 2H), 0.36-0.46 (m, 2H), 0.82-0.97 (m, 1H), 1.88-2.02 (m, 1H), 2.79 (d, J=6.4 Hz, 2H), 3.01 (d, J=7.6 Hz, 2H), 3.47 (s, 3H), 3.65 (dd, J=7.6, 11.6 Hz, 2H), 3.78 (s, 6H), 3.85 (s, 3H), 4.06 (dd, J=3.6, 11.2 Hz, 2H), 4.50 (s, 2H), 4.73 (d, J=6.4 Hz, 1H), 4.89 (d, J=6.4 Hz, 1H), 6.44 (s, 1H), 6.64 (s, 2H).

Example 12

Butyl-[3-(2,6-dimethoxy-4-methoxymethyl-phenyl)-6-methoxy-pyrazolo[5,1-b][1,3]thiazol-7-yl)-[1,3]dioxan-5-ylmethyl-amine

[Chemical Formula 103]

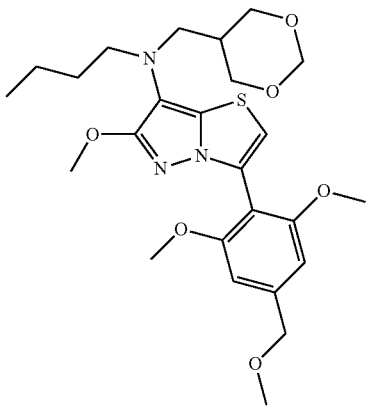

¹H-NMR (CDCl₃) δ: 0.88 (t, J=7.2 Hz, 3H), 1.22-1.47 (m, 4H), 1.87-2.00 (m, 1H), 2.85-2.95 (m, 4H), 3.47 (s, 3H), 3.63 (dd, J=8.0, 11.6 Hz, 2H), 3.79 (s, 6H), 3.85 (s, 3H), 4.05 (dd, J=4.0, 11.2 Hz, 2H), 4.50 (s, 2H), 4.73 (d, J=6.0 Hz, 1H), 4.90 (d, J=6.0 Hz, 1H), 6.41 (s, 1H), 6.64 (s, 2H).

Example 13

N-(Cyclopropylmethyl)-3-[2,6-dimethoxy-4-(methoxymethyl)phenyl]-6-methoxy-N-(tetrahydrofuran-3-yl)pyrazolo[5,1-b][1,3]thiazole-7-amine

[Chemical Formula 104]

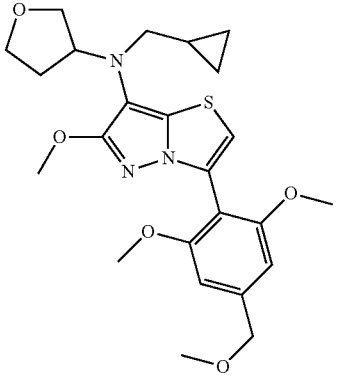

¹H-NMR (CDCl₃) δ: −0.02-0.06 (m, 2H), 0.36 (d, J=8.0 Hz, 2H), 0.81-0.93 (m, 1H), 1.86-2.08 (m, 2H), 2.76 (dd,

J=6.8, 12.8 Hz, 1H), 2.82 (dd, J=6.8, 12.8 Hz, 1H), 3.47 (s, 3H), 3.69 (t, J=7.0 Hz, 1H), 3.73-3.98 (m, 4H), 3.78 (s, 6H), 3.87 (s, 3H), 4.50 (s, 2H), 6.43 (s, 1H), 6.65 (s, 2H).

Example 14

3-[2,6-Dimethoxy-4-methoxymethylphenyl]-6-methoxy-N-propyl-N-(tetrahydrofuran-3-yl)pyrazolo[5,1-b][1,3]thiazole-7-amine

[Chemical Formula 105]

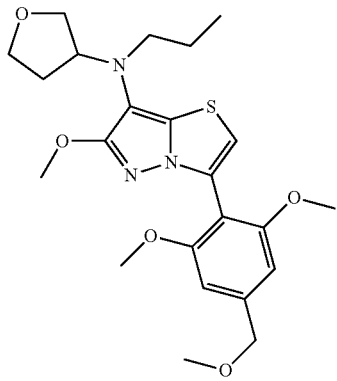

$^1$H-NMR (CDCl$_3$) δ: 0.88 (t, J=7.4 Hz, 3H), 1.40 (sext., J=7.4 Hz, 2H), 1.88-2.07 (m, 2H), 2.77-2.95 (m, 2H), 3.47 (s, 3H), 3.65-3.73 (m, 1H), 3.73-3.91 (m, 4H), 3.79 (s, 6H), 3.86 (s, 3H), 4.50 (s, 2H), 6.43 (s, 1H), 6.65 (s, 2H).

Example 15

[3-(6-Dimethylamino-4-methoxy-pyridin-3-yl)-6-methoxy-pyrazolo[5,1-b][1,3]thiazol-7-yl]-propyl-(tetrahydro-pyran-4-yl)amine

[Chemical Formula 106]

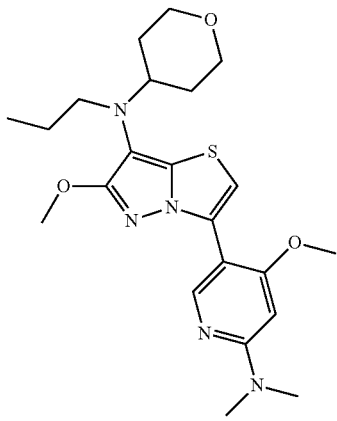

$^1$H-NMR (CDCl$_3$) δ: 0.86 (t, J=7.2 Hz, 3H), 1.28-1.44 (m, 2H), 1.50-1.70 (m, 2H), 1.76-1.88 (m, 2H), 2.94 (t, J=7.6 Hz, 2H), 2.99-3.12 (m, 1H), 3.17 (s, 6H), 3.37 (t, J=12.0 Hz, 2H), 3.92 (s, 3H), 3.97 (s, 3H), 3.92-4.04 (m, 2H), 6.02 (s, 1H), 6.76 (s, 1H), 9.17 (s, 1H).

Example 16

[3-(6-Dimethylamino-4-methoxy-pyridin-3-yl)-6-methoxy-pyrazolo[5,1-b][1,3]thiazol-7-yl]-propyl-(tetrahydro-furan-3-ylmethyl)-amine

[Chemical Formula 107]

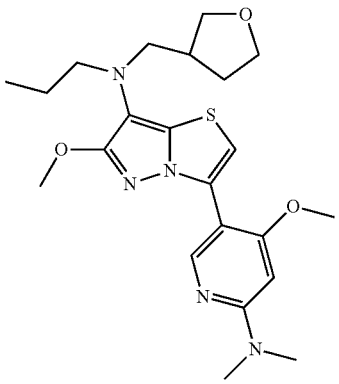

$^1$H-NMR (CDCl$_3$) δ: 0.01-0.10 (m, 2H), 0.34-0.45 (m, 2H), 0.80-0.95 (m, 1H), 1.54-1.70 (m, 1H), 1.88-2.01 (m, 1H), 2.24-2.36 (m, 1H), 2.81 (d, J=6.4 Hz, 2H), 2.94 (dd, J=8.0, 11.2 Hz, 1H), 3.06 (dd, 12.0 Hz, 1H), 3.17 (s, 6H), 3.57 (dd, J=6.0, 8.4 Hz, 1H), 3.62-3.72 (m, 1H), 3.75-3.87 (m, 2H), 3.92 (s, 3H), 3.98 (s, 3H), 6.02 (s, 1H), 6.76 (s, 1H), 9.18 (s, 1H).

Example 17

3-(2,6-Dimethoxy-4-methylphenyl)-6-methoxy-N-propyl-N-(tetrahydro-2H-pyran-4-yl)pyrazolo[5,1-b][1,3]thiazole-7-amine

[Chemical Formula 108]

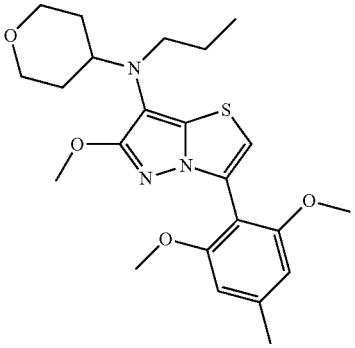

$^1$H-NMR (CDCl$_3$) δ: 0.87 (t, J=7.4 Hz, 3H), 1.38 (sext., J=7.6 Hz, 2H), 1.53-1.66 (m, 2H), 1.82 (dd, J=1.6, 12.8 Hz, 2H), 2.41 (s, 3H), 2.94 (t, J=7.4 Hz, 2H), 3.05 (tt, J=11.2, 4.0

Hz, 1H), 3.38 (dt, J=1.6, 12.0 Hz, 2H), 3.76 (s, 6H), 3.86 (s, 3H), 3.98 (dd, J=3.6, 6.8 Hz, 2H), 6.39 (s, 1H), 6.48 (s, 2H).

Example 18

3-[2,6-Dimethoxy-4-(1-methoxyethyl)phenyl]-6-methoxy-N-propyl-N-(tetrahydro-2H-pyran-4-yl)pyrazolo[5,1-b][1,3]thiazole-7-amine

[Chemical Formula 109]

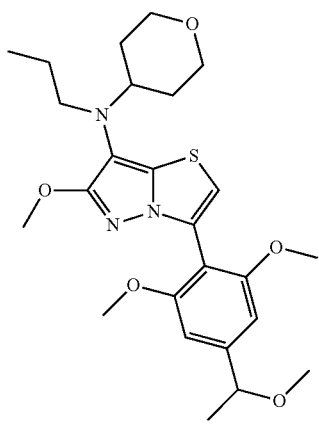

$^1$H-NMR (CDCl$_3$) δ: 0.87 (t, J=7.6 Hz, 3H), 1.31-1.43 (m, 2H), 1.49 (d, J=6.4 Hz, 3H), 1.52-1.71 (m, 2H), 1.76-1.87 (m, 2H), 2.88-2.98 (m, 2H), 3.00-3.12 (m, 1H), 3.33 (s, 3H), 3.34-3.43 (m, 2H), 3.79 (s, 6H), 3.88 (s, 3H), 3.93-4.04 (m, 2H), 4.27-4.38 (m, 1H), 6.43 (s, 1H), 6.62 (s, 2H).

Example 19

N-(Cyclopropylmethyl)-3-[2,6-dimethoxy-4-(1-methoxyethyl)phenyl]-6-methoxy-N-(tetrahydrofuran-3-ylmethyl)pyrazolo[5,1-b][1,3]thiazole-7-amine

[Chemical Formula 110]

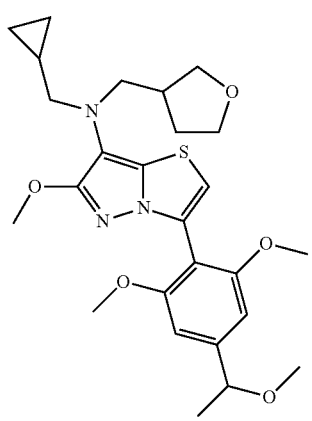

$^1$H-NMR (CDCl$_3$) δ: 0.02-0.09 (m, 2H), 0.37-0.45 (m, 2H), 0.85-0.96 (m, 1H), 1.49 (d, J=6.4 Hz, 3H), 1.60-1.70 (m, 1H), 1.91-2.02 (m, 1H), 2.27-2.40 (m, 1H), 2.81 (d, J=6.8 Hz, 2H), 2.91-3.00 (m, 1H), 3.03-3.12 (m, 1H), 3.32 (s, 3H), 3.52-3.61 (m, 1H), 3.65-3.74 (m, 1H), 3.75-3.92 (m, 11H), 4.32 (q, J=6.4 Hz, 1H), 6.43 (s, 1H), 6.61 (s, 2H).

Example 20

N-(Cyclopropylmethyl)-3-[6-(dimethylamino)-4-methylpyridin-3-yl]-6-methoxy-N-(tetrahydrofuran-3-ylmethyl)pyrazolo[5,1-b][1,3]thiazole-7-amine

[Chemical Formula 111]

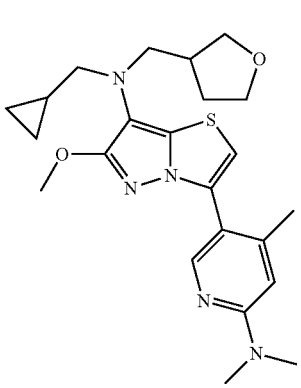

$^1$H-NMR (CDCl$_3$) δ: 0.03-0.07 (m, 2H), 0.38-0.43 (m, 2H), 0.83-0.95 (m, 1H), 1.56-1.69 (m, 1H), 1.93-2.01 (m, 1H), 2.25-2.38 (m, 1H), 2.28 (s, 3H), 2.81 (d, J=6.8 Hz, 2H), 2.95 (dd, J=12.0, 8.4 Hz, 1H), 3.07 (dd, J=12.0, 7.2 Hz, 1H), 3.14 (s, 6H), 3.57 (dd, J=8.0, 6.0 Hz, 1H), 3.69 (dd, J=15.6, 8.0 Hz, 1H), 3.78-3.87 (m, 2H), 3.90 (s, 3H), 6.31 (s, 1H), 6.44 (s, 1H), 8.27 (s, 1H).

Example 21

3-[6-(Dimethylamino)-4-methyl-pyridin-3-yl]-6-methoxy-N-propyl-N-(tetrahydro-2H-pyran-4-yl)pyrazolo[5,1-b][1,3]thiazole-7-amine

[Chemical Formula 112]

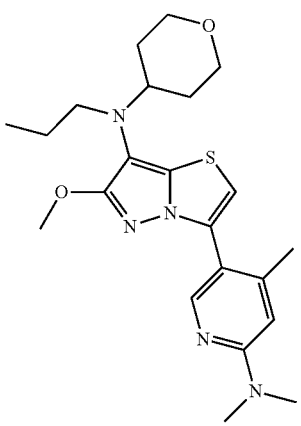

$^1$H-NMR (CDCl$_3$) δ: 0.88 (t, J=7.2 Hz, 3H), 1.32-1.42 (m, 2H), 1.52-1.64 (m, 2H), 1.79-1.86 (m, 2H), 2.29 (s, 3H), 2.92-2.96 (m, 2H), 3.01-3.11 (m, 1H), 3.14 (s, 6H), 3.38 (ddd, J=12.0, 11.6, 1.6 Hz, 2H), 3.89 (s, 3H), 3.95-4.01 (m, 2H), 6.31 (s, 1H), 6.44 (s, 1H), 8.28 (s, 1H).

Example 22

[3-(4-Ethyl-2,6-dimethoxyphenyl)-6-methoxypyrazolo[5,1-b][1,3]thiazol-7-yl]-propyl-(tetrahydropyran-4-yl)amine

[Chemical Formula 113]

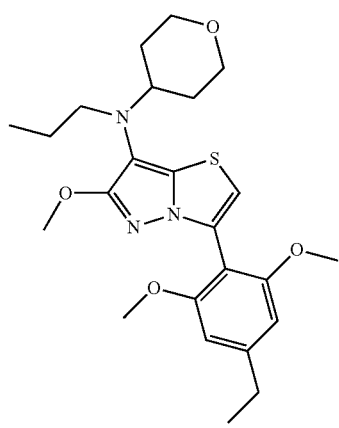

$^1$H-NMR (CDCl$_3$) δ: 0.87 (t, 3H), 1.31 (t, J=7.6 Hz, 3H), 1.32-1.44 (m, 2H), 1.53-1.66 (m, 2H), 1.78-1.87 (m, 2H), 2.71 (q, J=7.6 Hz, 2H), 2.94 (dd, 8.8 Hz, 2H), 3.00-3.11 (m, 1H), 338 (td, J=2.0, 12.0 Hz, 2H), 3.78 (s, 6H), 3.87 (s, 3H), 3.93-4.03 (m, 2H), 6.40 (s, 1H), 6.51 (s, 2H).

Example 23

Cyclopropylmethyl-[3-(4-ethyl-2,6-dimethoxy-phenyl)-6-methoxy-pyrazolo[5,1-b][1,3]thiazol-7-yl]-(tetrahydrofuran-3-ylmethyl)amine

[Chemical Formula 114]

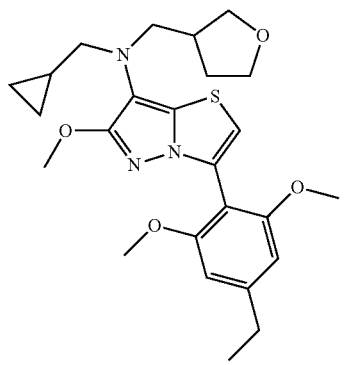

$^1$H-NMR (CDCl$_3$) δ: 0.01-0.10 (m, 2H), 0.36-0.46 (m, 2H), 0.84-0.97 (m, 1H), 1.30 (t, J=7.6 Hz, 3H), 1.57-1.70 (m, 1H), 1.90-2.03 (m, 1H), 2.27-2.42 (m, 1H), 2.70 (q, J=7.6 Hz, 2H), 2.81 (d, J=6.8 Hz, 2H), 2.95 (dd, J=8.4, 12.0 Hz, 1H), 3.06 (dd, J=6.8, 12.0 Hz, 1H), 3.56 (dd, J=6.0, 8.8 Hz, 1H), 3.64-3.74 (m, 1H), 3.77 (s, 6H), 3.76-3.87 (m, 2H), 3.88 (s, 3H), 6.40 (s, 1H), 6.51 (s, 2H).

Example 24

3-[2,6-Dimethoxy-4-(methoxymethyl)phenyl]-6-methoxy-N,N-dipropylpyrazolo[5,1-b][1,3]thiazole-7-amine

[Chemical Formula 115]

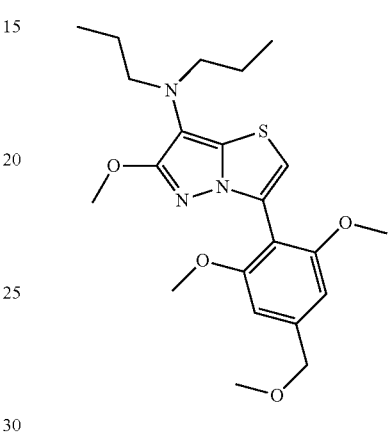

$^1$H-NMR (CDCl$_3$) δ: 0.88 (t, J=6.8 Hz, 6H), 1.40-1.52 (m, 4H), 2.88 (t, J=7.8 Hz, 4H), 3.47 (s, 3H), 3.78 (s, 6H), 3.87 (s, 3H), 4.50 (s, 2H), 6.40 (s, 1H), 6.64 (s, 2H).

Example 25

N-(Cyclopropylmethyl)-3-(2,6-dimethoxy-4-methylphenyl)-6-methoxy-N-(tetrahydro-2H-pyran-4-yl)pyrazolo[5,1-b][1,3]thiazole-7-amine

[Chemical Formula 116]

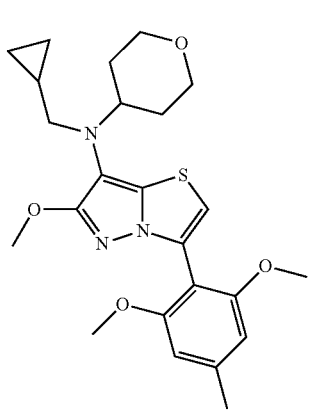

$^1$H-NMR (CDCl$_3$) δ: −0.03-0.04 (m, 2H), 0.30-0.37 (m, 2H), 0.78-0.92 (m, 1H), 1.51-1.66 (m, 2H), 1.76-1.87 (m, 2H), 2.41 (s, 3H), 2.88 (d, J=6.4 Hz, 2H), 3.15 (tt, J=11.2, 4.0

Hz, 1H), 3.39 (dt, J=11.6, 2.0 Hz, 2H), 3.76 (s, 6H), 3.87 (s, 3H), 3.93-4.02 (m, 2H), 6.39 (s, 1H), 6.48 (s, 2H).

Example 26

N-(Cyclopropylmethyl)-3-(2,6-dimethoxy-4-methylphenyl)-6-methoxy-N-(tetrahydrofuran-3-ylmethyl)pyrazolo[5,1-b][1,3]thiazole-7-amine

[Chemical Formula 117]

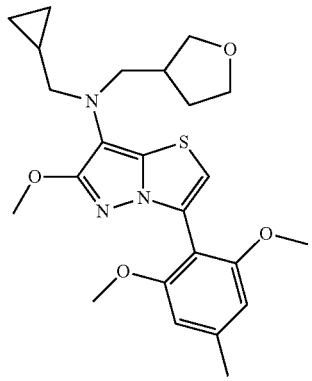

$^1$H-NMR (CDCl$_3$) δ: 0.02-0.08 (m, 2H), 0.35-0.45 (m, 2H), 0.84-0.96 (m, 1H), 1.58-1.70 (m, 1H), 1.91-2.02 (m, 1H), 2.27-2.40 (m, 1H), 2.41 (s, 3H), 2.81 (d, J=6.8 Hz, 2H), 2.95 (dd, J=12.0, 8.4 Hz, 1H), 3.06 (dd, J=12.0, 6.8, 1H), 3.56 (dd, J=8.6, 6.2 Hz, 1H), 3.65-3.73 (m, 1H), 3.76 (s, 6H), 3.78-3.86 (m, 2H), 3.87 (s, 3H), 6.39 (s, 1H), 6.48 (s, 2H).

Example 27

N-(Cyclopropylmethyl)-3-[2,6-dimethoxy-4-(methoxymethyl)phenyl]-6-methoxy-N-(2-methoxyethyl)pyrazolo[5,1-b][1,3]thiazole-7-amine

[Chemical Formula 118]

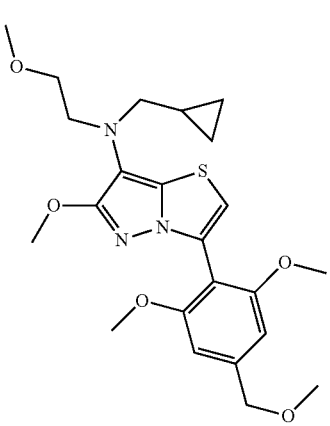

$^1$H-NMR (CDCl$_3$) δ: 0.03-0.10 (m, 2H), 0.36-0.45 (m, 2H), 0.89-0.98 (m, 1H), 2.87 (d, J=6.8 Hz, 2H), 3.25 (t, J=6.4 Hz, 2H), 3.33 (s, 3H), 3.41-3.50 (m, 5H), 3.78 (s, 6H), 3.87 (s, 3H), 4.50 (s, 2H), 6.41 (s, 1H), 6.65 (s, 2H).

Example 28

N-Butyl-3-[2,6-dimethoxy-4-(methoxymethyl)phenyl]-6-methoxy-N-(2-methoxyethyl)pyrazolo[5,1-b][1,3]thiazole-7-amine

[Chemical Formula 119]

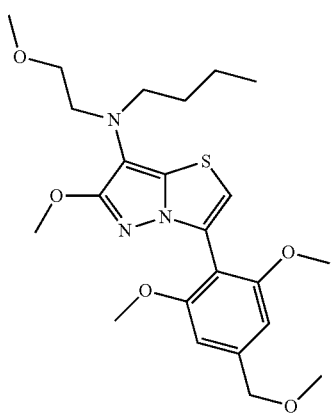

$^1$H-NMR (CDCl$_3$) δ: 0.88 (t, J=7.6 Hz, 3H), 126-1.38 (m, 2H), 1.39-1.48 (m, 2H), 2.95-3.02 (m, 2H), 3.16 (t, J=6.4 Hz, 2H), 3.32 (s, 3H), 3.44 (t, J=6.4 Hz, 2H), 3.47 (s, 3H), 3.79 (s, 6H), 3.87 (s, 3H), 450 (s, 2H), 6.42 (s, 1H), 6.65 (s, 2H).

Example 29

N-(Cyclobutylmethyl)-3-[2,6-dimethoxy-4-(methoxymethyl)phenyl]-6-methoxy-N-(tetrahydrofuran-3-yl)pyrazolo[5,1-b][1,3]thiazole-7-amine

[Chemical Formula 120]

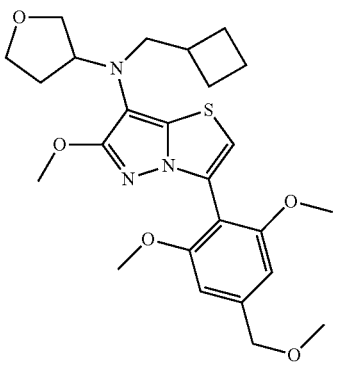

$^1$H-NMR (CDCl$_3$) δ: 1.54-1.65 (m, 2H), 1.67-2.05 (m, 6H), 2.30-2.42 (m, 1H), 2.82-2.90 (m, 1H), 2.91-2.98 (m,

1H), 3.47 (s, 3H), 3.63-3.69 (m, 1H), 3.72-3.91 (m, 13H), 4.70 (s, 2H), 6.42 (s, 1H), 6.64 (s, 2H).

Example 30

3-(4-Chloro-2,6-dimethoxyphenyl)-N-(cyclopropylmethyl)-6-methoxy-N-(tetrahydrofuran-3-ylmethyl)pyrazolo[5,1-b][1,3]thiazole-7-amine

[Chemical Formula 121]

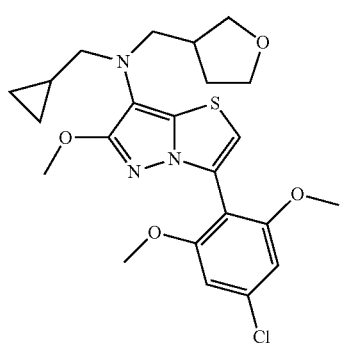

$^1$H-NMR (CDCl$_3$) δ: 0.03-0.07 (m, 2H), 0.36-0.44 (m, 2H), 0.84-0.94 (m, 1H), 1.58-1.68 (m, 1H), 1.92-2.00 (m, 1H), 2.27-2.39 (m, 1H), 2.81 (d, J=6.8 Hz, 2H), 2.94 (dd, J=12.0, 8.4 Hz, 1H), 3.07 (dd, J=12.0, 6.8 Hz, 1H), 3.58 (dd, J=8.8, 6.0 Hz, 1H), 3.66-3.73 (m, 1H), 3.76-3.86 (m, 2H), 3.77 (s, 6H), 3.87 (s, 3H), 6.41 (s, 1H), 6.66 (s, 2H).

Example 31

3-(4-Chloro-2,6-dimethoxymethylphenyl)-6-methoxy-N-propyl-N-(tetrahydro-2H-pyran-4-yl)pyrazolo[5,1-b][1,3]thiazole-7-amine

[Chemical Formula 122]

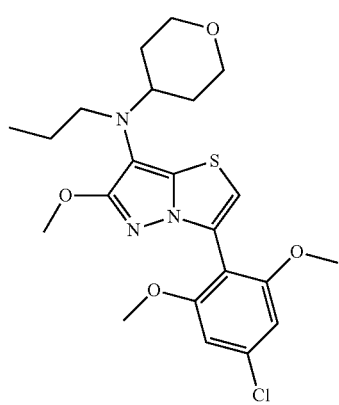

$^1$H-NMR (CDCl$_3$) δ: 0.87 (t, J=7.6 Hz, 3H), 1.37 (qt, J=7.6, 7.6 Hz, 2H), 1.52-1.65 (m, 2H), 1.78-1.86 (m, 2H), 2.94 (t, J=7.6 Hz, 2H), 3.01-3.10 (m, 1H), 3.38 (ddd, J=11.6, 11.6, 1.6 Hz, 2H), 3.77 (s, 6H), 3.86 (s, 3H), 3.94-4.01 (s, 2H), 6.41 (s, 1H), 6.67 (s, 2H).

Example 32

N-(Cyclopropylmethyl)-3-[2,6-dimethoxy-4-(methoxymethyl)phenyl]-6-methoxy-N-(3-methoxypropyl)pyrazolo[5,1-b][1,3]thiazole-7-amine

[Chemical Formula 123]

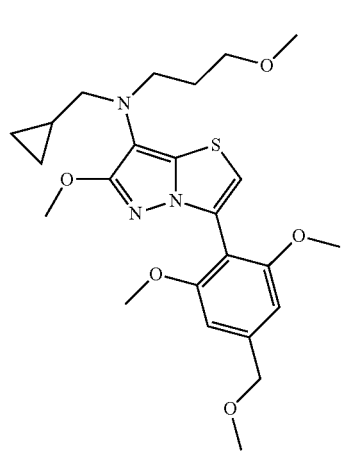

$^1$H-NMR (CDCl$_3$) δ: 0.03-0.07 (m, 2H), 0.38-0.42 (m, 2H), 0.87-0.96 (m, 1H), 1.73 (tt, J=7.2, 6.4 Hz, 2H), 2.82 (d, J=6.4 Hz, 2H), 3.09 (t, J=7.2 Hz, 2H), 3.31 (s, 3H), 3.45 (t, J=6.4 Hz, 2H), 3.47 (s, 3H), 3.78 (s, 6H), 3.87 (s, 3H), 4.50 (s, 2H), 6.39 (s, 1H), 6.64 (s, 2H).

Example 33

3-[2,6-Dimethoxy-4-(methoxymethyl)phenyl]-6-methoxy-N-(3-methoxypropyl)-N-(tetrahydro-2H-pyran-4-yl)pyrazolo[5,1-b][1,3]thiazole-7-amine

[Chemical Formula 124]

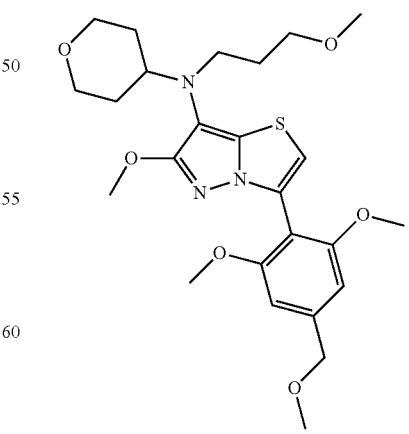

$^1$H-NMR (CDCl$_3$) δ: 1.54-1.67 (m, 4H), 1.79-1.86 (m, 2H), 3.00-3.10 (m, 3H), 3.29 (s, 3H), 3.33-3.46 (m, 4H), 3.47

(s, 3H), 3.79 (s, 6H), 3.85 (s, 3H), 3.94-4.01 (m, 2H), 4.50 (s, 2H), 6.41 (s, 1H), 6.65 (s, 2H).

Example 34

3-[2,6-Dimethoxy-4-(methoxymethyl)phenyl]-6-methoxy-N-oxepan-4-yl-N-propylpyrazolo[5,1-b][1,3]thiazole-7-amine

[Chemical Formula 125]

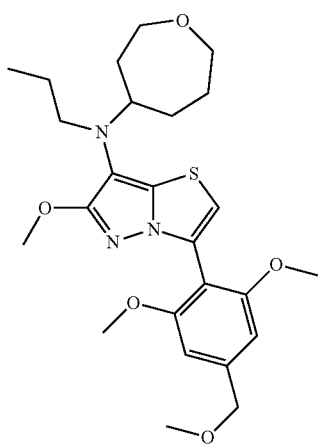

¹H NMR (CDCl₃) δ: 0.84-0.92 (m, 3H), 1.30-1.42 (m, 2H), 1.55-1.68 (m, 2H), 1.73-1.85 (m, 2H), 2.04-2.12 (m, 2H), 2.91 (t, J=7.4 Hz, 2H), 3.10-3.18 (m, 1H), 3.47 (s, 3H), 3.52-3.62 (m, 2H), 3.70-3.82 (m, 2H), 3.79 (s, 6H), 3.86 (s, 3H), 4.50 (s, 2H), 6.41 (s, 1H), 6.65 (s, 2H).

Example 35

[3-(4-Ethoxymethyl-2,6-dimethoxy-phenyl)-6-methoxy-pyrazolo[5,1-b][1,3]thiazol-7-yl]-(3-fluoro-propyl)-(tetrahydro-pyran-4-yl)-amine

[Chemical Formula 126]

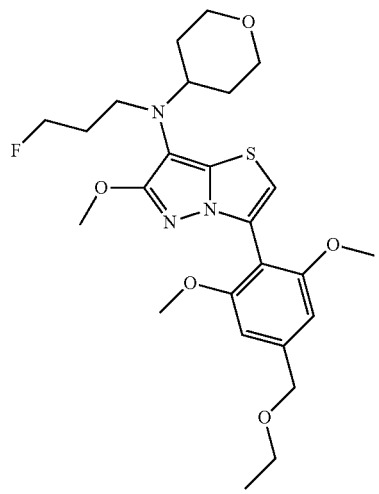

¹H-NMR (CDCl₃) δ: 1.30 (t, J=6.8 Hz, 3H), 1.52-1.88 (m, 6H), 2.99-3.12 (m, 1H), 3.13 (t, J=7.2 Hz, 2H), 3.37 (t, J=11.6 Hz, 2H), 3.63 (q, J=7.2 Hz, 2H), 3.79 (s, 6H), 3.85 (s, 3H), 3.93-4.04 (m, 2H), 4.47 (t, J=5.6 Hz, 1H), 4.55 (s, 2H), 4.58 (t, J=6.0 Hz, 1H), 6.42 (s, 1H), 6.66 (s, 2H).

Example 36

[3-(4-Ethoxymethyl-2,6-dimethoxy-phenyl)-6-methoxy-pyrazolo[5,1-b][1,3]thiazol-7-yl]-(4-fluoro-butyl)-(tetrahydro-pyran-4-yl)-amine

[Chemical Formula 127]

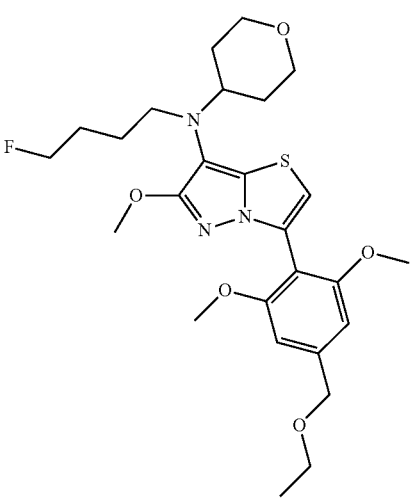

¹H-NMR (CDCl₃) δ: 1.30 (t, J=7.2 Hz, 3H), 1.40-1.51 (m, 2H), 1.52-1.87 (m, 6H), 2.98-3.11 (m, 1H), 3.03 (t, J=7.2 Hz, 2H), 3.37 (t, J=11.6 Hz, 2H), 3.62 (q, J=7.2 Hz, 2H), 3.79 (s, 6H), 3.85 (s, 3H), 3.93-4.04 (m, 2H), 4.35 (t, J=6.0 Hz, 1H), 4.47 (t, J=6.4 Hz, 1H), 4.55 (s, 2H), 6.41 (s, 1H), 6.66 (s, 2H).

Example 37

N-[(3,3-Difluorocyclobutyl)methyl]-3-[2,6-dimethoxy-4-(methoxymethyl)phenyl]-6-methoxy-N-(tetrahydrofuran-3-ylmethyl)pyrazolo[5,1-b][1,3]thiazole-7-amine

[Chemical Formula 128]

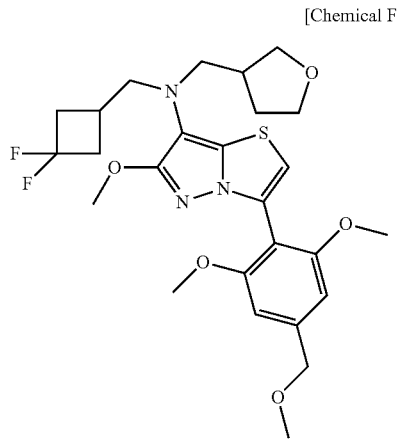

¹H-NMR (CDCl₃) δ: 1.56-1.67 (m, 1H), 1.92-2.00 (m, 1H), 2.12-2.35 (m, 4H), 2.46-2.60 (m, 2H), 2.85 (dd, J=12.0, 8.4 Hz, 1H), 2.95-3.04 (m, 3H), 3.47 (s, 3H), 3.55 (dd, 6.0 Hz, 1H), 3.66-3.73 (m, 1H), 3.76-3.86 (m, 2H), 3.78 (s, 6H), 3.85 (s, 3H), 4.50 (s, 2H), 6.43 (s, 1H), 6.65 (s, 2H).

Example 38

N-[(3,3-Difluorocyclobutyl)methyl]-3-[2,6-dimethoxy-4-(methoxymethyl)phenyl]-6-methoxy-N-(tetrahydro-2H-pyran-4-yl)pyrazolo[5,1-b][1,3]thiazole-7-amine

[Chemical Formula 129]

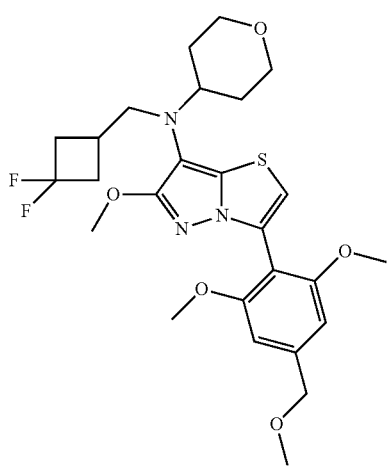

¹H-NMR (CDCl₃) δ: 1.52-1.64 (m, 2H), 1.78-1.84 (m, 2H), 2.08-2.24 (m, 3H), 2.41-2.53 (m, 2H), 2.97-3.09 (m, 3H), 3.37 (ddd, J=12.0, 12.0, 2.0 Hz, 2H), 3.47 (s, 3H), 3.79 (s, 6H), 3.84 (s, 3H), 3.94-4.01 (m, 2H), 4.50 (s, 2H), 6.43 (s, 1H), 6.65 (s, 2H).

Example 39

3-[2,6-Dimethoxy-4-(methoxymethyl)phenyl]-6-methoxy-N-(3-methoxypropyl)-N-propylpyrazolo[5,1-b][1,3]thiazole-7-amine

[Chemical Formula 130]

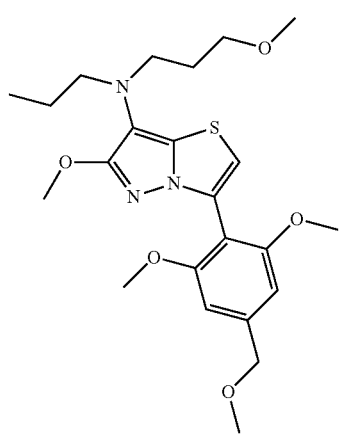

¹H-NMR (CDCl₃) δ: 0.89 (t, 77.6 Hz, 3H), 1.43-1.80 (m, 4H), 2.90-2.99 (m, 2H), 3.03-3.12 (m, 2H), 3.30 (s, 3H), 3.43 (t, J=6.0 Hz, 2H), 3.47 (s, 3H), 3.78 (s, 6H), 3.87 (s, 3H), 4.50 (s, 2H), 6.42 (s, 1H), 6.64 (s, 2H).

Example 40

N-(Cyclopropylmethyl)-3-[4-(ethoxymethyl)-2,6-dimethoxyphenyl]-6-methoxy-N-(2-methoxyethyl)pyrazolo[5,1-b][1,3]thiazole-7-amine

[Chemical Formula 131]

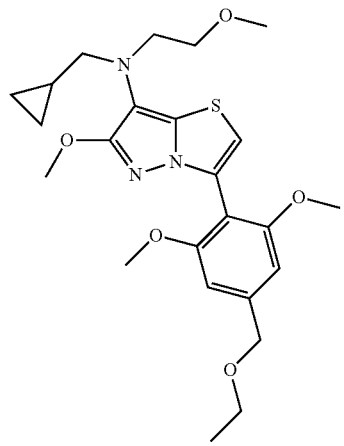

¹H-NMR (CDCl₃) δ: 0.04-0.08 (m, 2H), 0.38-0.43 (m, 2H), 0.87-0.99 (m, 1H), 1.30 (J=7.2 Hz, 3H), 2.87 (d, J=6.8 Hz, 2H), 3.25 (t, J=6.4 Hz, 2H), 3.33 (s, 3H), 3.46 (t, J=6.4 Hz, 2H), 3.62 (q, J=7.2 Hz, 2H), 3.78 (s, 6H), 3.87 (s, 3H), 4.54 (s, 2H), 6.40 (s, 1H), 6.66 (s, 2H).

Example 41

N-Butyl-3-[4-(ethoxymethyl)-2,6-dimethoxyphenyl]-6-methoxy-N-(2-methoxyethyl)pyrazolo[5,1-b][1,3]thiazole-7-amine

[Chemical Formula 132]

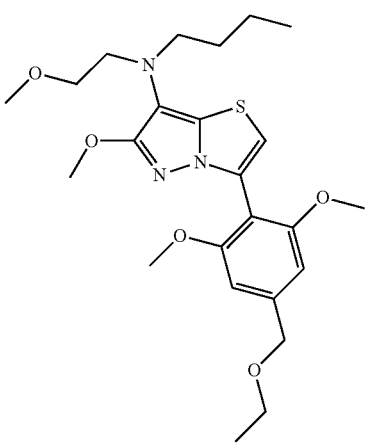

¹H-NMR (CDCl₃) δ: 0.88 (t, J=7.2 Hz, 3H), 1.25-1.38 (m, 5H), 1.39-1.48 (m, 2H), 2.98 (t, J=7.2 Hz, 2H), 3.16 (t, J=6.4

Hz, 2H), 3.32 (s, 3H), 3.44 (t, 2H), 3.62 (q, J=7.2 Hz, 2H), 3.79 (s, 6H), 3.87 (s, 3H), 4.54 (s, 2H), 6.41 (s, 1H), 6.66 (s, 2H).

Example 42

N-(Cyclopropylmethyl)-3-[4-(ethoxymethyl)-2,6-dimethoxyphenyl]-6-methoxy-N-(3-methoxypropyl)pyrazolo[5,1-b][1,3]thiazole-7-amine

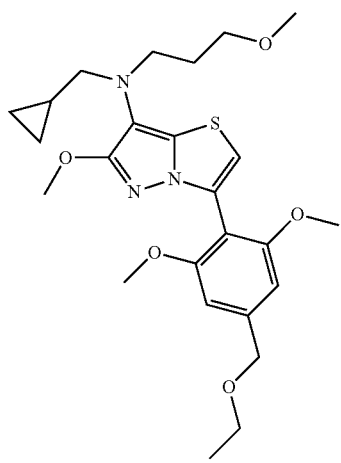

[Chemical Formula 133]

$^1$H-NMR (CDCl$_3$) δ: 0.02-0.08 (m, 2H), 0.37-0.43 (m, 2H), 0.85-0.96 (m, 1H), 1.30 (t, J=7.2 Hz, 3H), 1.68-1.78 (m, 2H), 2.82 (d, J=6.4 Hz, 2H), 3.09 (t, J=7.2 Hz, 2H), 3.31 (s, 3H), 3.45 (t, —6.4 Hz, 2H), 3.62 (q, J=7.2 Hz, 2H), 3.78 (s, 6H), 3.87 (s, 3H), 4.54 (s, 2H), 6.39 (s, 1H), 6.66 (s, 2H).

Example 43

[3-(2,6-Dimethoxy-4-methoxymethylphenyl)-6-methoxy-pyrazolo[5,1-b][1,3]thiazol-7-yl]-isobutyl-(tetrahydrofuran-3-yl)-amine

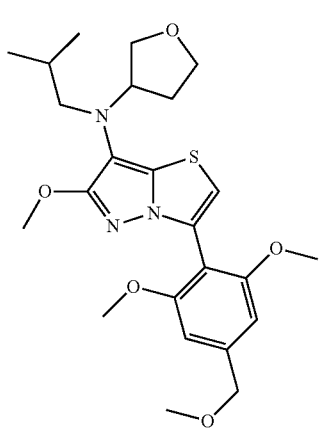

[Chemical Formula 134]

$^1$H-NMR (CDCl$_3$) δ: 0.89 (d, J=6.8 Hz, 6H), 1.47-1.59 (m, 1H), 1.87-2.04 (m, 2H), 2.62 (dd, J=7.2, 12.0 Hz, 1H), 2.72 (dd, 12.0 Hz, 1H), 3.47 (s, 3H), 3.64-3.90 (m, 5H), 3.78 (s, 6H), 3.86 (s, 3H), 4.50 (s, 2H), 6.43 (s, 1H), 6.64 (s, 2H).

Example 44

3-[2,6-Dimethoxy-4-(methoxymethyl)phenyl]-6-methoxy-N-propyl-N-(pyridin-4-ylmethyl)pyrazolo[5,1-b][1,3]thiazole-7-amine

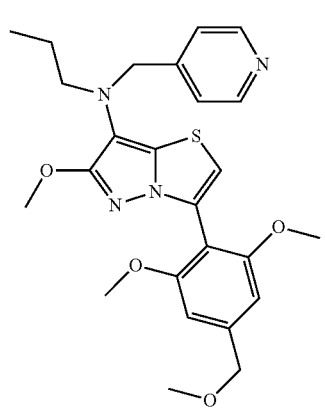

[Chemical Formula 135]

$^1$H-NMR (CDCl$_3$) δ: 0.89 (t, 37.4 Hz, 3H), 1.43-1.54 (m, 2H), 2.89 (t, J=7.4 Hz, 2H), 3.46 (s, 3H), 3.76 (s, 6H), 3.85 (s, 3H), 4.13 (s, 2H), 4.49 (s, 2H), 6.38 (s, 1H), 6.63 (s, 2H), 7.28-733 (m, 2H), 8.49 (m, 2H).

Example 45

N-(Cyclopropylmethyl)-3-[2,6-dimethoxy-4-(methoxymethyl)phenyl]-N-(2-ethoxyethyl)-6-methoxy-pyrazolo[5,1-b][1,3]thiazole-7-amine

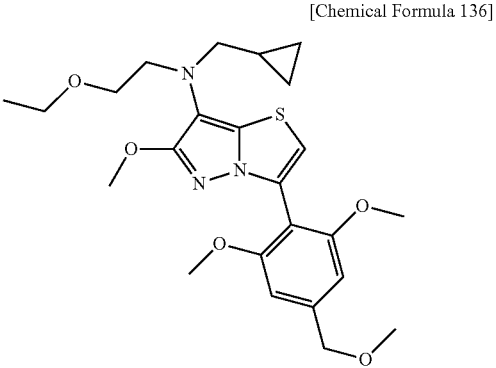 [SMILES: CCOCCN(CC1CC1)c1c(OC)nn2c(-c3c(OC)cc(COC)cc3OC)csc12]

[Chemical Formula 136]

$^1$H-NMR (CDCl$_3$) δ: 0.40-1.10 (m, 2H), 0.36-0.45 (m, 2H), 0.89-0.98 (m, 1H), 1.17 (t, J=7.0 Hz, 3H), 2.88 (d, J=6.4 Hz, 2H), 3.26 (t, J=6.8 Hz, 2H), 3.46 (t, J=6.8 Hz, 2H), 3.47

(s, 3H), 3.50 (q, J=7.0 Hz, 2H), 3.78 (s, 6H), 3.87 (s, 3H), 4.50 (s, 2H), 6.41 (s, 1H), 6.65 (s, 2H).

Example 46

3-[4-(Ethoxymethyl)-2,6-dimethoxyphenyl]-6-methoxy-N-propyl-N-(tetrahydrofuran-3-yl)pyrazolo[5,1-b][1,3]thiazole-7-amine

[Chemical Formula 137]

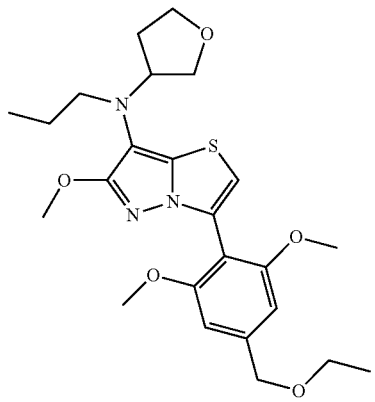

$^1$H-NMR (CDCl$_3$) δ: 0.88 (t, J=7.2 Hz, 3H), 1.30 (t, J=7.2 Hz, 3H), 1.34-1.45 (m, 2H), 1.89-2.06 (m, 2H), 2.77-2.95 (m, 2H), 3.62 (q, J=7.2 Hz, 2H), 3.65-3.72 (m, 1H), 3.74-3.90 (m, 13H), 4.54 (s, 2H), 6.42 (s, 1H), 6.66 (s, 2H).

Example 47

N-(Cyclobutylmethyl)-3-[4-(ethoxymethyl)-2,6-dimethoxyphenyl]-6-methoxy-N-(tetrahydrofuran-3-yl)pyrazolo[5,1-b][1,3]thiazole-7-amine

[Chemical Formula 138]

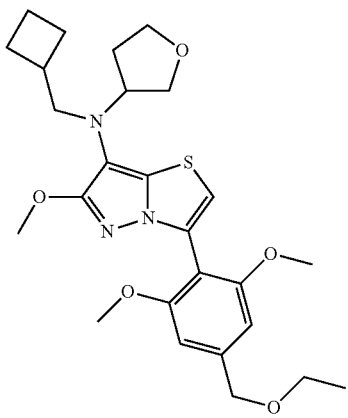

$^1$H-NMR (CDCl$_3$) δ: 1.30 (t, J=7.2 Hz, 3H), 1.53-1.64 (m, 2H), 1.68-2.06 (m, 6H), 2.31-2.42 (m, 1H), 2.86 (dd, J=11.6, 7.0 Hz, 1H), 2.94 (dd, J=11.6, 7.2 Hz, 1H), 3.62 (q, J=7.2 Hz, 2H), 3.65-3.69 (m, 1H), 3.73-3.92 (m, 13H), 4.54 (s, 2H), 6.42 (s, 1H), 6.65 (s, 2H).

Example 48

N-(Cyclobutylmethyl)-3-[2,6-dimethoxy-4-(methoxymethyl)phenyl]-6-methoxy-N-(2-methoxyethyl)pyrazolo[5,1-b][1,3]thiazole-7-amine

[Chemical Formula 139]

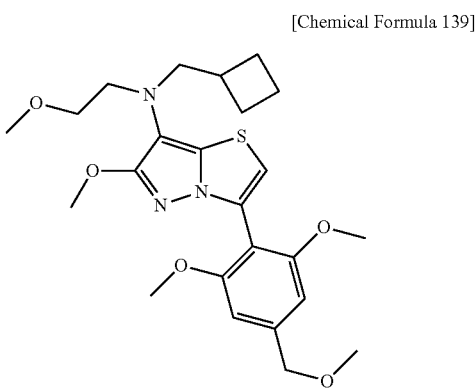

$^1$H-NMR (CDCl$_3$) δ: 1.56-1.68 (m, 2H), 1.69-1.96 (m, 4H), 2.40-2.52 (m, 1H), 3.01 (d, J=7.2 Hz, 2H), 3.14 (t, J=6.4 Hz, 2H), 3.32 (s, 3H), 3.43 (t, J=6.4 Hz, 2H), 3.47 (s, 3H), 3.78 (s, 6H), 3.87 (s, 3H), 4.50 (s, 2H), 6.42 (s, 1H), 6.64 (s, 2H).

Example 49

N-(Cyclopropylmethyl)-3-[2,6-dimethoxy-4-(methoxymethyl)phenyl]-N-(2-isopropoxyethyl)-6-methoxypyrazolo[5,1-b][1,3]thiazole-7-amine

[Chemical Formula 140]

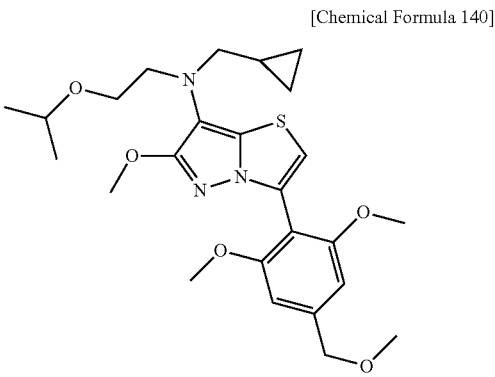 [SMILES: COCc1cc(OC)c(-c2csc3c(N(CCOC(C)C)CC4CC4)c(OC)nn23)c(OC)c1]

$^1$H-NMR (CDCl$_3$) δ: 0.03-0.11 (m, 2H), 0.37-0.45 (m, 2H), 0.88-0.99 (m, 1H), 1.11 (d, J=6.4 Hz, 6H), 2.89 (d, J=6.8

Hz, 2H), 3.26 (d, 2H), 3.47 (s, 3H), 3.48-3.57 (m, 3H), 3.78 (s, 6H), 3.89 (s, 3H), 4.50 (s, 2H), 6.41 (s, 1H), 6.64 (s, 2H).

Example 50

N-(Cyclopropylmethyl)-3-[2,6-dimethoxy-4-(methoxymethyl)phenyl]-6-methoxy-N-(3-methoxybutyl)pyrazolo[5,1-b][1,3]thiazole-7-amine

[Chemical Formula 141]

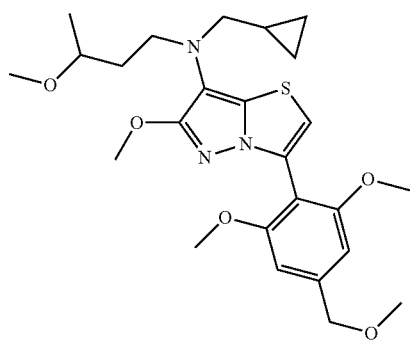

$^{1}$H-NMR (CDCl$_{3}$) δ: 0.02-0.09 (m, 2H), 0.36-0.45 (m, 2H), 0.85-0.97 (m, 1H), 1.13 (d, J=6.0 Hz, 3H), 1.48-1.59 (m, 1H), 1.65-1.77 (m, 1H), 2.81 (d, J=6.8 Hz, 2H), 3.08 (t, J=7.6 Hz, 2H), 3.28 (s, 3H), 3.40-3.48 (m, 4H), 3.78 (s, 6H), 3.87 (s, 3H), 4.50 (s, 2H), 6.40 (s, 1H), 6.64 (s,

Example 51

N-(Cyclopropylmethyl)-3-[2,6-dimethoxy-4-(methoxymethyl)phenyl]-6-methoxy-N-(2-methoxypropyl)pyrazolo[5,1-b][1,3]thiazole-7-amine

[Chemical Formula 142]

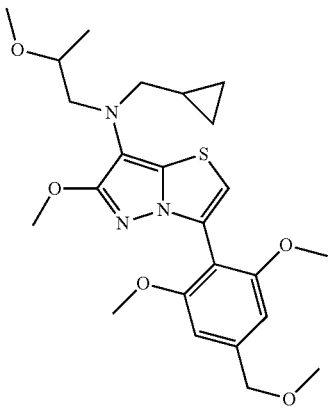

$^{1}$H-NMR (CDCl$_{3}$) δ: 0.02-0.08 (m, 2H), 0.36-0.44 (m, 2H), 0.86-0.97 (m, 1H), 1.16 (d, J=6.4 Hz, 3H), 2.82-2.87 (m, 2H), 2.91 (dd, 6.0 Hz, 1H), 3.30 (dd, J=12.8, 6.4 Hz, 1H), 3.30-3.38 (m, 4H), 3.47 (s, 3H), 3.78 (s, 6H), 3.87 (s, 3H), 4.50 (s, 2H), 6.41 (s, 1H), 6.65 (s, 2H).

Example 52

3-[2,6-Dimethoxy-4-(methoxymethyl)phenyl]-N-(1-ethylpropyl)-6-methoxy-N-(2-methoxyethyl)pyrazolo[5,1-b][1,3]thiazole-7-amine

[Chemical Formula 143]

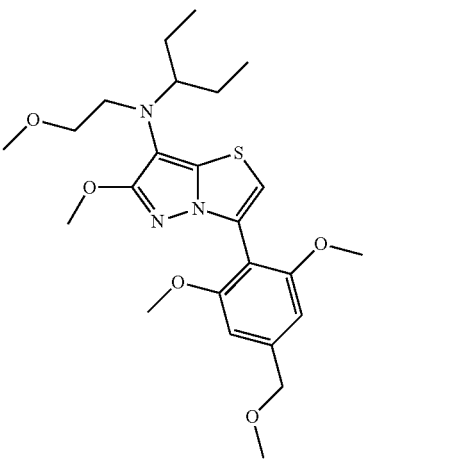

$^{1}$H-NMR (CDCl$_{3}$) δ: 0.92-1.02 (m, 6H), 1.31-1.61 (m, 4H), 2.60-2.71 (m, 1H), 3.17 (t, J=6.8 Hz, 2H), 3.32 (s, 3H), 3.38 (t, J=6.8 Hz, 2H), 3.47 (s, 3H), 3.79 (s, 6H), 3.84 (s, 3H), 4.50 (s, 2H), 6.40 (s, 1H), 6.64 (s, 2H).

Example 53

N-Cyclopentyl-3-[2,6-dimethoxy-4-(methoxymethyl)phenyl]-6-methoxy-N-(2-methoxyethyl)pyrazolo[5,1-b][1,3]thiazole-7-amine

[Chemical Formula 144]

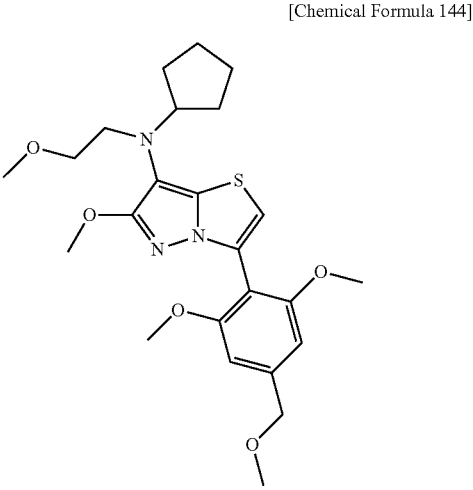

$^{1}$H-NMR (CDCl$_{3}$) δ: 1.43-1.87 (m, 8H), 3.15 (t, J=6.8 Hz, 2H), 3.30 (s, 3H), 3.38 (t, J=6.8 Hz, 2H), 3.42-3.52 (m, 4H, involving a singlet at 3.47), 3.79 (s, 6H), 3.87 (s, 3H), 4.50 (s, 2H), 6.43 (s, 1H), 6.65 (s, 2H).

Example 54

N-Cyclohexyl-3-[2,6-dimethoxy-4-(methoxymethyl)phenyl]-6-methoxy-N-(2-methoxyethyl)pyrazolo[5,1-b][1,3]thiazole-7-amine

[Chemical Formula 145]

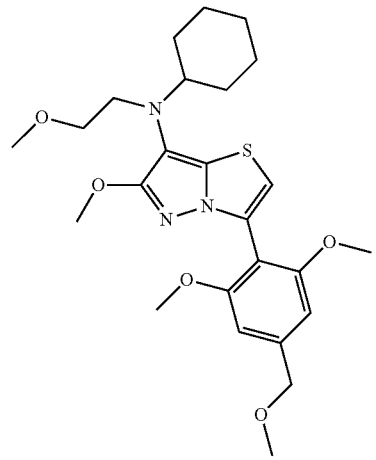

$^1$H-NMR (CDCl$_3$) δ: 0.95-1.31 (m, 5H), 1.48-1.62 (m, 1H), 1.69-1.80 (m, 2H), 1.89-2.01 (m, 2H), 2.75-2.88 (m, 1H), 3.20 (t, J=6.8 Hz, 2H), 3.30 (s, 3H), 3.36 (t, J=6.8 Hz, 2H), 3.47 (s, 3H), 3.79 (s, 6H), 3.86 (s, 3H), 4.50 (s, 2H), 6.43 (s, 1H), 6.65 (s, 2H).

Example 55

3-[2,6-Dimethoxy-4-(methoxymethyl)phenyl]-N-isobutyl-6-methoxy-N-(2-methoxyethyl)pyrazolo[5,1-b][1,3]thiazole-7-amine

[Chemical Formula 146]

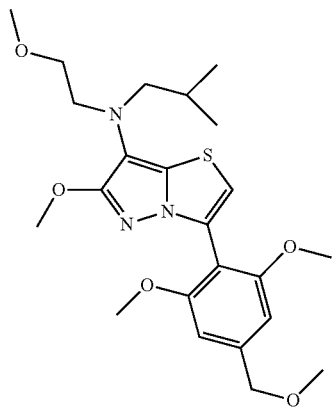

$^1$H-NMR (CDCl$_3$) δ: 0.91 (d, J=6.8 Hz, 6H), 1.57-1.67 (m, 1H), 2.78 (d, J=7.2 Hz, 2H), 3.15 (t, J=6.4 Hz, 2H), 3.33 (s, 3H), 3.45 (t, J=6.4 Hz, 2H), 3.47 (s, 3H), 3.79 (s, 6H), 3.86 (s, 3H), 4.50 (s, 2H), 6.41 (s, 1H), 6.64 (s, 2H).

Example 56

N-Cyclobutyl-3-[2,6-dimethoxy-4-(methoxymethyl)phenyl]-6-methoxy-N-(2-methoxyethyl)pyrazolo[5,1-b][1,3]thiazole-7-amine

[Chemical Formula 147]

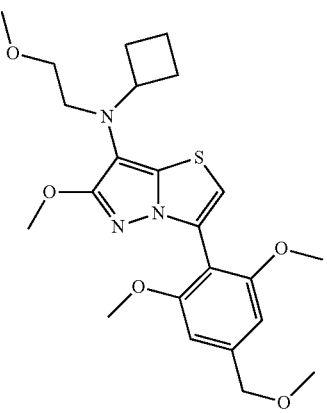

$^1$H-NMR (CDCl$_3$) δ: 1.53-1.67 (m, 2H), 1.88-2.07 (m, 4H), 3.05 (t, J=6.4 Hz, 2H), 3.31 (s, 3H), 3.39 (t, J=6.4 Hz, 2H), 3.47 (s, 3H), 3.63-3.75 (m, 1H), 3.79 (s, 6H), 3.87 (s, 3H), 4.50 (s, 2H), 6.43 (s, 1H), 6.65 (s, 2H).

Example 57

N-(Cyclopropylmethyl)-6-methoxy-N-(2-methoxyethyl)-3-[2-methoxy-4-(methoxymethyl)phenyl]pyrazolo[5,1-b][1,3]thiazole-7-amine

[Chemical Formula 148]

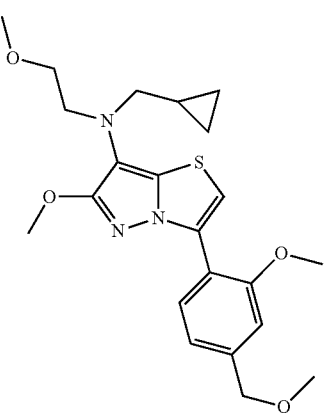

$^1$H-NMR (CDCl$_3$) δ: 0.04-0.11 (m, 2H), 0.35-0.43 (m, 2H), 0.83-0.93 (m, 1H), 2.88 (d, J=6.0 Hz, 2H), 3.25 (t, J=6.4 Hz, 2H), 3.32 (s, 3H), 3.43 (t, J=6.4 Hz, 2H), 3.44 (s, 3H), 3.92 (s, 3H), 3.98 (br.s, 3H), 4.52 (s, 2H), 6.98-7.02 (m, 1H), 7.03-7.07 (m, 2H), 8.43-8.46 (m, 1H).

Example 58

N-(Cyclopropylmethyl)-3-(2,4-dimethoxyphenyl)-6-methoxy-N-(2-methoxyethyl)pyrazolo[5,1-b][1,3]thiazole-7-amine

[Chemical Formula 149]

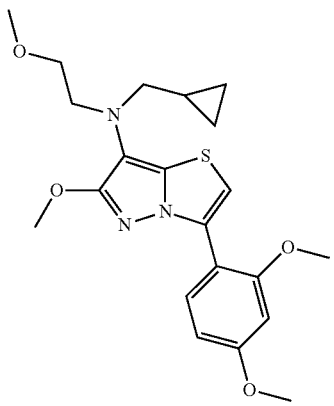

$^1$H-NMR (CDCl$_3$) δ: 0.03-0.10 (m, 2H), 0.36-0.43 (m, 2H), 0.85-0.95 (m, 1H), 2.88 (d, J=6.8 Hz, 2H), 3.25 (t, J=6.4 Hz, 2H), 3.31 (s, 3H), 3.42 (t, J=6.4 Hz, 2H), 3.88 (s, 3H), 3.88 (s, 3H), 3.99 (s, 3H), 6.58 (d, J=2.4 Hz, 1H), 6.64 (dd, J=8.4, 2.4 Hz, 1H), 6.89 (s, 1H), 8.43 (d, J=8.4 Hz, 1H).

Example 59

N-Cyclobutyl-3-[2,6-dimethoxy-4-(methoxymethyl)phenyl]-N-ethyl-6-methoxypyrazolo[5,1-b][1,3]thiazole-7-amine

[Chemical Formula 150]

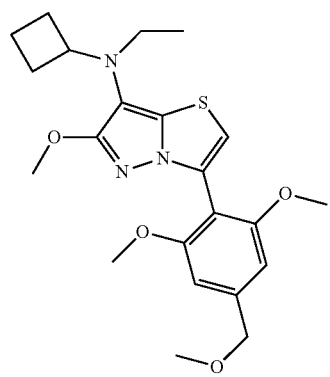

$^1$H-NMR (CDCl$_3$) δ: 0.98 (t, J=7.0 Hz, 3H), 1.52-1.68 (m, 2H), 1.87-2.06 (m, 4H), 2.88 (q, J=7.0 Hz, 2H), 3.47 (s, 3H), 3.56-3.67 (m, 1H), 3.78 (s, 6H), 3.87 (s, 3H), 4.50 (s, 2H), 6.42 (s, 2H), 7.26 (s, 1H).

Example 60

3-(4-Cyclopropyl-2,6-dimethoxyphenyl)-N-(cyclopropylmethyl)-6-methoxy-N-(tetrahydrofuran-3-ylmethyl)pyrazolo[5,1-b][1,3]thiazole-7-amine

[Chemical Formula 151]

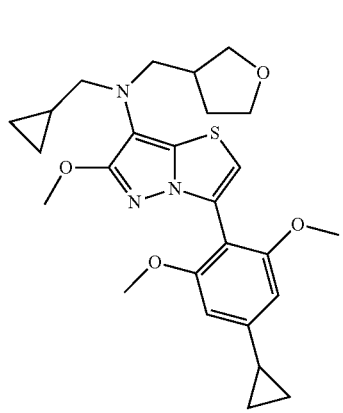

$^1$H-NMR (CDCl$_3$) δ: 0.03-0.08 (m, 2H), 0.37-0.43 (m, 2H), 0.75-0.81 (m, 2H), 0.86-0.94 (m, 1H), 0.99-1.05 (m, 2H), 1.59-1.70 (m, 1H), 1.90-2.01 (m, 2H), 2.28-2.40 (m, 1H), 2.80 (d, J=6.8 Hz, 2H), 2.94 (dd, J=12.0, 8.8 Hz, 1H), 3.06 (12.0, 6.8 Hz, 1H), 3.56 (dd, J=8.8, 6.4 Hz, 1H), 3.66-3.72 (m, 1H), 3.76 (s, 6H), 3.77-3.85 (m, 2H), 3.87 (s, 3H), 6.37 (s, 2H), 6.38 (s, 1H).

Example 61

3-(4-Cyclopropyl-2,6-dimethoxyphenyl)-6-methoxy-N-propyl-N-(tetrahydro-2H-pyran-4-yl)pyrazolo[5,1-b][1,3]thiazole-7-amine

[Chemical Formula 152]

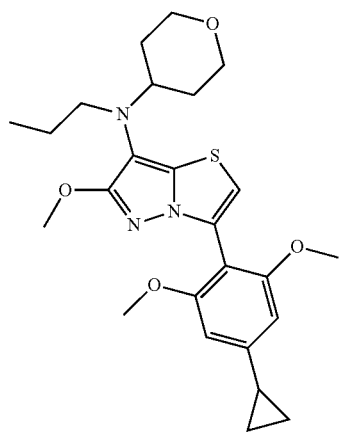

$^1$H-NMR (CDCl$_3$) δ: 0.77-0.81 (m, 2H), 0.87 (t, J=7.61 Hz, 3H), 1.00-1.05 (m, 2H), 1.38 (qt, J=7.6, 7.6 Hz, 2H), 1.50-

1.66 (m, 2H), 1.79-1.86 (m, 2H), 1.91-2.00 (m, 1H), 2.93 (t, J=7.6 Hz, 2H), 3.00-3.10 (m, 1H), 3.33-3.42 (m, 2H), 3.77 (s, 6H), 3.87 (s, 3H), 3.94-4.02 (m, 2H), 6.38 (s, 2H), 6.38 (s, 1H).

Example 62

N-Cyclobutyl-3-[2,6-dimethoxy-4-(methoxymethyl)phenyl]-6-methoxy-N-(3-methoxypropyl)pyrazolo[5,1-b][1,3]thiazole-7-amine

[Chemical Formula 153]

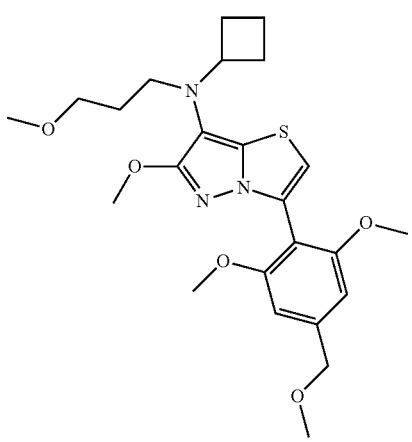

$^1$H-NMR (CDCl$_3$) δ: 1.52-1.72 (m, 4H), 1.85-2.08 (m, 4H), 2.83-2.93 (m, 2H), 3.30 (s, 3H), 3.38-3.46 (m, 2H), 3.47 (s, 3H), 3.57-3.68 (m, 1H), 3.79 (s, 6H), 3.86 (s, 3H), 4.50 (s, 2H), 6.42 (s, 1H), 6.65 (s, 2H).

Example 63

N-Cyclopentyl-3-[2,6-dimethoxy-4-(methoxymethyl)phenyl]-6-methoxy-N-(3-methoxypropyl)pyrazolo[5,1-b][1,3]thiazole-7-amine

[Chemical Formula 154]

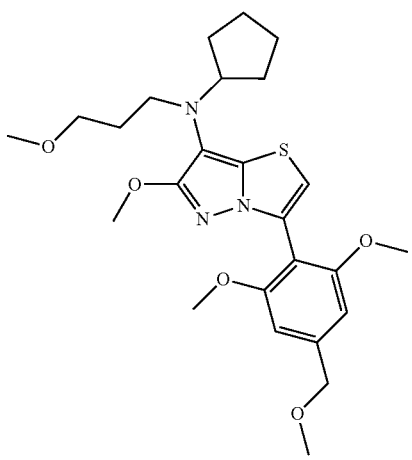

$^1$H-NMR (CDCl$_3$) δ: 1.42-1.86 (m, 10H), 2.95-3.05 (m, 2H), 3.30 (s, 3H), 3.37-3.46 (m, 2H), 3.47 (s, 3H), 3.73-3.83 (m, 7H, involving a singlet at 3.78), 3.86 (s, 3H), 4.50 (s, 2H), 6.41 (s, 1H), 6.64 (s, 2H).

Example 64

3-(4-Cyclopropyl-2,6-dimethoxyphenyl)-N-ethyl-6-methoxy-N-(tetrahydro-2H-pyran-4-yl)pyrazolo[5,1-b][1,3]thiazole-7-amine

[Chemical Formula 155]

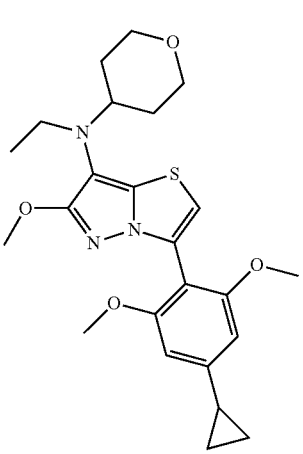

$^1$H-NMR (CDCl$_3$) δ: 0.77-0.81 (m, 2H), 0.99 (t, J=7.2 Hz, 3H), 1.02-1.05 (m, 2H), 1.52-1.65 (m, 2H), 1.80-1.86 (m, 2H), 1.92-1.99 (m, 1H), 3.02-3.11 (m, 1H), 3.05 (q, J=7.2 Hz, 2H), 3.38 (ddd, J=12.0, 12.0, 1.6 Hz, 2H), 3.77 (s, 6H), 3.87 (s, 3H), 3.95-4.01 (m, 2H), 6.38 (s, 2H), 6.39 (s, 1H).

Example 65

3-[2,6-Dimethoxy-4-(methoxymethyl)phenyl]-6-methoxy-N-[3-(methoxymethyl)cyclobutyl]-N-propylpyrazolo[5,1-b][1,3]thiazole-7-amine

[Chemical Formula 156]

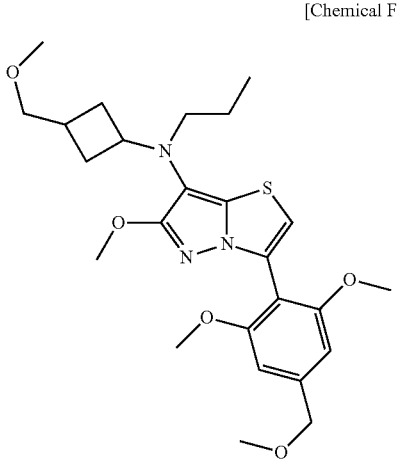

$^1$H-NMR (CDCl$_3$) δ: 0.86 (t, J=7.4 Hz, 3H), 1.33-1.46 (m, 2H), 1.81-1.90 (m, 2H), 2.07-2.22 (m, 2H), 2.29-2.41 (m,

1H), 2.71-2.80 (m, 2H), 3.18-3.44 (m, 5H), 3.47 (s, 3H), 3.66-3.76 (m, 1H), 3.78 (s, 6H), 3.86 (s, 3H), 4.50 (s, 2H), 6.42 (s, 1H), 6.64 (s, 2H).

Example 66

N-Cyclopentyl-3-[2,6-dimethoxy-4-(methoxymethyl)phenyl]-N-ethyl-6-methoxypyrazolo[5,1-b][1,3]thiazole-7-amine

[Chemical Formula 157]

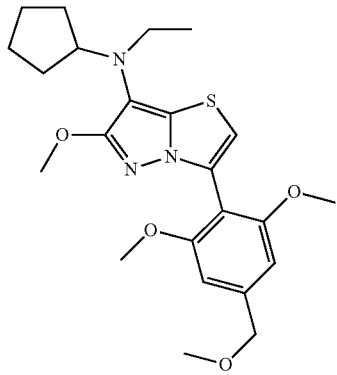

$^1$H-NMR (CDCl$_3$) δ: 0.98 (t, J=7.4 Hz, 3H), 1.44-1.85 (m, 8H), 2.99 (q, J=7.2 Hz, 2H), 3.37-3.47 (m, 1H), 3.47 (s, 3H), 3.78 (s, 6H), 3.87 (s, 3H), 4.50 (s, 2H), 6.42 (s, 1H), 6.65 (s, 2H).

Example 67

N-Cyclobutyl-3-[2,6-dimethoxy-4-(methoxymethyl)phenyl]-6-methoxy-N-(tetrahydrofuran-3-yl)pyrazolo[5,1-b][1,3]thiazole-7-amine

[Chemical Formula 158]

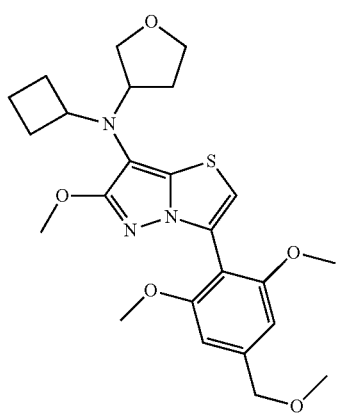

$^1$H-NMR (CDCl$_3$) δ: 1.51-1.62 (m, 2H), 1.84-2.05 (m, 6H), 3.47 (s, 3H), 3.60-3.73 (m, 2H), 3.74-3.83 (m, 9H), 3.84-3.91 (m, 4H), 4.50 (s, 2H), 6.44 (s, 1H), 6.65 (s, 2H).

Example 68

[3-(4-Isopropoxymethyl-2,6-dimethoxyphenyl)-6-methoxy-pyrazolo[5,1-b][1,3]thiazol-7-yl]-propyl-(tetrahydro-pyran-4-yl)-amine

[Chemical Formula 159]

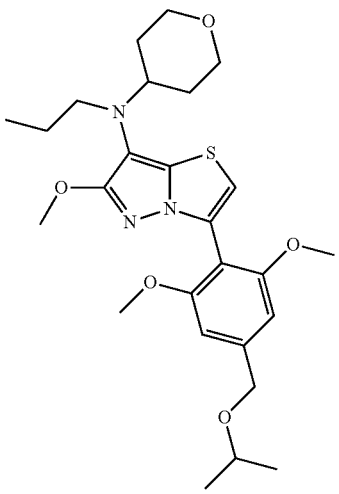

$^1$H-NMR (CDCl$_3$) δ: 0.87 (t, J=7.6 Hz, 3H), 1.27 (d, J=6.0 Hz, 6H), 1.30-1.45 (m, 2H), 1.52-1.67 (m, 2H), 1.78-1.87 (m, 2H), 2.94 (t, J=7.6 Hz, 2H), 2.99-3.11 (m, 1H), 3.38 (t, J=11.2 Hz, 2H), 3.79 (s, 6H), 3.85 (s, 3H), 3.70-3.90 (m, 1H), 3.93-4.04 (m, 2H), 4.55 (s, 2H), 6.40 (s, 1H), 6.66 (s, 2H).

Example 69

N-Cyclopentyl-3-(4-cyclopropyl-2,6-dimethoxyphenyl)-6-methoxy-N-(3-methoxypropyl)pyrazolo[5,1-b][1,3]-thiazole-7-amine

[Chemical Formula 160]

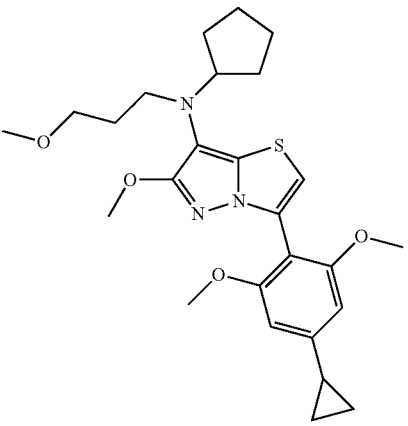

$^1$H-NMR (CDCl$_3$) δ: 0.76-0.80 (m, 2H), 1.00-1.05 (m, 2H), 1.44-1.69 (m, 8H), 1.71-1.82 (m, 2H), 1.92-1.98 (m, 1H), 3.00 (t, J=7.2 Hz, 2H), 3.29 (s, 3H), 3.41 (t, J=6.8 Hz, 2H), 3.36 (m, 1H), 3.76 (s, 6H), 3.87 (s, 3H), 6.37 (s, 2H), 6.38 (s, 1H).

Example 70

3-[2,6-Dimethoxy-4-(methoxymethyl)phenyl]-N-(3-fluoropropyl)-6-methoxy-N-(pyridin-4-ylmethyl)-pyrazolo[5,1-b][1,3]thiazole-7-amine

[Chemical Formula 161]

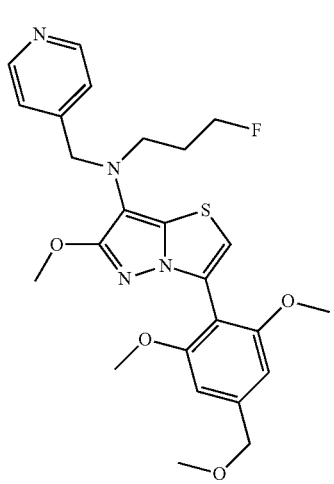

$^1$H-NMR (CDCl$_3$) δ: 1.76-1.90 (m, 2H), 3.08 (t, J=6.8 Hz, 2H), 3.47 (s, 3H), 3.76 (s, 6H), 3.85 (s, 3H), 4.14 (s, 2H), 4.49 (s, 2H), 4.55 (dt, J=47.6, 6.4 Hz, 2H), 6.40 (s, 1H), 6.63 (s, 2H), 7.24-7.32 (m, 2H), 8.47-8.52 (m, 2H).

Example 71

3-[2,6-Dimethoxy-4-(methoxymethyl)phenyl]-N-(3-fluoropropyl)-6-methoxy-N-(pyridin-3-ylmethyl)-pyrazolo[5,1-b][1,3]thiazole-7-amine

[Chemical Formula 162]

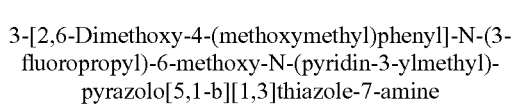

$^1$H-NMR (CDCl$_3$) δ: 1.74-1.90 (m, 2H), 3.08 (t, J=6.8 Hz, 2H), 3.46 (s, 3H), 3.76 (s, 6H), 3.84 (s, 3H), 4.13 (s, 2H), 4.49 (s, 2H), 4.52 (dt, J"47.2, 6.4, 2H), 6.38 (s, 1H), 6.63 (s, 2H), 7.20 (dd, J=8.0, 4.8 Hz, 1H), 7.63-7.69 (m, 1H), 8.46 (dd, J=4.8, 1.6 Hz, 1H), 8.52 (d, J=2.0 Hz, 1H).

Example 72

3-[2,6-Dimethoxy-4-(methoxymethyl)phenyl]-N-(3-fluoropropyl)-6-methoxy-N-(pyridin-2-ylmethyl)-pyrazolo[5,1-b][1,3]thiazole-7-amine

[Chemical Formula 163]

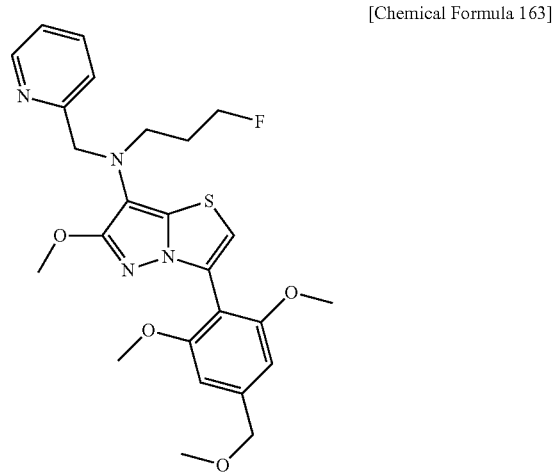 [SMILES: COCc1cc(OC)c(-c2csc3c(N(CCCF)Cc4ccccn4)c(OC)nn23)c(OC)c1]

$^1$H-NMR (CDCl$_3$) δ: 1.75-1.92 (m, 2H), 3.13 (t, J=7.0 Hz, 2H), 3.46 (s, 3H), 3.76 (s, 6H), 3.86 (s, 3H), 4.31 (s, 2H), 4.49 (s, 2H), 4.53 (dt, J=47.6, 2H), 6.39 (s, 1H), 6.63 (s, 2H), 7.09-7.16 (m, 1H), 7.54 (d, J=7.6 Hz, 1H), 7.63 (td, J=7.4 Hz, 1H), 8.47-8.53 (m, 1H).

Example 73

3-[2-Chloro-6-methoxy-4-(methoxymethyl)phenyl]-N-cyclopentyl-6-methoxy-N-(3-methoxypropyl)pyrazolo[5,1-b][1,3]thiazole-7-amine

[Chemical Formula 164]

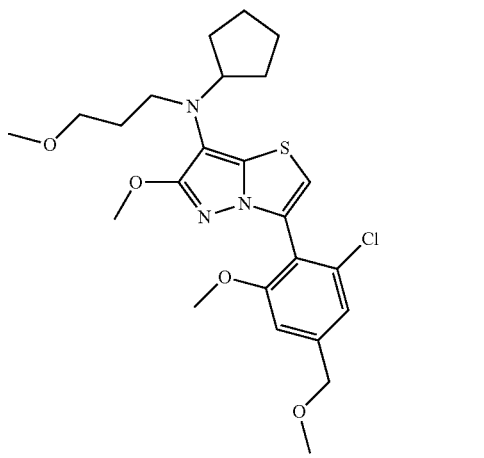

¹H-NMR (CDCl₃) δ: 1.44-1.84 (m, 10H), 3.01 (t, J=7.6 Hz, 2H), 3.30 (s, 3H), 3.38-3.48 (m, 1H), 3.42 (t, J=6.8 Hz, 2H), 3.47 (s, 3H), 3.79 (s, 3H), 3.86 (s, 3H), 4.49 (s, 2H), 6.46 (s, 1H), 6.93 (s, 1H), 7.09 (s, 1H).

Example 74

4-{7-[Cyclopentyl(2-methoxyethyl)amino]-6-methoxypyrazolo[5,1-b][1,3]thiazol-3-yl}-3,5-dimethoxybenzonitrile

[Chemical Formula 165]

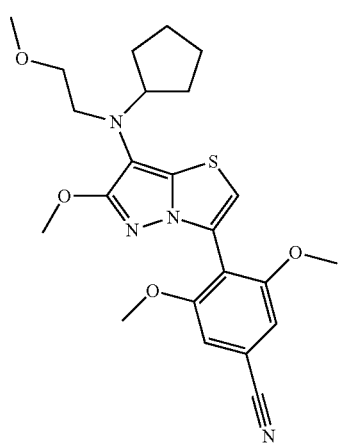

¹H-NMR (CDCl₃) δ: 1.43-1.71 (m, 6H), 1.73-1.86 (m, 2H), 3.15 (t, J=6.6 Hz, 2H), 3.30 (s, 3H), 3.38 (t, J=6.6 Hz, 2H), 3.43-3.54 (m, 1H), 3.82 (s, 6H), 3.86 (s, 3H), 6.50 (s, 1H), 6.93 (s, 2H).

Example 75

Butyl-[3-(4-isopropoxymethyl-2,6-dimethoxy-phenyl)-6-methoxy-pyrazolo[5,1-b][1,3]thiazol-7-yl]-(tetrahydro-pyran-4-yl)amine

[Chemical Formula 166]

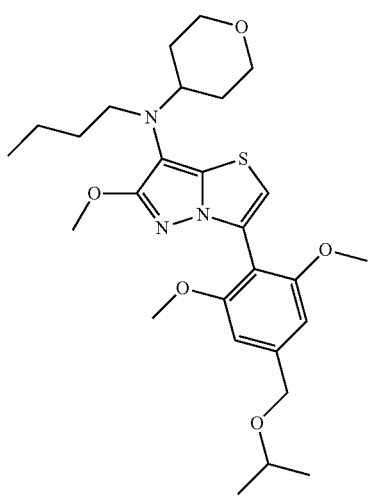

¹H-NMR (CDCl₃) δ: 0.86 (t, J=7.2 Hz, 3H), 1.27 (d, J=6.0 Hz, 6H), 1.22-1.40 (m, 4H), 1.52-1.66 (m, 2H), 1.78-1.87 (m, 2H), 2.97 (t, J=6.8 Hz, 2H), 2.99-3.10 (m, 1H), 3.38 (td, J=2.0, 12.0 Hz, 2H), 3.70-3.82 (m, 1H), 3.79 (s, 6H), 3.86 (s, 3H), 3.94-4.02 (m, 2H), 4.55 (s, 2H), 6.40 (s, 1H), 6.66 (s, 2H).

Example 76

3-[2,6-Dimethoxy-4-(methoxymethyl)phenyl]-N-isobutyl-6-methoxy-N-[(1-methoxycyclopropyl)methyl]pyrazolo[5,1-b][1,3]thiazole-7-amine (76a) N-{3-[2,6-Dimethoxy-4-(methoxymethyl)phenyl]-6-methoxypyrazolo[5,1-b][1,3]thiazol-7-yl}-1-hydroxycyclopropanecarboxamide

[Chemical Formula 167]

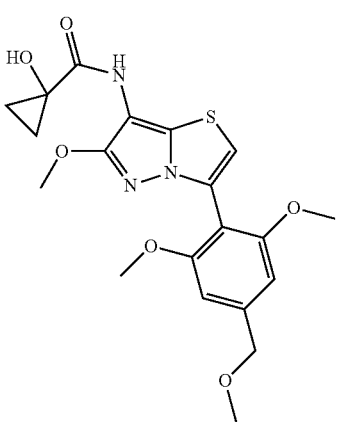

To a N,N-dimethylformamide (6 mL) solution of 3-[2,6-dimethoxy-4-(methoxymethyl)phenyl]-6-methoxypyrazolo[5,1-b][1,3]thiazole-7-amine (400 mg, 1.14 mmol) were added 1-ethyl-3-(3-dimethylaminopropyl)carbodiimide (0.236 mL, 1.33 mmol) and 1-hydroxybenzotriazole (180 mg, 1.33 mmol), and the mixture was stirred at room temperature over one day and night. Water was added to the reaction mixture, and the reaction mixture was extracted with ethyl acetate and dried over anhydrous magnesium sulfate. The mixture was filtered, and then the solvent in the filtrate was distilled off under reduced pressure. The residue was purified by silica gel column chromatography (a mixed solvent of n-heptane and ethyl acetate: n-heptane/ethyl acetate=1/1 then 1/2) to obtain the title compound (404 mg, 0.93 mmol).

¹H-NMR (CDCl₃) δ: 1.09-1.15 (m, 2H), 1.47-1.53 (m, 2H), 2.75 (s, 1), 3.46 (s, 3H), 3.76 (s, 6H), 3.90 (s, 3), 4.50 (s, 2H), 6.45 (s, 1H), 6.63 (s, 2H), 8.38 (s, 1H).

(76b) 1-[({3-[2,6-dimethoxy-4-(methoxymethyl)phenyl]-6-methoxypyrazolo[5,1-b][1,3]thiazol-7-yl}amino)methyl]cyclopropanol

[Chemical Formula 168]

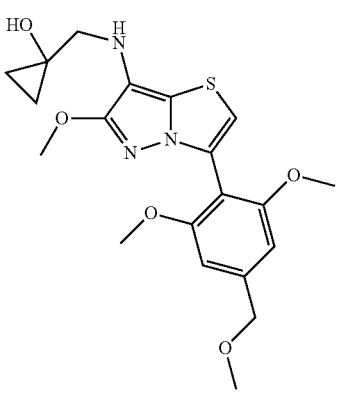

To a tetrahydrofuran (4 mL) solution of N-{3-[2,6-dimethoxy-4-(methoxymethyl)phenyl]-6-methoxypyrazolo[5,1-b][1,3]thiazol-7-yl}-1-hydroxycyclopropanecarboxamide (162 mg, 0.374 mmol) was added 0.99 M diborane (0.944 mL, 0.935 mmol), and the mixture was stirred at 55° C. for two hours. The temperature was made to be room temperature, and a 2N aqueous solution of hydrochloric acid (0.374 mL, 0.748 mmol) was added, and the mixture was stirred at 50° C. for one hour. Water was added to the reaction mixture at room temperature, and the reaction mixture was extracted with ethyl acetate, and dried over anhydrous magnesium sulfate. The mixture was filtered, and then the solvent in the filtrate was distilled off under reduced pressure. The residue was purified by silica gel column (NI-1) chromatography (a mixed solvent of n-heptane and ethyl acetate: n-heptane/ethyl acetate=1/1) to obtain the title compound (94.5 mg, 0.225 mmol).

$^1$H-NMR (CDCl$_3$) δ: 0.37-0.41 (m, 2H), 0.73-0.78 (m, 2H), 1.26 (t, J=7.2 Hz, 1H), 3.10 (s, 2H), 3.47 (s, 3H), 3.77 (s, 6H), 3.90 (s, 3H), 4.50 (s, 2H), 6.42 (s, 1H), 6.64 (s, 2H).

(76c) 3-[2,6-Dimethoxy-4-(methoxymethyl)phenyl]-N-isobutyl-6-methoxy-N-[(1-methoxycyclopropyl)methyl]pyrazolo[5,1-b][1,3]thiazole-7-amine

[Chemical Formula 169]

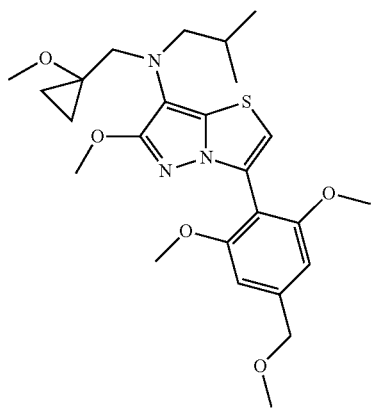

To a tetrahydrofuran (5 mL) solution of 1-[({3-[2,6-dimethoxy-4-(methoxymethyl)phenyl]-6-methoxypyrazolo[5,1-b][1,3]thiazol-7-yl}amino)methyl]cyclopropanol (94.5 mg, 0.225 mmol) were added isobutyl aldehyde (0.031 mL, 0.338 mmol) and sodium triacetoxyborohydride (71.5 mg, 0.338 mmol), and the mixture was stirred at room temperature for one hour. Water was added to the reaction mixture at room temperature, and the reaction mixture was extracted with ethyl acetate and dried over anhydrous magnesium sulfate. The mixture was filtered, and then the solvent in the filtrate was distilled off under reduced pressure to obtain a crude product. To a N,N-dimethylformamide (5 mL) solution of the crude product were added 60% sodium hydride (18.0 mg, 0.450 mmol) and iodomethane (0.028 mL, 0.450 mmol) at room temperature, and stirred at mom temperature over one day and night. After the reaction was completed, water was added, and the reaction mixture was extracted with ethyl acetate and dried over anhydrous magnesium sulfate. The mixture was filtered, and then the solvent in the filtrate was distilled off under reduced pressure. The residue was purified by silica gel column (N11) chromatography (a mixed solvent of n-heptane and ethyl acetate: n-heptane/ethyl acetate=2/1 then 1/1) to obtain the title compound (89.1 mg, 0.182 mmol).

$^1$H-NMR (CDCl$_3$) δ: 0.37-0.42 (m, 2H), 0.63-0.67 (m, 2H), 0.93 (d, J=6.8 Hz, 6H), 1.48-1.68 (m, 1H), 2.84 (d, J=7.2 Hz, 2H), 3.15 (s, 2H), 3.30 (s, 3H), 3.46 (s, 3H), 3.77 (s, 6H), 3.86 (s, 3H), 4.50 (s, 2H), 6.40 (s, 1H), 6.64 (s, 2H).

Example 77

3-[4-(2-Fluoroethoxy)-2,6-dimethoxyphenyl]-6-methoxy-N-propyl-N-(tetrahydro-2H-pyran-4-yl)pyrazolo[5,1-b][1,3]thiazole-7-amine (77a) tert-Butyl[3-(4-hydroxy-2,6-dimethoxyphenyl)-6-methoxypyrazolo[5,1-b][1,3]thiazol-7-yl]carbamate

[Chemical Formula 170]

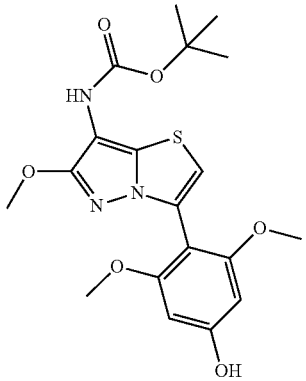

To a solution of tert-butyl(3-bromo-6-methoxypyrazolo[5,1-b][1,3]thiazol-7-yl)carbamate (375 mg, 1.08 mmol) in 1,4-dioxane (25 ml) and water (12.5 ml) were added (4-{[tert-butyl(dimethyl)silyl]oxy}-2,6-dimethoxyphenyl)boronic acid (505 mg, 1.61 mmol), tetrakis(triphenylphosphine)palladium(0) (125 mg, 0.108 mmol) and potassium carbonate (298 mg, 2.15 mmol), and the mixture was heated to reflux at 110° C. for two hours and 35 minutes. The reaction mixture was concentrated under reduced pressure. Water was added to the residue, and the mixture was extracted with ethyl acetate and dried over anhydrous magnesium sulfate, and then the solvent was distilled off under reduced pressure. The residue was purified by medium pressure silica gel column chromatography (n-heptane/ethyl acetate=10% then 70%) to obtain the title compound (242 mg, 0.574 mmol).

$^1$H-NMR (CDCl$_3$) δ: 1.54 (s, 9H), 3.61 (s, 6H), 3.99 (s, 3H), 5.93 (s, 2H), 6.10 (br.s, 1H), 6.38 (s, 1H).

(77b) tert-Butyl{3-[4-(2-fluoroethoxy)-2,6-dimethoxyphenyl]-6-methoxypyrazolo[5,1-b][1,3]thiazol-7-yl}carbamate

[Chemical Formula 171]

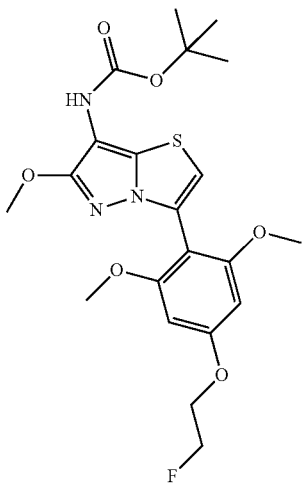

To a DMF (2.28 ml) solution of tert-butyl[3-(4-hydroxy-2,6-dimethoxyphenyl)-6-methoxypyrazolo[5,1-b][1,3]thiazol-7-yl]carbamate (115 mg, 0.273 mmol) were added potassium carbonate (49.0 mg, 0.355 mmol) and 1-iodo-2-fluoroethane (61.7 mg, 0.355 mmol), and the mixture was stirred at room temperature for 20 hours and 30 minutes. Water was added to the reaction mixture, and the mixture was extracted with diethyl ether. The organic layer was dried over anhydrous magnesium sulfate, and then the solvent was distilled off under reduced pressure to obtain a crude product of the title compound (128 mg, 0.273 mmol)

$^1$H-NMR (CDCl$_3$) δ: 1.52 (s, 9H), 3.72 (s, 6H), 3.89 (s, 3H), 4.22-4.27 (m, 1H), 4.29-4.34 (m, 1H), 4.70-4.75 (m, 1H), 4.82-4.87 (m, 1H), 6.23 (s, 2H), 6.40 (s, 1H).

(77c) 3-[4-(2-Fluoroethoxy)-2,6-dimethoxyphenyl]-6-methoxy-N-propyl-N-(tetrahydro-2H-pyran-4-yl)pyrazolo[5,1-b][1,3]thiazole-7-amine

[Chemical Formula 172]

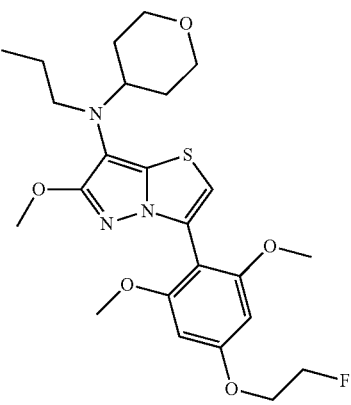

This compound was synthesized according to the procedure similar to Example 10.

$^1$H-NMR (CDCl$_3$) δ: 0.87 (t, J=7.4 Hz, 3H), 1.33-1.42 (m, 2H), 1.55-1.66 (m, 2H), 1.77-1.88 (m, 2H), 2.90-2.96 (m, 2H), 3.00-3.10 (m, 1H), 3.32-3.42 (m, 2H), 3.76 (s, 6H), 3.87 (s, 3H), 3.94402 (m, 2H), 4.23-4.28 (m, 1H), 4.30435 (m, 1H), 4.71-4.76 (m, 1H), 4.82-4.88 (m, 1H), 6.26 (s, 2H), 6.38 (s, 1H).

Example 78

3-[4-Ethoxy-2,6-dimethoxyphenyl]-6-methoxy-N-propyl-N-(tetrahydro-2H-pyran-4-yl)pyrazolo[5,1-b][1,3]thiazole-7-amine

[Chemical Formula 173]

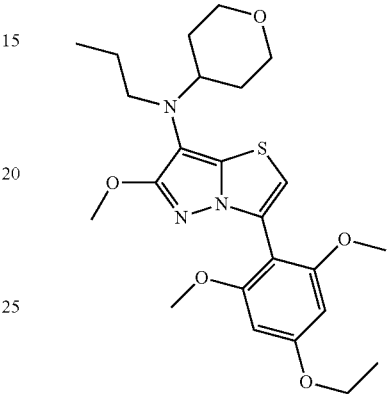

To a DMF (2.97 ml) solution of tert-butyl[3-(4-hydroxy-2,6-dimethoxyphenyl)-6-methoxypyrazolo[5,1-b][1,3]thiazol-7-yl]carbamate (150 mg, 0.356 mmol) were added potassium carbonate (78.7 mg, 0.570 mmol) and iodoethane (45.6 μl, 0.570 mmol), and the mixture was stirred at room temperature for 16 hours and 10 minutes. Water was added to the reaction mixture, and the mixture was extracted with diethyl ether. The organic layer was dried over anhydrous magnesium sulfate, and then the solvent was distilled off under reduced pressure. The residue was dissolved in DMF (1.88 ml), and sodium hydride (50% oil dispersion: 20.8 mg, 0.434 mmol) and 1-iodopropane (42.3 μl, 0.434 mmol) were added thereto, and the mixture was stirred at room temperature for 20 minutes. Ice was added to the reaction mixture, and the reaction mixture was extracted with diethyl ether. The organic layer was dried over anhydrous magnesium sulfate, and then the solvent was distilled off under reduced pressure. The residue was dissolved in a mixture of dichloromethane (4.69 ml) and trifluoroacetic acid (1.87 ml), and the reaction mixture was stirred at room temperature for 30 minutes. The reaction mixture was concentrated under reduced pressure. The residue was dissolved in a mixture of tetrahydrofuran (11.7 ml) and acetic acid (1.17 ml), tetrahydro-4H-pyran-4-one (61.5 μl, 0.670 mmol) and sodium triacetoxyborohydride (142 mg, 0.670 mmol) were added, and the mixture was stirred at mom temperature for 11 hours and 30 minutes. The reaction mixture was concentrated under reduced pressure, a saturated aqueous solution of sodium hydrogencarbonate was added to the residue, and the mixture was extracted with ethyl acetate. The organic layer was concentrated under reduced pressure, and the residue was purified by medium pressure silica gel column chromatography (n-heptane/ethyl acetate: 10% then 50%) to obtain the title compound (101 mg, 0.212 mmol).

$^1$H-NMR (CDCl$_3$) δ: 0.87 (t, J=7.2 Hz, 3H), 1.32-1.43 (m, 2H), 1.46 (t, J=7.0 Hz, 3H), 1.53-1.66 (m, 2H), 1.78-1.87 (m, 2H), 2.90-2.97 (m, 2H), 3.00-3.10 (m, 1H), 3.33-3.43 (m,

2H), 3.76 (s, 6H), 3.87 (s, 3H), 3.94-4.02 (m, 2H), 4.10 (q, J=7.2 Hz, 2H), 6.22 (s, 2H), 6.38 (s, 1H).

Example 79

3-[2,6-Dimethoxy-4-(methoxymethyl)phenyl]-6-ethoxy-N-propyl-N-(tetrahydro-2H-pyran-4-yl)pyrazolo[5,1-b][1,3]thiazole-7-amine

[Chemical Formula 174]

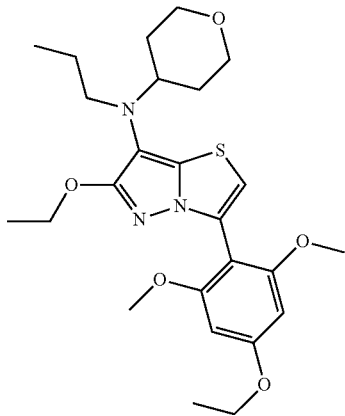

This compound was synthesized according to the procedure similar to Example 10 by using the compound obtained in Production Example 22-4.

¹H-NMR (CDCl₃) δ: 0.88 (J=7.6 Hz, 3H), 1.31 (t, J=7.2 Hz, 3H), 1.34-1.44 (m, 2H), 1.54-1.68 (m, 2H), 1.84 (br.d, J=12.4 Hz, 2H), 2.95 (t, J=7.2 Hz, 2H), 3.01-3.11 (m, 1H), 3.38 (t, 2H), 3.47 (s, 3H), 3.78 (s, 6H), 3.94-4.03 (m, 2H), 4.22 (q, J=7.2 Hz, 2H), 4.50 (s, 2H), 6.41 (s, 1H), 6.64 (s, 2H).

Hereinafter, the compounds of Example 80 to Example 84 were synthesized according to the procedure similar to Example 79.

Example 80

3-[2,6-Dimethoxy-4-(methoxymethyl)phenyl]-6-ethoxy-N-propyl-N-(tetrahydro-2H-pyran-4-ylmethyl)pyrazolo[5,1-b][1,3]thiazole-7-amine

[Chemical Formula 175]

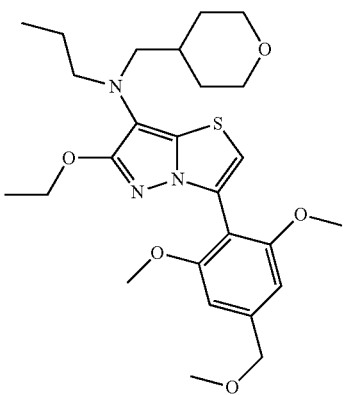

¹H-NMR (CDCl₃) δ: 0.89 (l, J=7.6 Hz, 3H), 1.20-1.34 (m, 2H), 1.31 (t, J=7.2 Hz, 3H), 1.38-1.50 (m, 2H), 1.55-1.66 (m, 1H), 1.76 (br.d, J=13.2 Hz, 2H), 2.80 (d, J=7.2 Hz, 2H), 2.88 (t, J=7.2 Hz, 2H), 3.36 (t, J=9.6 Hz, 2H), 3.47 (s, 3H), 3.78 (s, 6H), 3.94 (dd, J=11.4 Hz, 3.0 Hz, 2H), 4.20 (q, J=7.21 Hz, 2H), 4.50 (s, 2H), 6.41 (s, 1H), 6.64 (s, 2H).

Example 81

N-(Cyclopropylmethyl)-3-[2,6-dimethoxy-4-(methoxymethyl)phenyl]-6-ethoxy-N-(tetrahydro-2H-pyran-4-yl)-pyrazolo[5,1-b][1,3]thiazole-7-amine

[Chemical Formula 176]

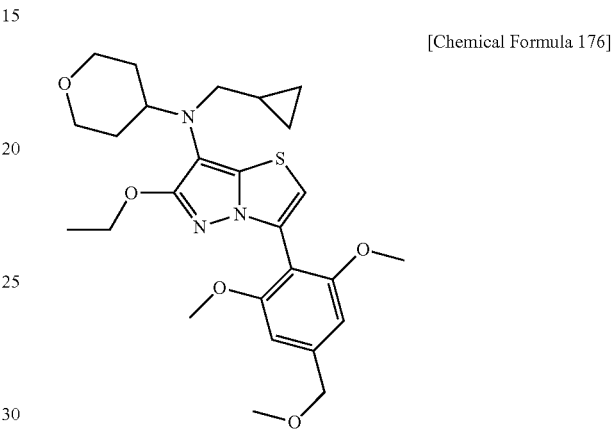

¹H-NMR (CDCl₃) δ: 0.00-0.05 (m, 2H), 0.30-0.37 (m, 2H), 0.78-0.90 (m, 1H), 1.31 (t, J=7.0 Hz, 3H), 1.52-1.65 (m, 2H), 1.78-1.88 (m, 2H), 2.89 (d, J=6.4 Hz, 2H), 3.16 (tt, J=11.2, 4.0 Hz, 1H), 3.39 (td, S=11.8, 1.8 Hz, 2H), 3.46 (s, 3H), 3.77 (s, 6H), 3.94-4.02 (m, 2H), 423 (q, J=7.0 Hz, 2H), 4.50 (s, 2H), 6.40 (s, 1H), 6.64 (s, 2H).

Example 82

N-Butyl-3-[2,6-dimethoxy-4-(methoxymethyl)phenyl]-6-ethoxy-N-(tetrahydro-2H-pyran-4-yl)-pyrazolo[5,1-b][1,3]thiazole-7-amine

[Chemical Formula 177]

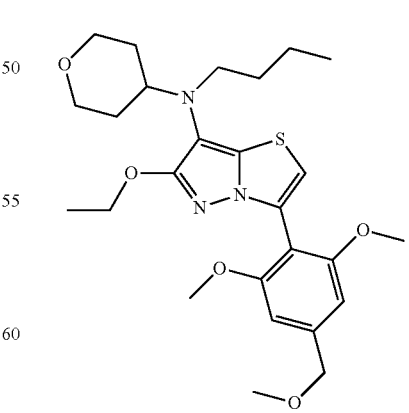

¹H-NMR (CDCl₃) δ: 0.86 (t, J=7.0 Hz, 3H), 1.24-1.40 (m, 4H), 1.31 (t, J=7.0 Hz, 3H), 1.54-1.66 (m, 2H), 1.79-1.87 (m, 2H), 2.94-3.02 (m, 2H), 3.06 (tt, J=11.2, 4.0 Hz, 1H), 3.38 (td,

J=11.8, 2.0 Hz, 2H), 3.47 (s, 3H), 3.78 (s, 6H), 3.94-4.02 (m, 2H), 4.22 (q, J=7.0 Hz, 2H), 4.50 (s, 2H), 6.41 (s, 1H), 6.64 (s, 2H).

Example 83

N-(Cyclobutylmethyl)-3-[2,6-dimethoxy-4-(methoxymethyl)phenyl]-6-ethoxy-N-(tetrahydro-2H-pyran-4-yl)-pyrazolo[5,1-b][1,3]thiazole-7-amine

[Chemical Formula 178]

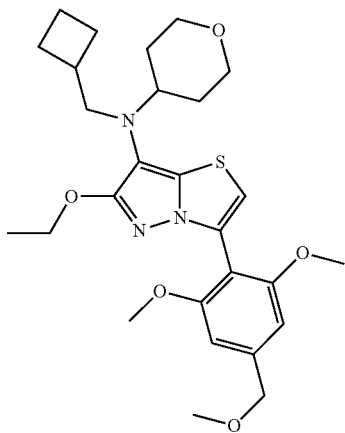

$^1$H-NMR (CDCl$_3$) δ: 1.31 (t, J=7.2 Hz, 3H), 1.51-1.64 (m, 4H), 1.66-1.90 (m, 6H), 2.26-2.40 (m, 1H), 2.96-3.07 (m, 3H), 3.37 (td, J=11.8, 1.8 Hz, 2H), 3.46 (s, 3H), 3.77 (s, 6H), 3.93-4.01 (m, 2H), 4.21 (q, J=7.0 Hz, 2H), 4.49 (s, 2H), 6.40 (s, 1H), 6.63 (s, 2H).

Example 84

3-[2,6-Dimethoxy-4-(methoxymethyl)phenyl]-6-ethoxy-N-propyl-N-(tetrahydrofuran-3-ylmethyl)pyrazolo[5,1-b][1,3]thiazole-7-amine

[Chemical Formula 179]

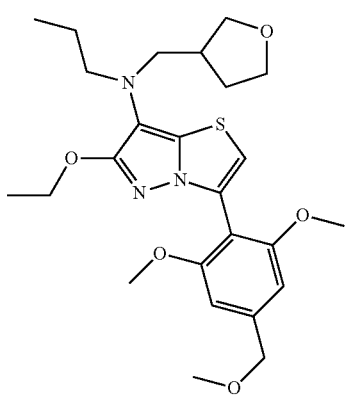

$^1$H-NMR (CDCl$_3$) δ: 0.90 (t, J=7.4 Hz, 3H), 1.32 (t, J=7.0 Hz, 3H), 1.38-1.49 (m, 2H), 1.56-1.68 (m, 1H), 1.91-2.01 (m, 1H), 2.28-2.40 (m, 1H), 2.82-2.93 (m, 3H), 2.99 (dd, J=12.2, 6.6 Hz, 1H), 3.47 (s, 3H), 3.56 (dd, J=8.6, 6.2 Hz, 1H), 3.69 (q, J=7.8 Hz, 1H), 3.78 (s, 6H), 3.74-3.86 (m, 2H), 4.21 (q, J=7.0 Hz, 2H), 4.50 (s, 2H), 6.41 (s, 1H), 6.64 (s, 2H).

Example 85

3-[2,6-Dimethoxy-4-(methoxymethyl)phenyl]-6-methoxy-N-propyl-N-pyridin-4-ylpyrazolo[5,1-b][1,3]thiazole-7-amine

[Chemical Formula 180]

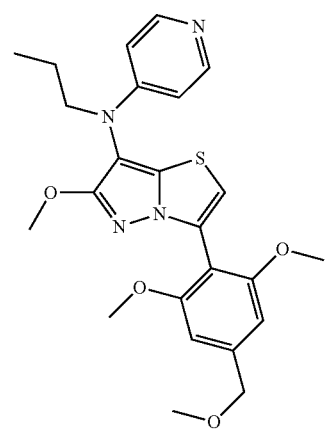

To a 1,4-dioxane (0.7 mL) solution of 3-[2,6-dimethoxy-4-(methoxymethyl)phenyl]-6-methoxy-N-propylpyrazolo[5,1-b][1,3]thiazole-7-amine (70 mg, 0.179 mmol) were added 4-chloropyridine hydrochloride (32.2 mg, 0.215 mmol), sodium tert-butoxide (20.6 mg, 0.215 mmol), potassium phosphate tribasic (64.6 mg, 0.304 mmol), tris(dibenzylideneacetone)dipalladium (8.2 mg, 0.009 mmol), and 4,5-bis(diphenylphosphino)-9,9-dimethylxanthene (7.77 mg, 0.0134 mmol), and the mixture was stirred at 100° C. for seven hours. After the reaction mixture was returned to room temperature, water was added to the reaction mixture, and the reaction mixture was extracted with ethyl acetate, and the solvent was distilled off under reduced pressure. The residue was purified by medium pressure amino silica gel column chromatography (n-heptane/ethyl acetate: 10% then 80%) to obtain the title compound (49.4 mg, 0.105 mmol).

$^1$H-NMR (CDCl$_3$) δ: 0.95 (t, J=7.4 Hz, 3H), 1.64-1.76 (m, 2H), 3.49 (s, 3H), 3.55 (t, J=7.8 Hz, 2H), 3.83 (s, 6H), 3.86 (s, 3H), 4.52 (s, 2H), 6.50-6.56 (m, 2H), 6.54 (s, 1H), 6.68 (s, 2H), 8.18-8.24 (m, 2H).

Example 86

3-[2,6-Dimethoxy-4-(methoxymethyl)phenyl]-6-methoxy-N-propyl-N-pyridin-2-ylpyrazolo[5,1-b][1,3]thiazole-7-amine

[Chemical Formula 181]

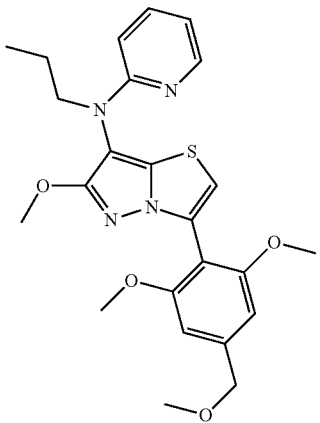

To a toluene (0.9 mL) solution of 3-[2,6-dimethoxy-4-(methoxymethyl)phenyl]-6-methoxy-N-propylpyrazolo[5,1-b][1,3]thiazole-7-amine (70 mg, 0.179 mmol) were added 2-bromopyridine (56.6 mg, 0.358 mmol), sodium tert-butoxide (25.8 mg, 0.269 mmol) and bis(tri-tert-butylphosphine)palladium (4.57 mg, 0.009 mmol), and the mixture was stirred at 100° C. for five hours. After the reaction mixture was returned to room temperature, water was added to the reaction mixture, and the reaction mixture was extracted with ethyl acetate, and the solvent was distilled off under reduced pressure. The residue was purified by medium pressure amino silica gel column chromatography (n-heptane/ethyl acetate: 10% then 50%) to obtain the title compound (18.2 mg, 0.0388 mmol).

$^1$H-NMR (CDCl$_3$) δ: 0.93 (t, J=7.6 Hz, 3H), 1.60-1.74 (m, 2H), 3.48 (s, 3H), 3.80-3.87 (m, 2H), 3.82 (s, 6H), 3.86 (s, 3H), 4.52 (s, 2H), 6.36 (d, J=8.8 Hz, 1H), 6.52 (s, 1H), 6.54-6.60 (m, 1H), 6.68 (s, 2H), 7.34 (ddd, J=2.0, 6.8, 8.8 Hz, 1H), 8.17-8.22 (m, 1H).

Example 87

3-[2,6-Dimethoxy-4-(methoxymethyl)phenyl]-6-methoxy-N-propyl-N-pyridin-3-ylpyrazolo[5,1-b][1,3]thiazole-7-amine

[Chemical Formula 182]

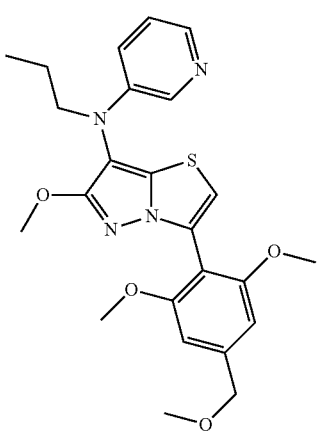

To a 1,4-dioxane (0.7 mL) solution of 3-[2,6-dimethoxy-4-(methoxymethyl)phenyl]-6-methoxy-N-propylpyrazolo[5,1-b][1,3]thiazole-7-amine (70 mg, 0.179 mmol) were added 3-bromopyridine (33.9 mg, 0.215 mmol), cesium carbonate (99.1 mg, 0.304 mmol), tris(dibenzylideneacetone)dipalladium (8.2 mg, 0.009 mmol) and 4,5-bis(diphenylphosphino)-9,9-dimethylxanthene (7.77 mg, 0.0134 mmol), and the mixture was stirred at 100° C. for eight hours. After the reaction mixture was returned to room temperature, water was added to the reaction mixture, and the reaction mixture was extracted with ethyl acetate, and the solvent was distilled off under reduced pressure. The residue was purified by medium pressure amino silica gel column chromatography (n-heptane/ethyl acetate: 10% then 60%) to obtain the title compound (32.4 mg, 0.0692 mmol).

$^1$H-NMR (CDCl$_3$) δ: 0.95 (t, J=7.4 Hz, 3H), 1.66-1.77 (m, 2H), 3.48 (s, 3H), 3.51-3.58 (m, 2H), 3.82 (s, 6H), 3.85 (s, 3H), 4.52 (s, 2H), 6.51 (s, 1H), 6.64 (s, 2H), 6.94 (ddd, J=1.2, 3.2, 8.4 Hz, 1H), 7.06-7.10 (m, 1H), 7.97 (dd, J=1.2, 4.4 Hz, 1H), 8.11 (d, J=2.4 Hz, 1H).

Hereinafter, the compounds of Example 88 and Example 89 were synthesized according to the procedure similar to Example 87.

Example 88

3-[2,6-Dimethoxy-4-(methoxymethyl)phenyl]-N-(3-fluoropropyl)-6-methoxy-N-pyridin-3-ylpyrazolo[5,1-b][1,3]thiazole-7-amine

[Chemical Formula 183]

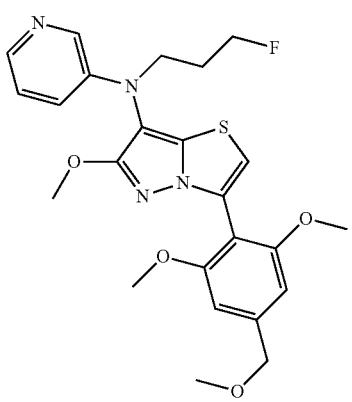

$^1$H-NMR (CDCl$_3$) δ: 1.97-2.14 (m, 2H), 3.49 (s, 3H), 3.77 (t, J=7.2 Hz, 2H), 3.82 (s, 6H), 3.85 (s, 3H), 4.52 (s, 2H), 4.57 (dt, J=47.2, 5.6 Hz, 2H), 6.52 (s, 1H), 6.67 (s, 2H), 6.97-7.04 (m, 1H), 7.07-7.13 (m, 1H), 8.00 (dd, J=4.4, 1.2 Hz, 1H), 8.12 (d, J=2.4 Hz, 1H).

Example 89

N-(Cyclopropylmethyl)-3-[2,6-dimethoxy-4-(methoxymethyl)phenyl]-6-methoxy-N-pyridin-3-ylpyrazolo[5,1-b][1,3]thiazole-7-amine

[Chemical Formula 184]

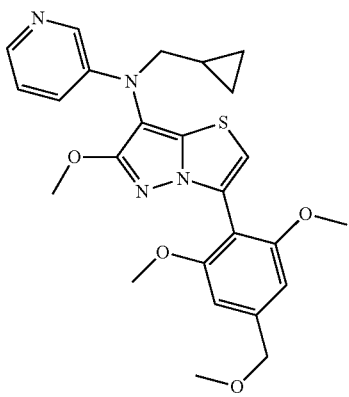

$^1$H-NMR (CDCl$_3$) δ: 0.15-0.21 (m, 2H), 0.45-0.52 (m, 2H), 1.10-1.20 (m, 1H), 3.45-3.50 (m, 2H), 3.48 (s, 3H), 3.82 (s, 6H), 3.85 (s, 3H), 4.52 (s, 2H), 6.51 (s, 1H), 6.67 (s, 2H), 6.96-7.02 (m, 1H), 7.06-7.11 (m, 1H), 7.98 (dd, J=4.2, 1.4 Hz, 1H), 8.17 (d, J=2.8 Hz, 1H).

Example 90

4-({Cyclopropylmethyl-[3-(2,6-dimethoxy-4-methoxymethyl-phenyl)-6-methoxy-pyrazolo[5,1-b][1,3]thiazol-7-yl]-amino}-methyl-tetrahydro-pyran-4-ol

[Chemical Formula 185]

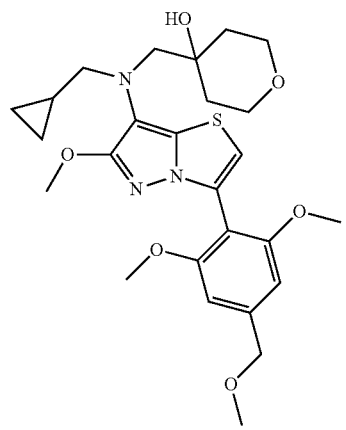

This compound was synthesized according to the procedure similar to Example 10.

$^1$H-NMR (CDCl$_3$) δ: 0.02-0.10 (m, 2H), 0.38-0.48 (m, 2H), 0.84-0.98 (m, 1H), 1.38-1.62 (m, 4H), 2.84 (d, J=6.8 Hz, 2H), 3.02 (s, 2H), 3.47 (s, 3H), 3.77 (s, 6H), 3.64-3.83 (m, 4H), 3.88 (s, 3H), 4.50 (s, 2H), 6.44 (s, 1H), 6.64 (s, 2H).

Example 91

Cyclopropylmethyl-[3-(2,6-dimethoxy-4-methoxymethyl-phenyl)-6-methoxy-pyrazolo[5,1-b][1,3]thiazol-7-yl]-(4-fluoro-tetrahydro-pyran-4-ylmethyl)-amine

[Chemical Formula 186]

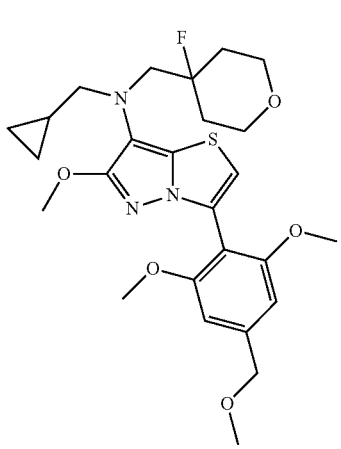

Example 92

Cyclopropylmethyl-(3,6-dihydro-2H-pyran-4-ylmethyl)-[3-(2,6-dimethoxy-4-methoxymethyl-phenyl)-6-methoxy-pyrazolo[5,1-b][1,3]thiazol-7-yl]-amine

[Chemical Formula 187]

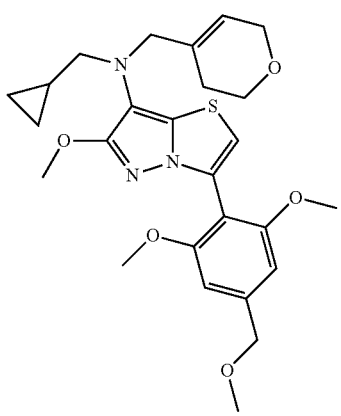

To a dichloromethane (4 mL) solution of 4-({cyclopropylmethyl-[3-(2,6-dimethoxy-4-methoxymethyl-phenyl)-6-methoxy-pyrazolo[5,1-b][1,3]thiazol-7-yl]-amino}-methyl)-tetrahydro-pyran-4-ol (64.5 mg, 0.124 mmol) was added dropwise diethylaminosulfur trifluoride (DAST) (24.6 μL, 0.186 mmol), and the mixture was stirred for five minutes. After the reaction was completed, a saturated aqueous solution of hydrogencarbonate was added to the reaction mixture, and the reaction mixture was extracted with ethyl acetate and dried over anhydrous magnesium sulfate. The mixture was filtered, and then the solvent in the filtrate was distilled off under reduced pressure. The residue was purified by HPLC to obtain cyclopropylmethyl-[3-(2,6-dimethoxy-4-methoxymethyl-phenyl)-6-methoxy-pyrazolo[5,1-b][1,3]thiazol-7-yl]-(4-fluoro-tetrahydro-pyran-4-ylmethyl)-amine (8.9 mg, 0.017 mmol) and cyclopropylmethyl-(3,6-dihydro-2H-pyran-4-ylmethyl)-[3-(2,6-dimethoxy-4-methoxymethyl-phenyl)-6-methoxy-pyrazolo[5,1-b][1,3]thiazol-7-yl]-amine (1.3 mg, 0.003 mmol).

$^1$H-NMR (CDCl$_3$) δ: 0.01-0.08 (m, 2H), 0.34-0.44 (m, 2H), 0.84-0.96 (m, 1H), 1.60-1.92 (m, 4H), 2.87 (d, J=7.2 Hz, 2H), 3.22 (d, J=−20.4 Hz, 2H), 3.47 (s, 3H), 3.78 (s, 6H), 3.64-3.83 (m, 4H), 3.87 (s, 3H), 4.50 (s, 2H), 6.41 (s, 1H), 6.64 (s, 2H).

$^1$H-NMR (CDCl$_3$) δ: 0.01-0.10 (m, 2H), 0.36-0.44 (m, 2H), 0.83-0.98 (m, 1H), 2.16-2.25 (m, 2H), 2.80 (d, J=6.8 Hz, 2H), 3.47 (s, 3H), 3.59 (s, 2H), 3.74 (t, J=5.6 Hz, 2H), 3.77 (s, 6H), 3.87 (s, 3H), 4.04-4.10 (m, 2H), 4.50 (s, 2H), 5.58-5.64 (m, 1H), 6.40 (s, 1H), 6.64 (s, 2H).

Hereinafter, the compounds of Examples 93 to 101 were synthesized according to the procedure similar to Example 10 by using the compound of Production Example 11-4 or Production Example 11-5.

Example 93

3-[2,6-Dimethoxy-4-(methoxymethyl)phenyl]-6-methoxy-N-[3-oxabicyclo[3.1.0]hex-6-ylmethyl]-N-propylpyrazolo[5,1-b][1,3]thiazole-7-amine (diastereomer 1)

[Chemical Formula 188]

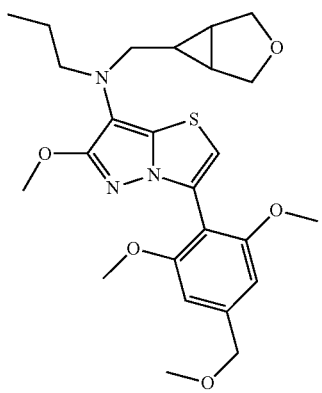

$^1$H-NMR (CDCl$_3$) δ: 0.87-0.94 (m, 1H), 0.90 (t, J=7.4 Hz, 3H), 129-1.34 (m, 2H), 1.41-1.52 (m, 2H), 2.85 (d, J=7.2 Hz, 2H), 2.93 (t, J=7.6 Hz, 2H), 3.46 (s, 3H), 3.59 (br.d, J=8.0 Hz, 2H), 3.75 (d, J=8.4 Hz, 2H), 3.78 (s, 6H), 3.88 (s, 3H), 4.50 (s, 2H), 6.39 (s, 1H), 6.42 (s, 2H).

Example 94

N-(Cyclopropylmethyl)-3-[2,6-dimethoxy-4-(methoxymethyl)phenyl]-6-methoxy-N-[3-oxabicyclo[3.1.0]hex-6-ylmethyl]-pyrazolo[5,1-b][1,3]thiazole-7-amine (diastereomer 1)

[Chemical Formula 189]

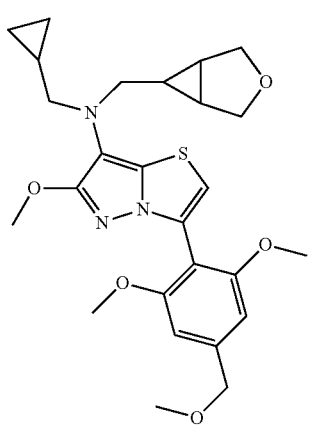

$^1$H-NMR (CDCl$_3$) δ: 0.06-0.12 (m, 2H), 0.37-0.44 (m, 2H), 0.85-0.96 (m, 2H), 1.30-1.36 (m, 2H), 2.86 (d, J=6.8 Hz, 2H), 2.92 (d, J=7.2 Hz, 2H), 3.47 (s, 3H), 3.59 (br.d, J=8.0 Hz, 2H), 3.73 (d, J=8.0 Hz, 2H), 3.78 (s, 6H), 3.88 (s, 3H), 4.50 (s, 2H), 6.40 (s, 1H), 6.64 (s, 2H).

Example 95

3-[2,6-Dimethoxy-4-(methoxymethyl)phenyl]-6-methoxy-N-[3-oxabicyclo[3.1.0]hex-6-ylmethyl]-N-propylpyrazolo[5,1-b][1,3]thiazole-7-amine (diastereomer 2)

[Chemical Formula 190]

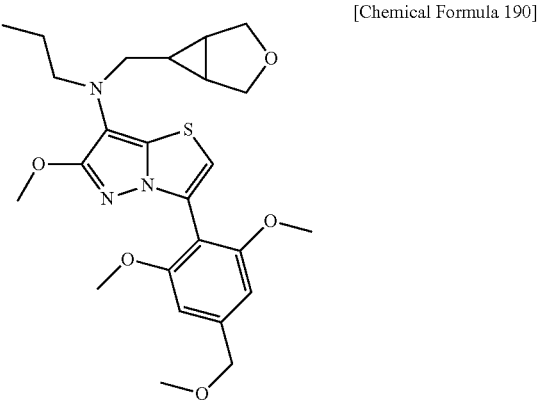 [SMILES: CCCN(CC1C2COCC21)c1c(OC)nn2c(-c3c(OC)cc(COC)cc3OC)csc12]

$^1$H-NMR (CDCl$_3$) δ: 0.84-0.94 (m, 3H), 1.04-1.15 (m, 1H), 1.40-1.53 (m, 2H), 1.62 (d, J=8.0 Hz, 2H), 2.96 (t, J=7.4

Hz, 2H), 3.03 (d, J=6.4 Hz, 2H), 3.47 (s, 3H), 3.70-3.82 (m, 4H), 3.78 (s, 6H), 3.87 (s, 3H), 4.50 (s, 2H), 6.40 (s, 1H), 6.64 (s, 2H).

Example 96

N-(Cyclopropylmethyl)-3-[2,6-dimethoxy-4-(methoxymethyl)phenyl]-6-methoxy-N-[3-oxabicyclo[3.1.0]hex-6-ylmethyl]-pyrazolo[5,1-b][1,3]thiazole-7-amine (diastereomer 2)

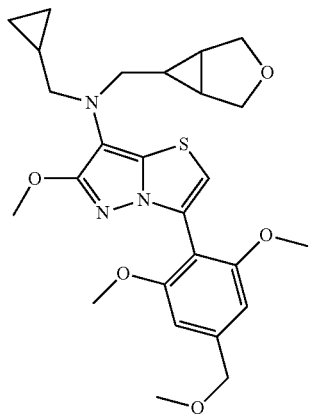

[Chemical Formula 191]

$^{1}$H NMR (CDCl$_3$) δ: 0.02-0.12 (m, 2H), 0.36-0.44 (m, 2H), 0.84-0.98 (m, 1H), 1.04-1.14 (m, 1H), 1.52-1.66 (m, 2H), 2.87 (d, J=6.4 Hz, 2H), 3.08 (d, J=6.0 Hz, 2H), 3.47 (s, 3H), 3.74-3.84 (m, 10H), 3.88 (s, 3H), 4.50 (s, 2H), 6.40 (s, 1H), 6.64 (s, 2H).

Example 97

3-(4-Cyclopropyl-2,6-dimethoxyphenyl)-N-ethyl-6-methoxy-N-[3-oxabicyclo[3.1.0]hex-6-ylmethyl]pyrazolo[5,1-b][1,3]thiazole-7-amine (diastereomer 1)

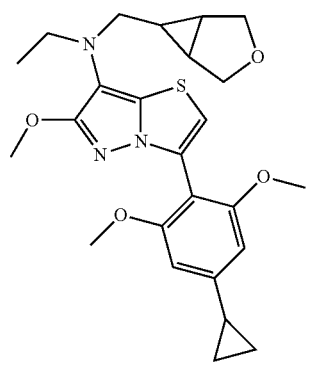

[Chemical Formula 192]

$^{1}$H-NMR (CDCl$_3$) δ: 0.76-0.80 (m, 2H), 0.87-0.94 (m, 1H), 1.00-1.07 (m, 2H), 1.05 (t, J=7.2 Hz, 3H), 1.29-1.34 (m, 2H), 1.92-1.98 (m, 1H), 2.85 (d, J=6.8 Hz, 2H), 3.03 (q, J=6.8 Hz, 2H), 3.59 (d, J=7.6 Hz, 2H), 3.73-3.77 (m, 2H), 3.75 (s, 6H), 3.88 (s, 3H), 6.37 (s, 1H), 6.37 (s, 2H).

Example 98

N-(Cyclobutylmethyl)-3-[2,6-dimethoxy-4-(methoxymethyl)phenyl]-6-methoxy-N-[3-oxabicyclo[3.1.0]hex-6-ylmethyl]-pyrazolo[5,1-b][1,3]thiazole-7-amine (diastereomer 1)

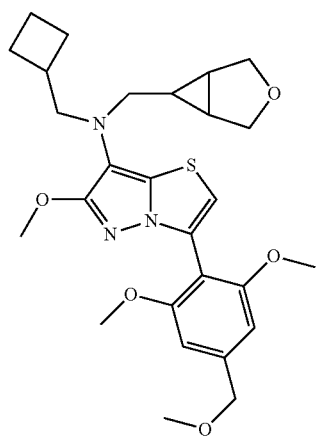

[Chemical Formula 193]

$^{1}$H-NMR (CDCl$_3$) δ: 0.84-0.92 (m, 1H), 1.29-1.34 (m, 2H), 1.59-1.97 (m, 6H), 2.36-2.50 (m, 1H), 2.83 (d, J=6.8 Hz, 2H), 2.98 (d, J=7.2 Hz, 2H), 3.46 (s, 3H), 3.54-3.62 (m, 2H), 3.73 (d, J=8.0 Hz, 2H), 3.77 (s, 6H), 3.86 (s, 3H), 4.50 (s, 2H), 6.39 (s, 1H), 6.64 (s, 2H).

Example 99

N-(Cyclobutylmethyl)-3-[2,6-dimethoxy-4-(methoxymethyl)phenyl]-6-methoxy-N-[3-oxabicyclo[3.1.0]hex-6-ylmethyl]-pyrazolo[5,1-b][1,3]thiazole-7-amine (diastereomer 2)

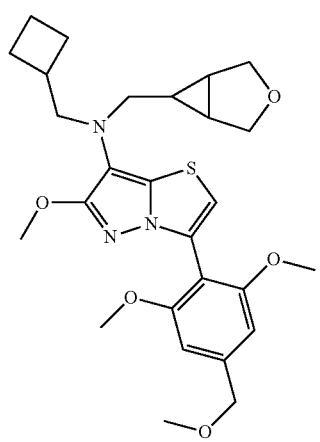

[Chemical Formula 194]

¹H-NMR (CDCl₃) δ: 1.10 (m, 1H), 1.57-1.98 (m, 8H), 2.38-2.50 (m, 1H), 2.96-3.04 (m, 4H), 3.46 (s, 3H), 3.75-3.84 (m, 4H), 3.77 (s, 6H), 3.87 (s, 3H), 4.50 (s, 2H), 6.40 (s, 1H), 6.64 (s, 2H).

Example 100

4-{7-{(Cyclopropylmethyl)[3-oxabicyclo[3.1.0]hex-6-ylmethyl]amino}-6-methoxypyrazolo[5,1-b][1,3]thiazol-3-yl)-3,5-dimethoxybenzonitrile (diastereomer 1)

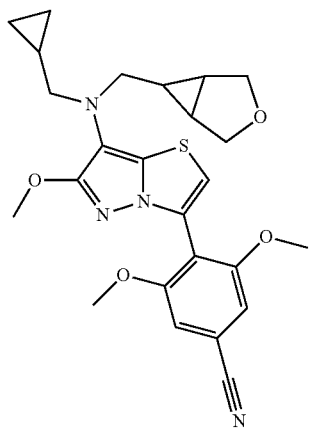

[Chemical Formula 195]

¹H-NMR (CDCl₃) δ: 0.04-0.11 (m, 2H), 0.37-0.44 (m, 2H), 0.85-0.93 (m, 2H), 1.32-1.38 (m, 2H), 2.85 (d, J=6.8 Hz, 2H), 2.92 (d, J=6.8 Hz, 2H), 3.59 (brd, J=8.0 Hz, 2H), 3.73 (d, J=8.0 Hz, 2H), 3.81 (s, 6H), 3.87 (s, 3H), 6.47 (s, 1H), 6.92 (s, 2H).

Example 101

3,5-Dimethoxy-4-{6-methoxy-7-[3-oxabicyclo[3.1.0]hex-6-ylmethyl](propyl)amino]pyrazolo[5,1-b][1,3]thiazol-3-yl}benzonitrile (diastereomer 1)

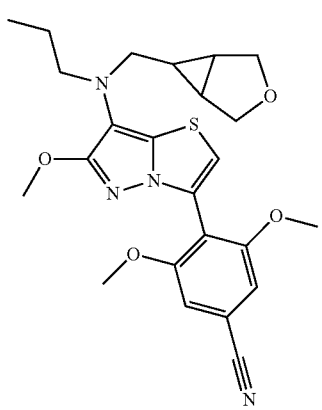

[Chemical Formula 196]

¹H-NMR (CDCl₃) δ: 0.91 (t, J=-7.2 Hz, 3H), 1.25-1.36 (m, 3H), 1.40-1.52 (m, 2H), 2.86 (d, J=6.8 Hz, 2H), 2.90-2.98 (m, 2H), 3.60 (bid, J=8.4 Hz, 2H), 3.74 (d, J=8.4 Hz, 2H), 3.81 (s, 6H), 3.86 (s, 3H), 6.47 (s, 1H), 6.92 (s, 2H).

Example 102

(4-{7-[Butyl(tetrahydro-2H-4-yl)amino]-6-methoxy-pyrazolo[5,1-b][1,3]thiazol-3-yl}-3,5-dimethoxyphenyl)methanol

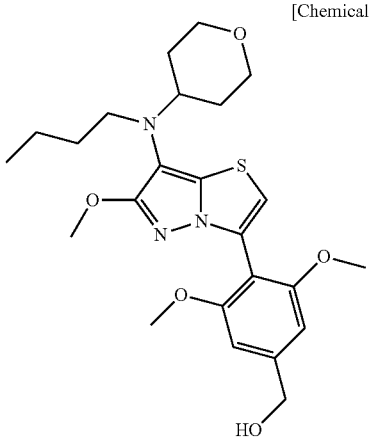

[Chemical Formula 197]

This compound was synthesized according to the procedure similar to Example 10.

¹H-NMR (CDCl₃) δ: 0.87 (t, J=7.2 Hz, 3H), 1.22-1.40 (m, 4H), 1.51-1.67 (m, 2H), 1.78-1.89 (m, 2H), 1.87 (t, J=6.0 Hz, 1H), 2.97 (t, J=6.8 Hz, 2H), 3.00-3.12 (m, 1H), 3.38 (td, J=1.6, 11.6 Hz, 2H), 3.80 (s, 6H), 3.86 (s, 3H), 3.94-4.03 (m, 2H), 4.74 (d, J=-6.0 Hz, 2H), 6.42 (s, 1H), 6.68 (s, 2H).

Example 103

(4-{7-[Butyl(tetrahydro-2H-4-yl)amino]-6-methoxy-pyrazolo[5,1-b][1,3]thiazol-3-yl}-3,5-dimethoxybenzaldehyde

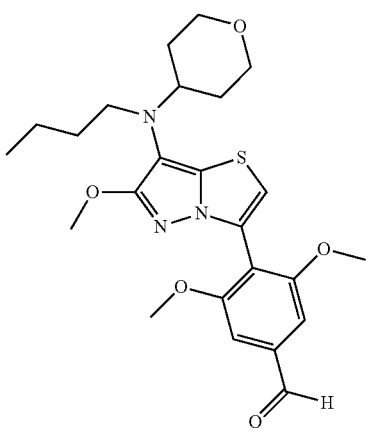

[Chemical Formula 198]

To a dichloromethane (70 mL) solution of (4-{7-[butyl(tetrahydro-2H-4-yl)amino]-6-methoxypyrazolo[5,1-b][1,3]thiazol-3-yl}-3,5-dimethoxyphenyl)methanol (1.22 g, 2.57 mmol) was added manganese dioxide (4.47 g, 51.4 mmol) at room temperature, and the mixture was stirred for 13 hours. After the reaction was completed, the reaction mixture was filtered with Celite, the solvent in the filtrate was distilled off under reduced pressure. The residue was purified by silica gel column chromatography (a mixed solvent of n-heptane and ethyl acetate: n-heptane/ethyl acetate=1/1) to obtain the title compound (256 mg, 0.540 mmol).

$^1$H-NMR (CDCl$_3$) δ: 0.87 (t, J=6.8 Hz, 3H), 1.24-1.40 (m, 4H), 1.52-1.67 (m, 2H), 1.78-1.88 (m, 2H), 2.98 (t, J=7.2 Hz, 2H), 3.00-3.12 (m, 1H), 3.38 (td, J=2.0, 12.0 Hz, 2H), 3.85 (s, 3H), 3.88 (s, 6H), 3.94-4.03 (m, 2H), 6.52 (s, 1H), 7.18 (s, 2H), 10.0 (s, 1H).

Example 104

4-{7-[Butyl(tetrahydro-2H-4-yl)amino]-6-methoxypyrazolo[5,1-b][1,3]thiazol-3-yl}-3,5-dimethoxybenzoic acid

[Chemical Formula 199]

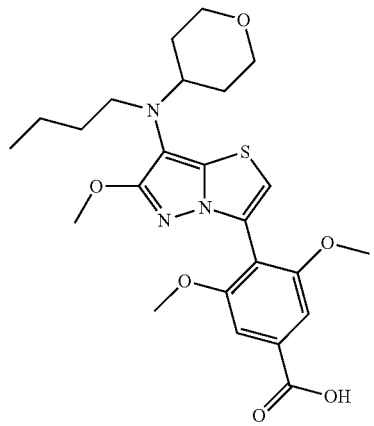

To a solution of (4-{7-[butyl(tetrahydro-2H-4-yl)amino]-6-methoxypyrazolo[5,1-b][1,3]thiazol-3-yl}-3,5-dimethoxybenzaldehyde (256 mg, 0.540 mmol) in a mixture of dioxane (16 mL) and water (11 mL) were added sulfamic acid (305 mg, 3.13 mmol) and sodium chlorite (48.8 mg, 0.432 mmol) while cooling on ice, and the mixture was stirred for 40 minutes. After the reaction was completed, water and acetic acid were added to make pH of the mixture 2, and the reaction mixture was extracted with ethyl acetate, and was distilled off under reduced pressure. The residue was purified by silica gel column chromatography (a mixed solvent of n-heptane and ethyl acetate: n-heptane/ethyl acetate=1/1) to obtain the title compound (256 mg, 0.540 mmol).

$^1$H-NMR (CDCl$_3$) δ: 0.83 (t, J=7.2 Hz, 3H), 1.16-1.42 (m, 6H), 1.66-1.76 (m, 2H), 2.93 (t, J=6.8 Hz, 2H), 2.94-3.06 (m, 1H), 3.18-3.44 (m, 2H), 3.72 (s, 3H), 3.78 (s, 6H), 3.78-3.88 (m, 2H), 6.88 (s, 1H), 7.31 (s, 2H).

Example 105

3-[4-(Ethoxymethyl)-2,6-dimethoxyphenyl]-6-methoxypyrazolo[5,1-b][1,3]thiazole-7-amine

[Chemical Formula 200]

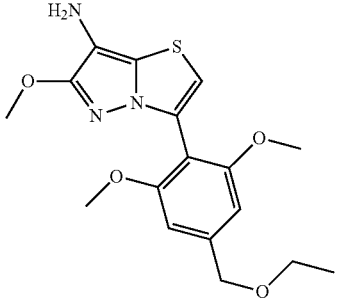

A precursor was synthesized according to the procedure similar to Example 10a, followed by deprotection by conventional methods to yield this compound.

$^1$H-NMR (CDCl$_3$) δ: 1.26 (t, J=7.2 Hz, 3H), 3.61 (q, J=7.2 Hz, 2H), 3.74 (s, 6H), 3.86 (s, 3H), 4.56 (s, 2H), 6.52 (s, 1H), 6.73 (s, 2H).

Example 106

N-Butyl-3-[2,6-dimethoxy-4-(methoxymethyl)phenyl]-6-(methylthio)-N-(tetrahydro-2H-pyran-4-yl)pyrazolo[5,1-b][1,3]thiazole-7-amine

[Chemical Formula 201]

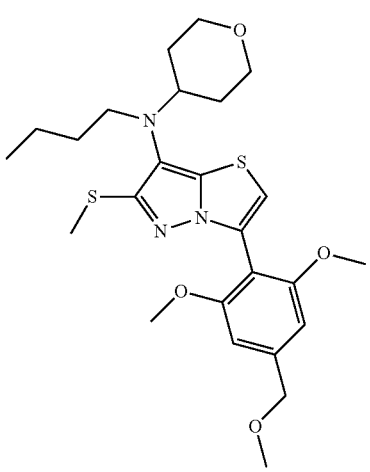

To a DMF (2 mL) solution of tert-butyl[3-[2,6-dimethoxy-4-(methoxymethyl)phenyl]-6-(methylthio)pyrazolo[5,1-b][1,3]thiazol-7-yl]carbamate (23 mg, 0.049 mmol) were added 60% sodium hydride (2.96 mg, 0.074 mmol) and 1-iodobutane (8.43 µl, 0.074 mmol), and the mixture was stirred at room temperature for 1.5 hours. Water was added to the reaction mixture, and then ethyl acetate was added, and a substance of interest was extracted with ethyl acetate. The organic layer was washed with water and brine, and dried over anhydrous magnesium sulfate. The mixture was filtered to yield a filtrate, and the solvent in the filtrate was distilled off under reduced pressure.

Dichloromethane (2 mL) was added to the obtained residue, and then trifluoroacetic acid (1 mL) was added, and the mixture was stirred at room temperature for one hour. The solvent in the reaction mixture was distilled off under reduced pressure. To the obtained residue, THF (2 mL) was added, and then, tetrahydro-4H-pyran-4-one (9.17 µl, 0.095 mmol), and sodium triacetoxyborohydride (20.1 mg, 0.095 mmol) were added in this order, and the mixture was stirred at room temperature for 4.5 hours. To the reaction mixture was added 5N aqueous sodium hydroxide to neutralize the mixture, and then ethyl acetate was added thereto. After thoroughly shaking the mixture, the organic layer was separated, the organic layer was washed with brine and dried over anhydrous magnesium sulfate, and the solvent was distilled off under reduced pressure. The residue was purified by silica gel column chromatography (n-heptane/ethyl acetate=3/2) to obtain the title compound (1.70 mg, 0.0034 mmol).

$^1$H-NMR (400 MHz, CDCl$_3$) δ: 0.87 (t, J=6.8 Hz, 3H), 1.20-1.40 (m, 4H), 1.48-1.72 (m, 2H), 1.78-1.88 (m, 2H), 2.44 (s, 3H), 3.00 (t, J=6.4 Hz, 2H), 3.06-3.18 (m, 1H), 3.37 (td, J=1.6, 11.6 Hz, 2H), 3.47 (s, 3H), 3.78 (s, 6H), 3.94-4.04 (m, 2H), 4.48 (s, 2H), 6.60 (s, 1H), 6.64 (s, 2H).

MS [M+H]$^+$=506

Pharmacological Test Example

The binding capacities of the compounds of the present invention for CRF1 receptor (CRFR1) were evaluated. The test methods and results were as described below.

Test Example 1

<CRFR1 Binding Test>
(1) Preparation of CRFR1-Expressing Cells

The membrane fraction of human CRFR1 high-expressing cells was used as the material for a CRFR1 binding experiment. The CRFR1-expressing cells were prepared in the following manner. The full-length CRFR1 gene was obtained by PCR by using human brain cDNA library (QuickClone™, Clontech). The obtained DNA fragment was inserted into a cloning vector and the base sequence was confirmed. cDNA having the proper base sequence was linked to an expression vector (pcDNA3.1™, Invitrogen). The CRFR1 expression vector was genetically introduced into HEK293 cell, and the resistant cells which proliferated in culture medium containing G418 (1 mg/ml) were cloned by the limiting dilution method. Out of the cloned cells, cells having high binding capacity between the membrane fraction per unit protein and sauvagine were selected according to the following binding experiment, and the selected cells were used for the experiments.

(2) Preparation of Membrane Fraction

The cloned cells obtained in (1) were collected and suspended in ice-cooled membrane buffer (50 mM Tris-HCl, 5 mM MgCl$_2$, 2 mM EGTA, 1 mM DTT, protease inhibitor cocktail (COMPLETE™, Roche Diagnostics) pH 7.3), and then the cells were disrupted with a Polytron (KINEMATICA) while cooling on ice (level 5, 10 seconds, 2-5 times, ice-cooling) and then centrifuged (2,000 rpm, 5 minutes, 4° C.), followed by collecting the supernatant. Membrane buffer was added to the precipitate, and the mixture was subjected to Polytron treatment (same conditions as mentioned above) and centrifuged (conditions as mentioned above), and the obtained supernatant was collected and combined with the previous supernatant. This was centrifuged (13,000 rpm (18,000×g), 30 minutes, 4° C.) to prepare cell membranes. The precipitated cell membranes were suspended in membrane buffer and disrupted with a Polytron (level 5, 10 seconds, 3-5 times, ice-cooling) to prepare a dispersed suspension The protein assay was carried out.

The following method (1) or (2) was carried out for use as the cell membrane fraction.

(1) The above dispersed suspension was diluted with membrane buffer containing 0.1% BSA to a protein concentration of 200 µg/ml, for use as the cell membrane fraction.

(2) The above dispersed suspension was freeze-preserved, and if necessary, thawed, re-dispersed and diluted for use as the cell membrane fraction.

(3) Binding Experiment:

A binding competition experiment with CRF was conducted by the SPA (GE Healthcare) method using a 96-well plate. Five µg of the cell membrane fraction protein, 1 mg of SPA beads and 100 pM $^{125}$I-CRF (Perkin Elmer) were allowed to stand at room temperature for at least two hours in the presence of a test compound, and the radioactivity of each well after centrifugation (1,200 rpm (260×g), five minutes, room temperature) was measured with a TopCount (registered trademark; Perkin Elmer).

(4) Calculation of Binding Capacity

The radioactivity with addition of a 4.000-fold excess of non-radioactive sauvagine as the nonspecific binding was subtracted from each value, and the resulting value was expressed as a percentage (% of control), with 100% as the radioactivity without addition of the test compound (control). The IC$_{50}$ value was calculated from a binding inhibition curve in which the abscissa axis shows the test compound concentration and the ordinate axis shows % (% of control).

<Test Results>

As shown in the following table, the compounds of the present invention exhibit excellent binding capacity with respect to CRFR1.

TABLE 1

| Compound No. (Example No.) | CRF1 receptor binding capacity IC$_{50}$(nM) | Compound No. (Example No.) | CRF1 receptor binding capacity IC$_{50}$(nM) |
| --- | --- | --- | --- |
| 1 | 93 | 53 | 18 |
| 2 | 39 | 54 | 20 |
| 3 | 297 | 55 | 19 |
| 4 | 46 | 56 | 31 |
| 5 | 76 | 59 | 24 |
| 7 | 94 | 60 | 33 |
| 8 | 51 | 61 | 39 |
| 9 | 116 | 62 | 73 |
| 11 | 92 | 63 | 61 |
| 12 | 71 | 64 | 61 |
| 13 | 56 | 66 | 26 |
| 14 | 51 | 67 | 52 |
| 16 | 132 | 68 | 77 |
| 17 | 56 | 69 | 48 |
| 19 | 52 | 70 | 61 |
| 22 | 64 | 71 | 58 |
| 23 | 44 | 72 | 75 |
| 24 | 26 | 73 | 66 |
| 25 | 43 | 74 | 52 |
| 26 | 33 | 75 | 74 |
| 27 | 48 | 76 | 37 |
| 28 | 40 | 79 | 76 |
| 29 | 45 | 81 | 89 |
| 30 | 49 | 82 | 63 |
| 31 | 74 | 83 | 47 |
| 32 | 57 | 84 | 51 |
| 34 | 130 | 86 | 33 |

TABLE 1-continued

| Compound No. (Example No.) | CRF1 receptor binding capacity IC$_{50}$(nM) | Compound No. (Example No.) | CRF1 receptor binding capacity IC$_{50}$(nM) |
|---|---|---|---|
| 35 | 89 | 87 | 36 |
| 37 | 95 | 88 | 53 |
| 39 | 57 | 89 | 52 |
| 40 | 32 | 91 | 61 |
| 41 | 25 | 92 | 47 |
| 42 | 35 | 93 | 45 |
| 43 | 45 | 94 | 45 |
| 44 | 53 | 95 | 80 |
| 45 | 48 | 96 | 62 |
| 46 | 26 | 97 | 80 |
| 47 | 32 | 98 | 88 |
| 48 | 25 | 100 | 89 |
| 49 | 59 | 101 | 99 |
| 50 | 87 | 103 | 101 |
| 51 | 36 | 106 | 83 |

Test Example 2

<Evaluation of Anxiolytic Effect in Light/Dark Box Test in Mice>

(1) Test Procedure:

The light/dark box test in mice was carried out according to a modified method of Belzung C., Misslin R., and Vogel E. et al. (Reference; Behavioural effects of the benzodiazepine receptor partial agonist RO16-6028 in mice, Psychopharmacology, 97, 388-391, 1989). The test apparatus used in this test was a light/dark box including a covered black acrylic box (dark box; 15×10×20 cm), a white acrylic box with top opened (light box; 15×20×20 cm) and a black acrylic tunnel (10×7×4.5 cm) that connects the dark box and the light box and enables a mouse to freely move back and forth between the dark box and light box. In this test apparatus, however, a transparent acrylic plate was used for the front side (20×20 cm) and back side (20×20 cm) of the light box to allow observation of the behavior. After setting illumination so that the light intensity of the floor surface of the light box became 150 Lux, 5-week-old male Balb/c mice (purchased from Nihon Charles River) were introduced into the dark box and the test was started. In the test, the tested compound was suspended in 5% dimethyl sulfoxide, 5% Cremopor EL and 90% physiological saline and orally administered to the test animals one hour prior to the start of the test.

(2) Calculation of Anxiolytic Effect:

The behavior of the mice was observed for 5 minutes after the start of the test. The time spent in the light box was measured as an index of the anxiolytic effect, with "spend in the light box" defined as the state in which all limbs of the mice were on the floor of the light box. The minimum dose which significantly prolonged the time spent in the light box in comparison with that of vehicle-treated group was determined as the minimum effective dose (MED). The statistical significance between the vehicle-treated group and the test compound-treated groups was analyzed by one-way layout analysis of variance followed by Dunnett multiple comparison when multiple doses were set for the same test, and by the Mann-Whitney U test when only one dose was set.

<Test Results>

The compounds of Examples 4, 11, 14, 42, 46, and 94 exhibited an excellent anxiolytic effects in the light/dark box test in mice, with statistically significant effects when the dose was 30 mg/kg (oral administration).

TABLE 2

| Compound No. (Example No.) | Effective Dose (mg/kg) |
|---|---|
| 4 | 30 |
| 11 | 30 |
| 14 | 30 |
| 42 | 30 |
| 46 | 30 |
| 94 | 30 |

Industrial Applicability

The present invention can provide pharmaceutical compositions comprising pyrazolothiazole compounds or pharmacologically acceptable salts thereof, which exhibit CRF receptor antagonism. The compounds or pharmacologically acceptable thereof according to the present invention have excellent CRF receptor antagonism, and sufficient pharmacological activity, safety and pharmacokinetic properties as medicines.

The pharmaceutical compositions of the present invention are useful for treatment or prevention of diseases associated with CRF and/or CRF receptors, and are particularly useful as therapeutic or prophylactic agents for depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder, dementia, or the like.

What is claimed is:

1. A compound represented by the formula (I) or pharmacologically acceptable salt thereof:

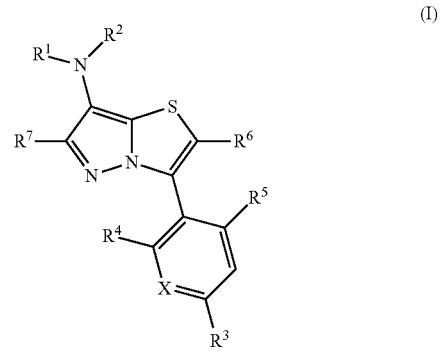

(I)

wherein X is CH;
$R^1$ is -$A^{11}$-$A^{12}$;
$A^{11}$ is a single bond or a C1-6 alkylene group;
$A^{12}$ is a hydrogen atom, (b) a C1-6 alkyl group optionally having 1 to 3 substituents selected from Substituent group A, or (c) a C3-6 cycloalkyl group optionally having 1 o 3 substituents selected from Substituent group A;
$R^2$ is -$A^{21}$-$A^{22}$.
$A^{21}$ is a single bond or a C1-6 alkylene group;
$A^{22}$ is (a) a hydrogen atom, (b) a C1-6 alkyl group optionally having 1 to 3 substituents selected from Substituent group A, (c) a C3-6 cycloalkyl group optionally having 1 to 3 substituents selected from Substituent group A; (d) a non-aromatic heterocyclic group selected from tetrahydropyranyl group, a dihydropyranyl group, a tetrahydrofuryl group, a dioxanyl group, a hexahydrooxepinyl group, an oxabicyclo[3.1.0]hexyl group, a tetrahydrothienyl group, a dithianyl group, and a hexahydrothiepinyl group, which optionally has 1 to 3 substituents selected from Substituent group A, or (c) a heteroaryl group selected from a pyridyl group, a pyrimidinyl group, and a thiazolyl group;

$R^3$ is (a) a C1-6 alkyl group optionally haying 1 to 3 substituents selected from Substituent group A, (b) a C3-6 cycloalkyl group, (c) a C1-6 alkoxy group optionally having 1 to 3 substituents selected from Substituent group A, (d) a C3-6 cycloalkoxy C1-6 alkyl group, (e) di-C1-6 alkyl amino group, (f) a halogen atom, (g) a cyano group, (h) a formyl group, or (i) a carboxyl group;

$R^4$ is a hydrogen atom or a C1-6 alkoxy group;

$R^5$ is a halogen atom, a C1-6 alkyl group, or a C1-6 alkoxy group;

$R^6$ is hydrogen atom, a C1-6 alkyl group, a C1-6 alkoxy group, a C1-6 alkythio group; or a C1-6 alkyl sulfinyl group; and $R^7$ is a C1-6 alkyl group, a C1-6 alkoxy group, or a C1-6 alkylthio group;

with the proviso that $R^3$ is (a) a C1-6 alkyl group optionally substituted with a hydroxyl group, (b) a C3-6 cycloalkyl group, (c) a C2-6 alkoxy group optionally having 1 to 3 substituents selected from Substituent group A, (d) a C3-6 alkoxy C1-6 alkyl group, (e) a C1-2 alkoxy C2-6 alkyl group, (f) a di-C1-6 alkyl amino group, (g) a halogen atom, (h) a formyl group or (i) a carboxyl group when $A^{12}$ is a C1-C6alkyl group or a C3-6 cycloalkyl group optionally having a methyl group, $R^2$ is a tetrahydrofurylmethyl group, a tetrahydropyranylmethyl group, or a tetrahydropyranyl group, $R^6$ is a hydrogen atom, and $R^7$ is a methoxy group; and wherein the Substitutent group A consists of a halogen atom, a hydroxyl group, a C1-6 alkyl group and a C1-6 alkoxy group.

2. The compound or pharmacologically acceptable salt thereof according to claim 1, wherein $A^{11}$ is a single bond, a methylene group or a 1,2-ethylene group;

$A^{12}$ is (a) a hydrogen atom, (b) a C1-6 alkyl group optionally having 1 to 3 substituents selected from Substituent group A, or (c) a C3-6 cycloalkyl group optionally having 1 to 3 substituents selected from Substituent group A;

$A^{21}$ is a single bond, a methylene group, or a 1, 2-ethylene group;

$A^{22}$ represents (a) a hydrogen atom, (b) a C1-6 alkyl group optionally having 1 to 3 substituents selected from Substituent group A, (c) a C3-6 cycloalkyl group optionally having 1 to 3 substituents selected from Substituent group A; (d) a tetrahydropyranyl group optionally having 1 to 3 substituents selected from Substituent group A; (e) a dihydropyranyl group, (f) a tetrahydrofuryl group, (g) a dioxanyl group, (h) a hexahydrooxepinyl group, (i) an oxabicyclo[3.1.0]hexyl group, or (j) a pyridyl group;

$R^3$ is (a) a methyl group, (b) an ethyl group, (c) a cyclopropyl group, (d) a C1-6 alkoxy group optionally substituted with 1 to 3 halogen atoms, (e) a C1-6 alkoxy methyl group, (f) a cyclobutoxymethyl group, (g) a dimethylamino group, (h) a halogen atom, (i) a cyano group, (j) hydroxymethyl group, (k) a formyl group, or (l) a carboxyl group;

$R^4$ is a hydrogen atom or a methoxy group;

$R^5$ is a halogen atom, a methyl group or a methoxy group;

$R^6$ is a hydrogen atom, a methyl group or an ethyl group; and $R^7$ is a methoxy group.

3. The compound or pharmacologically acceptable salt thereof according to claim 2, wherein $R^3$ is (a) a methyl group, (b) an ethyl group, (c) a cyclopropyl group, (d) a C1-6 alkoxy group optionally substituted with 1 to 3 halogen atoms, (e) a C1-6 alkoxy methyl group, or (f) a cyclobutoxymethyl group.

4. The compound or pharmacologically acceptable salt thereof according to claim 1, wherein $R^1$ is a hydrogen atom, a C1-6 alkyl group, a C3-6 cycloalkyl group, or a C3-6 cycloalkyl methyl group;

$R^2$ is a hydrogen atom, a C1-6 alkyl group, a tetrahydropranyl group, a tetrahydropyranylmethyl group, or a tetrahydrofurylmethyl group;

$R^3$ is a C1-6 alkoxy methyl group;

$R^4$ is a methoxy group;

$R^5$ is a methoxy group;

$R^6$ is a hydrogen atom, a methyl group, a methylthk group, or a methylsulfinyl group; and $R^7$ is a methyl group, an ethyl group, an ethoxy group, or a methylthio group.

5. The compound or pharmacologically acceptable salt thereof according to claim 4, wherein $R^7$ is a methyl group.

6. The compound or pharmacologically acceptable salt thereof according to claim 4, wherein $R^7$ is an ethoxy group.

7. A pharmaceutical composition comprising a compound or pharmacologically acceptable salt thereof according to claim 1 as an active ingredient.

8. The pharmaceutical composition according to claim 7, which is a CRF1 receptor antagonist.

9. A method for treating depression, depressive symptoms, anxiety, irritable bowel syndrome, sleep disorder, insomnia, alcohol dependence, alcohol withdrawal symptoms, drug dependence, drug withdrawal symptoms, stress-related gastrointestinal dysfunction, anorexia nervosa, eating disorder, postoperative ileus, ischemic neuropathy, apoplexy, excitotoxic neuropathy, convulsion, epilepsy, hypertension, schizophrenia, bipolar disorder or dementia, comprising administering a compound or pharmacologically acceptable salt thereof according to claim 1 to patient.

10. A method for treating depression, depressive symptoms, anxiety, irritable bowel syndrome, sleep disorder, insomnia, alcohol dependence, alcohol withdrawal symptom, drug dependence, drug withdrawal symptoms, stress-related gastrointestinal dysfunction, or dementia, comprising administering a compound. or pharmacologically acceptable salt thereof according to claim 1 to patient.

11. A method for treating depression, depressive symptoms, anxiety, or irritable bowel syndrome, comprising administering compound or pharmacologically acceptable salt thereof according to claim 1 to patient.

12. The compound or pharmacologically acceptable salt thereof according to claim 1, wherein the compound is N-(cyclopropylmethyl)-3-[2,6-dimethoxy-4-(methoxymethyl)phenyl]-6-methyl-N-(tetrahydro-2H-pyran-4-ylmethyl)pyrazolo[5,1-b][1,3]thiazole-7-amine:

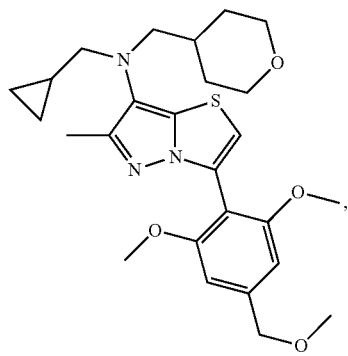 [SMILES: COCc1cc(OC)c(-c2csc3c(N(CC4CCOCC4)CC4CC4)c(C)nn23)c(OC)c1]

cyclopropylmethyl-[3-(2,6-dimethoxy-4-methoxymethyl-phenyl)-6-methoxy-pyrazolo[5,1-b][1,3 ]thiazol-7-yl]-[1,3]dioxan-5-ylmethyl-amine:

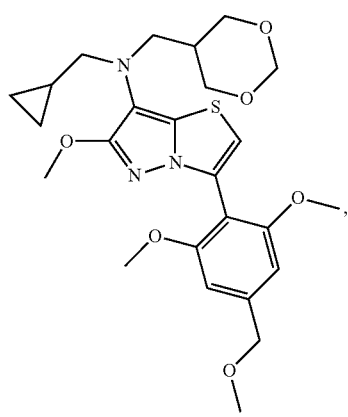 [SMILES: COCc1cc(OC)c(-c2csc3c(N(CC4CC4)CC4COCOC4)c(OC)nn23)c(OC)c1]

or
N-butyl-3-[2,6-dimethoxy-4-(methoxymethy)phenyl]-6-(methylthio)-N-(tetrahydro-2H-pyran-4-yl)pyrazolo[5,1-b] [1,3]thiazole-7-amine:

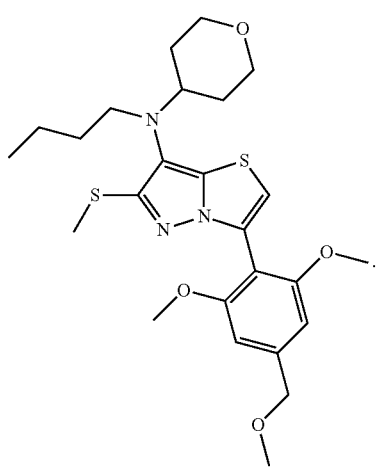 [SMILES: CCCCN(c1c(SC)nn2c(-c3c(OC)cc(COC)cc3OC)csc12)C1CCOCC1]

13. The compound or pharmacologically acceptable salt thereof according to claim 1, wherein compound is N-(cyclopropylmethyl)-3-dimethoxy-4-(methoxymethyl)phenyl]-6-methyl-N-(tetrahydro-2H-pyran-4-ylmethyl)pyrazolo[5,1-b][1,3]thiazole-7-amine:

14. The compound or pharmacologically acceptable salt thereof according to claim 1, wherein the compound is cyclopropylmethyl-[3(2,6-dimethoxy-4-methoxymethyl-phenyl)-6-methoxy-pyrazolo[5,1-b][1,3]thiazol-7-yl]-[1,3 ]dioxan-5-ylmethyl-amine:

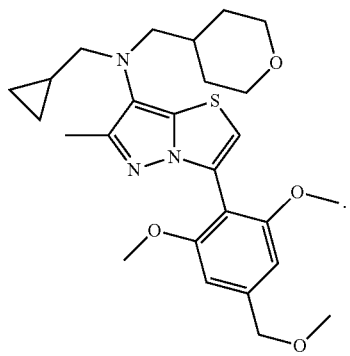 [SMILES: COCc1cc(OC)c(-c2csc3c(N(CC4CCOCC4)CC4CC4)c(C)nn23)c(OC)c1]

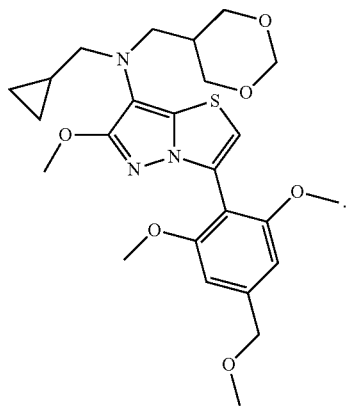 [SMILES: COCc1cc(OC)c(-c2csc3c(N(CC4CC4)CC4COCOC4)c(OC)nn23)c(OC)c1]

15. The compound or pharmacologically acceptable salt thereof according to claim 1, wherein the compound is N-butyl-3-[2,6-dimethoxy-4-(methoxymethyl)phenyl]-6-(methylthio)-N-(tetrahydro-2H-pyran-4-yl)pyrazolo[5,1-b][1,3] thiazole-7-amine:

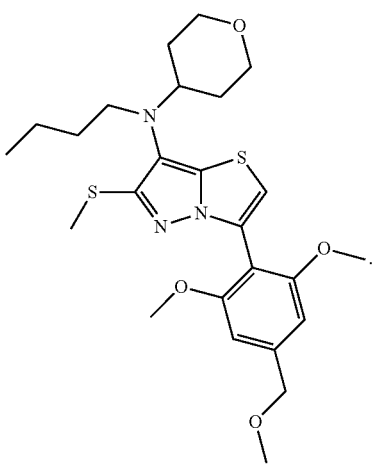 [SMILES: CCCCN(c1c(SC)nn2c(-c3c(OC)cc(COC)cc3OC)csc12)C1CCOCC1]

* * * * *